US011918578B2

(12) United States Patent
Jaecklin et al.

(10) Patent No.: US 11,918,578 B2
(45) Date of Patent: *Mar. 5, 2024

(54) METHODS FOR TREATING CHOLESTASIS

(71) Applicant: Mirum Pharmaceuticals, Inc., Foster City, CA (US)

(72) Inventors: Thomas Jaecklin, Delemont (CH); Alejandro Dorenbaum, Mill Valley, CA (US)

(73) Assignee: MIRUM PHARMACEUTICALS, INC., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,669

(22) Filed: Oct. 5, 2022

(65) Prior Publication Data

US 2023/0190742 A1 Jun. 22, 2023

Related U.S. Application Data

(63) Continuation of application No. 17/554,588, filed on Dec. 17, 2021, now Pat. No. 11,497,745, which is a continuation of application No. 16/994,368, filed on Aug. 14, 2020, now Pat. No. 11,229,647, which is a continuation of application No. PCT/US2020/017941, filed on Feb. 12, 2020.

(60) Provisional application No. 62/932,015, filed on Nov. 7, 2019, provisional application No. 62/908,431, filed on Sep. 30, 2019, provisional application No. 62/863,904, filed on Jun. 20, 2019, provisional application No. 62/804,523, filed on Feb. 12, 2019.

(51) Int. Cl.
*A61K 31/4995* (2006.01)
*A61K 31/554* (2006.01)
*A61K 31/7042* (2006.01)
*A61P 1/16* (2006.01)
*A61P 17/04* (2006.01)
*G01N 33/68* (2006.01)

(52) U.S. Cl.
CPC ........ *A61K 31/4995* (2013.01); *A61K 31/554* (2013.01); *A61K 31/7042* (2013.01); *A61P 1/16* (2018.01); *A61P 17/04* (2018.01); *G01N 33/6893* (2013.01); *G01N 2800/085* (2013.01)

(58) Field of Classification Search
None
See application file for complete search history.

(56) References Cited

U.S. PATENT DOCUMENTS

| 7,956,085 | B2 | 6/2011 | Frick et al. |
| 9,040,518 | B2 | 5/2015 | Aquino et al. |
| 11,229,647 | B2 | 1/2022 | Jaecklin et al. |
| 11,497,745 | B2* | 11/2022 | Jaecklin .................. A61P 1/16 |
| 2005/0009805 | A1 | 1/2005 | Sasahara et al. |
| 2010/0130472 | A1 | 5/2010 | Young et al. |
| 2013/0108573 | A1 | 5/2013 | Gedulin et al. |
| 2014/0243281 | A1 | 8/2014 | Gedulin et al. |
| 2014/0275090 | A1 | 9/2014 | Gedulin |
| 2016/0193277 | A1 | 7/2016 | Gillberg et al. |
| 2016/0310518 | A1* | 10/2016 | Gedulin .................. A61K 31/38 |
| 2017/0210717 | A1 | 7/2017 | Guo et al. |
| 2017/0368075 | A1 | 12/2017 | Sawai et al. |
| 2022/0265649 | A1 | 8/2022 | Gedulin et al. |
| 2023/0212211 | A1 | 7/2023 | Gedulin et al. |

FOREIGN PATENT DOCUMENTS

| CA | 2815749 | 5/2012 |
| EA | 29581 | 4/2018 |
| EA | 201792541 | 7/2018 |
| JP | 2014-532662 | 12/2014 |
| JP | 2014-532663 | 12/2014 |
| WO | 2000062810 | 10/2000 |
| WO | 2002050051 | 6/2002 |
| WO | 2003022286 | 3/2003 |
| WO | 2005027894 | 3/2005 |
| WO | 2008058628 | 5/2008 |
| WO | 2011137135 | 11/2011 |
| WO | 2012064266 | 5/2012 |
| WO | 201767935 | 10/2017 |
| WO | 2018193006 | 10/2017 |
| WO | 2017002827 | 4/2018 |
| WO | WO-2020167958 A1 * | 8/2020 ......... A61K 31/4995 |

OTHER PUBLICATIONS

Baker Alastair et al., "LB-3: A long-term phase 2 safety and efficacy study of the apical sodium-dependent bile acid transporter inhibitor maralixibat in children with Alagille syndrome: preliminary results from th IMAGINE study", Hepatology; 68th Annual Meeting of the American-Association-for-the-Study-of-Live R-Diseases (AASLD) / Liver Meeting; Oct. 20-24, 2017, vol. 66, No. 6., Nov. 30, 2017, pp. 1255A-1256A, XP009533601, ISSN: 0270-9139.

Supplementary European Search Report dated Nov. 21, 2022 in connection with EP Application No. 20756251.3.

Malatack Jeffrey et al., "Case Report a Drug Regimen for Progressive Familial Cholestasis Type 2" Pediatrics, Jan. 1, 2018, pp. 1-5, XP055975631.

Clinical Trials.Gov: "Study Record Versions History of Changes for Study: NCT03659916 Long Term Safety & Efficacy Study Evaluation the Effect of A4250 in Children With PFIC Types 1 & 2", clinical trials.gov, Feb. 11, 2019, pp. 1-11, XP055975930.

Clinical Trials.Gov: "Study Record Versions Contacts/Locations and Study Status History of Changes for Study: NCT03566238 This Study Will Investigate the Efficacy and Safety of A4250 in Children With PFIC 1 or 2 (PEDFIC 1)", clinical trials.gov, Feb. 8, 2019, pp. 1-16, XP055975866.

(Continued)

Primary Examiner — Leslie A. Royds Draper
(74) Attorney, Agent, or Firm — Troutman Pepper Hamilton Sanders LLP

(57) ABSTRACT

Provided herein are methods for treating cholestasis in a subject having a liver disease. The method includes administering to the subject an Apical Sodium-dependent Bile Acid Transporter (ASBTI). More specifically, the present invention relates to methods for treating cholestasis in a subject where the method includes administering an ASBTI to a subject at a dose of at least 10 μg/kg/day.

17 Claims, 55 Drawing Sheets

(56) References Cited

OTHER PUBLICATIONS

Anonymous: "Study Record Versions History of Changes for Study: NCT04185363 An Extension Study of Maralixibat in Patients With Progressive Familial Intrahepatic Cholestasis (PFIC)", Clinical trials. gov, Dec. 6, 2019, pp. 1-9, XP055977607.

Anonymous: "Study Record Versions History of Changes for Study: NCT04168385 MRX-800: A Long-Term Safety Study of Maralixibat in the Treatment of Cholestatic Liver Disease in Subject Who Previously Participated in a Maralixibat Study (MERGE)", clinicaltrials.gov, Jan. 22, 2020, pp. 1-9, XP055977617.

Melissa Palmer et al., "A randomised, double-blind, placebo-controlled phase 1 study of the safety, tolerability and pharmacodynamics of volixibat in overweight and obese but otherwise healthy adults: implications for treatment of non-alcoholic steathepatitis", BMC Pharmacology and Toxicology, Biomed Central Ltd, London, UK, vol. 19, No. 1, Mar. 16, 2018, pp. 1-13, XP021254505.

Supplementary European Search Report dated Nov. 22, 2022 in connection with EP Application No. 20755296.9.

Eudract 2015-001157-21: "Clinical Trial Results: An exploratory Phase II Study to demonstrate the Safety and Efficacy of A4250 in Children with Cholestatic Pruritus Summary", EU clinical Trials register, Oct. 14, 2017, pp. 1-19, XP055975770.

Strautnieks S. et al., "Severe Bile Salt Export Pump Deficiency: 82 Different ABCB11 Mutations in 109 Families", Gastroenterology, Elsevier Inc, US, vol. 134, No. 4, Apr. 1, 2008, pp. 1203-1214, XP022584853.

Baumann U, "Effects of the ileal bile acid transport inhibitor A4250 on pruritus and serum bile acids in patients with biliary atresia: phase 2 study results", Journal of Pediatric Gastroenterology and Nutrition May 1, 2019 Lippincott Williams and Wilkins NLD, vol. 68, No. Supplement 1, May 1, 2019, pp. 767.

Thompson Richard, "Oral Abstracts (Abstracts 1-288)", Hepatology, vol. 70, No. S1, Oct. 1, 2019, pp. 1-1, XP055977389.

Clinical Trials.Gov: "Study Record Versions History of Changes for Study: NCT02057718 Open Label Study to Evaluate Efficacy and Long Term Safety of LUM001 in the Treatment of Cholestatic Liver Disease in Patients With Progressive Familial Intrahepatic Cholestasis (INDIGO)", Sep. 5, 2017, pp. 1-13, XP055975938.

Hegade Vinod et al., "Effect of ileal bile acid transporter inhibitor GSK2330672 on pruritus in primary biliary cholangitis: a double-blind, randomised, placebo-controlled, crossover, phase 2a study" The Lancet Elsevier, Amsterdam, NL, vol. 389, No. 10074, Feb. 8, 2017, pp. 1114-1123, XP029946669.

Chen Huey-Ling et al., "Expression of Hepatocyte Transposters and Nuclear Receptors in Children With Early and Late-Stage Biliary Atresia", Pediatric Research, vol. 63, No. 6, Jun. 1, 2008, pp. 667-673, XP055978248.

Al-Dury et al., Ileal Bile Acid Transporter Inhibition for the Treatment of Chronic Constipation, Cholestatic Pruritus, and NASH, Frontiers in Pharmacology, 2018, vol. 9, Article 931, 8 pages, entire document, especially: abstract; p. 5, col. 2, para 4; p. 6, col. 1, pare 2; p. 6, col. 1, para 3.

International Search Report dated Jun. 26, 2020 in connection with PCT/US20/017951.

Written Opinion dated Jun. 26, 2020 in connection with PCT/US20/017951.

International Search Report dated May 11, 2020 in connection with PCT/US20/017970.

Written Opinion dated May 11, 2020 in connection with PCT/US20/017970.

Supplementary European Search Report issued in EP 20756138.2 dated Feb. 24, 2022.

Mirum Pharmaceuticals: "Mirum Pharmaceuticals Presents New Data Demonstrating Durable Improvements in ClinicalOutcome Measures in Patients with PFIC2 and Alagille Syndrome Treated with Maralixibat", Apr. 15, 2019; URL: https://www.prnewswire.com/news-releases/mirum-pharmaceuticals-presents-new-data-demonstrating-durable-improvements-in-clinical-outcome-measures-in-patients-with-pfic2-and alagille-syndrome-treated-with-maralixibat-300831721.html [retrieved on Feb. 15, 2022] *p. 2 para 2; p. 4 para 3; p. 4 para 2*.

Office Action dated Jun. 23, 2023 in connection with Russian Patent Application No. 2021126624.

Hegade VS et al. Apical Sodium-Dependent Transporter Inhibitors in Primary Biliary Cholangitis and Primary Sclerosing Cholangitis. Dig Dis., 2017, 35(3):267-274, doi: 10.1159/000450988.

Extended European Search Report dated Oct. 24, 2023 in connection with European Application No. 23184125.5.

Thompson Richard, "Oral Abstracts (Abstracts 1-263)", Hepatology, vol. 66, No. S1, Oct. 1, 2017, pp. 1-148, XP093090080.

Thompson Richard J. et al. "Phase 2 open-label efficacy and safety study of the apical sodium-dependent bile acid transporter inhibitor maralixibat in children with progressive familial intrahepatic cholestasis: 48-week interim efficacy analysis", Oct. 24, 2017, pp. 1-18, XP093090535.

Office Action dated Oct. 2, 2023 in connection with Russian Patent Application No. 2021126651.

Kamath B. M. et al. "Childhood Liver Disease Research Network (ChiLDReN). Quality of Life and Its Determinants in a Multicenter Cohort of Children with Alagille Syndrome" J. Pediatr. 2015, v.167, No. 2, p. 390-396.

Miloh T, Bulut P. "Primary sclerosing cholangitis during childhood and adolescence" Clin. Liver Dis. (Hoboken), 2013, v. 2, No. 5, p. 215-218.

Davit-Spraul et al., "ATP8B1 and ABCD11 Analysis in 62 Children with Normal Gamma-Glutamyl Transferase Progressive Familial Intrahepatic Cholestatis (PFIC): Phenotypic Differences Between PFIC1 and PFIC2 and Natural History" Hepatology, 2010, vol. 51, No. 5, pp. 1645-1655, abstract: p. 1652, col. 2, para 1.

Gonzales et al. "Phase 2 Open-Label Study with a Placebo-Controlled Drug Withdrawal Period of the Apical Sodium-Bile Acid Transporter Inhibitor Maralixibat in Children with Alagille Syndrome: 48-Week interim Efficacy Analysis", Journal of Hepatology, Apr. 2019; 70:e119-120, Abstract PS-193. (Year: 2019).

Gonzales et al. "Durability of Treatment Effect with Long-Term Maralixibat in Children with Alagille Syndrome: 4-Year Safety and Efficacy Results from the ICONIC Study", Hepatology, Nov. 29, 2019; 70(6,Suppl,); Abstract L03, p. 1479A, (Year: 2019).

Gonzales et al., "Efficacy and Safety of Maralixibat Treatment in Patients with Alagille Syndrome and Cholestatic Pruritus (ICONIC): A Randomised Phase 2 Study", Lancet, Oct. 30, 2021; 398: 1581-1592 (Year: 2021).

PubChem [Online] "Maralixibat Chloride" (CID 9831642). [Retrieved Mar. 2, 2021]. Retrieved from the Internet: <URL: https://pubchem.ncbi.nlm.nih.gov/compound/Maralixibat-chloride>. pp. 1-15. (Year: 2021).

Quiros-Tejeira et al. "Does Liver Transplantation Affect Growth Pattern in Alagille Syndrome?" Liver Transpl. 2000; 6:582-587. (Year: 2000).

(Anonymous: "Study Record Versions Contacts/Locations and Study Status Study Status and Study Identification Contacts/Locations and Study Status History of Changes for Study:NCT02160782 Safety and Efficacy Study of LUMO01 With a Drug Withdrawal Period in Participants With Alagille Syndrome (ALGS) (ICONIC)", Sep. 19, 2018 (Sep. 19, 2018), XP055892127)—Safety and Efficacy Study of LUM001 With a Dmg Withdrawal Period in Participants With Alagille Syndrome (ALGS) (ICONIC), https://www.clinicaltrials.gov/ct2/history/NCT02160782?V20=View.

Shneider et al. "Results of ITCH, A Multi-Center Randomized Double-Blind Placebo-Controlled Trial of Maralixibat, an Ileal Apical Sodium-Dependent Bile Acid Transporter Inhibitor (ASBTi), for Pruritus in Alagille Syndrome (ALGS)", Hepatology, Oct. 2017; 66(S1):84A, Abstract 144. (Year: 2017).

Shneider et al., "Placebo-Controlled Randomized Trial of an Intestinal Bile Salt Transport Inhibitor for Pruritus in Alagille Syndrome", Hepatology Communications, 2018, vol. 2 (10), pp. 1184-1198, entire document.

International Search Report dated Jul. 29, 2020 in connection with PCT/US20/017941.

Written Opinion dated Jul. 29, 2020 in connection with PCT/US20/017941.

(56) References Cited

OTHER PUBLICATIONS

Office Action dated Oct. 31, 2023 in connection with Canadian Patent Application No. 3,129,735.
Los et al., "Nutrition for Children with Cholestatic Liver Disease", Nestle Nutr Workshop Ser Pediatr Program, 59, pp. 147-157, 2007.
European Search Report dated Nov. 8, 2023 in connection with European Application No. 23190792.4.
Mayo Marlyn J. et al., "A Randomized, Controlled, Phase 2 Study of Maralixibat in the Treatment of Itching Associated with Primary Biliary Cholangitis", Hepatology Communications, vol. 3, No. 3, Feb. 1, 2019, pp. 365-381, XP093098015.
Al-Dury Samer et al., "Pilot study with IBAT inhibitor A4250 for the treatment of cholestatic pruritus in primary biliary cholangitis", Scientific Reports, vol. 8, No. 1, Apr. 27, 2018, XP093098023.
Anonymous: "EU Clinical Trials Register Clinical trial results: A Pilot, Open-Label Study to Evaluate the Safety, Tolerability and Efficacy of LUM001, an Apical Sodium-dependent Bile Acid Transporter Inhibitor (ASBTi), in Patients with Primary Sclerosing Cholangitis (PSC)", EU clinical trials, Jan. 7, 2017, pp. 1-15, XP093098090.
Bowlus Christopher, "Safety and efficacy of maralixibat in patients with primary sclerosing cholangitis: an open-label proof-of-concept study", Nov. 12, 2019, pp. 1-1, XP09309121.
Tiessen Renger G et al., "Safety, tolerability and pharmacodynamics of apical sodium-dependent bile acid transporter inhibition with volixibat in healthy adults and patients with type 2 diabetes mellitus: a randomised placebo-controlled trial", BMC Gastroenterology, vol. 18, No. 1, Jan. 5, 2018, XP093097755.
Poupon, R., et al. "Chronic cholestatic diseases", Journal of Hepatology 2000; 32 (suppl. 1): 129-140. doi: 10.1016/s0168-8278(00)80421-3. PMID: 10728800.
Morotti RA, et al. "Progressive familial intrahepatic cholestasis (PFIC) type 1, 2, and 3: a review of the liver pathology findings" Semin Liver Dis. Feb. 2011;31(1):3-10. doi: 10.1055/s-0031-1272831. Epub Feb. 2, 20112. PMID: 21344347.
Huang H.-C. et al., "Discovery of potent, nonsystemic apical sodium-co-dependent bile acid transporter inhibitors (Part 2)", Journal of Medicinal Chemistry, 48, pp. 5853-5868, Sep. 1, 2005.
Office Action dated Dec. 20, 2023 in connection with Canadian Application No. 3,129,827.
Malatack, J.J. et al., "A Drug Regimen for Progressive Familial Cholestasis Type 2", PEDIATRICS, vol. 141 (1), e20163877, Jan. 1, 2018.
Office Action dated Nov. 15, 2023 in connection with Japanese Application No. 2021-547793.
Baumann U., et al., "Effects of the ileal bile acid transport inhibitor A4250 on serum bile acids, pruritus and sleep in patients with Alagille syndrome: phase 2 study results", J. Pediatr. Gastroenterol. Nutr. (May 2019) vol. 68, Suppl. 1, p. 686-687(H-O-006).
Office Action dated Nov. 15, 2023 in connection with Japanese Patent Appln. No. 2021-547790.
Sturm E., "The ileal bile acid transport inhibitor A4250 reduced pruritus and serum bile acid levels in children with cholestatic liver disease and pruritus final results from a multiple-dose, open-label, multinational study", Hepatology (2017) vol. 66, No. 1, suppl., p. 646A-647A (1200).
Imagawa K., et al., Clinical phenotype and molecular analysis of a homozygous ABCB11 mutation responsible for progressive infantile cholestasis:, J. Hum. Genet. (2018) vol. 63, issue 5, p. 569-577 (a document cited as disclosing a common technical matter).
Liver (2003) vol. 44, No. 10, p. 12-20 (a document cited as disclosing a common technical matter).
Office Action dated Nov. 15, 2023 in connection with Japanese Patent Appln. No. 2021-547575.
Office Action dated Dec. 14, 2023 in connection with Russian Patent Application No. 2021126624.
https://www.fiercebiotech.com/biotech/shire-reports-topline-results-from- first-of-three-placebo-controlled-phase-2-studies-of Michael Gibney, Shire Reports Topline Results from First of Three Placebo-Controlled Phase 2 Studies of SHP625 (LUM001) in Children with Alagille Syndrome, 2015. found online at https://web.archive.org/web/20160506062040/, https://www.fiercebiotech.com/biotech/shire-reports-topline-results-from-first-of-three-placebo-controlled-phase-2-studies-of.
J.C.Bucuvalas et al. "Growth hormone insensitivity associated with elevated circulating growth hormone-binding protein in children with Alagille syndrome and short stature", Journal of Clinical Endocrinology and Metabolism, 1993, vol. 76, 6, p. 1477-1482.
E.V. Omelchenko et al. Arteriohepatic dysplasia (Alagille syndrome) in a child. 2015, No. 62, p. 129-132. English translation not attached.

* cited by examiner

ItchRO, Adult Itch Reported Outcome (0–10 daily score); sBA, serum bile acid; 7αC4, 7-α-hydroxy-cholesten-3-one ItchRO, Adult Itch Reported Outcome (0–10 daily score); LDL-C, low-density lipoprotein cholesterol

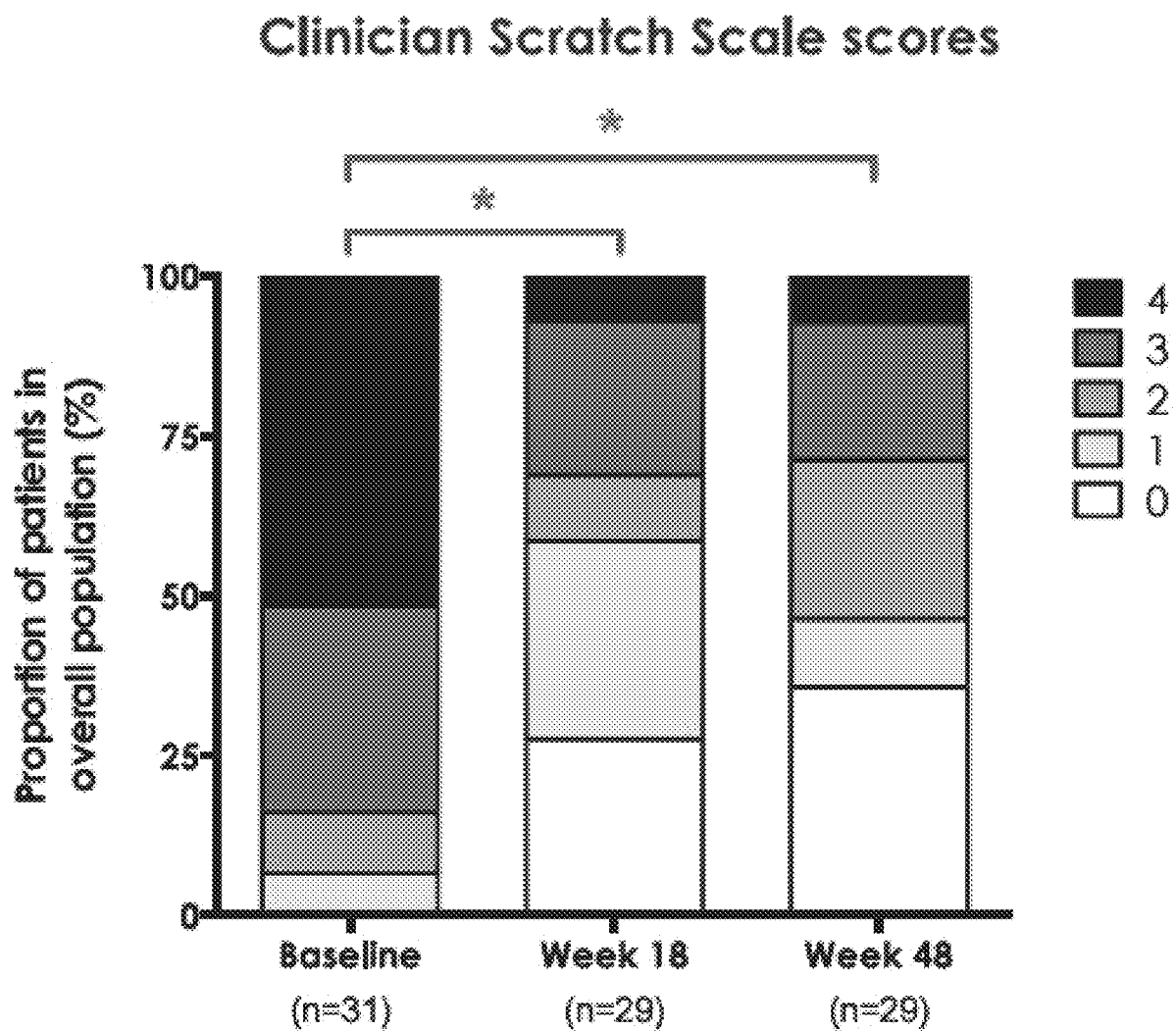

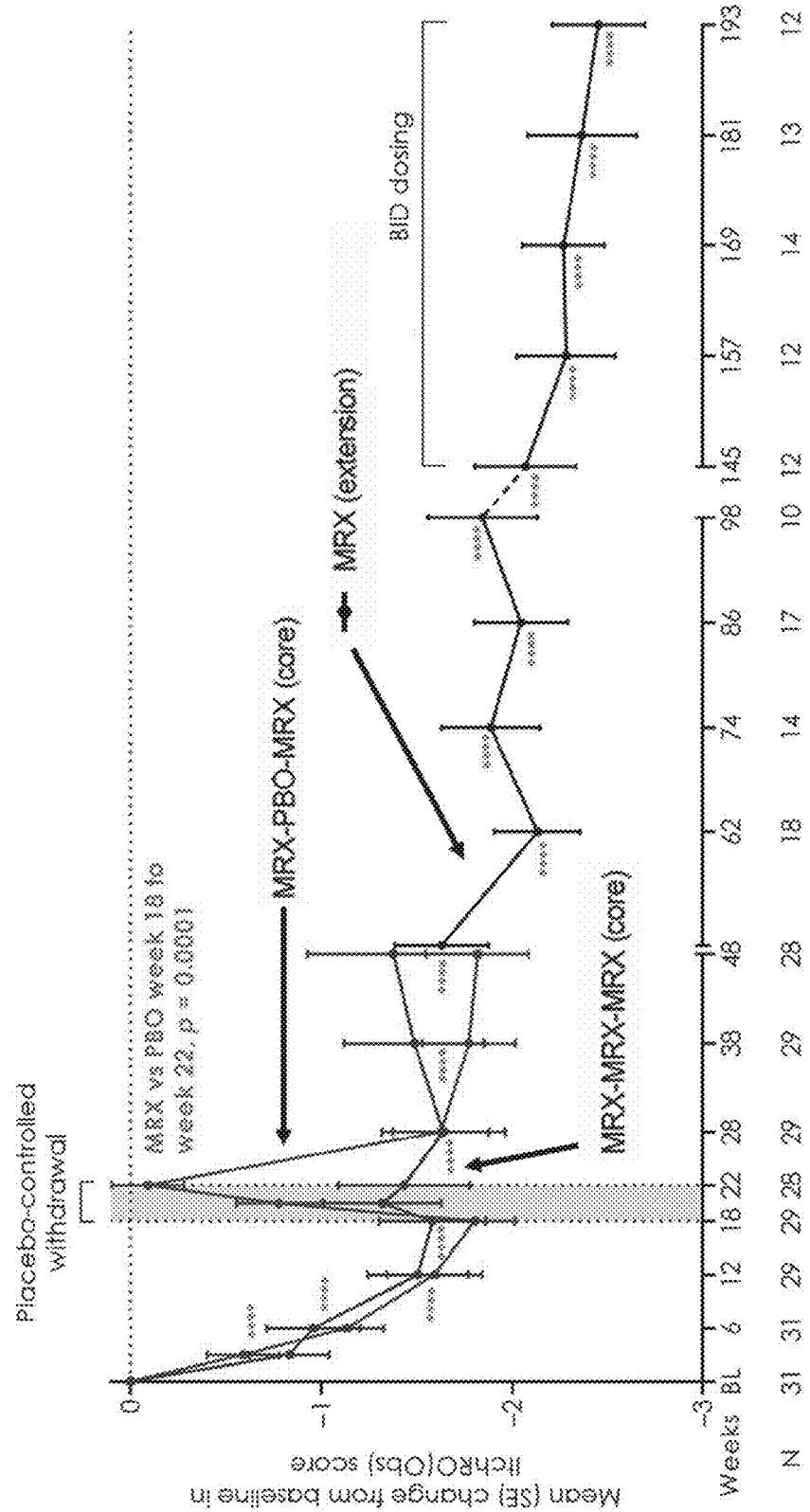

METHODS FOR TREATING CHOLESTASIS

CROSS REFERENCE TO RELATED APPLICATIONS

This application is a continuation of Ser. No. 17/554,588, filed Dec. 17, 2021, which is a continuation of Ser. No. 16/994,368, filed Aug. 14, 2020, now U.S. Pat. No. 11,229,647, issued Jan. 25, 2022, which is a continuation of PCT/US2020/017941, filed on Feb. 12, 2020, which claims the benefit under 35 U.S.C. § 119(e) of U.S. Provisional Application Nos. 62/804,523, filed Feb. 12, 2019, 62/863,904, filed Jun. 20, 2019, 62/908,431, filed Sep. 30, 2019, and 62/932,015, filed Nov. 7, 2019, which are incorporated herein by reference in their entirety for all purposes.

FIELD OF THE INVENTION

The present invention relates generally to methods for treating cholestasis in a subject having liver disease. More specifically, the present invention relates to methods for treating cholestasis in a subject where the method includes administering an ASBTI to a subject at a dose of at least 10 µg/kg/day.

BACKGROUND

Hypercholemia and cholestatic liver diseases are liver diseases associated with impaired bile secretion (i.e., cholestasis), associated with and often secondary to the intracellular accumulation of bile acids/salts in the hepatocyte. Hypercholemia is characterized by increased serum concentration of bile acid or bile salt. Cholestasis can be categorized clinicopathologically into two principal categories of obstructive, often extrahepatic, cholestasis, and nonobstructive, or intrahepatic, cholestasis. Nonobstructive intrahepatic cholestasis can further be classified into two principal subgroups of primary intrahepatic cholestasis that result from constitutively defective bile secretion, and secondary intrahepatic cholestasis that result from hepatocellular injury. Primary intrahepatic cholestasis includes diseases such as benign recurrent intrahepatic cholestasis, which is predominantly an adult form with similar clinical symptoms, and progressive familial intrahepatic cholestasis (PFIC) types 1, 2, and 3, which are diseases that affect children.

Neonatal respiratory distress syndrome and lung pneumonia is often associated with intrahepatic cholestasis of pregnancy. Active treatment and prevention are limited. Currently, effective treatments for hypercholemia and cholestatic liver diseases include surgery, liver transplantation, and rarely administration of ursodiol. Effective and safe medication for hypercholemia and cholestatic liver diseases is needed.

SUMMARY OF THE INVENTION

Various non-limiting aspects and embodiments of the invention are described below.

In one aspect, the present invention provides a method for treating cholestatic liver disease in a subject comprising administering to the subject an Apical Sodium-dependent Bile Acid Transporter Inhibitor (ASBTI). The ASBTI is administered in an amount of from about 10 µg/kg/day to about 1400 µg/kg/day.

In certain embodiments, the ASBTI is wherein the ASBTI is

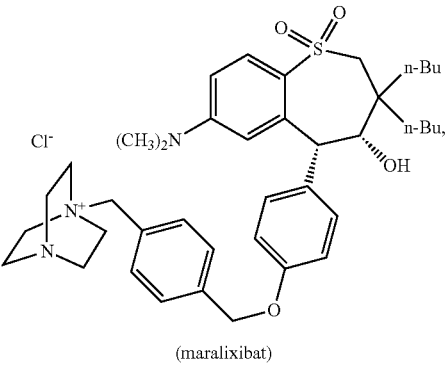

(maralixibat)

or a pharmaceutically acceptable alternative salt thereof,

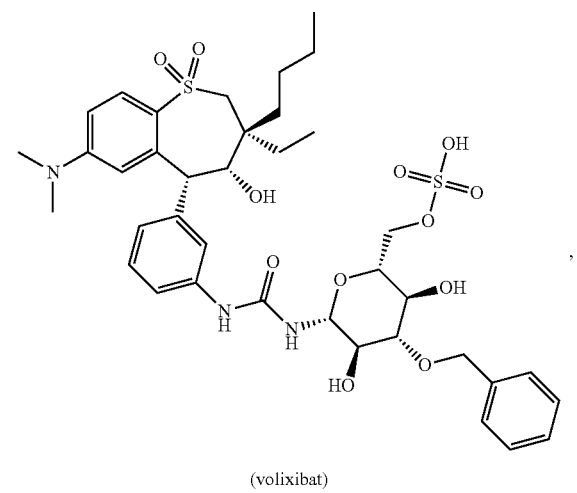 [SMILES: CCCC[C@]1(CC)CS(=O)(=O)c2ccc(N(C)C)cc2[C@@H](c2cccc(NC(=O)N[C@@H]3O[C@H](COS(=O)(=O)O)[C@@H](O)[C@H](OCc4ccccc4)[C@H]3O)c2)[C@H]1O]

(volixibat)

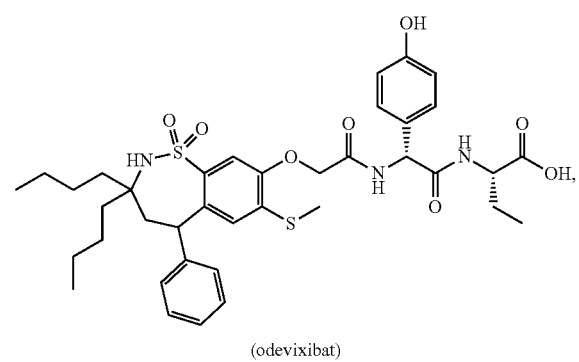

(odevixibat)

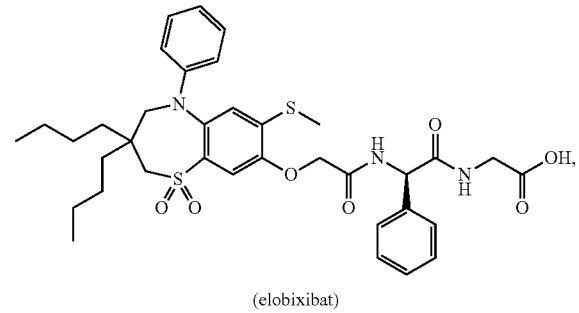

(elobixibat)

-continued (GSK2330672)

or a pharmaceutically acceptable salt thereof. In various embodiments, the ASBTI is maralixibat, or a pharmaceutically acceptable salt thereof. In some embodiments, the ASBTI is volixibat, or a pharmaceutically acceptable salt thereof. In certain embodiments, the ASBTI is odevixibat, or a pharmaceutically acceptable salt thereof. In various embodiments, the ASBTI is elobixibat, or a pharmaceutically acceptable salt thereof. In certain embodiments, the ASBTI is GSK2330672, or a pharmaceutically acceptable salt thereof.

In some embodiments, the cholestatic liver disease is a pediatric cholestatic liver disease that results in below normal growth, height, or weight. In various embodiments, the cholestatic liver disease is selected from progressive familial intrahepatic cholestasis (PFIC), Alagille Syndrome (ALGS), primary sclerosing cholangitis (PSC), biliary atresia, intrahepatic cholestasis of pregnancy (ICP), or primary biliary cholangitis (PBC). In some embodiments, the cholestatic liver disease is biliary atresia. In various embodiments, the cholestatic liver disease is ICP.

In certain embodiments, the cholestatic liver disease is PFIC. In some embodiments, the ASBTI is odevixibat. In certain embodiments, the ASBTI is maralixibat. In certain embodiments, the PFIC is selected from PFIC type 1, PFIC type 2 and PFIC type 3. In various embodiments, the PFIC is PFIC type 2. In some embodiments, the subject has a non-truncating mutation in ABCB11 gene. In various embodiments, the subject is a pediatric subject. In certain embodiments, the ASBTI is administered once daily (QD).

In various embodiments, the ASBTI is administered twice daily (BID). In some embodiments, the ASBTI is administered in an amount of from about 140 µg/kg/day to about 1400 µg/kg/day. In some embodiments, the ASBTI is administered in an amount of from about 280 µg/kg/day to about 1400 µg/kg/day.

In certain embodiments, administration of the ASBTI results in a reduction in a symptom or a change in a disease-relevant laboratory measure of the cholestatic liver disease that is maintained for at least one year. In various embodiments, the reduction in the symptom or a change in a disease-relevant laboratory measure comprises a reduction in sBA concentration, an increase in serum 7α-hydroxy-4-cholesten-3-one (7αC4) concentration, an increase in a ratio of serum 7αC4 concentration to serum bile acids (sBA) concentration (7αC4:sBA), a reduction in pruritis, an increase in a quality of life inventory score, an increase in a quality of life inventory score related to fatigue, an increase in growth, or a combination thereof. In some embodiments, the reduction in the symptom or a change in a disease-relevant laboratory measure is determined relative to a baseline level. In certain embodiments, the reduction in the symptom or a change in a disease-relevant laboratory measure comprises an increase in growth. In various embodiments, the increase in growth of the pediatric subject is measured as an increase in height Z-score or weight Z-score.

In certain embodiments, the administration of the ASBTI results in an increase in serum 7αC4 concentration. In some embodiments, the serum 7αC4 concentration is increased from about 1.5-fold to about 40-fold relative to baseline. In various embodiments, the serum 7αC4 concentration is increased by at least 100% relative to baseline. In some embodiments, the administration of the ASBTI results in an increase in a ratio of serum 7αC4 concentration to sBA concentration (7αC4:sBA). In certain embodiments, the 7αC4:sBA is increased by from about 2-fold to about 5,000-fold relative to baseline.

In various embodiments, the method further comprises administering a second dose of the ASBTI, wherein the second dose is greater than the first dose, if after the administration of the first dose of the ASBTI the 7αC4:sBA is not maintained at about >2-fold higher than the baseline ratio. In some embodiments, the method further comprises administering a second dose of the ASBTI, wherein the second dose is greater than the first dose, if the 7αC4:sBA initially increases by at least >2-fold higher than the baseline ratio and then begins to decrease back to the baseline ratio.

In various embodiments, the administration of the ASBTI results in a decrease in sBA concentration of at least about 70% relative to baseline. In certain embodiments, the administration of the ASBTI results in a reduction in severity of pruritis. In various embodiments, the reduction in severity of pruritis is measured as a reduction of at least 1.0 in an observer-reported itch reported outcome (ITCHRO(OBS)) score. In some embodiments, the administration of the ASBTI results in an ITCHRO(OBS) score of ≤1. In various embodiments, the administration of the ASBTI results in an increase in a quality of life inventory score, or in a quality of life inventory score related to fatigue. In certain embodiments, the quality of life inventory score is a health-related quality of life (HRQoL) score related to fatigue. In various embodiments, the quality of life inventory score is a Pediatric Quality of Life Inventory (PedsQL) score, and wherein the PedsQL score is increased by at least 10% relative to baseline.

In some embodiments, serum bilirubin concentration is at about pre-administration baseline level at about 4 months after first administration of the ASBTI. In some embodiments, serum alanine aminotransferase (ALT) concentration is at about pre-administration baseline level at about 4 months after first administration of the ASBTI. In certain embodiments, serum aspartate aminotransferase (AST) concentration, and serum bilirubin concentration are within a normal range at about 4 weeks after first administration of the ASBTI. In various embodiments, the administration of the ASBTI results in serum ALT concentration decreasing by at least about 10% relative to baseline.

In some embodiments, the cholestatic liver disease is ALGS. In various embodiments, the subject is a pediatric subject.

In certain embodiments, the ASBTI is administered once daily (QD). In various embodiments, the ASBTI is administered twice daily (BID). In some embodiments, the ASBTI is administered in an amount of from about 140 µg/kg/day to about 1400 µg/kg/day. In some embodiments, the ASBTI is administered in an amount of about 280 µg/kg/day to about 1400 µg/kg/day.

In certain embodiments, the administration of the ASBTI results in a reduction in a symptom or a change in a disease-relevant laboratory measure of the cholestatic liver disease that is maintained for at least 6 months. In various embodiments, the reduction in the symptom or a change in a disease-relevant laboratory measure comprises a reduction in sBA concentration, an increase in serum 7αC4 concentration, a reduction in pruritus, an increase in a quality of life inventory score, an increase in a quality of life inventory score related to fatigue, a reduction in xanthoma score, an increase in growth, or a combination thereof. In some embodiments, the reduction in the symptom or a change in a disease-relevant laboratory measure is determined relative to a baseline level. In various embodiments, the reduction in the symptom or a change in a disease-relevant laboratory measure comprises an increase in growth. In some embodiments, the increase in growth of the pediatric subject is measured as an increase in height Z-score or weight Z-score. In certain embodiments, the reduction in the symptom or a change in a disease-relevant laboratory measure is maintained for at least 2 years.

In various embodiments, the administration of the ASBTI results in a reduction of intensity of pruritus. In some embodiments, an ITCHRO(OBS) score of the subject is reduced by at least 40% relative to baseline. In certain embodiments, a CSS score of the subject is reduced by at least 50% relative to baseline. In various embodiments, the subject has an ITCHRO(OBS) score of ≤1 on at least 50% of days after 6 months. In certain embodiments, the administration of the ASBTI results in a maintained and progressive decrease in severity and frequency of pruritus over time.

In some embodiments, the administration of the ASBTI results in a reduction in sBA concentration of at least 30% by 18 weeks. In various embodiments, the administration of the ASBTI results in a reduction in sBA concentration of at least 50%. In certain embodiments, administration of the ASBTI coincides with a positive correlation between reduction in sBA concentration and reduction in severity of pruritus. In some embodiments, the administration results in a xanthoma score of the subject being reduced by at least 25%.

In various embodiments, the administration of the ASBTI results in an increase in a quality of life inventory score. In some embodiments, the quality of life inventory score is a health-related quality of life (HRQoL) score. In certain embodiments, the quality of life inventory score is a Pediatric Quality of Life Inventory (PedsQL) score, and wherein the PedsQL score is increased by at least 10% relative to baseline. In some embodiments, the administration of the ASBTI results in a reduction in serum cholesterol concentration of at least 15% by 18 weeks. In some embodiments, the administration of the ASBTI results in an increase in serum 7αC4 concentration of at least 50% by about 18 weeks.

In certain embodiments, the ASBTI is administered for up to 3 years. In various embodiments, the ASBTI is administered for up to 4 years.

In various embodiments, the cholestatic liver disease is PSC and the ASBTI is volixibat, or a pharmaceutically acceptable salt thereof. In some embodiments, the subject is an adult. In some embodiments, the ASBTI is administered once daily (QD). In various embodiments, the ASBTI is administered twice daily (BID). In various embodiments, the ASBTI is administered in an amount of about 0.5 mg/day to about 100 mg/day.

In some embodiments, the administration of the ASBTI results in a reduction in a symptom or a change in a disease-relevant laboratory measure of the cholestatic liver disease that is maintained for at least four weeks. In various embodiments, the reduction in the symptom or a change in a disease-relevant laboratory measure comprises a reduction in sBA concentration, an increase in serum 7αC4 concentration, a reduction in pruritus, an increase in a quality of life inventory score, an increase in a quality of life inventory score related to fatigue, or a combination thereof. In certain embodiments, the reduction in the symptom or a change in a disease-relevant laboratory measure is determined relative to a baseline level.

In some embodiments, a degree of the reduction in the symptom or a change in a disease-relevant laboratory measure demonstrates a positive correlation with a baseline ITCHRO score of the subject. In certain embodiments, the degree of the reduction in the symptom or a change in a disease-relevant laboratory measure is greater if the subject has a baseline ITCHRO score of at least four than if the subject has a baseline ITCHRO score of less than 4.

In various embodiments, the administration of the ASBTI results in a reduction in severity of pruritus. In various embodiments, an ITCHRO score of the subject is reduced by at least 40% relative to baseline by 14 weeks. In some embodiments, the ITCHRO score of the subject is reduced by at least 60% relative to a baseline ITCHRO score of 4 or higher.

In certain embodiments, the administration of the ASBTI results in a reduction in sBA concentration of at least 30% relative to baseline. In some embodiments, sBA concentration is reduced by at least 45% relative to baseline if the subject has a baseline ITCHRO score of at least 4. In various embodiments, administration of the ASBTI results in a reduction in total serum cholesterol concentration of at least 10 mg/dL. In some embodiments, reduction in total serum cholesterol concentration is at least 12.5 mg/dL if the subject has a baseline ITCHRO score of at least 4.

In certain embodiments, the administration of the ASBTI results in a reduction in serum LDL cholesterol concentration of at least 5%. In various embodiments, the administration of the ASBTI results in a reduction in serum LDL cholesterol concentration of at least 10 mg/dL. In some embodiments, the administration of the ASBTI results in an increase in serum 7αC4 concentration of at least 30% relative to baseline.

In certain embodiments, the administration of the ASBTI results in a reduction in serum autotaxin concentration of at least 50% if the subject has a baseline ITCHRO score of at least 4. In various embodiments, the administration of the ASBTI results in a reduction in serum autotaxin concentration of at least 10% by week 6 and 20% by week 14. In various embodiments, the administration of the ASBTI does not result in a significant change from baseline in serum conjugated bilirubin concentration if the subject has a baseline ITCHRO score of at least 4. In various embodiments, the administration of the ASBTI does not result in a significant change from baseline in serum bilirubin concentration, serum AST concentration, serum ALT concentration, serum alkaline phosphatase concentration, or some combination thereof.

In some embodiments, by day 28 of administration the subject's fecal bile acids (fBA) excretion increases by at least 250 μmol. In certain embodiments, upon day 7 of administration the subject's fBA excretion increases by at least 1,000 μmol. In some embodiments, upon day 7 of administration of the ASBTI the subject's fBA excretion increases by at least 1.5-fold relative to baseline. In various embodiments, administration of the ASBTI results in an at least 4-fold increase in fBA excretion relative to baseline. In some embodiments, administration of the ASBTI results in a dose-dependent increase in fBA excretion.

These and other aspects of the present invention will become apparent to those skilled in the art after a reading of the following detailed description of the invention, including the appended claims.

BRIEF DESCRIPTION OF THE DRAWINGS

FIG. 5A plots sBA concentrations over time for patients having non-truncating bile salt export pump (BSEP, which is encoded by the ABCB11 gene) mutations. FIG. 5B plots sBA concentrations over time for patients having truncating BSEP mutations. FIGS. 5A-5B demonstrate that sBA responses differed by BSEP mutation status. Black filled circles indicate termination. White filled circles indicate start of BID dosing (280 μg/kg BID). In FIGS. 5A and 5B lines corresponding to non-responders are marked with a star.

FIG. 6 demonstrates that ITCHRO(OBS) response was sustained over years and that >50% (10/19) patients demonstrated a ≥1.0 pt. reduction in ITCHRO(OBS) score. Black filled circles indicate termination. White filled circles indicate commencement of BID dosing (280 μg/kg BID). The ITCHRO(OBS) scale range is 0 to 4. In FIG. 6 lines corresponding to non-responders are marked with a star.

FIG. 7 demonstrates that non-truncating BSEP mutation responders showed significant increases in 7αC4 concentration. Black filled circles indicate termination. White filled circles indicate commencement of BID dosing (280 μg/kg BID). The ITCHRO(OBS) scale range is 0 to 4. In FIG. 7 lines corresponding to non-responders are marked with a star.

FIG. 8 demonstrates that non-truncating BSEP mutation responders had significantly different 7αC4:sBA ratios than non-responders. Two non-truncating BSEP mutation responders showed an increase in 7αC4:sBA ratio following dose elevation. Black filled circles indicate termination. White filled circles indicate commencement of BID dosing (280 μg/kg BID). The ITCHRO(OBS) scale range is 0 to 4. In FIG. 8 lines corresponding to non-responders are marked with a star.

FIG. 17A shows a graph plotting mean change in sBA concentration from baseline in all participants through week 48.

FIG. 17B shows a bar graph showing mean change in sBA from week 8-22 in sBA responders during a randomized withdrawal.

FIG. 20A shows mean change from baseline in ITCHRO(OBS) score for participants over time. FIG. 20B shows a plot of ITCHRO(OBS) score for participants during a placebo-controlled withdrawal period.

FIGS. 21A and 21B demonstrates improvements from baseline in clinician scratch scale (CSS) scores throughout the ICONIC clinical study. FIG. 21A shows proportions of total patients having indicated CSS scores at baseline, week 18, and week 48.

FIG. 21B shows proportions of total patients administered maralixibat or placebo having indicated CSS scores during a placebo-controlled withdrawal period at week 22.

FIGS. 23A-23D provide plots of weekly average ITCHRO(OBS) score over time for participants in the ICONIC clinical study during the core study and during the extension. FIG. 23A provides a scatter plot showing average ITCHRO(OBS) score over time. FIG. 23B shows that reductions in pruritus were maintained in the long-term extension. Each line represents ITCHRO(OBS) scores for an individual patient. FIGS. 23C and 23D show that reductions in pruritus were maintained with maralixibat but not with switch to placebo withdrawal period (indicated by boxed area of the plot). Each line represents ITCHRO(OBS) scores for an individual patient. MRX=maralixibat; PLA=placebo. N=number of participants measured at an indicated timepoint.

FIGS. 32A-32H show lattice plots of sBA concentration (blue; left axis; μmol/L) and ITCHRO(OBS) weekly average score (red; right axis) over time (lower axis) for each participant in the ICONIC clinical study. FIGS. 32A and 32D show lattice plots for patients in an MRX-MRX-MRX study group, which includes only those patients administered maralixibat before, during, and after a placebo-controlled drug-withdrawal period of the ICONIC clinical study. FIGS. 32E and 32H show lattice plots for patients in an MRX-Placebo-MRX study group, which includes only those patients administered maralixibat before, placebo during, and maralixibat again after the placebo-controlled drug-withdrawal period. Patient 090004 did not have post-baseline assessments done, so the baseline datapoint is not visible in a plot.

DETAILED DESCRIPTION

Figure 1:
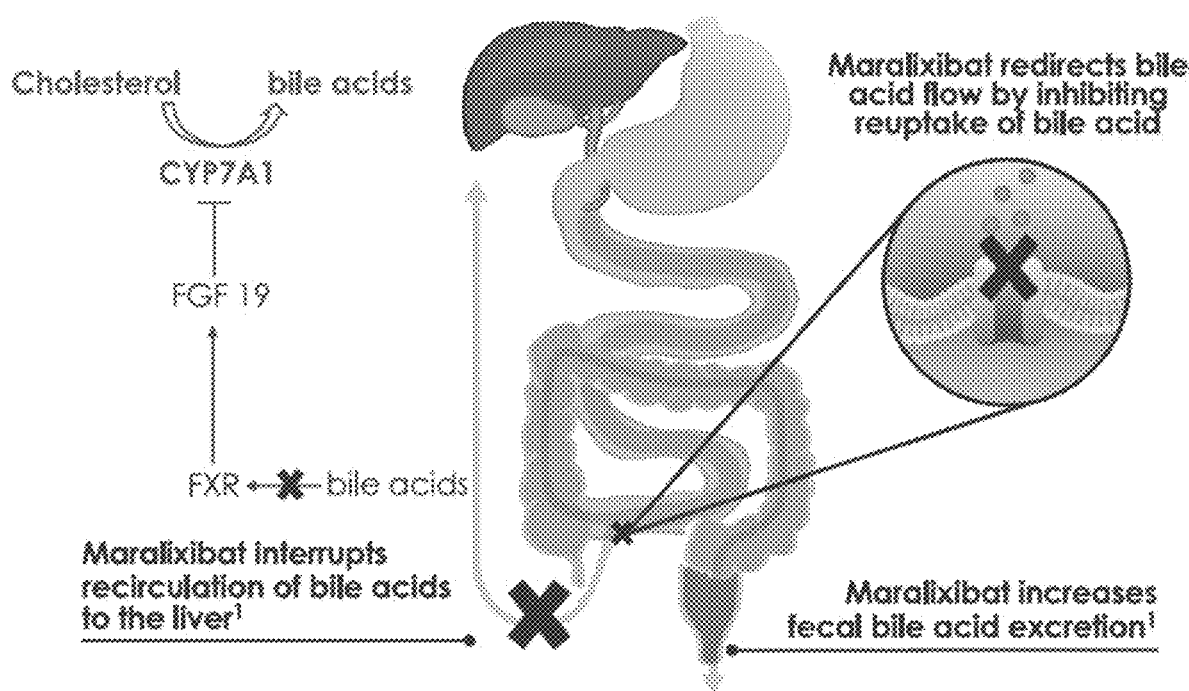
FIG. 1 provides a schematic diagram summarizing physiological effects of maralixibat administration in a patient. CYP7A1, cholesterol 7α-hydroxylase; FGF, fibroblast growth factor; FXR, farnesoid X receptor.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Bile acids/salts play a critical role in activating digestive enzymes and solubilizing fats and fat-soluble vitamins and are involved in liver, biliary, and intestinal disease. Bile acids are synthesized in the liver by a multistep, multiorganelle pathway. Hydroxyl groups are added to specific sites on the steroid structure, the double bond of the cholesterol B ring is reduced, and the hydrocarbon chain is shortened by three carbon atoms resulting in a carboxyl group at the end of the chain. The most common bile acids are cholic acid and chenodeoxycholic acid (the "primary bile acids"). Before exiting the hepatocytes and forming bile, the bile acids are conjugated to either glycine (to produce glycocholic acid or glycochenodeoxycholic acid) or taurine (to produce taurocholic acid or taurochenodeoxycholic acid). The conjugated bile acids are called bile salts and their amphipathic nature makes them more efficient detergents than bile acids. Bile salts, not bile acids, are found in bile.

Bile salts are excreted by the hepatocytes into the canaliculi to form bile. The canaliculi drain into the right and left hepatic ducts and the bile flows to the gallbladder. Bile is released from the gallbladder and travels to the duodenum, where it contributes to the metabolism and degradation of fat. The bile salts are reabsorbed in the terminal ileum and transported back to the liver via the portal vein. Bile salts often undergo multiple enterohepatic circulations before being excreted via feces. A small percentage of bile salts may be reabsorbed in the proximal intestine by either passive or carrier-mediated transport processes. Most bile salts are reclaimed in the distal ileum by a sodium-dependent apically located bile acid transporter referred to as apical sodium-dependent bile acid transporter (ASBT). At the basolateral surface of the enterocyte, a truncated version of ASBT is involved in vectoral transfer of bile acids/salts into the portal circulation. Completion of the enterohepatic circulation occurs at the basolateral surface of the hepatocyte by a transport process that is primarily mediated by a sodium-dependent bile acid transporter. Intestinal bile acid transport plays a key role in the enterohepatic circulation of bile salts. Molecular analysis of this process has recently led to important advances in understanding of the biology, physiology and pathophysiology of intestinal bile acid transport.

Within the intestinal lumen, bile acid concentrations vary, with the bulk of the reuptake occurring in the distal intestine. Described herein are certain compositions and methods that control bile acid concentrations in the intestinal lumen, thereby controlling the hepatocellular damage caused by bile acid accumulation in the liver.

Classes of Cholestasis and Cholestatic Liver Disease

As used herein, "cholestasis" means the disease or symptoms comprising impairment of bile formation and/or bile flow. As used herein, "cholestatic liver disease" means a liver disease associated with cholestasis. Cholestatic liver diseases are often associated with jaundice, fatigue, and pruritis. Biomarkers of cholestatic liver disease include elevated serum bile acid concentrations, elevated serum alkaline phosphatase (AP), elevated gamma-glutamyltranspeptidease, elevated conjugated hyperbilirubinemia, and elevated serum cholesterol.

Cholestatic liver disease can be sorted clinicopathologically between two principal categories of obstructive, often extrahepatic, cholestasis, and nonobstructive, or intrahepatic, cholestasis. In the former, cholestasis results when bile flow is mechanically blocked, as by gallstones or tumor, or as in extrahepatic biliary atresia.

The latter group who has nonobstructive intrahepatic cholestasis in turn fall into two principal subgroups. In the first subgroup, cholestasis results when processes of bile secretion and modification, or of synthesis of constituents of bile, are caught up secondarily in hepatocellular injury so severe that nonspecific impairment of many functions can be expected, including those subserving bile formation. In the second subgroup, no presumed cause of hepatocellular injury can be identified. Cholestasis in such patients appears to result when one of the steps in bile secretion or modification, or of synthesis of constituents of bile, is constitutively damaged. Such cholestasis is considered primary.

Accordingly, provided herein are methods and compositions for stimulating epithelial proliferation and/or regeneration of intestinal lining and/or enhancement of the adaptive processes in the intestine in individuals with hypercholemia and/or a cholestatic liver disease. In some of such embodiments, the methods comprise increasing bile acid concentrations and/or GLP-2 concentrations in the intestinal lumen.

Increased levels of bile acids, and elevated levels of AP (alkaline phosphatase), LAP (leukocyte alkaline phosphatase), gamma GT (gamma-glutamyl transpeptidase), and 5'-nucleotidase are biochemical hallmarks of cholestasis and cholestatic liver disease. Accordingly, provided herein are methods and compositions for stimulating epithelial proliferation and/or regeneration of intestinal lining and/or enhancement of the adaptive processes in the intestine in individuals with hypercholemia, and elevated levels of AP (alkaline phosphatase), LAP (leukocyte alkaline phosphatase), gamma GT (gamma-glutamyl transpeptidase or GGT), and/or 5'-nucleotidase. In some of such embodiments, the methods comprise increasing bile acid concentrations in the intestinal lumen. Further provided herein, are methods and compositions for reducing hypercholemia, and elevated levels of AP (alkaline phosphatase), LAP (leukocyte alkaline phosphatase), gamma GT (gamma-glutamyl transpeptidase), and 5'-nucleotidase comprising reducing overall serum bile acid load by excreting bile acid in the feces.

Pruritus is often associated with hypercholemia and cholestatic liver diseases. It has been suggested that pruritus results from bile salts acting on peripheral pain afferent nerves. The degree of pruritus varies with the individual (i.e., some individuals are more sensitive to elevated levels of bile acids/salts).

Administration of agents that reduce serum bile acid concentrations has been shown to reduce pruritus in certain individuals. Accordingly, provided herein are methods and compositions for stimulating epithelial proliferation and/or regeneration of intestinal lining and/or enhancement of the adaptive processes in the intestine in individuals with pruritus. In some of such embodiments, the methods comprise increasing bile acid concentrations in the intestinal lumen. Further provided herein, are methods and compositions for treating pruritus comprising reducing overall serum bile acid load by excreting bile acid in the feces.

Another symptom of hypercholemia and cholestatic liver disease is the increase in serum concentration of conjugated bilirubin. Elevated serum concentrations of conjugated bilirubin result in jaundice and dark urine. The magnitude of elevation is not diagnostically important as no relationship has been established between serum levels of conjugated bilirubin and the severity of hypercholemia and cholestatic liver disease. Conjugated bilirubin concentration rarely exceeds 30 mg/dL. Accordingly, provided herein are methods and compositions for stimulating epithelial proliferation and/or regeneration of intestinal lining and/or enhancement of the adaptive processes in the intestine in individuals with elevated serum concentrations of conjugated bilirubin. In some of such embodiments, the methods comprise increasing bile acid concentrations in the intestinal lumen. Further provided herein, are methods and compositions for treating elevated serum concentrations of conjugated bilirubin comprising reducing overall serum bile acid load by excreting bile acid in the feces.

Increased serum concentration of nonconjugated bilirubin is also considered diagnostic of hypercholemia and cholestatic liver disease. Portions of serum bilirubin and covalently bound to albumin (delta bilirubin or biliprotein). This fraction may account for a large proportion of total bilirubin in patients with cholestatic jaundice. The presence of large quantities of delta bilirubin indicates long-standing cholestasis. Delta bilirubin in cord blood or the blood of a newborn is indicative of cholestasis/cholestatic liver disease that antedates birth. Accordingly, provided herein are methods and compositions for stimulating epithelial proliferation and/or regeneration of intestinal lining and/or enhancement of the adaptive processes in the intestine in individuals with elevated serum concentrations of nonconjugated bilirubin or delta bilirubin. In some of such embodiments, the methods comprise increasing bile acid concentrations in the intestinal lumen. Further provided herein, are methods and compositions for treating elevated serum concentrations of nonconjugated bilirubin and delta bilirubin comprising reducing overall serum bile acid load by excreting bile acid in the feces.

Cholestasis and cholestatic liver disease results in hypercholemia. During metabolic cholestasis, the hepatocytes retains bile salts. Bile salts are regurgitated from the hepatocyte into the serum, which results in an increase in the concentration of bile salts in the peripheral circulation. Furthermore, the uptake of bile salts entering the liver in portal vein blood is inefficient, which results in spillage of bile salts into the peripheral circulation. Accordingly, provided herein are methods and compositions for stimulating epithelial proliferation and/or regeneration of intestinal lining and/or enhancement of the adaptive processes in the intestine in individuals with hypercholemia. In some of such embodiments, the methods comprise increasing bile acid concentrations in the intestinal lumen. Further provided herein, are methods and compositions for treating hypercholemia comprising reducing overall serum bile acid load by excreting bile acid in the feces.

Hyperlipidemia is characteristic of some but not all cholestatic diseases. Serum cholesterol is elevated in cholestasis due to the decrease in circulating bile salts which contribute to the metabolism and degradation of cholesterol. Cholesterol retention is associated with an increase in membrane cholesterol content and a reduction in membrane fluidity and membrane function. Furthermore, as bile salts are the metabolic products of cholesterol, the reduction in cholesterol metabolism results in a decrease in bile acid/salt synthesis. Serum cholesterol observed in children with cholestasis ranges between about 1,000 mg/dL and about 4,000 mg/dL. Accordingly, provided herein are methods and compositions for stimulating epithelial proliferation and/or regeneration of intestinal lining and/or enhancement of the adaptive processes in the intestine in individuals with hyperlipidemia. In some of such embodiments, the methods comprise increasing bile acid concentrations in the intestinal lumen. Further provided herein, are methods and compositions for treating hyperlipidemia comprising reducing overall serum bile acid load by excreting bile acid in the feces.

In individuals with hypercholemia and cholestatic liver diseases, xanthomas develop from the deposition of excess circulating cholesterol into the dermis. The development of xanthomas is more characteristic of obstructive cholestasis than of hepatocellular cholestasis. Planar xanthomas first occur around the eyes and then in the creases of the palms and soles, followed by the neck. Tuberous xanthomas are associated with chronic and long-term cholestasis. Accordingly, provided herein are methods and compositions for stimulating epithelial proliferation and/or regeneration of intestinal lining and/or enhancement of the adaptive processes in the intestine in individuals with xanthomas. In some of such embodiments, the methods comprise increasing bile acid concentrations in the intestinal lumen. Further provided herein, are methods and compositions for treating xanthomas comprising reducing overall serum bile acid load by excreting bile acid in the feces.

In children with chronic cholestasis, one of the major consequences of hypercholemia and cholestatic liver disease is failure to thrive. Failure to thrive is a consequence of reduced delivery of bile salts to the intestine, which contributes to inefficient digestion and absorption of fats, and reduced uptake of vitamins (vitamins E, D, K, and A are all malabsorbed in cholestasis). Furthermore, the delivery of fat into the colon can result in colonic secretion and diarrhea. Treatment of failure to thrive involves dietary substitution and supplementation with long-chain triglycerides, medium-chain triglycerides, and vitamins. Ursodeoxycholic acid, which is used to treat some cholestatic conditions, does not form mixed micelles and has no effect on fat absorption. Accordingly, provided herein are methods and compositions for stimulating epithelial proliferation and/or regeneration of intestinal lining and/or enhancement of the adaptive processes in the intestine in individuals (e.g., children) with failure to thrive. In some of such embodiments, the methods comprise increasing bile acid concentrations in the intestinal lumen. Further provided herein, are methods and compositions for treating failure to thrive comprising reducing overall serum bile acid load by excreting bile acid in the feces.

Primary Biliary Cirrhosis (PBC)

Primary biliary cirrhosis is an autoimmune disease of the liver characterized by the destruction of the bile canaliculi. Damage to the bile canaliculi results in the build-up of bile in the liver (i.e., cholestasis). The retention of bile in the liver damages liver tissue and may lead to scarring, fibrosis, and cirrhosis. PBC usually presents in adulthood (e.g., ages 40 and over). Individuals with PBC often present with fatigue, pruritus, and/or jaundice. PBC is diagnosed if the individual has elevated AP concentrations for at least 6 months, elevated gammaGT levels, antimitochondrial antibodies (AMA) in the serum (>1:40), and florid bile duct lesions. Serum ALT and serum AST and conjugated bilirubin may also be elevated, but these are not considered diagnostic. Cholestasis associated with PBC has been treated or ameliorated by administration of ursodeoxycholic acid (UDCA or Ursodiol). Corticosteroids (e.g., prednisone and budesonide) and immunosuppressive agents (e.g., azathioprine, cyclosporin A, methotrexate, chlorambucil and mycophenolate) have been used to treat cholestasis associated with PBC. Sulindac, bezafibrate, tamoxifen, and lamivudine have also been shown to treat or ameliorate cholestasis associated with PBC.

Progressive Familial Intrahepatic Cholestasis (PFIC)

PFIC is a rare genetic disorder that causes progressive liver disease typically leading to liver failure. In people with PFIC, liver cells are less able to secrete bile. The resulting buildup of bile causes liver disease in affected individuals. Signs and symptoms of PFIC typically begin in infancy. Patients experience severe itching, jaundice, failure to grow at the expected rate (failure to thrive), and an increasing inability of the liver to function (liver failure). The disease is estimated to affect one in every 50,000 to 100,000 births in the United States and Europe. Six types of PFIC have been genetically identified, all of which are similarly characterized by impaired bile flow and progressive liver disease.

PFIC 1

PFIC 1 (also known as, Byler disease or FIC1 deficiency) is associated with mutations in the ATP8B1 gene (also designated as FIC1). This gene, which encodes a P-type ATPase, is located on human chromosome 18 and is also mutated in the milder phenotype, benign recurrent intrahepatic cholestasis type 1 (BRIO) and in Greenland familial cholestasis. FIC1 protein is located on the canalicular membrane of the hepatocyte but within the liver it is mainly expressed in cholangiocytes. P-type ATPase appears to be an aminophospholipid transporter responsible for maintaining the enrichment of phosphatidylserine and phophatidylethanolamme on the inner leaflet of the plasma membrane in comparison of the outer leaflet. The asymmetric distribution of lipids in the membrane bilayer plays a protective role against high bile salt concentrations in the canalicular lumen. The abnormal protein function may indirectly disturb the biliary secretion of bile acids. The anomalous secretion of bile acids/salts leads to hepatocyte bile acid overload.

PFIC 1 typically presents in infants (e.g., age 6-18 months). The infants may show signs of pruritus, jaundice, abdominal distension, diarrhea, malnutrition, and shortened stature. Biochemically, individuals with PFIC 1 have elevated serum transaminases, elevated bilirubin, elevated serum bile acid levels, and low levels of gammaGT. The individual may also have liver fibrosis. Individuals with PFIC 1 typically do not have bile duct proliferation. Most individuals with PFIC 1 will develop end-stage liver disease by 10 years of age. No medical treatments have proven beneficial for the long-term treatment of PFIC 1. In order to reduce extrahepatic symptoms (e.g., malnutrition and failure to thrive), children are often administered medium chain triglycerides and fat-soluble vitamins. Ursodiol has not been demonstrated as effective in individuals with PFIC 1.

PFIC 2

PFIC 2 (also known as, Byler Syndrome or BSEP deficiency) is associated with mutations in the ABCB11 gene (also designated BSEP). The ABCB11 gene encodes the ATP-dependent canalicular bile salt export pump (BSEP) of human liver and is located on human chromosome 2. BSEP protein, expressed at the hepatocyte canalicular membrane, is the major exporter of primary bile acids/salts against extreme concentration gradients. Mutations in this protein responsible for the decreased biliary bile salt secretion described in affected patients, leading to decreased bile flow and accumulation of bile salts inside the hepatocyte with ongoing severe hepatocellular damage.

PFIC 2 typically presents in infants (e.g., age 6-18 months). The infants may show signs of pruritus. Biochemically, individuals with PFIC 2 have elevated serum transaminases, elevated bilirubin, elevated serum bile acid levels, and low levels of gammaGT. The individual may also have portal inflammation and giant cell hepatitis. Further, individuals often develop hepatocellular carcinoma. No medical treatments have proven beneficial for the long-term treatment of PFIC 2. In order to reduce extrahepatic symptoms (e.g., malnutrition and failure to thrive), children are often administered medium chain triglycerides and fat-soluble vitamins. The PFIC 2 patient population accounts for approximately 60% of the PFIC population.

PFIC 3

PFIC 3 (also known as MDR3 deficiency) is caused by a genetic defect in the ABCB4 gene (also designated MDR3) located on chromosome 7. Class III Multidrug Resistance (MDR3) P-glycoprotein (P-gp), is a phospholipid translocator involved in biliary phospholipid (phosphatidylcholine) excretion in the canlicular membrane of the hepatocyte. PFIC 3 results from the toxicity of bile in which detergent bile salts are not inactivated by phospholipids, leading to bile canaliculi and biliary epithelium injuries.

PFIC 3 also presents in early childhood. As opposed to PFIC 1 and PFIC 2, individuals have elevated gammaGT levels. Individuals also have portal inflammation, fibrosis, cirrhosis, and massive bile duct proliferation. Individuals may also develop intrahepatic gallstone disease. Ursodiol has been effective in treating or ameliorating PFIC 3.

Benign Recurrent Intrahepatic Cholestasis (BRIC)

BRIC 1

BRIC1 is caused by a genetic defect of the FIC1 protein in the canalicular membrane of hepatocytes. BRIC1 is typically associated with normal serum cholesterol and γ-glutamyltranspeptidase levels, but elevated serum bile salts. Residual FIC1 expression and function is associated with BRIC1. Despite recurrent attacks of cholestasis or cholestatic liver disease, there is no progression to chronic liver disease in a majority of patients. During the attacks, the patients are severely jaundiced and have pruritis, steatorrhea, and weight loss. Some patients also have renal stones, pancreatitis, and diabetes.

BRIC 2

BRIC2 is caused by mutations in ABCB11, leading to defective BSEP expression and/or function in the canalicular membrane of hepatocytes.

BRIC 3

BRIC3 is related to the defective expression and/or function of MDR3 in the canalicular membrane of hepatocytes. Patients with MDR3 deficiency usually display elevated serum γ-glutamyltranspeptidase levels in the presence of normal or slightly elevated bile acid levels.

Dubin-Johnson Syndrome (DJS)

DJS is characterized by conjugated hyperbilirubinemia due to inherited dysfunction of MRP2. Hepatic function is preserved in affected patients. Several different mutations have been associated with this condition, resulting either in the complete absence of immunohistochemically detectable MRP2 in affected patients or impaired protein maturation and sorting.

Acquired Cholestatic Disease

Primary Biliary Cirrhosis (PBC)

PBC is a chronic inflammatory hepatic disorder slowly progressing to end stage liver failure in most of the affected patients. In PBC, the inflammatory process affects predominantly the small bile ducts.

Primary Sclerosing Cholangitis (PSC)

PSC is a chronic inflammatory hepatic disorder slowly progressing to end stage liver failure in most of the affected patients. In PSC inflammation, fibrosis and obstruction of large and medium sized intra- and extrahepatic ductuli is predominant.

PSC is characterized by progressive cholestasis. Cholestasis can often lead to severe pruritus which significantly impairs quality of life.

Intrahepatic Cholestasis of Pregnancy (ICP)

ICP is characterized by occurrence of transient cholestasis or cholestatic liver disease in pregnant women typically occurring in the third trimester of pregnancy, when the circulating levels of estrogens are high. ICP is associated with pruritis and biochemical cholestasis or cholestatic liver disease of varying severity and constitutes a risk factor for prematurity and intrauterine fetal death. A genetic predisposition has been suspected based upon the strong regional clustering, the higher prevalence in female family members of patients with ICP and the susceptibility of ICP patients to develop intrahepatic cholestasis or cholestatic liver disease under other hormonal challenges such as oral contraception. A heterogeneous state for an MDR3 gene defect may represent a genetic predisposition.

Gallstone Disease

Gallstone disease is one of the most common and costly of all digestive diseases with a prevalence of up to 17% in Caucasian women. Cholesterol containing gallstones are the major form of gallstones and supersaturation of bile with cholesterol is therefore a prerequisite for gallstone formation. ABCB4 mutations may be involved in the pathogenesis of cholesterol gallstone disease.

Drug Induced Cholestasis

Inhibition of BSEP function by drugs is an important mechanism of drug-induced cholestasis, leading to the hepatic accumulation of bile salts and subsequent liver cell damage. Several drugs have been implicated in BSEP inhibition. Most of these drugs, such as rifampicin, cyclosporine, glibenclamide, or troglitazone directly cis-inhibit ATP-dependent taurocholate transport in a competitive manner, while estrogen and progesterone metabolites indirectly trans-inhibits BSEP after secretion into the bile canaliculus by Mrp2. Alternatively, drug-mediated stimulation of MRP2 can promote cholestasis or cholestatic liver disease by changing bile composition.

Total Parenteral Nutrition Associated Cholestasis

TPNAC is one of the most serious clinical scenarios where cholestasis or cholestatic liver disease occurs rapidly and is highly linked with early death. Infants, who are usually premature and who have had gut resections are dependent upon TPN for growth and frequently develop cholestasis or cholestatic liver disease that rapidly progresses to fibrosis, cirrhosis, and portal hypertension, usually before 6 months of life. The degree of cholestasis or cholestatic liver disease and chance of survival in these infants have been linked to the number of septic episodes, likely initiated by recurrent bacterial translocation across their gut mucosa. Although there are also cholestatic effects from the intravenous formulation in these infants, septic mediators likely contribute the most to altered hepatic function.

Alagille Syndrome (ALGS)

Alagille syndrome is a genetic disorder that affects the liver and other organs. ALGS is also known as syndromic intrahepatic bile duct paucity or arteriohepatic dysplasia. ALGS is a rare genetic disorder in which bile ducts are abnormally narrow, malformed, and reduced in number, which leads to bile accumulation in the liver and ultimately progressive liver disease. ALGS is autosomal dominant, caused by mutations in JAG1 (>90% of cases) or NOTCH2. The estimated incidence of ALGS is one in every 30,000 or 50,000 births in the United States and Europe. In patients with ALGS, multiple organ systems may be affected by the mutation, including the liver, heart, kidneys and central nervous system. The accumulation of bile acids prevents the liver from working properly to eliminate waste from the bloodstream and leads to progressive liver disease that ultimately requires liver transplantation in 15% to 47% of patients. Signs and symptoms arising from liver damage in ALGS may include jaundice, pruritus and xanthomas, and decreased growth. The pruritus experienced by patients with ALGS is among the most severe in any chronic liver disease and is present in most affected children by the third year of life.

ALGS often presents during infancy (e.g., age 6-18 months) through early childhood (e.g., age 3-5 years) and may stabilize after the age of 10. Symptoms may include chronic progressive cholestasis, ductopenia, jaundice, pruritus, xanthomas, congenital heart problems, paucity of intrahepatic bile ducts, poor linear growth, hormone resistance, posterior embryotoxon, Axenfeld anomaly, retinitis pigmentosa, pupillary abnormalities, cardiac murmur, atrial septal defect, ventricular septal defect, patent ductus arteriosus, and Tetralogy of Fallot. Individuals diagnosed with Alagille syndrome have been treated with ursodiol, hydroxyzine, cholestyramine, rifampicin, and phenobarbital. Due to a reduced ability to absorb fat-soluble vitamins, individuals with Alagille Syndrome are further administered high dose multivitamins.

Biliary Atresia

Biliary atresia is a life-threatening condition in infants in which the bile ducts inside or outside the liver do not have normal openings. With biliary atresia, bile becomes trapped, builds up, and damages the liver. The damage leads to scarring, loss of liver tissue, and cirrhosis. Without treatment, the liver eventually fails, and the infant needs a liver transplant to stay alive. The two types of biliary atresia are fetal and perinatal. Fetal biliary atresia appears while the baby is in the womb. Perinatal biliary atresia is much more common and does not become evident until 2 to 4 weeks after birth.

Post-Kasai Biliary Atresia

Biliary atresia is treated with surgery called the Kasai procedure or a liver transplant. The Kasai procedure is usually the first treatment for biliary atresia. During a Kasai procedure, the pediatric surgeon removes the infant's damaged bile ducts and brings up a loop of intestine to replace them. While the Kasai procedure can restore bile flow and correct many problems caused by biliary atresia, the surgery doesn't cure biliary atresia. If the Kasai procedure is not successful, infants usually need a liver transplant within 1 to 2 years. Even after a successful surgery, most infants with biliary atresia slowly develop cirrhosis over the years and require a liver transplant by adulthood. Possible complications after the Kasai procedure include ascites, bacterial cholangitis, portal hypertension, and pruritis.

Post Liver Transplantation Biliary Atresia

If the atresia is complete, liver transplantation is the only option. Although liver transplantation is generally successful at treating biliary atresia, liver transplantation may have complications such as organ rejection. Also, a donor liver may not become available. Further, in some patients, liver transplantation may not be successful at curing biliary atresia.

Xanthoma

Xanthoma is a skin condition associated with cholestatic liver diseases, in which certain fats build up under the surface of the skin. Cholestasis results in several disturbances of lipid metabolism resulting in formation of an abnormal lipid particle in the blood called lipoprotein X. Lipoprotein X is formed by regurgitation of bile lipids into the blood from the liver and does not bind to the LDL receptor to deliver cholesterol to cells throughout the body as does normal LDL. Lipoprotein X increases liver cholesterol production by fivefold and blocks normal removal of lipoprotein particles from the blood by the liver.

General Definitions

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "baseline" or "pre-administration baseline," as used herein, refers to information gathered at the beginning of a study or an initial known value which is used for comparison with later data. A baseline is an initial measurement of a measurable condition that is taken at an early time point and used for comparison over time to look for changes in the measurable condition. For example, serum bile acid concentration in a patient before administration of a drug (baseline) and after administration of the drug. Baseline is an observation or value that represents the normal or beginning level of a measurable quality, used for comparison with values representing response to intervention or an environmental stimulus. The baseline is time "zero", before participants in a study receive an experimental agent or intervention, or negative control. For example, "baseline" may refer in some instances 1) to the state of a measurable quantity just prior to the initiation of a clinical study or 2) the state of a measurable quantity just prior to altering a dosage level or composition administered to a patient from a first dosage level or composition to a second dosage level or composition.

The terms "level" and "concentration," as used herein, are used interchangeably. For example, "high serum levels of bilirubin" may alternatively be phrased "high serum concentrations of bilirubin."

The terms "normalized" or "normal range," as used herein, indicates age-specific values that are within a range corresponding to a healthy individual (i.e., normal or normalized values). For example, the phrase "serum bilirubin concentrations were normalized within three weeks" means that serum bilirubin concentrations fell within a range known in the art to correspond to that of a healthy individual (i.e., within a normal and not e.g. an elevated range) within three weeks. In various embodiments, a normalized serum bilirubin concentration is from about 0.1 mg/dL to about 1.2 mg/dL. In various embodiments, a normalized serum bile acid concentration is from about 0 μmol/L to about 25 μmol/L.

The terms "ITCHRO(OBS)" and "ITCHRO" (alternatively, "ItchRO(Pt)") as used herein, are used interchangeably with the qualification that the ITCHRO(OBS) scale is used to measure severity of pruritus in children under the age of 18 and the ITCHRO scale is used to measure severity of pruritus in adults of at least 18 years of age. Therefore, where ITCHRO(OBS) scale is mentioned with regard to an adult patient, the ITCHRO scale is the scale being indicated. Similarly, whenever the ITCHRO scale is mentioned with regard to a pediatric patient, the ITCHRO(OBS) scale is usually the scale being indicated (some older children were permitted to report their own scores as ITCHRO scores. The ITCHRO(OBS) scale ranges from 0 to 4 and the ITCHRO scale ranges from 0 to 10.

The term "bile acid" or "bile acids," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hydroxycholate, glycocholic acid, glycocholate, taurocholic acid, taurocholate, chenodeoxycholic acid, ursodeoxycholic acid, ursodiol, a tauroursodeoxycholic acid, a glycoursodeoxycholic acid, a 7-B-methyl cholic acid, a methyl lithocholic acid, chenodeoxycholate, lithocholic acid, lithocholate, and the like. Taurocholic acid and/or taurocholate are referred to herein as TCA. Any reference to a bile acid used herein includes reference to a bile acid, one and only one bile acid, one or more bile acids, or to at least one bile acid. Therefore, the terms "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, pharmaceutically acceptable bile acid esters are optionally utilized as the "bile acids" described herein, e.g., bile acids/salts conjugated to an amino acid (e.g., glycine or taurine). Other bile acid esters include, e.g., substituted or unsubstituted alkyl ester, substituted or unsubstituted heteroalkyl esters, substituted or unsubstituted aryl esters, substituted or unsubstituted heteroaryl esters, or the like. For example, the term "bile acid" includes cholic acid conjugated with either glycine or taurine:glycocholate and taurocholate, respectively (and salts thereof). Any reference to a bile acid used herein includes reference to an identical compound naturally or synthetically prepared. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted.

The term "subject", "patient", "participant", or "individual" are used interchangeably herein and refer to mammals and non-mammals, e.g., suffering from a disorder described herein. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The term "about," as used herein, includes any value that is within 10% of the described value.

The term "composition," as used herein includes the disclosure of both a composition and a composition administered in a method as described herein. Furthermore, in some embodiments, the composition of the present invention is or comprises a "formulation," an oral dosage form or a rectal dosage form as described herein.

The terms "treat," "treating" or "treatment," and other grammatical equivalents as used herein, include alleviating, inhibiting or reducing symptoms, reducing or inhibiting severity of, reducing incidence of, reducing or inhibiting recurrence of, delaying onset of, delaying recurrence of, abating or ameliorating a disease or condition symptoms, ameliorating the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "effective amount" or "therapeutically effective amount" as used herein, refer to a sufficient amount of at least one agent (e.g., a therapeutically active agent) being administered which achieve a desired result in a subject or individual, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study. In some embodiments, a "therapeutically effective amount," or an "effective amount" of an ASBTI refers to a sufficient amount of an ASBTI to treat cholestasis or a cholestatic liver disease in a subject or individual.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical Sciences (current edition), Mack Publishing Co., Easton, Pa, all of which are incorporated herein by reference in their entirety for all purposes. In certain embodiments, the agents and compositions described herein are administered orally.

The term "ASBT inhibitor" refers to a compound that inhibits apical sodium-dependent bile transport or any recuperative bile salt transport. The term Apical Sodium-dependent Bile Transporter (ASBT) is used interchangeably with the term Ileal Bile Acid Transporter (IBAT).

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, subsalicylate, maleate, laurate, malate, fumarate, succinate, tartrate, amsonate, pamoate, p-toluene-sulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

Bile Acid

Bile contains water, electrolytes and a numerous organic molecules including bile acids, cholesterol, phospholipids and bilirubin. Bile is secreted from the liver and stored in the gall bladder, and upon gall bladder contraction, due to ingestion of a fatty meal, bile passes through the bile duct into the intestine. Bile acids/salts are critical for digestion and absorption of fats and fat-soluble vitamins in the small intestine. Adult humans produce 400 to 800 mL of bile daily. The secretion of bile can be considered to occur in two stages. Initially, hepatocytes secrete bile into canaliculi, from which it flows into bile ducts and this hepatic bile contains large quantities of bile acids, cholesterol and other organic molecules. Then, as bile flows through the bile ducts, it is modified by addition of a watery, bicarbonate-rich secretion from ductal epithelial cells. Bile is concentrated, typically five-fold, during storage in the gall bladder.

The flow of bile is lowest during fasting, and a majority of that is diverted into the gallbladder for concentration. When chyme from an ingested meal enters the small intestine, acid and partially digested fats and proteins stimulate secretion of cholecystokinin and secretin, both of which are important for secretion and flow of bile. Cholecystokinin (cholecysto=gallbladder and kinin=movement) is a hormone which stimulates contractions of the gallbladder and common bile duct, resulting in delivery of bile into the gut. The most potent stimulus for release of cholecystokinin is the presence of fat in the duodenum. Secretin is a hormone secreted in response to acid in the duodenum, and it simulates biliary duct cells to secrete bicarbonate and water, which expands the volume of bile and increases its flow out into the intestine.

Bile acids/salts are derivatives of cholesterol. Cholesterol, ingested as part of the diet or derived from hepatic synthesis, are converted into bile acids/salts in the hepatocyte. Examples of such bile acids/salts include cholic and chenodeoxycholic acids, which are then conjugated to an amino acid (such as glycine or taurine) to yield the conjugated form that is actively secreted into canaliculi. The most abundant of the bile salts in humans are cholate and deoxycholate, and they are normally conjugated with either glycine or taurine to give glycocholate or taurocholate respectively.

Free cholesterol is virtually insoluble in aqueous solutions, however in bile it is made soluble by the presence of bile acids/salts and lipids. Hepatic synthesis of bile acids/salts accounts for the majority of cholesterol breakdown in the body. In humans, roughly 500 mg of cholesterol are converted to bile acids/salts and eliminated in bile every day. Therefore, secretion into bile is a major route for elimination of cholesterol. Large amounts of bile acids/salts are secreted into the intestine every day, but only relatively small quantities are lost from the body. This is because approximately 95% of the bile acids/salts delivered to the duodenum are absorbed back into blood within the ileum, by a process is known as "Enterohepatic Recirculation".

Venous blood from the ileum goes straight into the portal vein, and hence through the sinusoids of the liver. Hepatocytes extract bile acids/salts very efficiently from sinusoidal blood, and little escapes the healthy liver into systemic circulation. Bile acids/salts are then transported across the hepatocytes to be resecreted into canaliculi. The net effect of this enterohepatic recirculation is that each bile salt molecule is reused about 20 times, often two or three times during a single digestive phase. Bile biosynthesis represents the major metabolic fate of cholesterol, accounting for more than half of the approximate 800 mg/day of cholesterol that an average adult uses up in metabolic processes. In comparison, steroid hormone biosynthesis consumes only about 50 mg of cholesterol per day. Much more that 400 mg of bile salts is required and secreted into the intestine per day, and this is achieved by re-cycling the bile salts. Most of the bile salts secreted into the upper region of the small intestine are absorbed along with the dietary lipids that they emulsified at the lower end of the small intestine. They are separated from the dietary lipid and returned to the liver for re-use. Recycling thus enables 20-30 g of bile salts to be secreted into the small intestine each day.

Bile acids/salts are amphipathic, with the cholesterol-derived portion containing both hydrophobic (lipid soluble) and polar (hydrophilic) moieties while the amino acid conjugate is generally polar and hydrophilic. This amphipathic nature enables bile acids/salts to carry out two important functions: emulsification of lipid aggregates and solubilization and transport of lipids in an aqueous environment. Bile acids/salts have detergent action on particles of dietary fat which causes fat globules to break down or to be emulsified. Emulsification is important since it greatly increases the surface area of fat available for digestion by lipases which cannot access the inside of lipid droplets. Furthermore, bile acids/salts are lipid carriers and are able to solubilize many lipids by forming micelles and are critical for transport and absorption of the fat-soluble vitamins.

The term "non-systemic" or "minimally absorbed," as used herein, refers to low systemic bioavailability and/or absorption of an administered compound. In some embodiments a non-systemic compound is a compound that is substantially not absorbed systemically. In some embodiments, ASBTI compositions described herein deliver the ASBTI to the distal ileum, colon, and/or rectum and not systemically (e.g., a substantial portion of the ASBTI is not systemically absorbed. In some embodiments, the systemic absorption of a non-systemic compound is <0.1%, <0.3%, <0.5%, <0.6%, <0.7%, <0.8%, <0.9%, <1%, <1.5%, <2%, <3%, or <5% of the administered dose (wt. % or mol %). In some embodiments, the systemic absorption of a non-systemic compound is <10% of the administered dose. In some embodiments, the systemic absorption of a non-systemic compound is <15% of the administered dose. In some embodiments, the systemic absorption of a non-systemic compound is <25% of the administered dose. In an alternative approach, a non-systemic ASBTI is a compound that has lower systemic bioavailability relative to the systemic bioavailability of a systemic ASBTI (e.g., compound 100A, 100C). In some embodiments, the bioavailability of a non-systemic ASBTI described herein is <30%, <40%, <50%, <60%, or <70% of the bioavailability of a systemic ASBTI (e.g., compound 100A, 100C).

In another alternative approach, compositions described herein are formulated to deliver <10% of the administered dose of the ASBTI systemically. In some embodiments, the compositions described herein are formulated to deliver <20% of the administered dose of the ASBTI systemically. In some embodiments, the compositions described herein are formulated to deliver <30% of the administered dose of the ASBTI systemically. In some embodiments, the compositions described herein are formulated to deliver <40% of the administered dose of the ASBTI systemically. In some embodiments, the compositions described herein are formulated to deliver <50% of the administered dose of the ASBTI systemically. In some embodiments, the compositions described herein are formulated to deliver <60% of the administered dose of the ASBTI systemically. In some embodiments, the compositions described herein are formulated to deliver <70% of the administered dose of the ASBTI systemically. In some embodiments, systemic absorption is determined in any suitable manner, including the total circulating amount, the amount cleared after administration, or the like.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halo, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a C1-C6 alkyl. A "heteroalkyl" group substitutes any one of the carbons of the alkyl group with a heteroatom having the appropriate number of hydrogen atoms attached (e.g., a $CH_2$ group to an NH group or an O group).

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{10}$alkylene. In another aspect, an alkylene is a $C_1$-$C_6$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and the like.

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

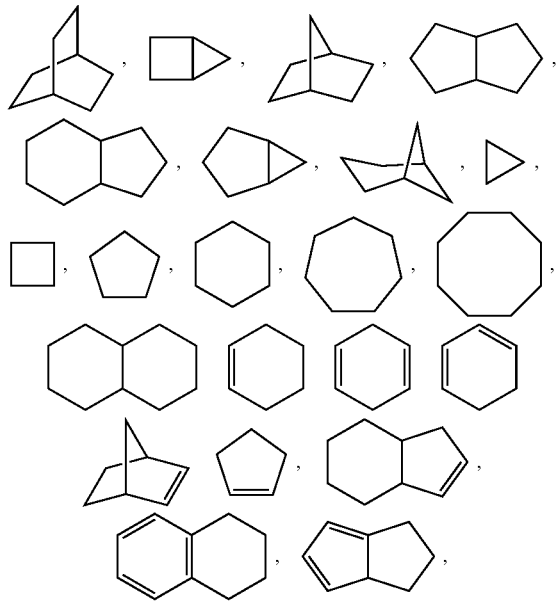

and the like. Monocyclic cycloalkyls include, but are not limited to, cyclopropyl, cyclobutyl, cyclopentyl, cyclohexyl, cycloheptyl, and cyclooctyl.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

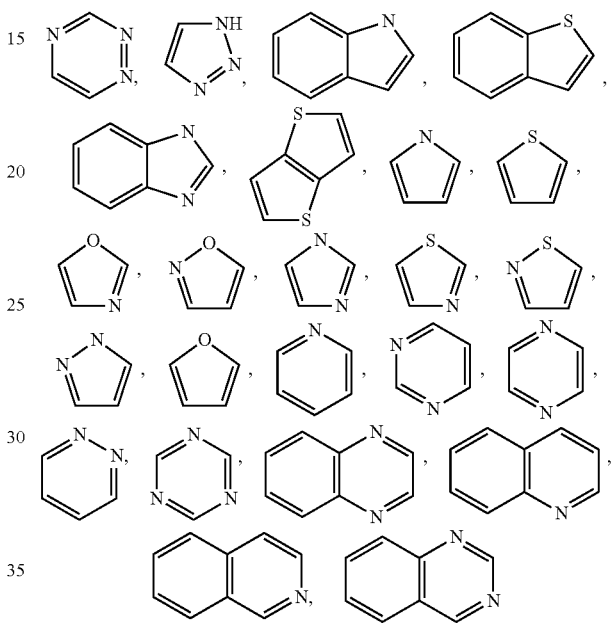

and the like.

A "heteroalicyclic" group or "heterocyclo" group refers to a cycloalkyl group, wherein at least one skeletal ring atom is a heteroatom selected from nitrogen, oxygen and sulfur. In various embodiments, the radicals are with an aryl or heteroaryl. Illustrative examples of heterocyclo groups, also referred to as non-aromatic heterocycles, include:

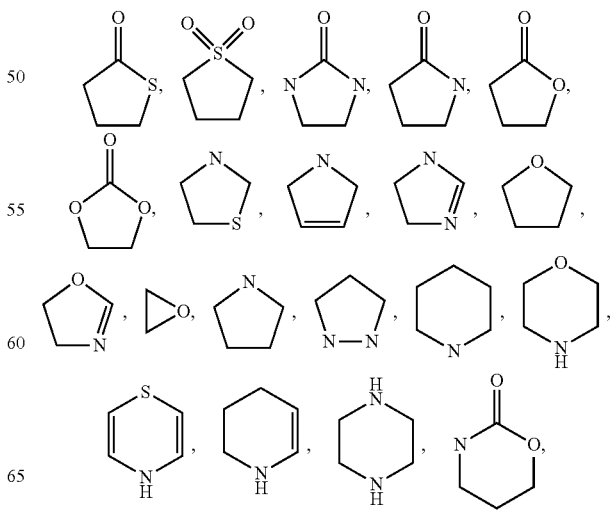

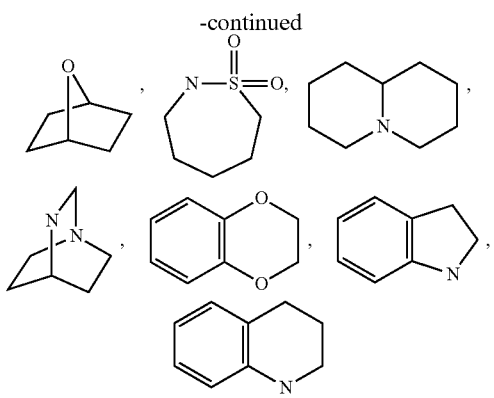

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In some embodiments, up to two heteroatoms are consecutive, such as, by way of example, —$CH_2$—NH—$OCH_3$ and —$CH_2$—O—Si($CH_3$)$_3$.

A "cyano" group refers to a —CN group.
An "isocyanato" group refers to a —NCO group.
A "thiocyanato" group refers to a —CNS group.
An "isothiocyanato" group refers to a —NCS group.
"Alkoyloxy" refers to a RC(=O)O— group.
"Alkoyl" refers to a RC(=O)— group.

The term "modulate," as used herein refers to having some affect on (e.g., increasing, enhancing or maintaining a certain level).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, arylalkoxy, aralkyloxy, arylalkyloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art and may be found in references such as Greene and Wuts, above. In some embodiments, alkyl groups described herein are optionally substituted with an O that is connected to two adjacent carbon atoms (i.e., forming an epoxide).

ASBT Inhibitors

In various embodiments of methods of the present invention, ASBT inhibitors are administered to a subject. ASBT inhibitors (ASBTIs) reduce or inhibit bile acid recycling in the distal gastrointestinal (GI) tract, including the distal ileum, the colon and/or the rectum. Inhibition of the apical sodium-dependent bile acid transport interrupts the enterohepatic circulation of bile acids and results in more bile acids being excreted in the feces, see FIG. 1, leading to lower levels of bile acids systemically, thereby reducing bile acid mediated liver damage and related effects and complications. In certain embodiments, the ASBTIs are systemically absorbed. In certain embodiments, the ASBTIs are not systemically absorbed. In some embodiments, ASBTIs described herein are modified or substituted (e.g., with a -L-K group) to be non-systemic. In certain embodiments, any ASBT inhibitor is modified or substituted with one or more charged groups (e.g., K) and optionally, one or more linker (e.g., L), wherein L and K are as defined herein.

In some embodiments, an ASBTI suitable for the methods described herein is a compound of Formula I:

Formula I

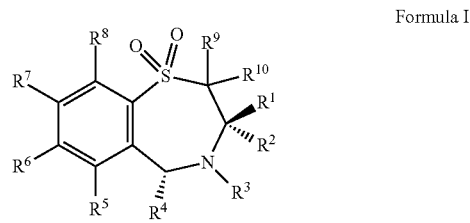

wherein:
$R^1$ is a straight chained $C_{1-6}$ alkyl group;
$R^2$ is a straight chained $C_{1-6}$ alkyl group;
$R^3$ is hydrogen or a group $OR^{11}$ in which $R^{11}$ is hydrogen, optionally substituted $C_{1-6}$ alkyl or a $C_{1-6}$ alkylcarbonyl group;
$R^4$ is pyridyl or optionally substituted phenyl or -$L_z$-$K_z$; wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;
$R^5$, $R^6$, $R^7$ and $R^8$ are the same or different and each is selected from hydrogen, halogen, cyano, $R^5$-acetylide, $OR^{15}$, optionally substituted $C_{1-6}$ alkyl, $COR^{15}$, $CH(OH)R^{15}$, $S(O)_nR^{15}$, $P(O)(OR^{15})_2$, $OCOR^{15}$, OCF3, OCN, SCN, NHCN, CH$_2$OR$^{15}$, CHO, (CH$_2$)$_p$CN, CONR$^{12}$R$^{13}$, (CH$_2$)$_p$CO$_2$R$^{15}$, (CH$_2$)$_p$NR$^{12}$R$^{13}$, CO$_2$R$^{15}$, NHCOCF$_3$, NHSO$_2$R$^{15}$, OCH$_2$OR$^{15}$, OCH=CHR$^{15}$, O(CH$_2$CH$_2$O)$_n$R$^{15}$, O(CH$_2$)$_p$SO$_3$R$^{15}$, O(CH$_2$)$_p$NR$^{12}$R$^{13}$, O(CH$_2$)$_p$N$^+$R$^{12}$R$^{13}$R$^{14}$ and —W—R$^{31}$, wherein W is O or NH and R$^{31}$ is selected from

[chemical structures shown]

wherein p is an integer from 1-4, n is an integer from 0-3 and, R$^{12}$, R$^{13}$, R$^{14}$ and R$^{15}$ are independently selected from hydrogen and optionally substituted C$_{1-6}$ alkyl; or R$^6$ and R$^7$ are linked to form a group —O—(CR$^{12}$R$^{13}$)$_m$—O— wherein R$^{12}$ and R$^{13}$ are as hereinbefore defined and m is 1 or 2; and
R$^9$ and R$^{10}$ are the same or different and each is selected from hydrogen or C$_{1-6}$ alkyl; and
salts, solvates and physiologically functional derivatives thereof.

In some embodiments of the methods, the compound of Formula I is a compound
wherein
R$^1$ is a straight chained C$_{1-6}$ alkyl group;
R$^2$ is a straight chained C$_{1-6}$ alkyl group;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is optionally substituted phenyl;
R$^5$, R$^6$ and R$^8$ are independently selected from hydrogen, C$_{1-4}$ alkyl optionally substituted by fluorine, C$_{1-4}$ alkoxy, halogen, or hydroxy;
R$^7$ is selected from halogen, cyano, R$^{15}$-acetylide, OR$^{15}$, optionally substituted C$_{1-6}$ alkyl, COR$^{15}$, CH(OH)R$^{15}$, S(O)$_n$R$^{15}$, P(O)(OR$^{15}$)$_2$, OCOR$^{15}$, OCF$_3$, OCN, SCN, HNCN, CH$_2$OR$^{15}$, CHO, (CH$_2$)$_p$CN, CONR$^{12}$R$^{13}$, (CH$_2$)$_p$CO$_2$R$^{15}$, (CH$_2$)$_p$NR$^{12}$R$^{13}$, CO$_2$R$^{15}$, NHCOCF$_3$, NHSO$_2$R$^{15}$, OCH$_2$OR$^{15}$, OCH=CHR$^{15}$, O(CH$_2$CH$_2$O)$_p$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$;
wherein n, p and R$^{12}$ to R$^{15}$ are as hereinbefore defined;
with the proviso that at least two of R$^5$ to R$^8$ are not hydrogen; and
salts solvates and physiologically functional derivatives thereof.

In some embodiments of the methods described herein, the compound of Formula I is a compound
wherein
R$^1$ is a straight chained C$_{1-6}$ alkyl group;
R$^2$ is a straight chained C$_{1-6}$ alkyl group;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is un-substituted phenyl;
R$^5$ is hydrogen or halogen;
R$^6$ and R$^8$ are independently selected from hydrogen, C$_{1-4}$ alkyl optionally substituted by fluorine, C$_{1-4}$ alkoxy, halogen, or hydroxy;
R$^7$ is selected from OR$^{15}$, S(O)$_n$R$^{15}$, OCOR$^{15}$, OCF$_3$, OCN, SCN, CHO, OCH$_2$OR$^{15}$, OCH=CHR$^{15}$, O(CH$_2$CH$_2$O)$_n$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein p is an integer from 1-4, n is an integer from 0-3, and R$^{12}$, R$^{13}$, R$^{14}$, and R$^{15}$ are independently selected from hydrogen and optionally substituted C$_{1-6}$ alkyl;
R$^9$ and R$^{10}$ are the same or different and each is selected from hydrogen or C$_{1-6}$ alkyl; and
salts, solvates and physiologically functional derivatives thereof.

In some embodiments of the methods, wherein the compound of Formula I is a compound
wherein
R$^1$ is methyl, ethyl or n-propyl;
R$^2$ is methyl, ethyl, n-propyl, n-butyl or n-pentyl;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is un-substituted phenyl;
R$^5$ is hydrogen;
R$^6$ and R$^8$ are independently selected from hydrogen, C$_{1-4}$ alkyl optionally substituted by fluorine, C$_{1-4}$ alkoxy, halogen, or hydroxy;
R$^7$ is selected from OR$^{15}$, S(O)$_n$R$^{15}$, OCOR$^{15}$, OCF$_3$, OCN, SCN, CHO, OCH$_2$OR$^{15}$, OCH=CHR$^{15}$, O(CH$_2$CH$_2$O)$_n$R$^{15}$, O(CH$_2$)$_p$SO$_3$R$^{15}$, O(CH$_2$)$_p$NR$^{12}$R$^{13}$ and O(CH$_2$)$_p$N$^+$R$^{12}$R$^{13}$R$^{14}$ wherein p is an integer from 1-4, n is an integer from 0-3, and R$^{12}$, R$^{13}$, R$^{14}$, and R$^{15}$ are independently selected from hydrogen and optionally substituted C$_{1-6}$ alkyl;
R$^9$ and R$^{10}$ are the same or different and each is selected from hydrogen or C$_{1-6}$ alkyl; and salts, solvates and physiologically functional derivatives thereof.

In some embodiments of the methods, the compound of Formula I is a compound
wherein
R$^1$ is methyl, ethyl or n-propyl;
R$^2$ is methyl, ethyl, n-propyl, n-butyl or n-pentyl;
R$^3$ is hydrogen or a group OR$^{11}$ in which R$^{11}$ is hydrogen, optionally substituted C$_{1-6}$ alkyl or a C$_{1-6}$ alkylcarbonyl group;
R$^4$ is un-substituted phenyl;
R$^5$ is hydrogen;
R$^6$ is C$_{1-4}$ alkoxy, halogen, or hydroxy;

R[7] is OR[15], wherein R[15] is hydrogen or optionally substituted $C_{1-6}$ alkyl;

R[8] is hydrogen or halogen;

R[9] and R[10] are the same or different and each is selected from hydrogen or $C_{1-6}$ alkyl; and salts, solvates and physiologically functional derivatives thereof.

In some embodiments of the methods, the compound of Formula I is (3R,5R)-3-Butyl-3-ethyl-2,3,4,5-tetrahydro-7,8-dimethoxy-5-phenyl-1,4-benzothiazepine 1,1-dioxide; (3R,5R)-3-Butyl-3-ethyl-2,3,4,5-tetrahydro-7,8-dimethoxy-5-phenyl-1,4-benzothiazepin-4-ol 1,1-dioxide; (±)-Trans-3-butyl-3-ethyl-2,3,4,5-tetrahydro-7,8-dimethoxy-5-phenyl-1,4-benzothiazepine 1,1-dioxide; (±)-Trans-3-butyl-3-ethyl-2,3,4,5-tetrahydro-7,8-dimethoxy-5-phenyl-1,4,-benzothiazepin-4-ol 1,1-dioxide; (3R,5R)-7-Bromo-3-butyl-3-ethyl-2,3,4,5-tetrahydro-8-methoxy-5-phenyl-1,4-benzothiazepine 1,1-dioxide; (3R,5R)-7-Bromo-3-butyl-3-ethyl-2,3,4,5-tetrahydro-8-methoxy-5-phenyl-1,4-benxothiaxepin-4-ol 1,1-dioxide; (3R,5R)-3-Butyl-3-ethyl-2,3,4,5-tetrahydro-5-phenyl-1, 4-benzothiazepine-7,8-diol 1,1-dioxide; (3R,5R)-3-Butyl-3-ethyl-2,3,4,5-tetrahydro-8-methoxy-5-phenyl-1,4-benzothiazepin-7-ol 1,1-dioxide; (3R,5R)-3-Butyl-3-ethyl-2,3,4,5-tetrahydro-7-methoxy-5-phenyl-1,4-benzothiazepin-8-ol 1,1-dioxide; (±)-Trans-3-butyl-3-ethyl-2,3,4,5-tetrahydro-8-methoxy-5-phenyl-1,4-benzothiazepine 1,1-dioxide; (±)-Trans-3-butyl-3-ethyl-2,3,4,5-tetrahydro-5-phenyl-1,4-benzothiazepin-8-ol 1,1-dioxide; (±)-Trans-3-butyl-3-ethyl-2,3,4,5-tetrahydro-5-phenyl-1,4-benzothiazepine-4,8-diol; (±)-Trans-3-butyl-3-ethyl-2,3,4,5-tetrahydro-5-phenyl-1,4-benzothiazepin-8-thiol 1,1-dioxide; (±)-Trans-3-butyl-3-ethyl-2,3,4,5-tetrahydro-5-phenyl-1,4-benzothiazepin-8-sulfonic acid 1,1-dioxide; (±)-Trans-3-butyl-3-ethyl-2,3,4,5-tetrahydro-8,9-dimethoxy-5-phenyl-1,4-benzothiazepine 1, 1-dioxide; (3R,5R)-3-butyl-7,8-diethoxy-2,3,4,5-tetrahydro-5-phenyl-1,4-benzothiazepine 1,1-dioxide; (±)-Trans-3-butyl-8-ethoxy-3-ethyl-2,3,4,5-tetrahydro-5-phenyl-1,4-benzothiazepine 1,1-dioxide; (±)-Trans-3-butyl-3-ethyl-2,3,4,5-tetrahydro-8-isopropoxy-5-phenyl-1,4-benzothiazepine 1,1-dioxide hydrochloride; (±)-Trans-3-butyl-3-ethyl-2,3,4,5-tetrahydro-5-phenyl-1,4-benzothiazepin-8-carbaldehyde-1,1-dioxide; 3,3-Diethyl-2,3,4,5-tetrahydro-7,8-dimethoxy-5-phenyl-1,4-benzothiazepine 1,1-dioxide; 3,3-Diethyl-2,3,4,5-tetrahydro-8-methoxy-5-phenyl-1,4-benzothiazepine 1,1-dioxide; 3,3-Diethyl-2,3,4,5-tetrahydro-5-phenyl-1,4-benzothiazpin-4,8-diol 1,1-dioxide; (RS)-3,3-Diethyl-2,3,4,5-tetrahydro-4-hydroxy-7,8-dimethoxy-5-phenyl-1,4-benzothiazepine 1,1-dioxide; (±)-Trans-3-butyl-8-ethoxy-3-ethyl-2,3,4,5-tetrahydro-5-phenyl-1,4-benzothiazepin-4-ol-1-dioxide; (±)-Trans-3-butyl-3-ethyl-2,3,4,5-tetrahydro-8-isopropoxy-5-phenyl-1,4-benzothiazepin-4-ol 1,1-dioxide; (±)-Trans-3-butyl-3-ethyl-2,3,4,5-tetrahydro-7,8,9-trimethoxy-5-phenyl-1,4-benzothiazepin-4-ol 1,1-dioxide; (3R,5R)-3-butyl-3-ethyl-2,3,4,5-tetrahydro-5-phenyl-1,4-benzothiazepin-4,7,8-triol 1,1-dioxide; (±)-Trans-3-butyl-3-ethyl-2,3,4,5-tetrahydro-4,7,8-trimethoxy-5-phenyl-1,4-benzothiazepine 1,1-dioxide; 3,3-Diethyl-2,3,4,5-tetrahydro-5-phenyl-1,4-benzothiazepin-8-ol 1,1-dioxide; 3,3-Diethyl-2,3,4,5-tetrahydro-7-methoxy-5-phenyl-1,4-benzothiazepin-8-ol 1,1-dioxide; 3,3Dibutyl-2,3,4,5-tetrahydro-5-phenyl-1,4-benzothiazepin-8-ol 1,1-dioxide; (±)-Trans-Butyl-3-ethyl-2,3,4,5-tetrahydro-1,1-dioxo-5-phenyl-1,4-benzothiazepin-8-yl hydrogen sulfate; or 3,3-Diethyl-2,3,4,5-tetrahydro-1,1-dioxo-5-phenyl-1,4-benzothiazepin-8-yl hydrogen sulfate.

In some embodiments, the compound of Formula I is

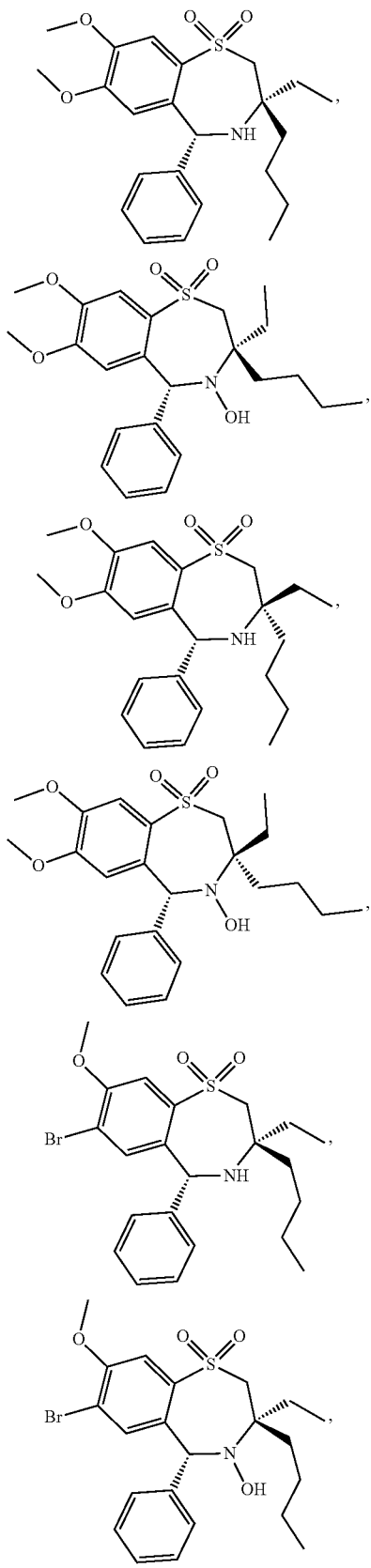

33
-continued
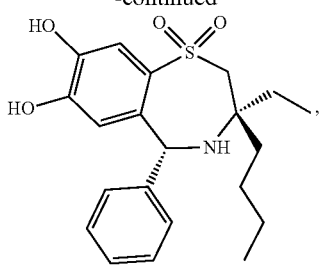
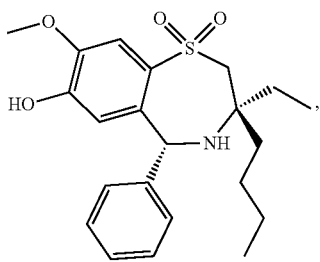
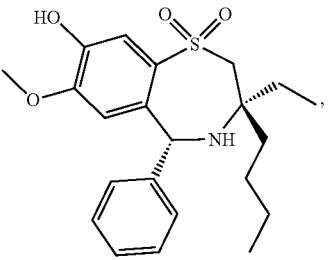
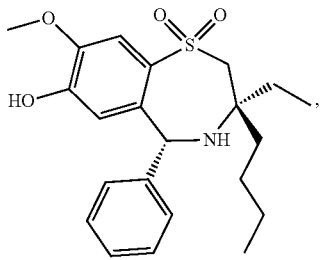
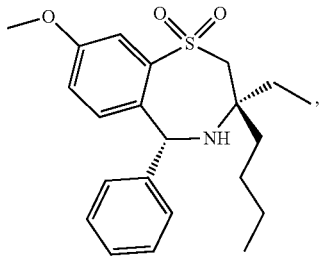
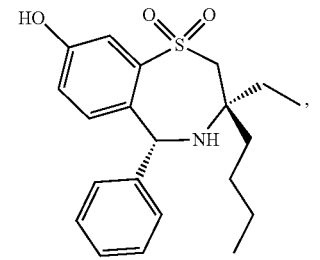
34
-continued
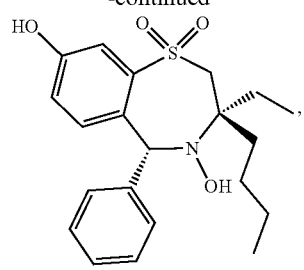
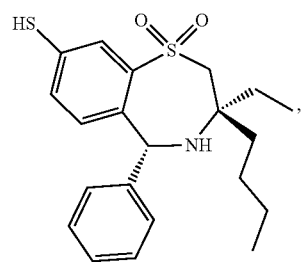
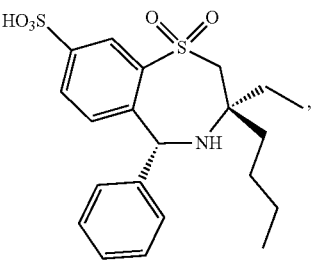
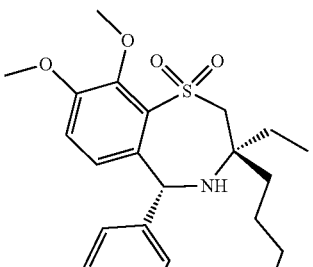
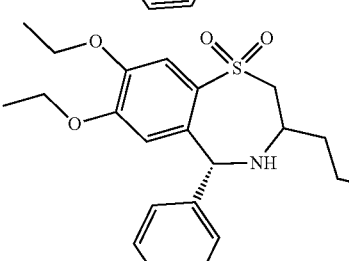
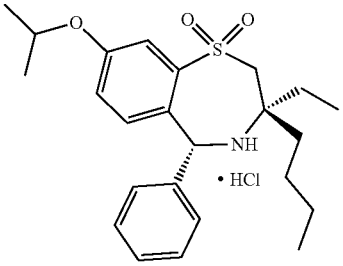

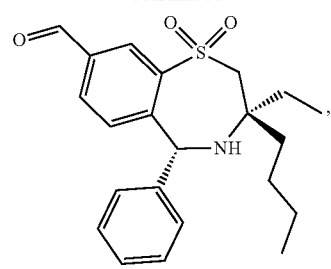,
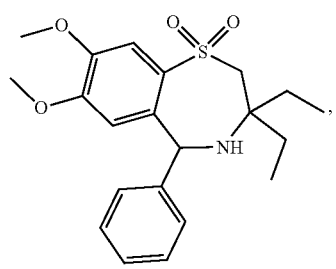,
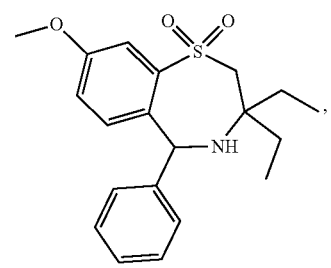,
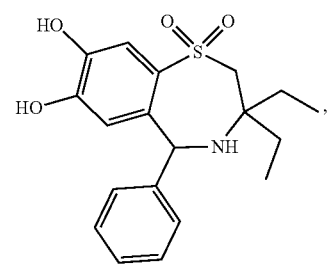,
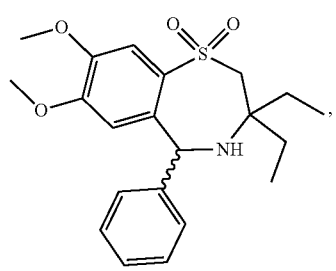,
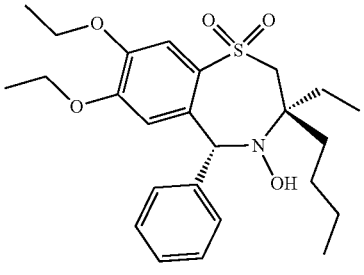,
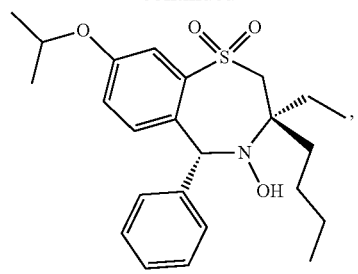,
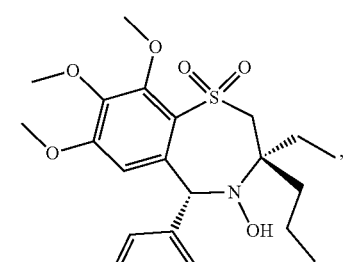,
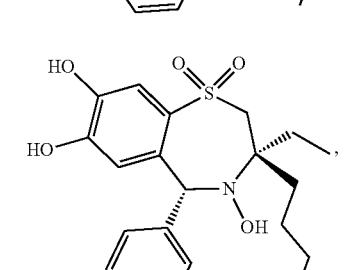,
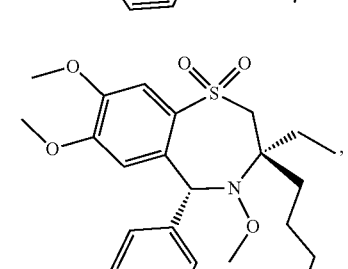,
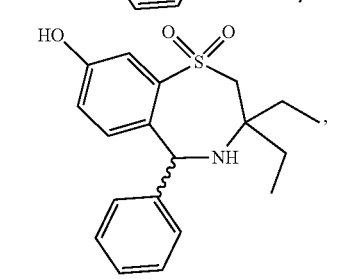,
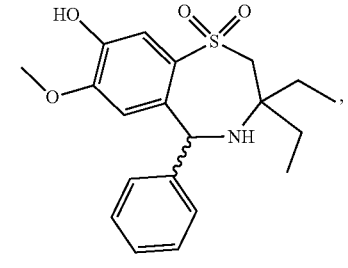,

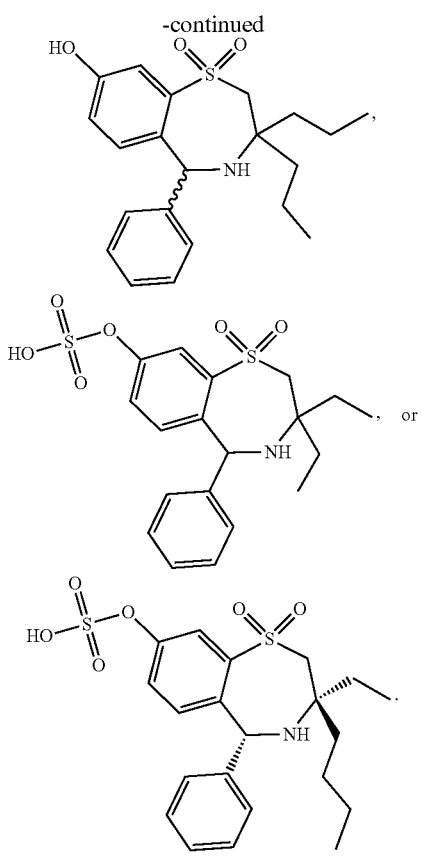

In some embodiments of the methods, the compound of Formula I is

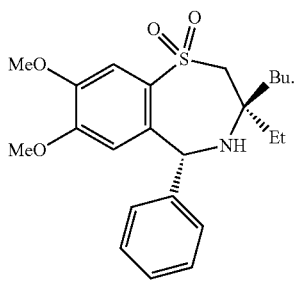

In some embodiments, the compound of Formula I is not a structure shown as:

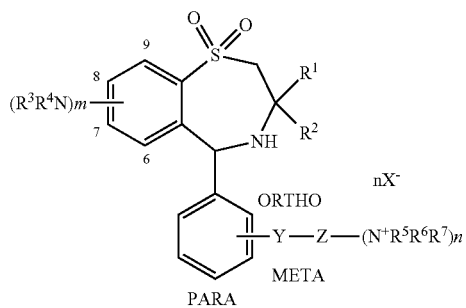

wherein m represents an integer of 1 or 2, and $R^3$ and $R^4$, which may be mutually different, each represents an alkyl group having 1 to 5 carbon atoms.

In some embodiments, an ASBTI suitable for the methods described herein is a compound of Formula II Formula II

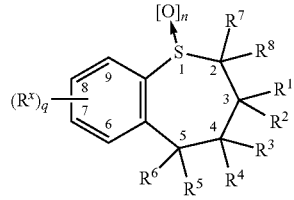

wherein:

q is an integer from 1 to 4;

n is an integer from 0 to 2;

$R^1$ and $R^2$ are independently selected from the group consisting of H, alkyl, alkenyl, alkynyl, haloalkyl, alkylaryl, arylalkyl, alkoxy, alkoxyalkyl, dialkylamino, alkylthio, (polyalkyl)aryl, and cycloalkyl, wherein alkyl, alkenyl, alkynyl, haloalkyl, alkylaryl, arylalkyl, alkoxy, alkoxyalkyl, dialkylamino, alkylthio, (polyalkyl)aryl, and cycloalkyl optionally are substituted with one or more substituents selected from the group consisting of $OR^9$, $NR^9R^{10}$, $N^+R^9R^{10}R^wA^-$, $SR^9$, $S^+R^9R^{10}A^-$, $P^+R^9R^{10}R^{11}A^-$, $S(O)R^9$, $SO_2R^9$, $SO_3R^9$, $CO_2R^9$, CN, halogen, oxo, and $CONR^9R^{10}$, wherein alkyl, alkenyl, alkynyl, alkylaryl, alkoxy, alkoxyalkyl, (polyalkyl)aryl, and cycloalkyl optionally have one or more carbons replaced by O, $NR^9$, $N^+R^9R^{10}A^-$, S, SO, $SO_2$, $S^+R^9A^-$, $P^+R^9R^{10}A^-$, or phenylene, wherein $R^9$, $R^{10}$, and $R^w$ are independently selected from the group consisting of H, alkyl, alkenyl, alkynyl, cycloalkyl, aryl, acyl, heterocycle, ammoniumalkyl, arylalkyl, and alkylammoniumalkyl; or $R^1$ and $R^2$ taken together with the carbon to which they are attached form $C_3$-$C_{10}$ cycloalkyl;

$R^3$ and $R^4$ are independently selected from the group consisting of H, alkyl, alkenyl, alkynyl, acyloxy, aryl, heterocycle, $OR^9$, $NR^9R^{10}$, $SR^9$, $S(O)R^9$, $SO_2R^9$, and $SO_3R^9$, wherein $R^9$ and $R^{10}$ are as defined above; or $R^3$ and $R^4$ together =O, =$NOR^{11}$, =S, =$NNR^{11}R^{12}$, =$NR^9$, or =$CR^{11}R^{12}$, wherein $R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ and $R^6$ are independently selected from the group consisting of H, alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and -$L_z$-$K_z$;

wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$ wherein:

$A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted from the one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)$ $OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{11}R^{12}A^-$, $P^+R^9R^{10}R^{11}A^-$, $OS(O)_2OM$, or $S^+R^9R^{10}A^-$, and $R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, S(O) $R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more R are independently selected from the group consisting of H, alkyl, alkenyl, alkynyl, polyalkyl, acyloxy, aryl, arylalkyl, halogen, haloalkyl, cycloalkyl, heterocycle, heteroaryl, polyether, quaternary heterocycle, quaternary heteroaryl, $OR^{13}$, $NR^{13}R^{14}$, $SR^{13}$, $S(O)R^{13}$, $S(O)_2R^{13}$, $SO_3R^{13}$, $S^+R^{13}R^{14}A^-$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $NR^{14}C(O)R^{13}$, $C(O)NR^{13}R^{14}$, $NR^{14}C(O)R^{13}$, C(O)OM, $COR^{13}$, $OR^{18}$, $S(O)_n$ $NR^{18}$, $NR^{13}R^{18}$, $NR^{18}R^{14}$, $N^+R^9R^{11}R^{12}A^-$, $P^+R^9R^{11}R^{12}A^-$, amino acid, peptide, polypeptide, and carbohydrate, wherein alkyl, alkenyl, alkynyl, cycloalkyl, aryl, polyalkyl, heterocycle, acyloxy, arylalkyl, haloalkyl, polyether, quaternary heterocycle, and quaternary heteroaryl can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{11}R^{12}A^-$, $S^+R^9R^{10}A^-$, or C(O)M, and wherein $R^{18}$ is selected from the group consisting of acyl, arylalkoxycarbonyl, arylalkyl, heterocycle, heteroaryl, alkyl, wherein acyl, arylalkoxycarbonyl, arylalkyl, heterocycle, heteroaryl, alkyl, quaternary heterocycle, and quaternary heteroaryl optionally are substituted with one or more substituents selected from the group consisting of $OR^9$, $NR^9R^{10}$, $N^+R^9R^{11}R^{12}A^-$, $SR^9$, $S(O)R^9$, $SO_2R^9$, $SO_3R^9$, oxo, $CO_3R^9$, CN, halogen, $CONR^9R^{10}$, $SO_3R^9$, $SO_2OM$, $SO_2NR^9R^{10}$, $PO(OR^{16})OR^{17}$, and C(O)OM, wherein in $R^x$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, wherein in said polyalkyl, phenylene, amino acid, peptide, polypeptide, and carbohydrate, one or more carbons are optionally replaced by O, $NR^9$, $R^9R^{10}A^-$, S, SO, $SO_2$, $S^+R^9A^-$, $PR^9$, $P^+R^9R^{10}A^-$, or $P(O)R^9$;

wherein quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$, provided that both $R^5$ and $R^6$ cannot be hydrogen or SH;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

In some embodiments of the methods, the compound of Formula II is a compound wherein q is an integer from 1 to 4;

n is 2;

$R^1$ and $R^2$ are independently selected from the group consisting of H, alkyl, alkoxy, dialkylamino, and alkylthio, wherein alkyl, alkoxy, dialkylamino, and alkylthio are optionally substituted with one or more substituents selected from the group consisting of $OR^9$, $NR^9R^{10}$, $SR^9$, $SO_2R^9$, $CO_2R^9$, CN, halogen, oxo, and $CONR^9R^{10}$;

each $R^9$ and $R^{10}$ are each independently selected from the group consisting of H, alkyl, cycloalkyl, aryl, acyl, heterocycle, and arylalkyl;

$R^3$ and $R^4$ are independently selected from the group consisting of H, alkyl, acyloxy, $OR^9$, $NR^9R^{10}$, $SR^9$, and $SO_2R^9$, wherein $R^9$ and $R^{10}$ are as defined above;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^5$ and $R^6$ are independently selected from the group consisting of H, alkyl, aryl, cycloalkyl, heterocycle, and $-L_z-K_z$;

wherein z is 1 or 2; each L is independently a substituted or unsubstituted alkyl, a substituted or unsubstituted heteroalkyl, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, aryl, cycloalkyl, and heterocycle can be substituted with one or more substituent groups independently selected from the group consisting of alkyl, aryl, haloalkyl, cycloalkyl, heterocycle, arylalkyl, quaternary heterocycle, quaternary heteroaryl, halogen, oxo, $OR^{13}$, $OR^{13}R^{14}$, $NR^{13}R^{14}$, $SR^{13}$, $SO_2R^{13}$, $NR^{13}NR^{14}R^{15}$, $NO_2$, $CO_2R^{13}$, CN, OM, and $CR^{13}$, wherein:

$A^-$ is a pharmaceutically acceptable anion and M is a pharmaceutically acceptable cation;

$R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl, wherein $R^{13}$, $R^{14}$ and $R^{15}$ are optionally substituted with one or more groups selected from the group consisting of quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, and $CONR^9R^{10}$; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl; and $R^7$ and $R^8$ are independently selected from the group consisting of hydrogen and alkyl; and one or more R are independently selected from the group consisting of H, alkyl, acyloxy, aryl, alkyl, halogen, haloalkyl, cycloalkyl, heterocycle, heteroaryl, $OR^{13}$, $NR^{13}R^{14}$, $SR^{13}$, $S(O)_2R^{13}$, $NR^{13}NR^{14}R^{15}$, $NO_2$, $CO_2R^{13}$, CN, $SO_2NR^{13}R^{14}$, $NR^{14}C(O)R^{13}$, $C(O)NR^{13}R^{14}$, $NR^{14}C(O)R^{13}$, and $COR^{13}$;

provided that both $R^5$ and $R^6$ cannot be hydrogen;

provided that when $R^5$ or $R^6$ is phenyl, only one of $R^1$ or $R^2$ is H;

provided that when q=1 and $R^x$ is styryl, anilido, or anilinocarbonyl, only one of $R^5$ or $R^6$ is alkyl; or a pharmaceutically acceptable salt, solvate, or prodrug thereof.

In some embodiments, the compound of Formula II is a compound wherein q is 1;

n is 2;

$R^x$ is $N(CH_3)_2$;

$R^7$ and $R^8$ are independently H;

$R^1$ and $R^2$ is alkyl;

$R^3$ is H, and $R^4$ is OH;

$R^5$ is H, and $R^6$ is selected from the group consisting of alkyl, alkenyl, alkynyl, aryl, cycloalkyl, heterocycle, quaternary heterocycle, quaternary heteroaryl, $OR^9$, $SR^9$, $S(O)R^9$, $SO_2R^9$, $SO_3R^9$, and $-L_z-K_z$;

wherein z is 1, 2 or 3; each L is independently a substituted or unsubstituted alkyl, a substituted or unsubstituted heteroalkyl, a substituted or unsubstituted alkoxy, a substituted or unsubstituted aminoalkyl group, a substituted or unsubstituted aryl, a substituted or unsubstituted heteroaryl, a substituted or unsubstituted cycloalkyl, or a substituted or unsubstituted heterocycloalkyl; each K is a moiety that prevents systemic absorption;

wherein alkyl, alkenyl, alkynyl, aryl, cycloalkyl, heterocycle, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, $C(O)OM$, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$.

wherein $A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R_8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7)OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{11}R^{12}A^-$, $P^+R^9R^{10}R^{11}A^-$, $OS(O)_2OM$, or $S^+R^9R^{10}A^-$, and $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O) R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl;

or a pharmaceutically acceptable salt, solvate, or prodrug thereof.

In some embodiments, the compound of Formula II is a compound wherein q is 1;

n is 2;

$R^x$ is $N(CH_3)_2$;

$R^7$ and $R^8$ are independently H;

$R^1$ and $R^2$ is independently $C_1$-$C_4$ alkyl;

$R^3$ is H, and $R^4$ is OH;

$R^5$ is H, and $R^6$ is arylsubstituted with one or more substituent groups independently selected from the group consisting of alkyl, alkenyl, alkynyl, polyalkyl, polyether, aryl, haloalkyl, cycloalkyl, heterocycle, arylalkyl, quaternary heterocycle, quaternary heteroaryl, halogen, oxo, $R^{15}$, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$.

wherein $A^-$ is a pharmaceutically acceptable anion and M is a pharmaceutically acceptable cation, said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8R^9A^-$, and $P(O)(OR^7) OR^8$ and wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene, and $R^{13}$, $R^{14}$, and $R^{15}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, quaternary heteroarylalkyl, and -G-T-V-W, wherein alkyl, alkenyl, alkynyl, arylalkyl, heterocycle, and polyalkyl optionally have one or more carbons replaced by O, $NR^9$, $N^+R^9R^{10}A^-$, S, SO, $SO_2$, $S^+R^9A^-$, PR, $P^+R^9R^{10}A^-$, $P(O)R^9$, phenylene, carbohydrate, $C_2$-$C_7$ polyol, amino acid, peptide, or polypeptide, and G, T and V are each independently a bond, —O—, —S—, —N(H)—, substituted or unsubstituted alkyl, —O-alkyl, —N(H)-alkyl, —C(O)N(H)—, —N(H)C(O)—, —N(H)C(O)N(H)—, substituted or unsubstituted alkenyl, substituted or unsubstituted alkynyl, substituted or unsubstituted aryl, substituted or unsubstituted arylalkyl, substituted or unsubstituted alkenylalkyl, alkynylalkyl, substituted or unsubstituted heteroalkyl, substituted or unsubstituted heterocycle, substituted or unsubstituted carboxyalkyl, substituted or unsubstituted carboalkoxyalkyl, or substituted or unsubstituted cycloalkyl, and W is quaternary heterocycle, quaternary heteroaryl, quaternary heteroarylalkyl, $N^+R^9R^{11}R^{12}A^-$, $P^+R^9R^{10}R^{11}A^-$, $OS(O)_2OM$, or $S^+R^9R^{10}A^-$, and $R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;

$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH, or $R^{11}$ and $R^{12}$ together with the nitrogen or carbon atom to which they are attached form a cyclic ring;

$R^{13}$, $R^{14}$ and $R^{15}$ are optionally substituted with one or more groups selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O) R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM, wherein $R^{16}$ and $R^{17}$ are independently selected from the substituents constituting $R^9$ and M; or $R^{14}$ and $R^{15}$, together with the nitrogen atom to which they are attached, form a cyclic ring; and is selected from the group consisting of alkyl, alkenyl, alkynyl, cycloalkyl, aryl, acyl, heterocycle, ammoniumalkyl, alkylammoniumalkyl, and arylalkyl;

or a pharmaceutically acceptable salt, solvate, or prodrug thereof.

In some embodiments of the methods, the compound of Formula II is a compound
wherein
$R^5$ and $R^6$ are independently selected from the group consisting of H, aryl, heterocycle, quaternary heterocycle, and quaternary heteroaryl
wherein the aryl, heteroaryl, quaternary heterocycle and quaternary heteroaryl are optionally substituted with one or more groups selected from the group consisting of alkyl, alkenyl, alkynyl, polyalkyl, polyether, aryl, haloalkyl, cycloalkyl, heterocycle, arylalkyl, halogen, oxo, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$ and $-L_z-K_z$.

In some embodiments of the methods, the compound of Formula II is a compound
wherein
$R^5$ or $R^6$ is $-Ar-(R^y)_t$
t is an integer from 0 to 5;
Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl; and
one or more $R^y$ are independently selected from the group consisting of alkyl, alkenyl, alkynyl, polyalkyl, polyether, aryl, halo alkyl, cycloalkyl, heterocycle, arylalkyl, halogen, oxo, $OR^{13}$, $OR^{13}R^{14}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, $N^+R^9R^{11}R^{12}A^-$ and $-L_z-K_z$;
wherein said alkyl, alkenyl, alkynyl, polyalkyl, polyether, aryl, haloalkyl, cycloalkyl, and heterocycle can be further substituted with one or more substituent groups selected from the group consisting of $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$, and or phenylene;
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene.

In some embodiments of the methods, the compound of Formula II is a compound wherein
$R^5$ or $R^6$ is

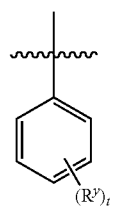

In some embodiments of the methods, the compound of Formula II is a compound wherein n is 1 or 2. In some embodiments of the methods, the compound of Formula II is a compound wherein $R^1$ and $R^2$ are independently H or $C_{1-7}$ alkyl. In some embodiments of the methods, the compound of Formula II is a compound wherein each $C_{1-7}$ alkyl is independently ethyl, n-propyl, n-butyl, or isobutyl. In some embodiments of the methods, the compound of Formula II is a compound wherein $R^3$ and $R^4$ are independently H or $OR^9$. In some embodiments of the methods, compound of Formula II is a compound wherein $R^9$ is H In some embodiments of the methods, the compound of Formula II is a compound wherein one or more $R^x$ are in the 7-, 8- or 9-position of the benzo ring of Formula II. In some embodiments of the methods, the compound of Formula II is a compound wherein $R^x$ is in the 7-position of the benzo ring of Formula II. In some embodiments of the methods, the compound of Formula II is a compound wherein one or more $R^x$ are independently selected from $OR^{13}$ and $NR^{13}R^{14}$.

In some embodiments of the methods, the compound of Formula II is a compound
wherein:
q is 1 or 2;
n is 2;
$R^1$ and $R^2$ are each alkyl;
$R^3$ is hydroxy;
$R^4$ and $R^6$ are hydrogen;
$R^5$ has the formula

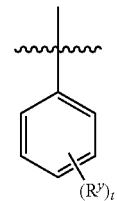

wherein
t is an integer from 0 to 5;
one or more $R^Y$ are $OR^{13}$ or $OR^{13}R^{14}$;
$R^{13}$ and $R^{14}$ are independently selected from the group consisting of hydrogen, alkyl, alkenyl, alkynyl, polyalkyl, aryl, arylalkyl, cycloalkyl, heterocycle, heteroaryl, quaternary heterocycle, quaternary heteroaryl, and quaternary heteroarylalkyl;
wherein said alkyl, alkenyl, alkynyl, arylalkyl, heterocycle, and polyalkyl groups optionally have one or more carbons replaced by O, $NR^9$, $N^+R^9R^{10}A^-$, S, SO, $SO_2$, $S^+R^9A^-$, $PR^9$, $P^+R^9R^{10}A^-$, $P(O)R^9$, phenylene, carbohydrate, amino acid, peptide, or polypeptide;
$R^{13}$ and $R^{14}$ are optionally substituted with one or more groups independently selected from the group consisting of sulfoalkyl, quaternary heterocycle, quaternary heteroaryl, $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}$, $SO_2OM$, $SO_2NR^9R^{10}$, $PO(OR^{16})OR^{17}$, $P^+R^9R^{10}R^{11}A^-$, $S^+R^9R^{10}A^-$, and C(O)OM,
wherein A is a pharmaceutically acceptable anion, and M is a pharmaceutically acceptable cation,
$R^9$ and $R^{10}$ are independently selected from the group consisting of H, alkyl, alkenyl, alkynyl, cycloalkyl, aryl, acyl, heterocycle, ammoniumalkyl, arylalkyl, and alkylammoniumalkyl;
$R^{11}$ and $R^{12}$ are independently selected from the group consisting of H, alkyl, alkenyl, alkynyl, aryl, arylalkyl, alkenylalkyl, alkynylalkyl, heterocycle, carboxyalkyl, carboalkoxyalkyl, cycloalkyl, cyanoalkyl, $OR^9$, $NR^9R^{10}$, $SR^9$, $S(O)R^9$, $SO_2R^9$, $SO_3R^9$, $CO_2R^9$, CN, halogen, oxo, and $CONR^9R^{10}$, wherein $R^9$ and $R^{10}$ are as defined above, provided that both $R^3$ and $R^4$ cannot be OH, $NH_2$, and SH; or $R^{11}$ and $R^{12}$ together with the nitrogen or carbon atom to which they are attached form a cyclic ring; and $R^{16}$ and $R^{17}$ are independently selected from the substituents constituting $R^9$ and M;

$R^7$ and $R^8$ are hydrogen; and one or more $R^x$ are independently selected from the group consisting of alkoxy, alkylamino and dialkylamino and —W—$R^{31}$, wherein W is O or NH and $R^{31}$ is selected from

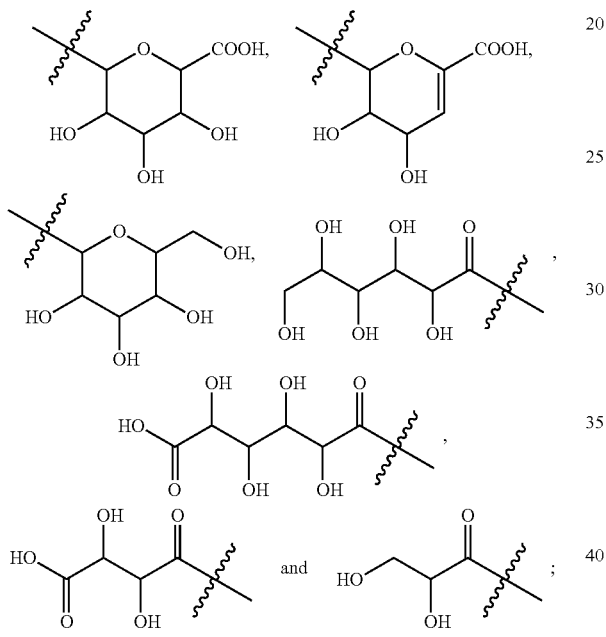

or a pharmaceutically acceptable salt, solvate, or prodrug thereof.

In some embodiments, a compound of Formula II is

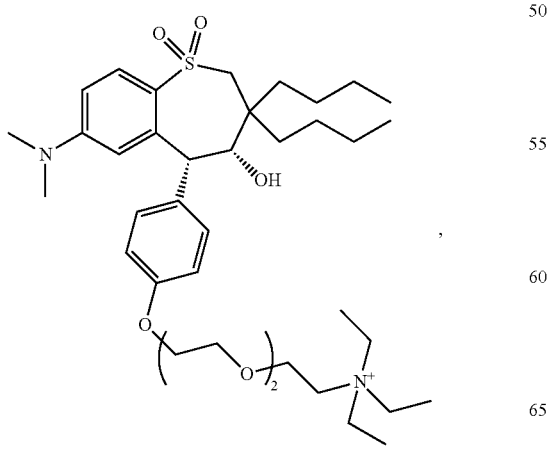

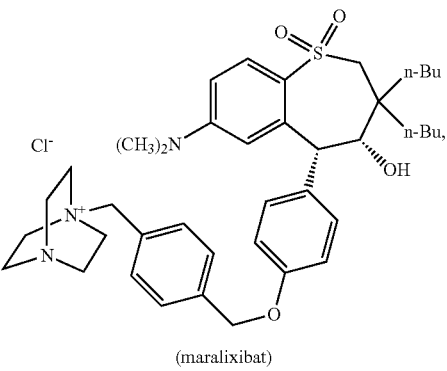

(maralixibat)

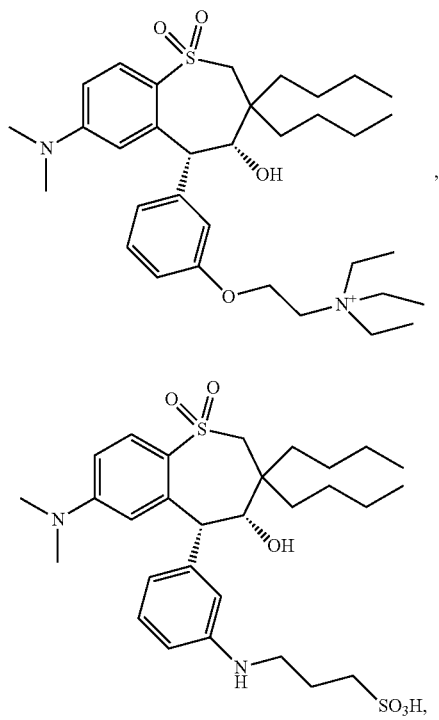

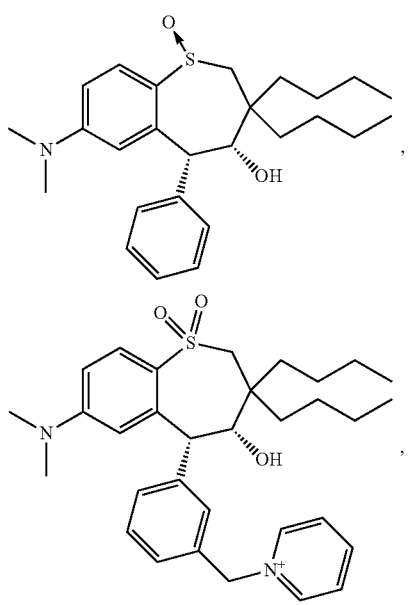

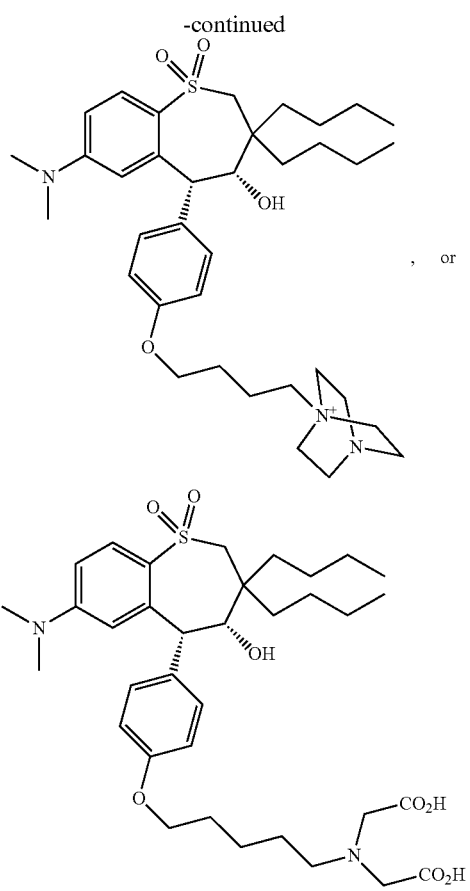

, or

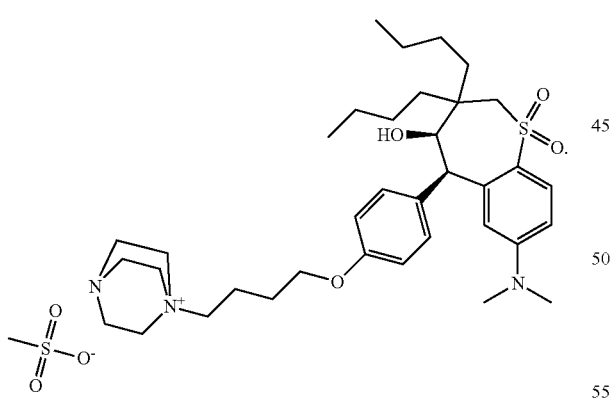

or the like.

In some embodiments of the methods, the compound of Formula II is

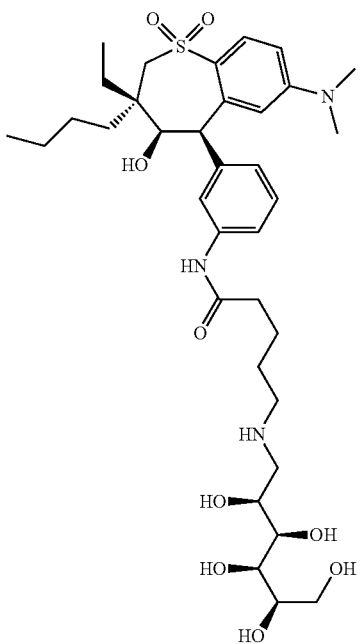

In some embodiments, a compound of Formula II is 1-[[5-[[3-[(3S,4R,5R)-3-butyl-7-(dimethylamino)-3-ethyl-2,3,4,5-tetrahydro-4-hydroxy-1,1-dioxido-1-benzothiepin-5yl]phenyl]amino]-5-oxopentyl]amino]-1-deoxy-D-glucitol or SA HMR1741 (a.k.a. BARI-1741).

In some embodiments, a compound of Formula II is

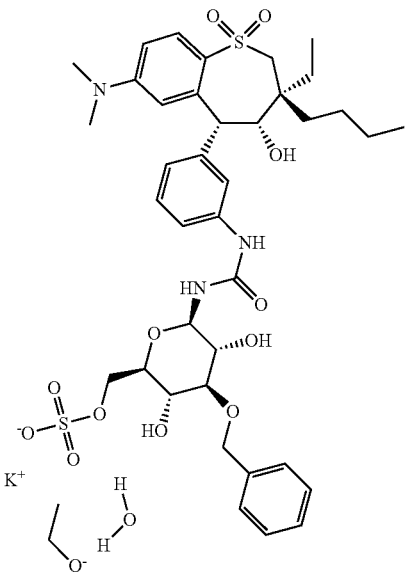

(volixibat potassium)

In some embodiments, a compound of Formula II is potassium((2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl) sulphate ethanolate, hydrate or SAR548304B (a.k.a. SAR-548304).

In certain embodiments, ASBTIs suitable for the methods described herein are non-systemic analogs of Compound 100C. Certain compounds provided herein are Compound 100C analogues modified or substituted to comprise a charged group. In specific embodiments, the Compound 100C analogues are modified or substituted with a charged group that is an ammonium group (e.g., a cyclic ar acyclic ammonium group). In certain embodiments, the ammonium group is a non-protic ammonium group that contains a quaternary nitrogen.

In some embodiments, an ASBTI suitable for the methods described herein is a compound of Formula III:

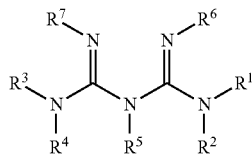

Formula III wherein:
each $R^1$, $R^2$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;
each $R^3$, $R^4$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;
$R^5$ is H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl,
each $R^6$, $R^7$ is independently H, hydroxy, alkyl, alkoxy, —C(=X)YR$^8$, —YC(=X)R$^8$, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;
each X is independently NH, S, or O;
each Y is independently NH, S, or O;
$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein
each A is independently NR$^1$, S(O)$_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;
n is 0-7;
K is a moiety that prevents systemic absorption;
provided that at least one of $R^1$, $R^2$, $R^3$ or $R^4$ is -L-K;
or a pharmaceutically acceptable prodrug thereof.

In some embodiments of a compound of Formula III, $R^1$ and $R^3$ are -L-K. In some embodiments, $R^1$, $R^2$ and $R^3$ are -L-K.

In some embodiments, at least one of $R^1$, $R^2$, $R^3$, $R^4$, $R^5$, $R^6$ and $R^7$ is H. In certain embodiments, $R^5$, $R^6$, $R^7$ are H and $R^1$, $R^2$, $R^3$ and $R^4$ are alkyl, aryl, alkyl-aryl, or heteroalkyl. In some embodiments, $R^1$ and $R^2$ are H. In some embodiments, $R^1$, $R^2$, $R^5$, $R^6$ and $R^7$ are H. In some embodiments, $R^6$ and $R^7$ together form a bond. In certain embodiments, $R^5$, $R^6$ and $R^7$ are H, alkyl or O-alkyl.

In some embodiments, $R^1$ and $R^3$ are -L-K. In some embodiments, $R^1$, $R^2$ and $R^3$ are -L-K. In some embodiments, $R^3$ and $R^4$ are -L-K. In some embodiments, $R^1$ and $R^2$ together with the nitrogen to which they are attached form a 3-8 membered ring and the ring is substituted with -L-K. In some embodiments, $R^1$ or $R^2$ or $R^3$ or $R^4$ are aryl optionally substituted with -L-K. In some embodiments, $R^1$ or $R^2$ or $R^3$ or $R^4$ are alkyl optionally substituted with -L-K. In some embodiments, $R^1$ or $R^2$ or $R^3$ or $R^4$ are alky-aryl optionally substituted with -L-K. In some embodiments, $R^1$ or $R^2$ or $R^3$ or $R^4$ are heteroalkyl optionally substituted with -L-K.

In some embodiments, L is a $C_1$-$C_7$alkyl. In some embodiments, L is heteroalkyl. In certain embodiments, L is $C_1$-$C_7$alkyl-aryl. In some embodiments, L is $C_1$-$C_7$alkyl-aryl-$C_1$-$C_7$alkyl.

In certain embodiments, K is a non-protic charged group. In some specific embodiments, each K is a ammonium group. In some embodiments, each K is a cyclic non-protic ammonium group. In some embodiments, each K is an acyclic non-protic ammonium group.

In certain embodiments, each K is a cyclic non-protic ammonium group of structure:

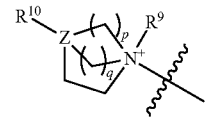

In certain embodiments, K is an acyclic non-protic ammonium group of structure:

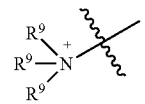

wherein p, q, $R^9$, $R^{10}$ and Z are as defined above. In certain embodiments, p is 1. In other embodiments, p is 2. In further embodiments, p is 3. In some embodiments, q is 0. In other embodiments, q is 1. In some other embodiments, q is 2.

The compounds further comprise 1, 2, 3 or 4 anionic counterions selected from Cl⁻, Br⁻, I⁻, $R^{11}SO_3^-$, $(SO_3^-$—$R^{11}$—$SO_3^-)$, $R^{11}CO_2^-$, $(CO_2^-$—$R^{11}$—$CO_2^-)$, $(R^{11})_2(P=O)$ $O^-$ and $(R^{11})(P=O)O_2^{2-}$ wherein $R^{11}$ is as defined above. In some embodiments, the counterion is Cl⁻, Br⁻, I⁻, $CH_2CO_2^-$, $CH_3SO_3^-$, or $C_6H_5SO_3^-$ or $CO_2^-$—$(CH_2)_2$—$CO_2^-$. In some embodiments, the compound of Formula III has one K group and one counterion. In other embodiments, the compound of Formula III has one K group, and two molecules of the compound of Formula III have one counterion. In yet other embodiments, the compound of Formula III has two K groups and two counterions. In some other embodiments, the compound of Formula III has one K group comprising two ammonium groups and two counterions.

Also described herein are compounds having the Formula IIIA:

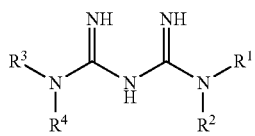

Formula IIIA wherein:
each $R^1$, $R^2$ is independently H, substituted or unsubstituted alkyl, or -L-K; or $R^1$ and $R^2$ together with the nitrogen to which they are attached form a 3-8-membered ring that is optionally substituted with $R^8$;
and $R^3$, $R^4$, $R^8$, L and K are as defined above.

In some embodiments of compounds of Formula IIIA, L is $A_n$, wherein each A is substituted or unsubstituted alkyl, or substituted or unsubstituted heteroalkyl, and n is 0-7. In certain specific embodiments of the compound of Formula IIIA, $R^1$ is H. In some embodiments of Formula IIIA, $R^1$ and $R^2$ together with the nitrogen to which they are attached form a 3-8-membered ring that is optionally substituted with -L-K.

Also described herein are compounds having the Formula IIIB:

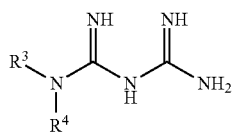

Formula IIIB wherein:
each $R^3$, $R^4$ is independently H, substituted or unsubstituted alkyl, substituted or unsubstituted heteroalkyl, substituted or unsubstituted aryl, substituted or unsubstituted alkyl-aryl, or -L-K;
and $R^1$, $R^2$, L and K are as defined above.

In certain embodiments of Formula IIIB, $R^3$ is H. In certain embodiments, $R^3$ and $R^4$ are each -L-K. In some embodiments, $R^3$ is H and $R^4$ is substituted or unsubstituted alkyl, substituted or unsubstituted heteroalkyl, substituted or unsubstituted aryl, substituted or unsubstituted alkyl-aryl containing one or two -L-K groups.

In some embodiments, an ASBTI suitable for the methods described herein is a compound of Formula IIIC

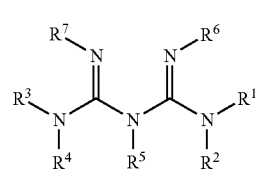

Formula IIIC wherein:
each $R^1$, $R^2$ is independently H, hydroxy, alkyl, alkoxy, —C(=X)YR⁸, —YC(=X)R⁸, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^1$ and $R^2$ together with the nitrogen to which they are attached form a 3-8-membered ring that is optionally substituted with $R^8$;
each $R^3$, $R^4$ is independently H, hydroxy, alkyl, alkoxy, —C(=X)YR⁸, —YC(=X)R⁸, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;
$R^5$ is H, hydroxy, alkyl, alkoxy, —C(=X)YR⁸, —YC(=X)R⁸, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl,
each $R^6$, $R^7$ is independently H, hydroxy, alkyl, alkoxy, —C(=X)YR⁸, —YC(=X)R⁸, substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K; or $R^6$ and $R^7$ taken together form a bond;
each X is independently NH, S, or O;
each Y is independently NH, S, or O;
$R^8$ is substituted or unsubstituted alkyl, substituted or unsubstituted heteroalkyl, substituted or unsubstituted aryl, substituted or unsubstituted alkyl-aryl, substituted or unsubstituted cycloalkyl, substituted or unsubstituted alkyl-cycloalkyl, substituted or unsubstituted heteroaryl, substituted or unsubstituted alkyl-heteroaryl, substituted or unsubstituted heterocycloalkyl, substituted or unsubstituted alkyl-heterocycloalkyl, or -L-K;

L is $A_n$, wherein each A is independently $NR^1$, $S(O)_m$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each m is independently 0-2;

n is 0-7;

K is a moiety that prevents systemic absorption;

or a pharmaceutically acceptable salt thereof.

In some specific embodiments of Formula I, II or III, K is selected from

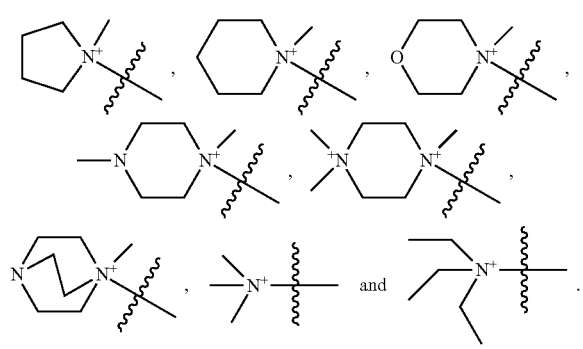

In some embodiments, an ASBTI suitable for the methods described herein is a compound of Formula IV:

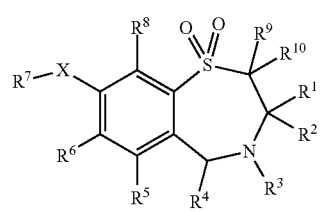

wherein $R^1$ is a straight chain $C_{1-6}$ alkyl group;

$R^2$ is a straight chain $C_{1-6}$ alkyl group;

$R^3$ is hydrogen or a group $OR^{11}$ in which $R^{11}$ is hydrogen, optionally substituted $C_{1-6}$ alkyl or a $C_{1-6}$ alkylcarbonyl group;

$R^4$ is pyridyl or an optionally substituted phenyl;

$R^5$, $R^6$ and $R^8$ are the same or different and each is selected from:

hydrogen, halogen, cyano, $R^{15}$-acetylide, $OR^{15}$, optionally substituted $C_{1-6}$ alkyl, $COR^{15}$, $CH(OH)R^{15}$, $S(O)_n R^{15}$, $P(O)(OR^{15})_2$, $OCOR^{15}$, $OCF_3$, OCN, SCN, NHCN, $CH_2OR^{15}$, CHO, $(CH_2)_pCN$, $CONR^{12}R^{13}$, $(CH_2)_pCO_2R^{15}$, $(CH_2)_pNR^{12}R^{13}$, $CO_2R^{15}$, $NHCOCF_3$, $NHSO_2R^{15}$, $OCH_2OR^{15}$, $OCH=CHR^{15}$, $O(CH_2CH_2O)_nR^{15}$, $O(CH_2)_pSO_3R^{15}$, $O(CH_2)_p NR^{12}R^{13}$ and $O(CH_2)_p N^+R^{12}R^{13}R^{14}$ wherein p is an integer from 1-4, n is an integer from 0-3 and $R^{12}$, $R^{13}$, $R^{14}$ and $R^{15}$ are independently selected from hydrogen and optionally substituted $C^{1-6}$ alkyl;

$R^7$ is a group of the formula

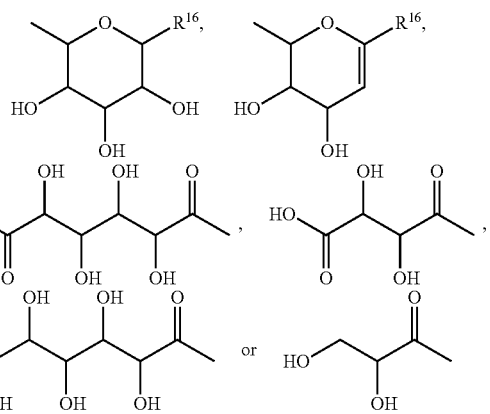

wherein the hydroxyl groups may be substituted by acetyl, benzyl, or $-(C_1-C_6)$-alkyl-$R^{17}$, wherein the alkyl group may be substituted with one or more hydroxyl groups;

$R^{16}$ is —COOH, —CH$_2$—OH, —CH$_2$—O-Acetyl, —COOMe or —COOEt;

$R^{17}$ is H, —OH, —NH$_2$, —COOH or $COOR^{18}$;

$R^{18}$ is $(C_1-C_4)$-alkyl or —NH—$(C_1-C_4)$-alkyl;

X is —NH— or —O—; and $R^9$ and $R^{10}$ are the same or different and each is hydrogen or $C_1-C_6$ alkyl; and salts thereof.

In some embodiments, a compound of Formula IV has the structure of Formula IVA or Formula IVB:

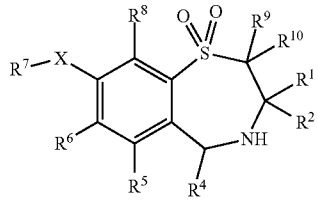

Formula IVA

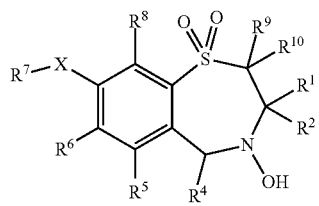

Formula IVB

In some embodiments, a compound of Formula IV has the structure of Formula IVC:

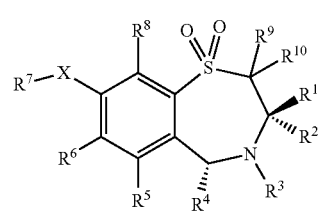

IVC

In some embodiments of Formula IV, X is O and $R^7$ is selected from

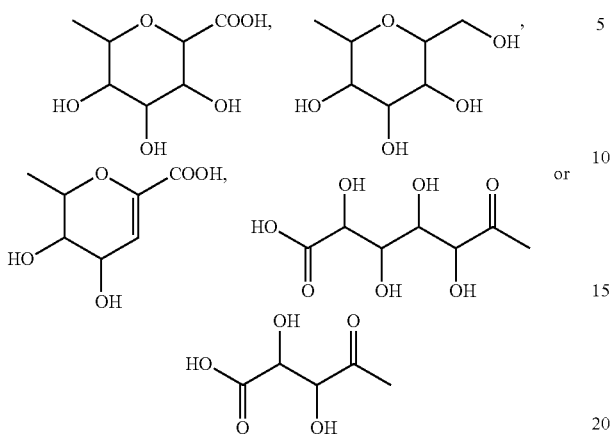

In some embodiments, a compound of Formula IV is:

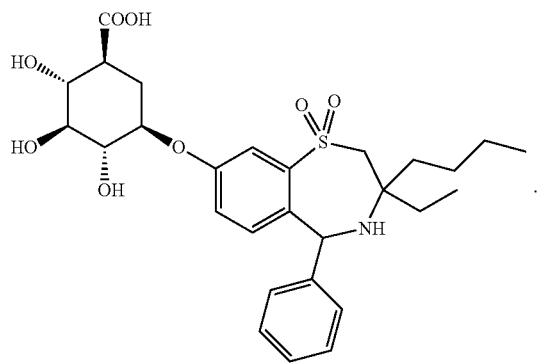 [SMILES: CCCCC1(CC)CS(=O)(=O)c2cc(O[C@@H]3C[C@H](C(=O)O)[C@@H](O)[C@H](O)[C@H]3O)ccc2C(c2ccccc2)N1]

In some embodiments, an ASBTI suitable for the methods described herein is a compound of Formula V:

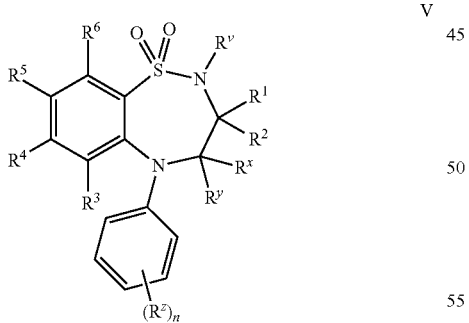

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$-alkyl)sulphamoyl and N,N—($C_{1-6}$alkyl)$_2$sulphamoyl;

n is 0-5;

one of $R^4$ and $R^5$ is a group of formula (VA):

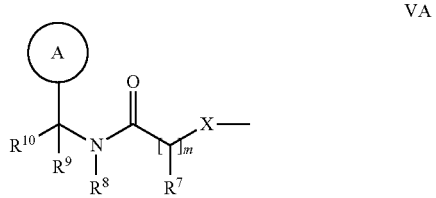

VA $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—;

wherein $R^a$ is hydrogen or $C_{1-6}$alkyl and b is 0-2;

Ring A is aryl or heteroaryl;

wherein Ring A is optionally substituted on carbon by one or more substituents selected from $R^{18}$;

$R^7$ is hydrogen, $C_{1-6}$alkyl, carbocyclyl or heterocyclyl;

wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$-alkyl;

$R^9$ is hydrogen or $C_{1-6}$alkyl;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkynyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$amino, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (VB):

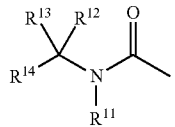

wherein:

$R^{11}$ is hydrogen or $C_{1-6}$-alkyl;

$R^{12}$ and $R^{13}$ are independently selected from hydrogen, halo, carbamoyl, sulphamoyl, $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, carbamoyl, sulphamoyl, hydroxyaminocarbonyl, $C_{1-10}$alkyl, $C_{2-10}$alkenyl, $C_{2-10}$alkynyl, $C_{1-10}$alkanoyl, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$- $R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (VC):

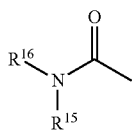

$R^{15}$ is hydrogen or $C_{1-6}$alkyl; and $R^{16}$ is hydrogen or $C_{1-6}$alkyl; wherein $R^{16}$ may be optionally substituted on carbon by one or more groups selected from $R^{31}$;

or $R^{15}$ and $R^{16}$ together with the nitrogen to which they are attached form a heterocyclyl; wherein said heterocyclyl may be optionally substituted on carbon by one or more $R^{37}$; and wherein if said heterocyclyl contains an —NH— group, that nitrogen may be optionally substituted by a group selected from $R^{38}$;

m is 1-3; wherein the values of $R^7$ may be the same or different;

$R^{17}$, $R^{18}$, $R^{19}$, $R^{23}$, $R^{25}$, $R^{29}$, $R^{31}$ and $R^{37}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$amino, $C_{1-10}$alkanoylamino, N—($C_{1-10}$alkyl)carbamoyl, N,N—($C_{1-10}$alkyl)$_2$ carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$, $R^{31}$ and $R^{37}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —$NR^{36}$—S(O)$_x$—, —$NR^{36}$C(O)$NR^{36}$—, —$NR^{36}$C(S)$NR^{36}$—, —OC(O)N=C—, —$NR^{36}$C(O)— or —C(O)$NR^{36}$—; wherein $R^{36}$ is selected from hydrogen or $C_{1-6}$alkyl, and x is 0-2;

p, q, r and s are independently selected from 0-2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$, $R^{35}$ and $R^{38}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; and wherein a "heteroaryl" is a totally unsaturated, mono or bicyclic ring containing 3-12 atoms of which at least one atom is chosen from nitrogen, sulphur and oxygen, which heteroaryl may, unless otherwise specified, be carbon or nitrogen linked;

wherein a "heterocyclyl" is a saturated, partially saturated or unsaturated, mono or bicyclic ring containing 3-12 atoms of which at least one atom is chosen from nitrogen, sulphur and oxygen, which heterocyclyl may, unless otherwise specified, be carbon or nitrogen linked, wherein a —$CH_2$— group can optionally be replaced by a —C(O)— group, and a ring sulphur atom may be optionally oxidised to form an S-oxide; and wherein a "carbocyclyl" is a saturated, partially saturated or unsaturated, mono or bicyclic carbon ring that contains 3-12 atoms; wherein a —$CH_2$— group can optionally be replaced by a —C(O) group;

or a pharmaceutically acceptable salt or in vivo hydrolysable ester or amide formed on an available carboxy or hydroxy group thereof.

In some embodiments, compound of Formula V is 1,1-dioxo-3,3-dibutyl-5-phenyl-7-methylthio-8-(N—{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]-4- hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—{(S)-1-[N—((S)-2-hydroxy-1-carboxyethyl)carbamoyl]propyl}carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-[N—{(R)-α-carboxy4-hydroxybenzyl}carbamoylmethoxy]-2,3,4,5-tetrahydro-1,2,5-benzothiadiazepine; or 1,1-dioxo-3,3-dibutyl-5-phenyl-7-methylthio-8-(N—{(R)-α-[N-(carboxymethyl)carbamoyl]benzyl} carbamoylmethoxy)-2,3,4,5-tetrahydro-1,2,5-benzothiadiazepine, or a salt thereof.

In some embodiments, compound of Formula V is

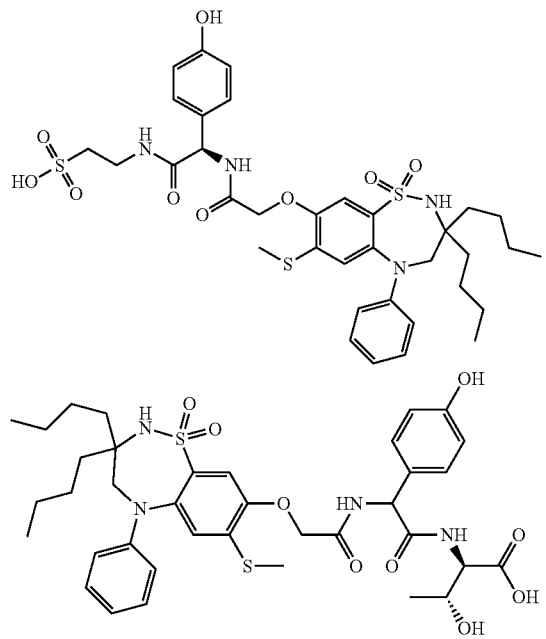

or

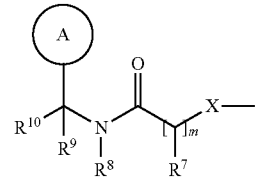

In some embodiments, an ASBTI suitable for the methods described herein is a compound of Formula VI:

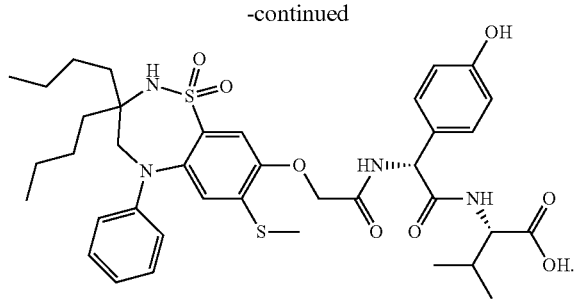

VI wherein:
$R^v$ and $R^w$ are independently selected from hydrogen or $C_{1-6}$alkyl;
one of $R^1$ and $R^2$ is selected from hydrogen or $C_{1-6}$alkyl and the other is selected from $C_{1-6}$alkyl;
$R^x$ and $R^y$ are independently selected from hydrogen or $C_{1-6}$alkyl, or one of R and $R^y$ is hydrogen or $C_{1-6}$alkyl and the other is hydroxy or $C_{1-6}$alkoxy;
$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
n is 0-5;
one of $R^4$ and $R^5$ is a group of formula (VIA):

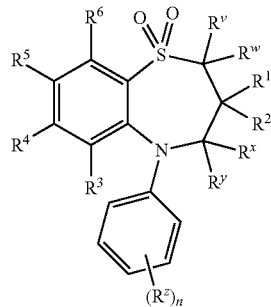

VIA $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS (O)$_a$ wherein a is 0 to 2, C$_{1-6}$alkoxycarbonyl, N—(C$_{1-6}$alkyl)sulphamoyl and N,N—(C$_{1-6}$alkyl)$_2$sulphamoyl; wherein R$^3$ and R$^6$ and the other of R$^4$ and R$^5$ may be optionally substituted on carbon by one or more R$^{17}$;

X is —O—, —N(R$^a$)—, —S(O)$_b$— or —CH(R$^a$)—; wherein R$^a$ is hydrogen or C$_{1-6}$alkyl and b is 0-2;

Ring A is aryl or heteroaryl; wherein Ring A is optionally substituted on carbon by one or more substituents selected from R$^{18}$;

R$^7$ is hydrogen, C$_{1-6}$alkyl, carbocyclyl or heterocyclyl; wherein R$^7$ is optionally substituted on carbon by one or more substituents selected from R$^{19}$; and wherein if said heterocyclyl contains an —NH— group, that nitrogen may optionally substituted by a group selected from R$^{20}$;

R$^8$ is hydrogen or C$_{1-6}$alkyl;

R$^9$ is hydrogen or C$_{1-6}$alkyl;

R$^{10}$ is hydrogen, halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$amino, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{21}$—(C$_{1-10}$alkylene)$_q$- or heterocyclyl-(C$_{1-10}$alkylene)$_r$-R$^{22}$—(C$_{1-10}$alkylene)$_s$-; wherein R$^{10}$ is optionally substituted on carbon by one or more substituents selected from R$^{23}$; and wherein if said heterocyclyl contains an —NH— group, that nitrogen may be optionally substituted by a group selected from R$^{24}$; or R$^{10}$ is a group of formula (VIB):

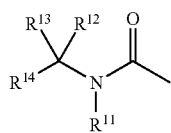

VIB wherein:

R$^{11}$ is hydrogen or C$_{1-6}$alkyl;

R$^{12}$ and R$^{13}$ are independently selected from hydrogen, halo, nitro, cyano, hydroxy, amino, carbamoyl, mercapto, sulphamoyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, carbocyclyl or heterocyclyl; wherein R$^{12}$ and R$^{13}$ may be independently optionally substituted on carbon by one or more substituents selected from R$^{25}$; and wherein if said heterocyclyl contains an —NH— group, that nitrogen may be optionally substituted by a group selected from R$^{26}$;

R$^{14}$ is selected from hydrogen, halo, nitro, cyano, hydroxy, amino, carbamoyl, mercapto, sulphamoyl, hydroxyaminocarbonyl, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, N—(C$_{1-10}$alkyl)amino, N,N—(C$_{1-10}$alkyl)$_2$amino, N,N,N—(C$_{1-10}$alkyl)$_3$amino, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{27}$—(C$_{1-10}$alkylene)$_q$- or heterocyclyl-(C$_{1-10}$alkylene)$_r$-R$^{28}$—(C$_{1-10}$alkylene)$_s$-; wherein R$^{14}$ may be optionally substituted on carbon by one or more substituents selected from R$^{29}$; and wherein if said heterocyclyl contains an —NH— group, that nitrogen may be optionally substituted by a group selected from R$^{30}$; or R$^{14}$ is a group of formula (VIC):

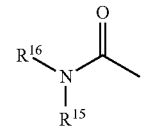

VIC

R$^{15}$ is hydrogen or C$_{1-6}$alkyl;

R$^{16}$ is hydrogen or C$_{1-6}$alkyl; wherein R$^{16}$ may be optionally substituted on carbon by one or more groups selected from R$^{31}$;

n is 1-3; wherein the values of R$^7$ may be the same or different;

R$^{17}$, R$^{18}$, R$^{19}$, R$^{23}$, R$^{25}$, R$^{29}$ or R$^{31}$ are independently selected from halo, nitro, cyano, hydroxy, amino, carbamoyl, mercapto, sulphamoyl, hydroxyaminocarbonyl, amidino, C$_{1-10}$alkyl, C$_{2-10}$alkenyl, C$_{2-10}$alkynyl, C$_{1-10}$alkoxy, C$_{1-10}$alkanoyl, C$_{1-10}$alkanoyloxy, (C$_{1-10}$alkyl)$_3$silyl, N—(C$_{1-10}$alkyl)amino, N,N—(C$_{1-10}$alkyl)$_2$ amino, N,N,N—(C$_{1-10}$alkyl)$_3$amino, C$_{1-10}$alkanoylamino, N—(C$_{1-10}$alkyl)carbamoyl, N,N—(C$_{1-10}$alkyl)$_2$carbamoyl, C$_{1-10}$alkylS(O)$_a$ wherein a is 0 to 2, N—(C$_{1-10}$alkyl)sulphamoyl, N,N—(C$_{1-10}$alkyl)$_2$ sulphamoyl, N—(C$_{1-10}$alkyl)sulphamoylamino, N,N—(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_p$-R$^{32}$—(C$_{1-10}$alkylene)$_q$- or heterocyclyl-(C$_{1-10}$alkylene)$_r$-R$^{33}$—(C$_{1-10}$alkylene)$_s$-; wherein R$^{17}$, R$^{18}$, R$^{19}$, R$^{23}$, R$^{25}$, R$^{29}$ or R$^{31}$ may be independently optionally substituted on carbon by one or more R$^{34}$; and wherein if said heterocyclyl contains an —NH— group, that nitrogen may be optionally substituted by a group selected from R$^{35}$;

R$^{21}$, R$^{22}$, R$^{27}$, R$^{28}$, R$^{32}$ or R$^{33}$ are independently selected from —O—, —NR$^{36}$—S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein R$^{36}$ is selected from hydrogen or C$_{1-6}$alkyl, and x is 0-2;

p, q, r and s are independently selected from 0-2;

R$^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$ or $R^{35}$ are independently selected from $C_{1-6}$alkyl, $C_{1-6}$alkanoyl, $C_{1-6}$alkylsulphonyl, C1-6alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate or solvate of such a salt, or an in vivo hydrolysable ester formed on an available carboxy or hydroxy thereof, or an in vivo hydrolysable amide formed on an available carboxy thereof.

In some embodiments, a compound of Formula VID has the structure of Formula VID:

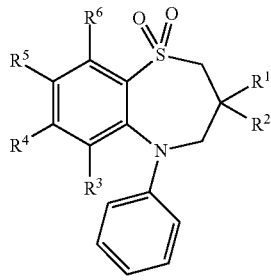

VID wherein:

$R^1$ and $R^2$ are independently selected from $C_{1-6}$alkyl; one of $R^4$ and $R^5$ is a group of formula (VIE):

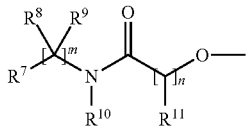

VIE $R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{14}$;

$R^7$ is carboxy, sulpho, sulphino, phosphono, —P(O)(OR$^a$)(OR$^b$), P(O)(OH)(OR$^a$), —P(O)(OH)(R$^a$) or P(O)(OR$^a$)(R$^b$), wherein R$^a$ and R$^b$ are independently selected from $C_{1-6}$alkyl; or $R^7$ is a group of formula (VIF):

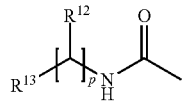

VIF $R^8$ and $R^9$ are independently hydrogen, $C_{1-4}$alkyl or a saturated cyclic group, or $R^8$ and $R^9$ together form $C_{2-6}$alkylene; wherein $R^8$ and $R^9$ or $R^8$ and $R^9$ together may be independently optionally substituted on carbon by one or more substituents selected from $R^{15}$; and wherein if said saturated cyclic group contains an —NH— moiety, that nitrogen may be optionally substituted by one or more $R^{20}$;

$R^{10}$ is hydrogen or $C_{1-4}$alkyl; wherein $R^{10}$ is optionally substituted on carbon by one or more substituents selected from $R^{24}$;

$R^{11}$ is hydrogen, $C^{1-4}$alkyl, carbocyclyl or heterocyclyl; wherein $R^{11}$ is optionally substituted on carbon by one or more substituents selected from $R^{16}$; and wherein if said heterocyclyl contains an —NH— moiety, that nitrogen may be optionally substituted by one or more $R^{21}$;

$R^{12}$ is hydrogen or $C_{1-4}$alkyl, carbocyclyl or heterocyclyl; wherein $R^{12}$ optionally substituted on carbon by one or more substituents selected from $R^{17}$; and wherein if said heterocyclyl contains an —NH— moiety, that nitrogen may be optionally substituted by one or more $R^{22}$;

$R^{13}$ is carboxy, sulpho, sulphino, phosphono, —P(O)(OR$^c$)(OR$^d$), —P(O)(OH)(OR$^c$), —P(O)(OH)(R$^c$) or —P(O)(OR$^c$)(R$^d$) wherein R$^c$ and R$^d$ are independently selected from $C_{1-6}$alkyl;

m is 1-3; wherein the values of $R^8$ and $R^9$ may be the same or different;

n is 1-3; wherein the values of $R^{11}$ may be the same or different;

p is 1-3; wherein the values of $R^{12}$ may be the same or different;

$R^{14}$ and $R^{16}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{14}$ and $R^{16}$ may be independently optionally substituted on carbon by one or more $R^{18}$;

$R^{15}$ and $R^{17}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl, sulpho, sulphino, amidino, phosphono, —P(O)(OR$^e$)(OR$^f$), —P(O)(OH)(OR$^e$), —P(O)(OH)(R$^e$) or —P(O)(OR$^e$)(R$^f$), wherein R$^e$ and R$^f$ are independently selected from $C_{1-6}$alkyl; wherein $R^{15}$ and $R^{17}$ may be independently optionally substituted on carbon by one or more $R^{19}$; and wherein if said heterocyclyl contains an —NH— moiety, that nitrogen may be optionally substituted by one or more $R^{23}$;

$R^{18}$, $R^{19}$ and $R^{25}$ are independently selected from halo, hydroxy, cyano, carbamoyl, ureido amino nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{20}$, $R^{21}$, $R^{22}$, $R^{23}$ and $R^{26}$ are independently $C_{1-4}$alkyl, $C_{1-4}$alkanoyl, $C_{1-4}$alkylsulphonyl, sulphamoyl, N—($C_{1-4}$alkyl)sulphamoyl, N,N—($C_{1-4}$alkyl)$_2$sulphamoyl, $C_{1-4}$alkoxycarbonyl, carbamoyl, N—($C_{1-4}$alkyl)carbamoyl, N,N—($C_{1-4}$alkyl)$_2$carbamoyl, benzyl, phenethyl, benzoyl, phenylsulphonyl and phenyl;

$R^{24}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl, carbocyclyl, heterocyclyl; wherein $R^{24}$ may be independently optionally substituted on carbon by one or more $R^{25}$; and wherein if said heterocyclyl contains an —NH— moiety, that nitrogen may be optionally substituted by one or more $R^{26}$;

wherein any saturated cyclic group is a totally or partially saturated, mono or bicyclic ring containing 3-12 atoms of which 0-4 atoms are chosen from nitrogen, sulphur or oxygen, which may be carbon or nitrogen linked;

wherein any heterocyclyl is a saturated, partially saturated or unsaturated, mono or bicyclic ring containing 3-12 atoms of which at least one atom is chosen from nitrogen, sulphur or oxygen, which may be carbon or nitrogen linked, wherein a —CH$_2$— group can optionally be replaced by a —C(O)— or a ring sulphur atom may be optionally oxidised to form the S-oxides; and wherein any carbocyclyl is a saturated, partially saturated or unsaturated, mono or bicyclic carbon ring that contains 3-12 atoms, wherein a —CH$_2$— group can optionally be replaced by a —C(O)—;

or a pharmaceutically acceptable salt thereof.

In some embodiments, a compound of Formula IV is 1,1-dioxo-3,3-dibutyl-5-phenyl-7-methylthio-8-(N—{(R)-1'-phenyl-1'-[N'-(carboxymethyl) carbamoyl]methyl}carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxypropyl)carbamoyl]-4-hydroxybenzyl}carbamoylmethoxy)-2,3,4,5-tetrahydro-1,5-benzothiazepine; 1,1-dioxo-3,3-dibutyl-5-phenyl-7-methylthio-8-(N—{(R)-1'-phenyl-1'-[N'-(carboxymethyl) carbamoyl] methyl}carbamoylmethoxy)-2,3,4,5-tetrahydro-1,5-benzothiazepine; 1,1-dioxo-3,3-dibutyl-5-phenyl-7-methylthio-8-(N—{(R)-α-[N'—((S)-1-carboxyethyl)carbamoyl]benzyl} carbamoylmethoxy)-2,3,4,5-tetrahydro-1,5-benzothiazepine; or a salt thereof.

In some embodiments, any compound described herein is covalently conjugated to a bile acid using any suitable method. In some embodiments, compounds described herein are covalently bonded to a cyclodextrin or a biodegradable polymer (e.g., a polysaccharide).

In certain embodiments compounds described herein are not systemically absorbed. Moreover, provided herein are compounds that inhibit bile salt recycling in the gastrointestinal tract of an individual. In some embodiments, compounds described herein, may not be transported from the gut lumen and/or do not interact with ASBT. In some embodiments, compounds described herein, do not affect, or minimally affect, fat digestion and/or absorption. In certain embodiments, the administration of a therapeutically effective amount of any compound described herein does not result in gastrointestinal disturbance or lactic acidosis in an individual. In certain embodiments, compounds described herein are administered orally. In some embodiments, an ASBTI is released in the distal ileum. An ASBTI compatible with the methods described herein may be a direct inhibitor, an allosteric inhibitor, or a partial inhibitor of the Apical Sodium-dependent Bile acid Transporter.

In certain embodiments, compounds that inhibit ASBT or any recuperative bile acid transporters are compounds that are described in EP1810689, U.S. Pat. Nos. 6,458,851, 7,413,536, 7,514,421, US Appl. Publication Nos. 2002/0147184, 2003/0119809, 2003/0149010, 2004/0014806, 2004/0092500, 2004/0180861, 2004/0180860, 2005/0031651, 2006/0069080, 2006/0199797, 2006/0241121, 2007/0065428, 2007/0066644, 2007/0161578, 2007/0197628, 2007/0203183, 2007/0254952, 2008/0070888, 2008/0070892, 2008/0070889, 2008/0070984, 2008/0089858, 2008/0096921, 2008/0161400, 2008/0167356, 2008/0194598, 2008/0255202, 2008/0261990, WO 2002/50027, WO2005/046797, WO2006/017257, WO2006/105913, WO2006/105912, WO2006/116499, WO2006/117076, WO2006/121861, WO2006/122186, WO2006/124713, WO2007/050628, WO2007/101531, WO2007/134862, WO2007/140934, WO2007/140894, WO2008/028590, WO2008/033431, WO2008/033464, WO2008/031501, WO2008/031500, WO2008/033465, WO2008/034534, WO2008/039829, WO2008/064788, WO2008/064789, WO2008/088836, WO2008/104306, WO2008/124505, and WO2008/130616; the compounds described therein that inhibit recuperative bile acid transport are hereby incorporated herein by reference.

In certain embodiments, compounds that inhibit ASBT or any recuperative bile acid transporters are compounds described in WO93/16055, WO94/18183, WO94/18184, WO96/05188, WO96/08484, WO96/16051, WO97/33882, WO98/38182, WO99/35135, WO98/40375, WO99/64409, WO99/64410, WO00/01687, WO00/47568, WO00/61568, DE 19825804, WO00/38725, WO00/38726, WO00/38727 (including those compounds with a 2,3,4,5-tetrahydro-1-benzothiepine 1,1-dioxide structure), WO00/38728, WO01/66533, WO02/50051, EP0864582 (e.g. (3R,5R)-3-butyl-3-ethyl-1,1-dioxido-5-Phenyl-2,3,4,5-tetrahydro-1,4-benzothiazepin-8-yl (0-D-glucopyranosiduronic acid, WO94/24087, WO98/07749, WO98/56757, WO99/32478, WO99/35135, WO00/20392, WO00/20393, WO00/20410, WO00/20437, WO01/34570, WO00/35889, WO01/68637, WO01/68096, WO02/08211, WO03/020710, WO03/022825, WO03/022830, WO03/0222861, JP10072371, U.S. Pat. Nos. 5,910,494; 5,723,458; 5,817,652; 5,663,165; 5,998,400; 6,465,451, 5,994,391; 6,107,494; 6,387,924; 6,784,201; 6,875,877; 6,740,663; 6,852,753; 5,070,103, 6,114,322, 6,020,330, 7,179,792, EP251315, EP417725, EP489-423, EP549967, EP573848, EP624593, EP624594, EP624595, EP869121, EP1070703, WO04/005247, compounds disclosed as having IBAT activity in Drugs of the Future, 24, 425-430 (1999), Journal of Medicinal Chemistry, 48, 5837-5852, (2005) and Current Medicinal Chemistry, 13, 997-1016, (2006); the compounds described therein that inhibit recuperative bile acid transport are hereby incorporated herein by reference.

In some embodiments, compounds that inhibit ASBT or any recuperative bile acid transporter are benzothiepines, benzothiazepines (including 1,2-benzothiazepines; 1,4-benzothiazepines; 1,5-benzothiazepines; and/or 1,2,5-benzothiadiazepines). In some embodiments, compounds that inhibit ASBT or any recuperative bile acid transporter include and are not limited to S-8921 (disclosed in EP597107, WO 93/08155), 264W94 (GSK) disclosed in WO 96/05188;

SC-435 (1-[4-[4-[(4R,5R)-3,3-dibutyl-7-(dimethylamino)-2,3,4,5-tetrahydro-4-hydroxy-1,1-dioxido-1-benzothiepin-5-yl]phenoxy]butyl]4-aza-1-azoniabicyclo[2.2.2]octane methanesulfonate salt), SC-635 (Searle); 2164U90 (3-butyl-3-ethyl-2,3,4,5-tetrahydro-5-phenyl-1,4-benzothiazepine 1,1-dioxide); BARI-1741 (Aventis SA), AZD 7508 (Astra Zeneca); barixibat (11-(D-gluconamido)-N-{2-[(1S,2R,3S)-3-hydroxy-3-phenyl-2-(2-pyridyl)-1-(2-pyridylamino)propyl]phenyl}undecanamide) or the like, or combinations thereof. In some embodiments, an ASBTI is:

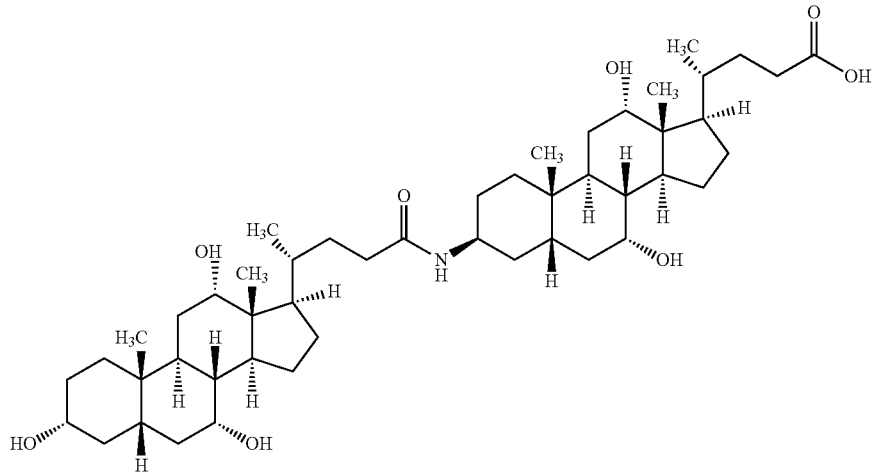

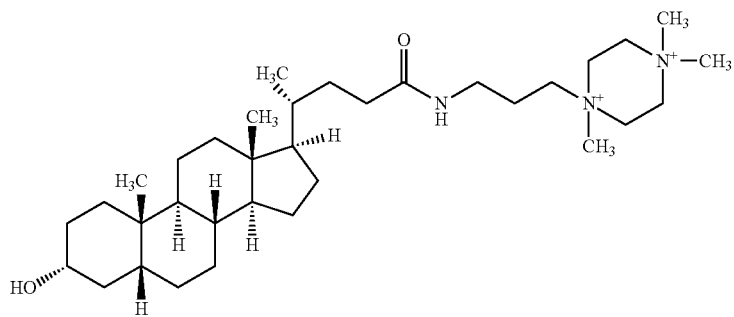

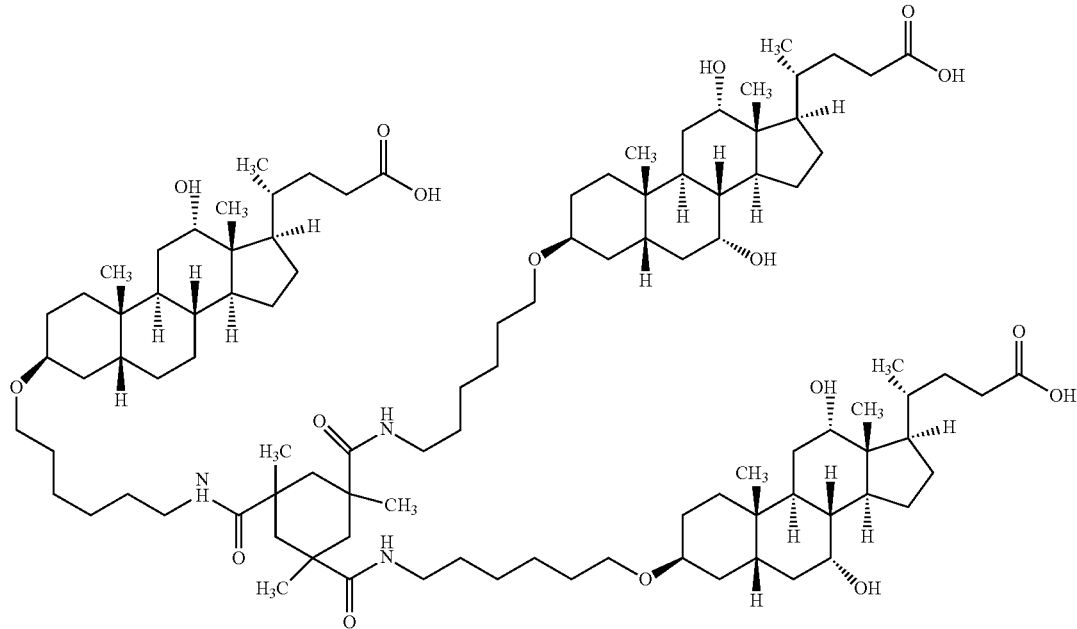

-continued
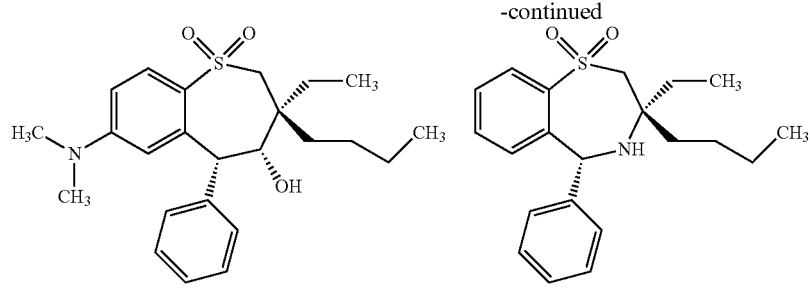
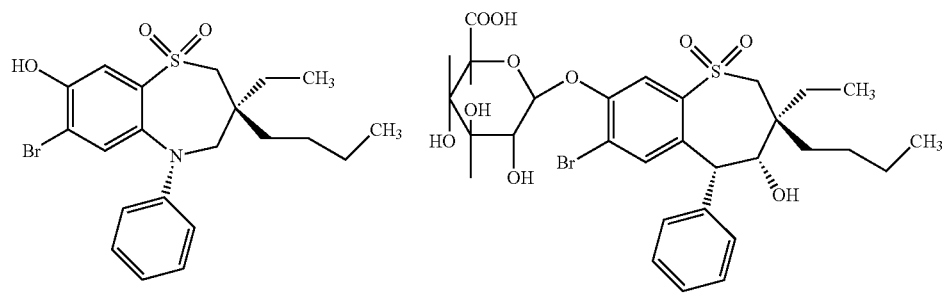
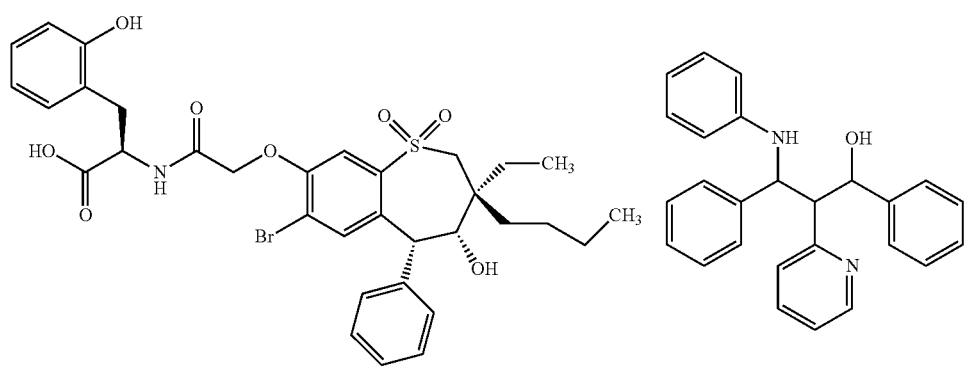
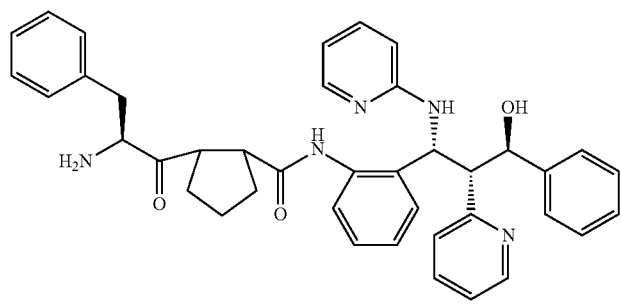
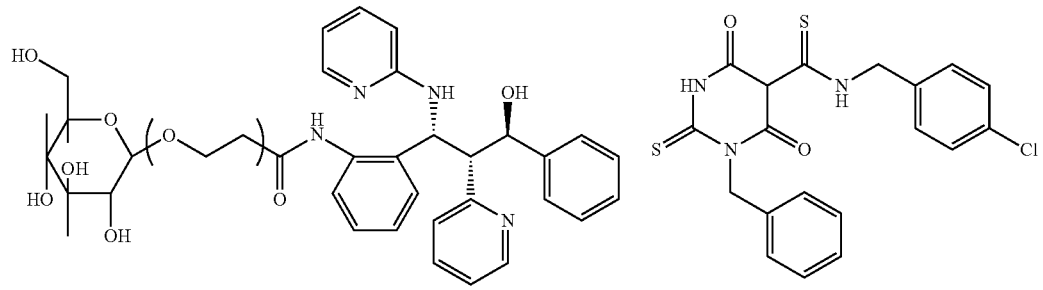

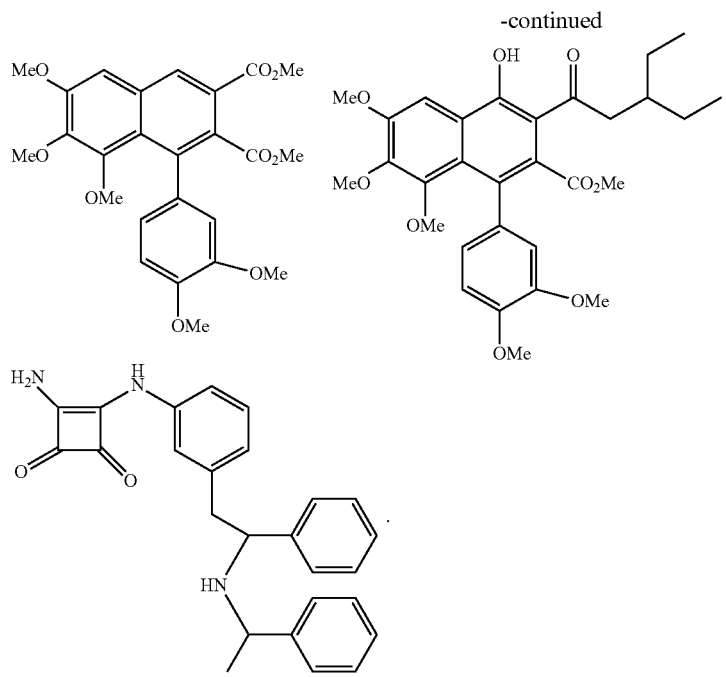
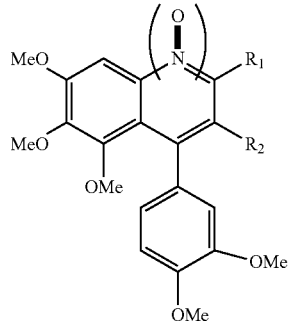

In certain embodiments, compounds described herein have one or more chiral centers. As such, all stereoisomers are envisioned herein. In various embodiments, compounds described herein are present in optically active or racemic forms. It is to be understood that the compounds of the present invention encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

In some embodiments, the ASBTI is

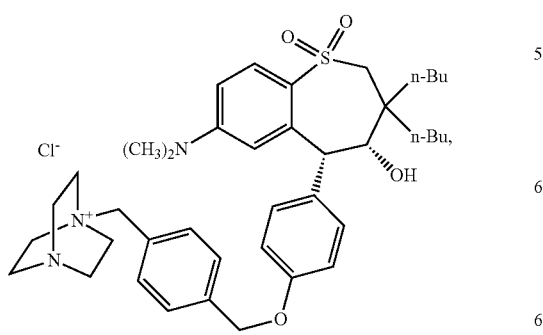

(maralixibat, LUM-001, SHP625, lopixibat chloride), or an alternative pharmaceutically acceptable salt thereof.

In some embodiments, the ASBTI is

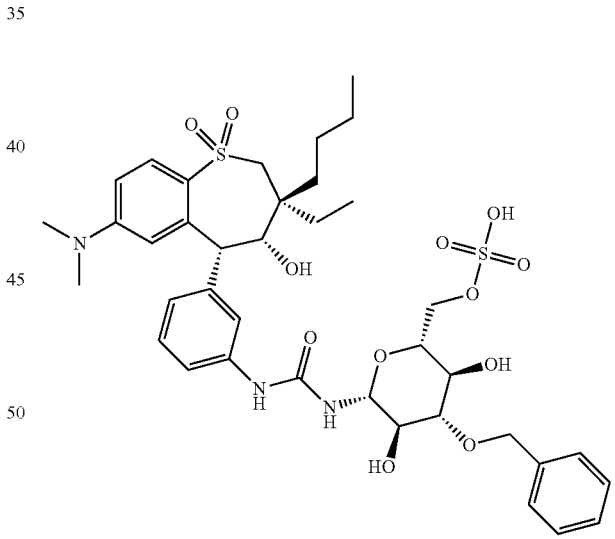

(volixibat, (2R,3R,4S,5R,6R)-4-benzyloxy-6-{3-[3-((3S,4R,5R)-3-butyl-7-dimethylamino-3-ethyl-4-hydroxy-1,1-dioxo-2,3,4,5-tetrahydro-1H-benzo[b]thiepin-5-yl)-phenyl]-ureido}-3,5-dihydroxy-tetrahydro-pyran-2-ylmethyl) hydrogen sulfate), or a pharmaceutically acceptable salt thereof.

In some embodiments, the ASBTI is

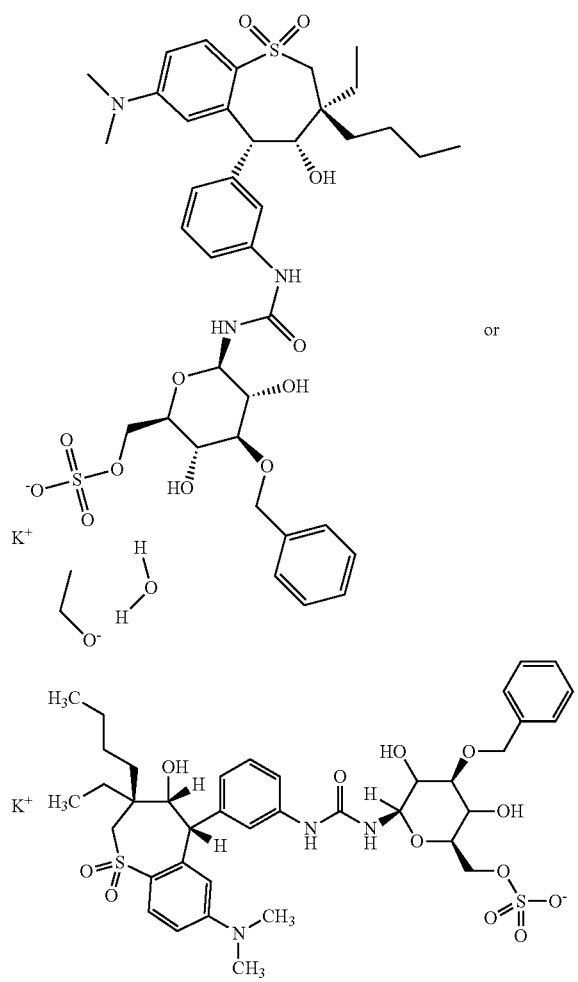

or

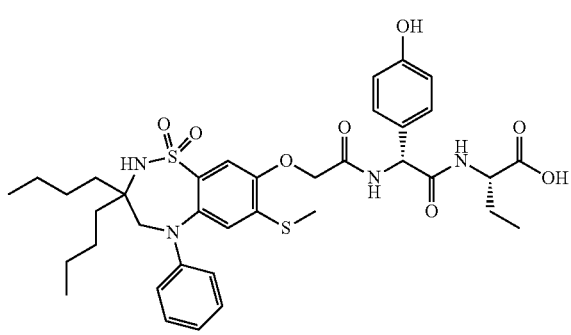 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1]

(LUM-002; SHP626; SAR548304; volixibat potassium) or an alternative pharmaceutically acceptable salt thereof.

In various embodiments the ASBTI is

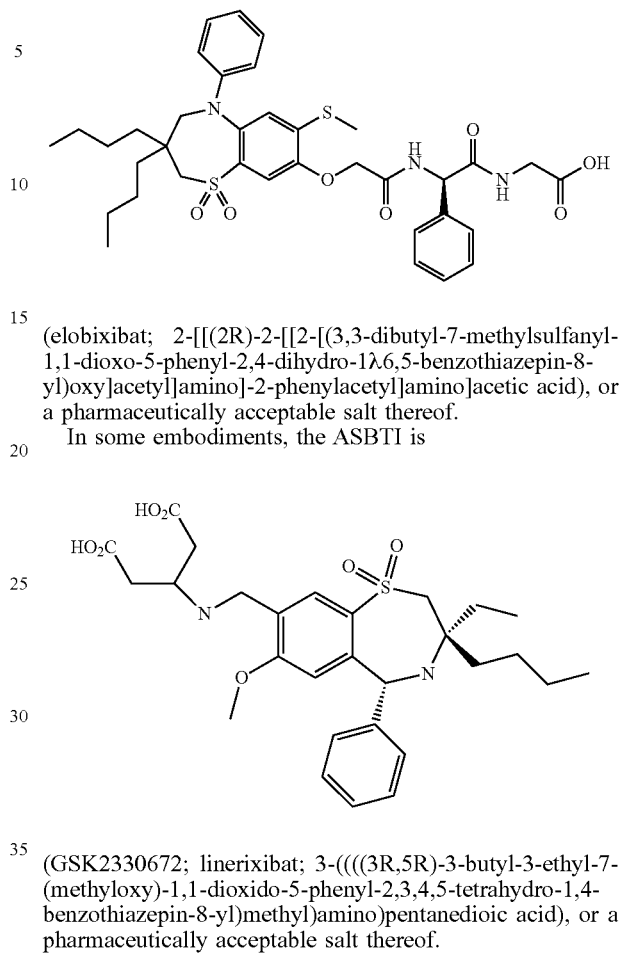

(odevixibat; AZD8294; WHO10706; AR-H064974; SCHEMBL946468; A4250; 1,1-dioxo-3,3-dibutyl-5-phenyl-7-methylthio-8-(N—{(R)-α-[N—((S)-1-carboxypropyl) carbamoyl]-4-hydroxybenzyl}carbamoylmethoxy)-2,3,4,5-tetrahydro-1,2,5-benzothiadiazepine), or a pharmaceutically acceptable salt thereof.

In some embodiments, the ASBTI is (elobixibat; 2-[[(2R)-2-[[2-[(3,3-dibutyl-7-methylsulfanyl-1,1-dioxo-5-phenyl-2,4-dihydro-1λ6,5-benzothiazepin-8-yl)oxy]acetyl]amino]-2-phenylacetyl]amino]acetic acid), or a pharmaceutically acceptable salt thereof.

In some embodiments, the ASBTI is (GSK2330672; linerixibat; 3-(((((3R,5R)-3-butyl-3-ethyl-7-(methyloxy)-1,1-dioxido-5-phenyl-2,3,4,5-tetrahydro-1,4-benzothiazepin-8-yl)methyl)amino)pentanedioic acid), or a pharmaceutically acceptable salt thereof.

In some embodiments, the ASBTI used in the methods or compositions of the present invention is maralixibat (SHP625), volixibat (SHP626), or odevixibat (A4250), or a pharmaceutically acceptable salt thereof.

In some embodiments, the ASBTI used in the methods or compositions of the present invention is maralixibat, or a pharmaceutically acceptable salt thereof.

In some embodiments, the ASBTI used in the methods or compositions of the present invention is volixibat, or a pharmaceutically acceptable salt thereof.

In some embodiments, the ASBTI used in the methods or compositions of the present invention is odevixibat, or a pharmaceutically acceptable salt thereof.

In some embodiments, the ASBTI used in the methods or compositions of the present invention is elobixibat, or a pharmaceutically acceptable salt thereof.

In some embodiments, the ASBTI used in the methods or compositions of the present invention is GSK2330672, or a pharmaceutically acceptable salt thereof.

In some embodiments, the ASBTI may comprise a mixture of different ASBTIs; for example, the ASBTI may be a composition comprising maralixibat, volixibat, odevixibat, GSK2330672, elobixibat, or various combinations thereof.

Methods for Treating Cholestasis

Provided herein is a method for treating cholestasis in a subject having a liver disease. The method includes administering to a subject in need of treatment an Apical Sodium-dependent Bile Acid Transporter Inhibitor (ASBTI). The ASBTI is maralixibat or volixibat, or a pharmaceutically acceptable salt thereof. The ASBTI is administered in an amount of from about 140 µg/kg/day to about 1400 µg/kg/day.

In various embodiments, the liver disease is a cholestatic liver disease. In some embodiments, the liver disease is PFIC, ALGS, PSC, biliary atresia, intrahepatic cholestasis of pregnancy, PBC, any of the cholestatic liver diseases discussed above, or various combinations thereof.

In certain embodiments, the cholestatic liver disease is progressive familial intrahepatic cholestasis (PFIC), PFIC type 1, PFIC type 2, PFIC type 3, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, pediatric primary sclerosing cholangitis, MRP2 deficiency syndrome, neonatal sclerosing cholangitis, a pediatric obstructive cholestasis, a pediatric non-obstructive cholestasis, a pediatric extrahepatic cholestasis, a pediatric intrahepatic cholestasis, a pediatric primary intrahepatic cholestasis, a pediatric secondary intrahepatic cholestasis, benign recurrent intrahepatic cholestasis (BRIC), BRIP type 1, BRIC type 2, BRIC type 3, total parenteral nutrition associated cholestasis, paraneoplastic cholestasis, Stauffer syndrome, drug-associated cholestasis, infection-associated cholestasis, or gallstone disease. In some embodiments, the cholestatic liver disease is a pediatric form of liver disease. In some embodiments, the subject has intrahepatic cholestasis of pregnancy (ICP).

In certain embodiments, a cholestatic liver disease is characterized by one or more symptoms selected from jaundice, pruritis, cirrhosis, hypercholemia, neonatal respiratory distress syndrome, lung pneumonia, increased serum concentration of bile acids, increased hepatic concentration of bile acids, increased serum concentration of bilirubin, hepatocellular injury, liver scarring, liver failure, hepatomegaly, xanthomas, malabsorption, splenomegaly, diarrhea, pancreatitis, hepatocellular necrosis, giant cell formation, hepatocellular carcinoma, gastrointestinal bleeding, portal hypertension, hearing loss, fatigue, loss of appetite, anorexia, peculiar smell, dark urine, light stools, steatorrhea, failure to thrive, and/or renal failure.

In various embodiments the liver disease is PFIC 2 and the subject has a non-truncating mutation in the ABCB11 gene. In various embodiments the non-truncating mutation in the ABCB11 gene is a missense mutation. In various embodiments the missense mutation may be selected from one of those mutations listed in Byrne, et al., "Missense Mutations and Single Nucleotide Polymorphisms in ABCB11 Impair Bile Salt Export Pump Processing and Function or Disrupt Pre-Messenger RNA Splicing," *Hepatology*, 49:553-567 (2009), which is incorporated herein by reference in its entirety for all purposes.

In various embodiments the subject has a condition associated with, caused by or caused in part by a BSEP deficiency. In certain embodiments, the condition associated with, caused by or caused in part by the BSEP deficiency is neonatal hepatitis, primary biliary cirrhosis (PBC), primary sclerosing cholangitis (PSC), PFIC 2, benign recurrent intrahepatic cholestasis (BRIC), intrahepatic cholestasis of pregnancy (ICP), drug-induced cholestasis, oral-contraceptive-induced cholestasis, biliary atresia, or a combination thereof.

In various embodiments, the patient is a pediatric patient under the age of 1, 2, 3, 4, 5, 6, 7, 8, 9, 10, 11, 12, 13, 14, 15, 16, 17, or 18 years old. In certain embodiments, the pediatric subject is a newborn, a pre-term newborn, an infant, a toddler, a preschooler, a school-age child, a pre-pubescent child, post-pubescent child, an adolescent, or a teenager under the age of eighteen. In some embodiments, the pediatric subject is a newborn, a pre-term newborn, an infant, a toddler, a preschooler, or a school-age child. In some embodiments, the pediatric subject is a newborn, a pre-term newborn, an infant, a toddler, or a preschooler. In some embodiments, the pediatric subject is a newborn, a pre-term newborn, an infant, or a toddler. In some embodiments, the pediatric subject is a newborn, a pre-term newborn, or an infant. In some embodiments, the pediatric subject is a newborn. In some embodiments, the pediatric subject is an infant. In some embodiments, the pediatric subject is a toddler. In various embodiments, the pediatric patient has PFIC 2, PFIC 1, or ALGS. In some embodiments, the patient is an adult over the age of 18, 20, 30, 40, 50, 60, or 70. In some patients, the adult patient has PSC. In some embodiments, the pediatric patient has any pediatric cholestatic condition resulting in below normal growth, height, or weight.

In certain embodiments, methods of the present invention comprise non-systemic administration of a therapeutically effective amount of an ASBTI. In certain embodiments, the methods comprise contacting the gastrointestinal tract, including the distal ileum and/or the colon and/or the rectum, of an individual in need thereof with an ASBTI. In various embodiments, the methods of the present invention cause a reduction in intraenterocyte bile acids, or a reduction in damage to hepatocellular or intestinal architecture caused by cholestasis or a cholestatic liver disease.

In various embodiments, methods of the present invention comprise delivering to ileum or colon of the individual a therapeutically effective amount of any ASBTI described herein.

In various embodiments, methods of the present invention comprise reducing damage to hepatocellular or intestinal architecture or cells from cholestasis or a cholestatic liver disease comprising administration of a therapeutically effective amount of an ASBTI. In certain embodiments, the methods of the present invention comprise reducing intraenterocyte bile acids/salts through administration of a therapeutically effective amount of an ASBTI to an individual in need thereof.

In some embodiments, methods of the present invention provide for inhibition of bile salt recycling upon administration of any of the compounds described herein to an individual. In some embodiments, an ASBTI described herein is systemically absorbed upon administration. In some embodiments, an ASBTI described herein is not absorbed systemically. In some embodiments, an ASBTI herein is administered to the individual orally. In some embodiments, an ASBTI described herein is delivered and/or released in the distal ileum of an individual.

In various embodiments, contacting the distal ileum of an individual with an ASBTI (e.g., any ASBTI described herein) inhibits bile acid reuptake and increases the concentration of bile acids/salts in the vicinity of L-cells in the distal ileum and/or colon and/or rectum, thereby reducing intraenterocyte bile acids, reducing serum and/or hepatic bile acid levels, reducing overall serum bile acid load, and/or reducing damage to ileal architecture caused by cholestasis or a cholestatic liver disease. Without being limited to any particular theory, reducing serum and/or hepatic bile acid levels ameliorates hypercholemia and/or cholestatic disease.

Administration of a compound described herein may be achieved in any suitable manner including, by way of non-limiting example, by oral, enteric, parenteral (e.g., intravenous, subcutaneous, intramuscular), intranasal, buccal, topical, rectal, or transdermal administration routes. Any compound or composition described herein may be administered in a method or formulation appropriate to treat a newborn or an infant. Any compound or composition described herein may be administered in an oral formulation (e.g., solid or liquid) to treat a newborn or an infant. Any compound or composition described herein may be administered prior to ingestion of food, with food or after ingestion of food.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, the individual's health status, weight, and response to the drugs, and the judgment of the treating physician.

In prophylactic applications, compounds or compositions containing compounds described herein may be administered to an individual susceptible to or otherwise at risk of a particular disease, disorder or condition. In certain embodiments of this use, the precise amounts of compound administered depend on the individual's state of health, weight, and the like. Furthermore, in some instances, when a compound or composition described herein is administered to an individual, effective amounts for this use depend on the severity and course of the disease, disorder or condition, previous therapy, the individual's health status and response to the drugs, and the judgment of the treating physician.

In certain embodiments of the methods of the present invention, wherein following administration of a selected dose of a compound or composition described herein, an individual's condition does not improve, upon the doctor's discretion the administration of a compound or composition described herein is optionally administered chronically, that is, for an extended period of time, including throughout the duration of the individual's life in order to ameliorate or otherwise control or limit the symptoms of the individual's disorder, disease or condition.

In certain embodiments of the methods of the present invention, an effective amount of a given agent varies depending upon one or more of a number of factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In some embodiments, doses administered include those up to the maximum tolerable dose. In some embodiments, doses administered include those up to the maximum tolerable dose by a newborn or an infant.

In various embodiments of the methods of the present invention, a desired dose is conveniently presented in a single dose or in divided doses administered simultaneously (or over a short period of time) or at appropriate intervals, for example as two, three, four or more sub-doses per day. In various embodiments, a single dose of an ASBTI is administered every 6 hours, every 12 hours, every 24 hours, every 48 hours, every 72 hours, every 96 hours, every 5 days, every 6 days, or once a week. In some embodiments the total single dose of an ASBTI is in a range described below.

In various embodiments of methods of the present invention, in the case wherein the patient's status does improve, upon the doctor's discretion an ASBTI is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100% of the original dose, including, by way of example only, 10%, 15%, 20%, 25%, 30%, 35%, 40%, 45%, 50%, 55%, 60%, 65%, 70%, 75%, 80%, 85%, 90%, 95%, or 100% of the original dose. In some embodiments the total single dose of an ASBTI is in a range described below.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are prefer ed. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

In certain embodiments, the composition used or administered comprises an absorption inhibitor, a carrier, and one or more of a cholesterol absorption inhibitor, an enteroendocrine peptide, a peptidase inhibitor, a spreading agent, and a wetting agent.

In some embodiments of methods of the present invention, the composition used to prepare an oral dosage form or administered orally comprises an absorption inhibitor, an orally suitable carrier, an optional cholesterol absorption inhibitor, an optional enteroendocrine peptide, an optional peptidase inhibitor, an optional spreading agent, and an optional wetting agent. In certain embodiments, the orally administered compositions evoke an anorectal response. In specific embodiments, the anorectal response is an increase in secretion of one or more enteroendocrine by cells in the colon and/or rectum (e.g., in L-cells the epithelial layer of the colon, ileum, rectum, or a combination thereof). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

Dosages

In various embodiments the ASBTI is maralixibat or volixibat, or a pharmaceutically acceptable salt thereof.

In various embodiments, efficacy and safety of ASBTI administration to the patient is monitored by measuring serum levels of 7α-hydroxy-4-cholesten-3-one (7αC4), sBA concentration, a ratio of 7αC4 to sBA (7αC4:sBA), serum conjugated bilirubin concentration, serum autotaxin concentration, serum bilirubin concentration, serum total cholesterol concentration, serum LDL-C concentration, serum ALT concentration, serum AST concentration, or a combination thereof. In various embodiments, efficacy of ASBTI administration is measured by monitoring observer-reported itch reported outcome (ITCHRO(OBS)) score, a HRQoL (e.g., PedsQL) score, a CSS score, a xanthoma score, a height Z-score, a weight Z-score, or various combinations thereof. In various embodiments, the method includes monitoring serum levels of 7α-hydroxy-4-cholesten-3-one (7αC4), sBA concentration, a ratio of 7αC4 to sBA (7αC4:sBA), serum conjugated bilirubin concentration, serum total cholesterol concentration, serum LDL-C concentration, serum autotaxin concentration, serum bilirubin concentration, serum ALT concentration, serum AST concentration, or a combination thereof. In various embodiments, the method includes monitoring observer-reported itch reported outcome (ITCHRO(OBS)) score, a weight Z-score, a HRQoL (e.g., PedsQL) score, a xanthoma score, a CSS score, a height Z-score, or various combinations thereof.

In some embodiments, the ASBTI is administered at a dose of about or at least about 0.5 µg/kg, 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 100 µg/kg, 140 µg/kg, 150 µg/kg, 200 µg/kg, 240 µg/kg, 280 µg/kg, 300 µg/kg, 250 µg/kg, 280 µg/kg, 300 µg/kg, 400 µg/kg, 500 µg/kg, 560 µg/kg, 600 µg/kg, 700 µg/kg, 800 µg/kg, 900 µg/kg, 1,000 µg/kg, 1,100 µg/kg, 1,200 µg/kg, 1,300 µg/kg, 1,400 µg/kg, 1500 µg/kg, 1,600 µg/kg, 1,700 µg/kg, 1,800 µg/kg, 1,900 µg/kg, or 2,000 µg/kg. In various embodiments, the ASBTI is administered at a dose not exceeding about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 100 µg/kg, 140 µg/kg, 150 µg/kg, 200 µg/kg, 240 µg/kg, 280 µg/kg, 300 µg/kg, 250 µg/kg, 280 µg/kg, 300 µg/kg, 400 µg/kg, 500 µg/kg, 560 µg/kg, 600 µg/kg, 700 µg/kg, 800 µg/kg, 900 µg/kg, 1,000 µg/kg, 1,100 µg/kg, 1,200 µg/kg, 1,300 µg/kg, 1,400 µg/kg, 1,500 µg/kg, 1,600 µg/kg, 1,700 µg/kg, 1,800 µg/kg, 1,900 µg/kg, 2,000, or 2,100 µg/kg. In various embodiments, the ASBTI is administered at a dose of about or of at least about 0.5 mg/day, 1 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 30 mg/day, 40 mg/day, 50 mg/day, 60 mg/day, 70 mg/day, 80 mg/day, 90 mg/day, 100 mg/day, 150 mg/day, 200 mg/day, 300 mg/day, 500 mg/day, 600 mg/day, 700 mg/day, 800 mg/day, 900 mg/day, 1000 mg/day. In various embodiments, the ASBTI is administered at a dose of not more than about 1 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 30 mg/day, 40 mg/day, 50 mg/day, 60 mg/day, 70 mg/day, 80 mg/day, 90 mg/day, 100 mg/day, 150 mg/day, 200 mg/day, 300 mg/day, 500 mg/day, 600 mg/day, 700 mg/day, 800 mg/day, 900 mg/day, 1,000 mg/day, 1,100 mg/day.

In some embodiments, the ASBTI is administered at a dose of from about 140 µg/kg/day to about 1400 µg/kg/day. In various embodiments, the ASBTI is administered at a dose of about or at least about 0.5 µg/kg/day, 1 µg/kg/day, 2 µg/kg/day, 3 µg/kg/day, 4 µg/kg/day, 5 µg/kg/day, 6 µg/kg/day, 7 µg/kg/day, 8 µg/kg/day, 9 µg/kg/day 10 µg/kg/day, 15 µg/kg/day, 20 µg/kg/day, 25 µg/kg/day, 30 µg/kg/day, 35 µg/kg/day, 40 µg/kg/day, 45 µg/kg/day, 50 µg/kg/day, 100 µg/kg/day, 140 µg/kg/day, 150 µg/kg/day, 200 µg/kg/day, 240 µg/kg/day, 280 µg/kg/day, 300 µg/kg/day, 250 µg/kg/day, 280 µg/kg/day, 300 µg/kg/day, 400 µg/kg/day, 500 µg/kg/day, 560 µg/kg/day, 600 µg/kg/day, 700 µg/kg/day, 800 µg/kg/day, 900 µg/kg/day, 1,000 µg/kg/day, 1,100 µg/kg/day, 1,200 µg/kg/day, or 1,300 µg/kg/day. In various embodiments, the ASBTI is administered at a dose not exceeding about 1 µg/kg/day, 2 µg/kg/day, 3 µg/kg/day, 4 µg/kg/day, 5 µg/kg/day, 6 µg/kg/day, 7 µg/kg/day, 8 µg/kg/day, 9 µg/kg/day 10 µg/kg/day, 15 µg/kg/day, 20 µg/kg/day, 25 µg/kg/day, 30 µg/kg/day, 35 µg/kg/day, 40 µg/kg/day, 45 µg/kg/day, 50 µg/kg/day, 100 µg/kg/day, 140 µg/kg/day, 150 µg/kg/day, 200 µg/kg/day, 240 µg/kg/day, 280 µg/kg/day, 300 µg/kg/day, 250 µg/kg/day, 280 µg/kg/day, 300 µg/kg/day, 400 µg/kg/day, 500 µg/kg/day, 560 µg/kg/day, 600 µg/kg/day, 700 µg/kg/day, 800 µg/kg/day, 900 µg/kg/day, 1,000 µg/kg/day, 1,100 µg/kg/day, 1,200 µg/kg/day, 1,300 µg/kg/day, or 1,400 µg/kg/day. In various embodiments, the ASBTI is administered at a dose of from about 0.5 µg/kg/day to about 500 µg/kg/day, from about 0.5 µg/kg/day to about 250 µg/kg/day, from about 1 µg/kg/day to about 100 µg/kg/day, from about 10 µg/kg/day to about 50 µg/kg/day, from about 10 µg/kg/day to about 100 µg/kg/day, from about 0.5 µg/kg/day to about 2000 µg/kg/day, from about 280 µg/kg/day to about 1400 µg/kg/day, from about 420 µg/kg/day to about 1400 µg/kg/day, from about 250 to about 550 µg/kg/day, from about 560 µg/kg/day to about 1400 µg/kg/day, from 700 µg/kg/day to about 1400 µg/kg/day, from about 560 µg/kg/day to about 1200 µg/kg/day, from about 700 µg/kg/day to about 1200 µg/kg/day, from about 560 µg/kg/day to about 1000 µg/kg/day, from about 700 µg/kg/day to about 1000 µg/kg/day, from about 800 µg/kg/day to about 1000 µg/kg/day, from about 200 µg/kg/day to about 600 µg/kg/day, from about 300 µg/kg/day to about 600 µg/kg/day, from about 400 µg/kg/day to about 500 µg/kg/day, from about 400 µg/kg/day to about 600 µg/kg/day, from about 400 µg/kg/day to about 700 µg/kg/day, from about 400 µg/kg/day to about 800 µg/kg/day, from about 500 µg/kg/day to about 800 µg/kg/day, from about 500 µg/kg/day to about 900 µg/kg/day, from about 600 µg/kg/day to about 900 µg/kg/day, from about 700 µg/kg/day to about 900 µg/kg/day, from about 200 µg/kg/day to about 600 µg/kg/day, from about 800 µg/kg/day to about 900 µg/kg/day, from about 100 µg/kg/day to about 1500 µg/kg/day, from about 300 µg/kg/day to about 2,000 µg/kg/day, or from about 400 µg/kg/day to about 2000 µg/kg/day.

In some embodiments, the ASBTI is administered at a dose of from about 30 µg/kg to about 1400 µg/kg per dose. In some embodiments, the ASBTI is administered at a dose of from about 0.5 µg/kg to about 2000 µg/kg per dose, from about 0.5 µg/kg to about 1500 µg/kg per dose, from about 100 µg/kg to about 700 µg/kg per dose, from about 5 µg/kg to about 100 µg/kg per dose, from about 10 µg/kg to about 500 µg/kg per dose, from about 50 µg/kg to about 1400 µg/kg per dose, from about 300 µg/kg to about 2,000 µg/kg per dose, from about 60 µg/kg to about 1200 µg/kg per dose, from about 70 µg/kg to about 1000 µg/kg per dose, from about 70 µg/kg to about 700 µg/kg per dose, from 80 µg/kg to about 1000 µg/kg per dose, from 80 µg/kg to about 800 µg/kg per dose, from 100 µg/kg to about 800 µg/kg per dose, from 100 µg/kg to about 600 µg/kg per dose, from 150 µg/kg to about 700 µg/kg per dose, from 150 µg/kg to about 500 µg/kg per dose, from 200 µg/kg to about 400 µg/kg per dose, from 200 µg/kg to about 300 µg/kg per dose, or from 300 µg/kg to about 400 µg/kg per dose.

In some embodiments, the ASBTI is administered at a dose of from about 0.5 mg/day to about 550 mg/day. In various embodiments, the ASBTI is administered at a dose of from about 1 mg/day to about 500 mg/day, from about 1 mg/day to about 300 mg/day, from about 1 mg/day to about 200 mg/day, from about 2 mg/day to about 300 mg/day, from about 2 mg/day to about 200 mg/day, from about 4 mg/day to about 300 mg/day, from about 4 mg/day to about 200 mg/day, from about 4 mg/day to about 150 mg/day, from about 5 mg/day to about 150 mg/day, from about 5 mg/day to about 100 mg/day, from about 5 mg/day to about 80 mg/day, from about 5 mg/day to about 50 mg/day, from about 5 mg/day to about 40 mg/day, from about 5 mg/day to about 30 mg/day, from about 5 mg/day to about 20 mg/day, from about 5 mg/day to about 15 mg/day, from about 10 mg/day to about 100 mg/day, from about 10 mg/day to about 80 mg/day, from about 10 mg/day to about 50 mg/day, from about 10 mg/day to about 40 mg/day, from about 10 mg/day to about 20 mg/day, from about 20 mg/day to about 100 mg/day, from about 20 mg/day to about 80 mg/day, from about 20 mg/day to about 50 mg/day, or from about 20 mg/day to about 40 mg/day, or from about 20 mg/day to about 30 mg/day.

In some embodiments, the ASBTI is administered twice daily (BID) in an amount of about 200 µg/kg to about 400 µg/kg per dose. In some embodiments, the ASBTI is administered in an amount of about 280 µg/kg/day to about 1400 µg/kg/day. In some embodiments, the ASBTI is administered in an amount of about 400 µg/kg/day to about 800 µg/kg/day. In some embodiments, the ASBTI is administered in an amount of about 20 mg/day to about 50 mg/day. In some embodiments, the ASBTI is administered in an amount of from about 5 mg/day to about 15 mg/day. In some embodiments, the ASBTI is administered in an amount of from about 560 µg/kg/day to about 1,400 µg/kg/day. In some embodiments, the ASBTI is administered in an amount of from about 700 µg/kg/day to about 1,400 µg/kg/day. In some embodiments, the ASBTI is administered in an amount of from about 400 µg/kg/day to about 800 µg/kg/day. In some embodiments, the ASBTI is administered in an amount of from about 700 µg/kg/day to about 900 µg/kg/day. In some embodiments, the ASBTI is administered in an amount of from about 560 µg/kg/day to about 1400 µg/kg/day. In some embodiments, the ASBTI is administered in an amount from 700 µg/kg/day to about 1400 µg/kg/day. In some embodiments, the ASBTI is administered in an amount of from about 200 µg/kg/day to about 600 µg/kg/day. In some embodiments, the ASBTI is administered in an amount of from about 400 µg/kg/day to about 600 µg/kg/day.

In various embodiments, the dose of the ASBTI is a first dose level. In various embodiments, the dose of the ASBTI is a second dose level. In some embodiments, the second dose level is greater than the first dose level. In some embodiments, the second dose level is about or at least about 1.5, 2, 3, 4, 5, 6, 7, 8, 9, 10, 15, 20, 30, 40, 50, 60, 70, 80, 90 or 100 times or fold greater than the first dose level. In some embodiments, the second dose level is not in excess of about 1.5, 2, 3, 4, 5, 6, 7, 8, 9, 10, 15, 20, 30, 40, 50, 60, 70, 80, 90, 100, or 150 times or fold greater than the first dose level.

In various embodiments, the ASBTI is administered once daily (QD) at one of the above doses or within one of the above dose ranges. In various embodiments, the ASBTI is administered twice daily (BID) at one of the above doses or within one of the above dose ranges. In various embodiments, an ASBTI dose is administered daily, every other day, twice a week, or once a week.

In various embodiments, the ASBTI is administered regularly for a period of about or of at least about 1, 2, 3, 4, 5, 6, 7, 8, 9, 10, 15, 20, 30, 40, 48, 50, 75, 100, 150, 200, 250, 300, 350, 400, 450, 500, 600, 700, or 800 weeks. In various embodiments, the ASBTI is administered for not more than about 1, 2, 3, 4, 5, 6, 7, 8, 9, 10, 15, 20, 30, 40, 48, 50, 75, 100, 150, 200, 250, 300, 350, 400, 450, 500, 600, 700, 800, or 1000 weeks. In various embodiments, the ASBTI is administered regularly for a period of about or of at least about 0.5, 1, 1.5, 2, 3, 4, 5, 6, 7, 8, 9, or 10 years. In various embodiments, the ASBTI is administered regularly for a period not in excess of about 0.5, 1, 1.5, 2, 3, 4, 5, 6, 7, 8, 9, 10, or 15 years.

Reduction in Symptoms or a Change in a Disease-Relevant Laboratory Measures of Cholestatic Liver Disease In various embodiments of the above methods of the invention, administration of the ASBTI results in a reduction in a symptom or a change in a disease-relevant laboratory measure of the cholestatic liver disease (i.e., improvement in the patient's condition) that is maintained for about or for at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 6 months, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 1 year, 13 months, 14 months, 15 months, 16 months, 17 months, 18 months, 19 months, 20 months, 21 months, 22 months, 23 months, 23 months, 2 years, 2.5 years, 3 years, 3.5 years, 4 years, 4.5 years, 5 years, 5.5 years, 6 years, 6.5 years, 7 years, 8 years, 9 years, or 10 years. In various embodiments, the reduction in the symptom or a change in a disease-relevant laboratory measure comprises a reduction in sBA concentration, an increase in serum 7αC4 concentration, an increase in the 7αC4:sBA ratio, an increase in fBA excretion, a reduction in pruritis, a decrease in serum total cholesterol concentration, a decrease in serum LDL-C cholesterol concentration, a reduction in ALT levels, an increase in a quality of life inventory score, an increase in a quality of life inventory score related to fatigue, a reduction in a xanthoma score, a reduction in serum autotaxin concentration, an increase in growth, or a combination thereof. In various embodiments, the reduction in the symptom or a change in a disease-relevant laboratory measure is determined relative to a baseline level. That is, the reduction in the symptom or a change in a disease-relevant laboratory measure is determined relative to a measurement of the symptom or a change in a disease-relevant laboratory measure prior to 1) changing a dose level of the ASBTI administered to the patient, 2) changing a dosing regimen followed for the patient, 3) commencing administration of the ASBTI, or 4) any other of various alterations made with the intention of reducing the symptom or a change in a disease-relevant laboratory measure in the patient. In various embodiments, the reduction in symptom or a change in a disease-relevant laboratory measure is a statistically significant reduction.

In various embodiments, the reduction in a symptom or a change in a disease-relevant laboratory measure of the cholestatic liver disease is measured as a progressive decrease in the symptom or a change in a disease-relevant laboratory measure for about or for at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 6 months, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 1 year, 13 months, 14 months, 15 months, 16 months, 17 months, 18 months, 19 months, 20 months, 21 months, 22 months, 23 months, 23 months, 2 years, 2.5 years, 3 years, 3.5 years, 4 years, 4.5 years, 5 years, 5.5 years, 6 years, 6.5 years, 7 years, 8 years, 9 years, or 10 years.

In some embodiments, the patient is the pediatric patient and the reduction in symptom or a change in a disease-relevant laboratory measure comprises an increase or improvement in growth. In some embodiments, the increase in growth is measured relative to baseline. In various embodiments, increase in growth is measured as an increase in height Z-score or in weight Z-score. In various embodiments, the increase in height Z-score or in weight Z-score is statistically significant. In various embodiments, the height Z-score, the weight Z-score, or both is increased by at least 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29 0.3, 0.31, 0.32, 0.33, 0.34, 0.35, 0.36, 0.37, 0.38, 0.39 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.7, 0.8, or 0.9 relative to baseline. In some embodiments, the height Z-score, the weight Z-score, or both progressively increases during administration of the ASBTI for a period of about or of at least about 1, 2, 3, 4, 5, 6, 7, 8, 9, 10, 20, 30, 40, 48, 50, 60, 70, or 72 weeks.

In various embodiments, the administration of the ASBTI results in an increase in serum 7αC4 concentration. In various embodiments, the serum 7αC4 concentration is increased by about or at least about 1.5, 2, 3, 4, 5, 6, 7, 8, 9, 10, 15, 20, 30, 40, 50, 60, 70, 80, 90, 100, 200, 300, 400, or 500 times or fold relative to baseline. In various embodiments the serum 7αC4 concentration is increased about or at least about 10%, 20%, 30%, 40%, 50%, 60%, 70%, 80%, 90%, 100%, 150%, 200%, 300%, 400%, 500%, 600%, 700%, 800%, 900%, 1,000%, or 10,000% relative to baseline.

In various embodiments, the administration of the ASBTI results in an increase in the 7αC4:sBA ratio to about or by at least about 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold relative to baseline.

In various embodiments, the administration of the ASBTI results in an increase in fBA excretion. In some embodiments, the administration of the ASBTI results in an increase in fBA excretion of about or of at least about 100%, 110%, 115%, 120%, 130%, 150%, 200%, 250%, 275%, 300%, 400%, 500%, 600%, 700%, 800%, 1,000%, 5,000%, 10,000% or 15,000% relative to baseline. In various embodiments, fBA excretion is increased by about or by at least about 1, 1.5, 2, 3, 4, 5, 6, 7, 8, 9, 10, 20, 30, 40, 50, 60, 70, 80, 90, or 100 fold or times relative to baseline. In some embodiments, fBA excretion is increased by about or by at least about 100 µmol, 150 µmol, 200 µmol, 250 µmol, 300 µmol, 400 µmol, 500 µmol, 600 µmol, 700 µmol, 800 µmol, 900 µmol, 1,000 µmol, or 1,500 µmol relative to baseline. In various embodiments, administration of the ASBTI results in a dose-dependent increase in fBA excretion so that administration of a higher dose of the ASBTI results in a corresponding higher level of fBA excretion. In various embodiments, the ASBTI is administered at a dose sufficient to result in an increase in bile acid secretion relative to baseline of at least about or of about 1, 2, 3, 4, 5, 6, 7, 8, 9, 10, 20, 30, 40, 50, 60, 70, 80, 90, or 100 fold or times relative to baseline.

In various embodiments, the administration of the ASBTI results in a decrease in sBA concentration of about or of at least about 5%, 10%, 15%, 20%, 25%, 30%, 31%, 35%, 40%, 45%, 50%, 55%, 57%, 60%, 65%, 70%, 75%, 80%, 85%, 90%, or 95% relative to baseline.

In some embodiments, the administration of the ASBTI results in a reduction in severity of pruritus. In various embodiments, the severity of pruritus is measured using an ITCHRO(OBS) score, an ITCHRO score, a CSS score, or a combination thereof. In various embodiments, the administration of the ASBTI results in a reduction in the ITCHRO (OBS) score on a scale of 1 to 4 of about or of at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.25, 2.5, or 3 relative to baseline. In various embodiments, the administration of the ASBTI results in a reduction in the ITCHRO score on a scale of 1 to 10 of about or of at least about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, or 10. In various embodiments, the administration of the ASBTI results in a reduction of the ITCHRO(OBS) score, the ITCHRO score, or both to zero. In various embodiments, the administration of the ASBTI results in a reduction of the ITCHRO(OBS) score or ITCHRO score to 1.0 or lower. In various embodiments, the administration of the ASBTI results in a reduction of the CSS score by about of at least about 0.1, 0.2, 0.3, 0.4, 0.4, 0.5, 0.6, 0.7, 0.8, 0.9, 1, 1.1, 1.2, 1.3, 1.4, 1.5, 1.6, 1.7, 1.8, 1.9, 2, 2.25, 2.5, or 3 relative to baseline. In various embodiments, the administration of the ASBTI results in a reduction of the CSS score to zero. In various embodiments, the administration of the ASBTI results in a reduction in the CSS score, the ITCHRO(OBS) score, the ITCHRO score, or a combination thereof by about or by at least about 10%, 15%, 20%, 25%, 30%, 35%, 40%, 45%, 50%, 55%, 60%, 65%, 70%, 75%, 80%, 85%, 90%, 95%, or 100% relative to baseline. In various embodiments, a reduced value relative to baseline of the CSS score, the ITCHRO(OBS) score, the ITCHRO score, or a combination thereof is observed on 10%, 20%, 30%, 40%, 50%, 60%, 70%, 75%, 80%, 85%, 90%, 91%, 92%, 93%, 94%, 95%, 96%, 97%, 98%, 99%, or 100% of days.

In some embodiments, patients with a higher baseline ITCHRO(OBS) score demonstrate a greater reduction in the symptom or a change in a disease-relevant laboratory measure than patients having a lower baseline ITCHRO(OBS) score. In some embodiments, patients with a baseline ITCHRO(OBS) score of at least 2, 3, or 4 or an ITCHRO score of at least 4, 5, 6, 7, 8, 9, or 10 have a greater reduction in the symptom or a change in a disease-relevant laboratory measure relative to baseline than a lower reduction in patients having a lower baseline severity of pruritus score. In various embodiments, patients having PSC and baseline ITCHRO scores of at least 4 demonstrate a greater reduction in the symptom or a change in a disease-relevant laboratory measure than patients having a baseline ITCHRO score of less than 4. In various embodiments, the method includes predicting that a patient will have a greater reduction in the symptom or a change in a disease-relevant laboratory measure if a baseline ITCHRO score of the patient is at least 4 as compared to a patient having a baseline ITCHRO score of less than 4. In various embodiments the lower reduction is about or less than about 5%, 10%, 15%, 20%, 25%, 30%, 35%, 40%, 45%, 50%, 55%, or 60% the greater reduction. In various embodiments a difference in the reduction in the symptom or a change in a disease-relevant laboratory measure (i.e., between the greater reduction and the lower reduction) between patients having an ITCHRO score of at least 4 at baseline and patients having an ITCHRO score of less than 4 at baseline is measured at about or at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 6 months, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 1 year, 13 months, 14 months, 15 months, 16 months, 17 months, 18 months, 19 months, 20 months, 21 months, 22 months, 23 months, 23 months, 2 years, 2.5 years, 3 years, 3.5 years, 4 years, 4.5 years, 5 years, 5.5 years, 6 years, 6.5 years, 7 years, 8 years, 9 years, or 10 years following first administration of the ASBTI at the first dose or at the second dose.

In various embodiments, reduction in severity of pruritus caused by administration of the ASBTI to the patient is positively correlated with a reduction in sBA concentration in the patient. In various embodiments, a greater reduction in sBA concentration in the patient correlates with a corresponding greater reduction in severity of pruritus.

In various embodiments, the administration of the ASBTI results in a reduction in serum LDL-C concentration relative to baseline. In some embodiments the serum LDL-C concentration is reduced by about or by at least about 1%, 2%, 3%, 4%, 5%, 10%, 15%, 20%, 25%, 25%, 30%, 35%, 40%, 45%, 50%, 55%, 60%, 65%, 70%, 75%, or 80% relative to baseline.

In some embodiments, the administration of the ASBTI results in a reduction in serum total cholesterol concentration relative to baseline. In some embodiments, the administration of the ASBTI results in a reduction in serum LDL-C levels relative to baseline. In some embodiments the serum total cholesterol concentration, the serum LDL-C levels, or both is reduced by about or by at least about 1%, 2%, 3%, 4%, 5%, 10%, 15%, 20%, 25%, 25%, 30%, 35%, 40%, 45%, 50%, 55%, 60%, 65%, 70%, 75%, or 80% relative to baseline. In various embodiments, the administration of the ASBTI results in a reduction in serum total cholesterol concentration, of serum LDL-C levels, or both of about or of at least about 1 mg/dL, 2 mg/dL, 3 mg/dL, 4 mg/dL, 5 mg/dL, 10 mg/dL, 12.5 mg/dL, 15 mg/dL, 20 mg/dL, 30 mg/dL, 40 mg/dL or 50 mg/dL relative to baseline.

In various embodiments, the administration of the ASBTI results in a decrease in serum autotaxin concentration. In some embodiments, the administration of the ASBTI results in a reduction in autotaxin concentration of about or of at least about 5%, 10%, 15%, 20%, 25%, 30%, 35%, 40%, 45%, 50%, 55%, 60%, 65%, 70%, 75%, or 80% relative to baseline.

In various embodiments, administration of the ASBTI results in an increase in a quality of life inventory score or in a quality of life inventory score related to fatigue. The quality of life inventory score can be a health-related quality of life (HRQoL) score. In some embodiments, the HRQoL score is a PedsQL score. In various embodiments, the administration of the ASBTI results an increase in the PedsQL score or in a PedsQL score related to fatigue of about or of at least about 5%, 10%, 15%, 20%, 25%, 30%, 45%, or 50% relative to baseline.

In various embodiments, administration of the ASBTI results in a decrease in a xanthoma score relative to baseline. In some embodiments, the xanthoma score is reduced by about or by at least about 2.5%, 5%, 10%, 15%, 20%, 35%, 30%, 35%, 40%, 45%, 50%, 55%, 60%, 65%, 70%, 75%, 80%, 85%, 90%, 95%, or 100% relative to baseline.

In various embodiments, the administration of the ASBTI results in the reduction in the symptom or a change in a disease-relevant laboratory measure by about 1 day, 2 days, 3 days, 4 days, 5 days, 6 days, 7 days, 8 days, 9 days, 10 days, 11 days, 12, days, 13 days, 14 days, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year.

In various embodiments, serum bilirubin concentration is at pre-administration baseline levels or at normal levels at about or by about 1 day, 2 days, 3 days, 4 days, 5 days, 6 days, 1 week, 2 weeks, 3 weeks, 4 weeks, 1 month, 5 weeks, 6 weeks, 7 weeks, 8 weeks, 2 months, 9 weeks 10 weeks, 11 weeks, 12 weeks, 13 weeks, 14 weeks, 15 weeks, 16 weeks, 4 months, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year.

In various embodiments, serum ALT concentration is at pre-administration baseline levels or at normal levels at about or by about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 4 months, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year. In some embodiments, the administration of the ASBTI results in a reduction in ALT levels relative to baseline of about or of at least about 1%, 2%, 3%, 4%, 5%, 6%, 7%, 8%, 9%, 10%, 11%, 12%, 13%, 14%, or 15%.

In various embodiments, serum ALT concentration, serum AST concentration, serum bilirubin concentration, serum conjugated bilirubin concentration, or various combinations thereof are within normal range or at pre-administration baseline levels at about or by about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 4 months, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year. In various embodiments, the administration of the ASBTI does not result in a statistically significant change from baseline in serum bilirubin concentration, serum AST concentration, serum ALT concentration, serum alkaline phosphatase concentration, or some combination thereof for a period of at least about or of about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 4 months, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year. In various embodiments, for adult patients with an ITCHRO score of at least 4 at baseline, the administration of the ASBTI does not result in a significant change from baseline in serum conjugated bilirubin concentration for a period of at least about or of about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks 10 weeks, 11 weeks, 12 weeks, 13 weeks, 14 weeks, 15 weeks, 16 weeks, 4 months, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or 1 year.

Dose Modulation

In various embodiments, the method includes modulating a dosage of the ASBTI administered to the patient. The modulation includes determining the 7αC4:sBA ratio for the patient at a baseline (e.g., prior to administration of the ASBTI or prior to modulating (e.g., increasing) a dosage of the ASBTI), and further determining the 7αC4:sBA ratio after administering the ASBTI at a first dose or modulating (e.g., increasing) a dosage amount of the ASBTI to a second dose. If the 7αC4:sBA ratio does not increase by at least 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold from baseline, the dose of the ASBTI is increased until the ratio increases at least about 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold relative to baseline. In various embodiments, the dose of the ASBTI is increased or decreased to achieve and maintain a particular 7αC4:sBA ratio.

In various embodiments, the modulating includes increasing a dose of the ASBTI from a first dose level to a second dose level greater than the first dose level if the 7αC4:sBA ratio initially increases by at least 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold from baseline and then begins to decrease or decreases to less than 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold or greater higher than baseline. The dose level is increased until the 7αC4:sBA ratio increases to at least 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold from the baseline.

In some embodiments, the modulation includes administering a first dose of the ASBTI to the patient. If the 7αC4:sBA ratio does not increase or increase by at least 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold from baseline, the patient is then administered a second dose of the ASBTI higher than the first dose. The dose administered to the patient continues to be increased until the 7αC4:sBA ratio increases by at least 1, 1.25, 1.5, 1.75, 2, 2.5, 3, 4, 5, 6, 7, 8, 9, 10, 15, 20, 30, 40, 50, 75, 100, 150, 200, 300, 500, 750, 1,000, 2,000, 3,000, 4,000, 5,000 or 10,000-fold from baseline.

In various embodiments, the 7αC4:sBA ratio is measured about daily, bi-weekly, weekly, bi-monthly, monthly, every two months, every three months, every four months, every five months, every six months, or annually, and the dose of the ASBTI is modulated as necessary each time the ratio is measured.

Pharmaceutical Compositions

In some embodiments, the ASBTI is administered as a pharmaceutical composition comprising an ASBTI (the composition or the pharmaceutical composition). Any composition described herein can be formulated for ileal, rectal and/or colonic delivery. In more specific embodiments, the composition is formulated for non-systemic or local delivery to the rectum and/or colon. It is to be understood that, as used herein, delivery to the colon includes delivery to sigmoid colon, transverse colon, and/or ascending colon. In still more specific embodiments, the composition is formulated for non-systemic or local delivery to the rectum and/or colon is administered rectally. In other specific embodiments, the composition is formulated for non-systemic or local delivery to the rectum and/or colon is administered orally.

Provided herein, in certain embodiments, is a pharmaceutical composition comprising a therapeutically effective amount of any compound described herein. In certain instances, the pharmaceutical composition comprises an ASBT inhibitor (e.g., any ASBTI described herein).

In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in Remington: *The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Mareel Decker, New York, N.Y., 1980; and *Pharmaceutical Dosage Forms and Drug Delivery Systems*, Seventh Ed. (Lippincott Williams & Wilkins 1999), all of which references are incorporated herein in their entirety for all purposes.

A pharmaceutical composition, as used herein, refers to a mixture of a compound described herein, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disease, disorder, or condition to be treated. In specific embodiments, the individual is a human. As discussed herein, the compounds described herein are either utilized singly or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

In certain embodiments, a pharmaceutical compositions described herein includes one or more compound described herein as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be described herein.

A "carrier" includes, in some embodiments, a pharmaceutically acceptable excipient and is selected on the basis of compatibility with compounds described herein, such as, compounds of any of Formula I-VI, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Mareel Decker, New York, N.Y., 1980; and *Pharmaceutical Dosage Forms* and Drug Delivery Systems, Seventh Ed. (Lippincott Williams & Wilkins 1999), all of which references are incorporated herein in their entirety for all purposes.

Moreover, in certain embodiments, the pharmaceutical compositions described herein are formulated as a dosage form. As such, in some embodiments, provided herein is a dosage form comprising a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, provided herein is a composition comprising an enteroendocrine peptide secretion enhancing agent and, optionally, a pharmaceutically acceptable carrier for alleviating symptoms of cholestasis or a cholestatic liver disease in an individual.

In certain embodiments, the composition comprises an enteroendocrine peptide secretion enhancing agent and an absorption inhibitor. In specific embodiments, the absorption inhibitor is an inhibitor that inhibits the absorption of the (or at least one of the) specific enteroendocrine peptide secretion enhancing agent with which it is combined. In some embodiments, the composition comprises an enteroendocrine peptide secretion enhancing agent, an absorption inhibitor and a carrier (e.g., an orally suitable carrier or a rectally suitable carrier, depending on the mode of intended administration). In certain embodiments, the composition comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In other embodiments, the compositions described herein are administered orally for non-systemic delivery of the ASBTI to the rectum and/or colon, including the sigmoid colon, transverse colon, and/or ascending colon. In specific embodiments, compositions formulated for oral administration are, by way of non-limiting example, enterically coated or formulated oral dosage forms, such as, tablets and/or capsules.

Absorption Inhibitors

In certain embodiments, the composition described herein as being formulated for the non-systemic delivery of ASBTI further includes an absorption inhibitor. As used herein, an absorption inhibitor includes an agent or group of agents that inhibit absorption of a bile acid/salt.

Suitable bile acid absorption inhibitors (also described herein as absorption inhibiting agents) may include, by way of non-limiting example, anionic exchange matrices, polyamines, quaternary amine containing polymers, quaternary ammonium salts, polyallylamine polymers and copolymers, colesevelam, colesevelam hydrochloride, Cholesta-Gel (N,N,N-trimethyl-6-(2-propenylamino)-1-hexanaminium chloride polymer with (chloromethyl) oxirane, 2-propen-1-amine and N-2-propenyl-1-decanamine hydrochloride), cyclodextrins, chitosan, chitosan derivatives, carbohydrates which bind bile acids, lipids which bind bile acids, proteins and proteinaceous materials which bind bile acids, and antibodies and albumins which bind bile acids. Suitable cyclodextrins include those that bind bile acids/salts such as, by way of non-limiting example, β-cyclodextrin and hydroxypropyl-β-cyclodextrin. Suitable proteins, include those that bind bile acids/salts such as, by way of non-limiting example, bovine serum albumin, egg albumin, casein, α-acid glycoprotein, gelatin, soy proteins, peanut proteins, almond proteins, and wheat vegetable proteins.

In certain embodiments the absorption inhibitor is cholestyramine. In specific embodiments, cholestyramine is combined with a bile acid. Cholestyramine, an ion exchange resin, is a styrene polymer containing quaternary ammonium groups crosslinked by divinylbenzene. In other embodiments, the absorption inhibitor is colestipol. In specific embodiments, colestipol is combined with a bile acid. Colestipol, an ion exchange resin, is a copolymer of diethylenetriamine and 1-chloro-2,3-epoxypropane.

In certain embodiments of the compositions and methods described herein the ASBTI is linked to an absorption inhibitor, while in other embodiments the ASBTI and the absorption inhibitor are separate molecular entities.

Cholesterol Absorption Inhibitors

In certain embodiments, a composition described herein optionally includes at least one cholesterol absorption inhibitor. Suitable cholesterol absorption inhibitors include, by way of non-limiting example, ezetimibe (SCH 58235), ezetimibe analogs, ACT inhibitors, stigmastanyl phosphorylcholine, stigmastanyl phosphorylcholine analogues, β-lactam cholesterol absorption inhibitors, sulfate polysaccharides, neomycin, plant sponins, plant sterols, phytostanol preparation FM-VP4, Sitostanol, β-sitosterol, acyl-CoA:cholesterol-O-acyltransferase (ACAT) inhibitors, Avasimibe, Implitapide, steroidal glycosides and the like. Suitable enzetimibe analogs include, by way of non-limiting example, SCH 48461, SCH 58053 and the like. Suitable ACT inhibitors include, by way of non-limiting example, trimethoxy fatty acid anilides such as Cl-976, 3-[decyldimethylsilyl]-N-[2-(4-methylphenyl)-1-phenylethyl]-propanamide, melinamide and the like. β-lactam cholesterol absorption inhibitors include, by way of non-limiting example, DR-4S)-1,4-bis-(4-methoxyphenyl)-3-β-phenylpropyl)-2-azetidinone and the like.

Peptidase Inhibitors

In some embodiments, the compositions described herein optionally include at least one peptidase inhibitor. Such peptidase inhibitors include, but are not limited to, dipeptidyl peptidase-4 inhibitors (DPP-4), neutral endopeptidase inhibitors, and converting enzyme inhibitors. Suitable dipeptidyl peptidase-4 inhibitors (DPP-4) include, by way of non-limiting example, Vildaglipti, 2.S)-1-{2-[β-hydroxy-1-adamantyl)amino]acetyl}pyrrolidine-2-carbonitrile, Sitagliptin, βR)-3-amino-1-[9-(trifluoromethyl)-1,4,7,8-tetrazabicyclo[4.3.0]nona-6,8-dien-4-yl]-4-(2,4,5-trifluorophenyl)butan-1-one, Saxagliptin, and (1S,3S,5S)-2-[(2S)-2-amino-2-β-hydroxy-1-adamantyl)acetyl]-2-azabicyclo[3.1.0]hexane-3-carbonitrile. Such neutral endopeptidase inhibitors include, but are not limited to, Candoxatrilat and Ecadotril.

Spreading Agents/Wetting Agents

In certain embodiments, the composition described herein optionally comprises a spreading agent. In some embodiments, a spreading agent is utilized to improve spreading of the composition in the colon and/or rectum. Suitable spreading agents include, by way of non-limiting example, hydroxyethylcellulose, hydroxypropymethyl cellulose, polyethylene glycol, colloidal silicon dioxide, propylene glycol, cyclodextrins, microcrystalline cellulose, polyvinylpyrrolidone, polyoxyethylated glycerides, polycarbophil, di-n-octyl ethers, Cetiol™OE, fatty alcohol polyalkylene glycol ethers, Aethoxal™B), 2-ethylhexyl palmitate, Cegesoft™C 24), and isopropyl fatty acid esters.

In some embodiments, the compositions described herein optionally comprise a wetting agent. In some embodiments, a wetting agent is utilized to improve wettability of the composition in the colon and rectum. Suitable wetting agents include, by way of non-limiting example, surfactants. In some embodiments, surfactants are selected from, by way of non-limiting example, polysorbate (e.g., 20 or 80), stearyl hetanoate, caprylic/capric fatty acid esters of saturated fatty alcohols of chain length $C_{12}$-$C_{18}$, isostearyl digylcerol isostearic acid, sodium dodecyl sulphate, isopropyl myristate, isopropyl palmitate, and isopropyl myristate/isopropyl stearate/isopropyl palmitate mixture.

Vitamins

In some embodiments, the methods provided herein further comprise administering one or more vitamins.

In some embodiments, the vitamin is vitamin A, B1, B2, B3, B5, B6, B7, B9, B12, C, D, E, K, folic acid, pantothenic acid, niacin, riboflavin, thiamine, retinol, beta carotene, pyridoxine, ascorbic acid, cholecalciferol, cyanocobalamin, tocopherols, phylloquinone, menaquinone.

In some embodiments, the vitamin is a fat-soluble vitamin such as vitamin A, D, E, K, retinol, beta carotene, cholecalciferol, tocopherols, phylloquinone. In a preferred embodiment, the fat-soluble vitamin is tocopherol polyethylene glycol succinate (TPGS).

Bile Acid Sequestrants Binders

In some embodiments, a labile bile acid sequestrant is an enzyme dependent bile acid sequestrant. In certain embodiments, the enzyme is a bacterial enzyme. In some embodiments, the enzyme is a bacterial enzyme found in high concentration in human colon or rectum relative to the concentration found in the small intestine. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

In certain embodiments, a labile bile acid sequestrant is a time-dependent bile acid sequestrant. In some embodiments, a labile bile acid sequestrant releases a bile acid or is degraded after 1, 2, 3, 4, 5, 6, 7, 8, 9, or 10 seconds of sequestration. In some embodiments, a labile bile acid sequestrant releases a bile acid or is degraded after 15, 20, 25, 30, 35, 40, 45, 50, or 55 seconds of sequestration. In some embodiments, a labile bile acid sequestrant releases a bile acid or is degraded after 1, 2, 3, 4, 5, 6, 7, 8, 9, or 10 minutes of sequestration. In some embodiments, a labile bile acid sequestrant releases a bile acid or is degraded after about 15, 20, 25, 30, 35, 45, 50, or 55 minutes of sequestration. In some embodiments, a labile bile acid sequestrant releases a bile acid or is degraded after about 1, 2, 3, 4, 5, 6, 7, 8, 9, 10, 11, 12, 13, 14, 15, 16, 17, 18, 19, 20, 21, 22, 23, or 24 hours of sequestration. In some embodiments, a labile bile acid sequestrant releases a bile acid or is degraded after 1, 2, or 3 days of sequestration.

In some embodiments, the labile bile acid sequestrant has a low affinity for bile acid. In certain embodiments, the labile bile acid sequestrant has a high affinity for a primary bile acid and a low affinity for a secondary bile acid.

In some embodiments, the labile bile acid sequestrant is a pH dependent bile acid sequestrant. In certain embodiments, the pH dependent bile acid sequestrant has a high affinity for bile acid at a pH of 6 or below and a low affinity for bile acid at a pH above 6. In certain embodiments, the pH dependent bile acid sequestrant has a high affinity for bile acid at a pH of 6.5 or below and a low affinity for bile acid at a pH above 6.5. In certain embodiments, the pH dependent bile acid sequestrant has a high affinity for bile acid at a pH of 7 or below and a low affinity for bile acid at a pH above 7. In certain embodiments, the pH dependent bile acid sequestrant has a high affinity for bile acid at a pH of 7.1 or below and a low affinity for bile acid at a pH above 7.1. In certain embodiments, the pH dependent bile acid sequestrant has a high affinity for bile acid at a pH of 7.2 or below and a low affinity for bile acid at a pH above 7.2. In certain embodiments, the pH dependent bile acid sequestrant has a high affinity for bile acid at a pH of 7.3 or below and a low affinity for bile acid at a pH above 7.3. In certain embodiments, the pH dependent bile acid sequestrant has a high affinity for bile acid at a pH of 7.4 or below and a low affinity for bile acid at a pH above 7.4. In certain embodiments, the pH dependent bile acid sequestrant has a high affinity for bile acid at a pH of 7.5 or below and a low affinity for bile acid at a pH above 7.5. In certain embodiments, the pH dependent bile acid sequestrant has a high affinity for bile acid at a pH of 7.6 or below and a low affinity for bile acid at a pH above 7.6. In certain embodiments, the pH dependent bile acid sequestrant has a high affinity for bile acid at a pH of 7.7 or below and a low affinity for bile acid at a pH above 7.7. In certain embodiments, the pH dependent bile acid sequestrant has a high affinity for bile acid at a pH of 7.8 or below and a low affinity for bile acid at a pH above 7.8. In some embodiments, the pH dependent bile acid sequestrant degrades at a pH above 6. In some embodiments, the pH dependent bile acid sequestrant degrades at a pH above 6.5. In some embodiments, the pH dependent bile acid sequestrant degrades at a pH above 7. In some embodiments, the pH dependent bile acid sequestrant degrades at a pH above 7.1. In some embodiments, the pH dependent bile acid sequestrant degrades at a pH above 7.2. In some embodiments, the pH dependent bile acid sequestrant degrades at a pH above 7.3. In some embodiments, the pH dependent bile acid sequestrant degrades at a pH above 7.4. In some embodiments, the pH dependent bile acid sequestrant degrades at a pH above 7.5. In some embodiments, the pH dependent bile acid sequestrant degrades at a pH above 7.6. In some embodiments, the pH dependent bile acid sequestrant degrades at a pH above 7.7. In some embodiments, the pH dependent bile acid sequestrant degrades at a pH above 7.8. In some embodiments, the pH dependent bile acid sequestrant degrades at a pH above 7.9.

In certain embodiments, the labile bile acid sequestrant is lignin or a modified lignin. In some embodiments, the labile bile acid sequestrant is a polycationic polymer or copolymer. In certain embodiments, the labile bile acid sequestrant is a polymer or copolymer comprising one or more N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof. In some embodiments, the bile acid binder is cholestyramine, and various compositions including cholestyramine, which are described, for example, in U.S. Pat. Nos. 3,383,281; 3,308,020; 3,769,399; 3,846,541; 3,974,272; 4,172,120; 4,252,790; 4,340,585; 4,814,354; 4,874,744; 4,895,723; 5,695,749; and 6,066, 336, all of which are incorporated herein by reference in their entirety for all purposes. In some embodiments, the bile acid binder is cholestipol or colesevelam.

Routes of Administration, Dosage Forms, and Dosing Regimens

In some embodiments, the compositions described herein, and the compositions administered in the methods described herein are formulated to inhibit bile acid reuptake or reduce serum or hepatic bile acid levels. In certain embodiments, the compositions described herein are formulated for rectal or oral administration. In some embodiments, such formulations are administered rectally or orally, respectively. In some embodiments, the compositions described herein are combined with a device for local delivery of the compositions to the rectum and/or colon (sigmoid colon, transverse colon, or ascending colon). In certain embodiments, for rectal administration the composition described herein are formulated as enemas, rectal gels, rectal foams, rectal aerosols, suppositories, jelly suppositories, or retention enemas. In some embodiments, for oral administration the compositions described herein are formulated for oral administration and enteric delivery to the colon.

In certain embodiments, the compositions or methods described herein are non-systemic. In some embodiments, compositions described herein deliver the ASBTI to the distal ileum, colon, and/or rectum and not systemically (e.g., a substantial portion of the enteroendocrine peptide secretion enhancing agent is not systemically absorbed). In some embodiments, oral compositions described herein deliver the ASBTI to the distal ileum, colon, and/or rectum and not systemically (e.g., a substantial portion of the enteroendocrine peptide secretion enhancing agent is not systemically absorbed). In some embodiments, rectal compositions described herein deliver the ASBTI to the distal ileum, colon, and/or rectum and not systemically (e.g., a substantial portion of the enteroendocrine peptide secretion enhancing agent is not systemically absorbed). In certain embodiments, non-systemic compositions described herein deliver less than 90% w/w of the ASBTI systemically. In certain embodiments, non-systemic compositions described herein deliver less than 80% w/w of the ASBTI systemically. In certain embodiments, non-systemic compositions described herein deliver less than 70% w/w of the ASBTI systemically. In certain embodiments, non-systemic compositions described herein deliver less than 60% w/w of the ASBT1 systemically. In certain embodiments, non-systemic compositions described herein deliver less than 50% w/w of the ASBTI systemically. In certain embodiments, non-systemic compositions described herein deliver less than 40% w/w of the ASBTI systemically. In certain embodiments, non-systemic compositions described herein deliver less than 30% w/w of the ASBTI systemically. In certain embodiments, non-systemic compositions described herein deliver less than 25% w/w of the ASBTI systemically. In certain embodiments, non-systemic compositions described herein deliver less than 20% w/w of the ASBTI systemically. In certain embodiments, non-systemic compositions described herein deliver less than 15% w/w of the ASBTI systemically. In certain embodiments, non-systemic compositions described herein deliver less than 10% w/w of the ASBTI systemically. In certain embodiments, non-systemic compositions described herein deliver less than 5% w/w of the ASBTI systemically. In some embodiments, systemic absorption is determined in any suitable manner, including the total circulating amount, the amount cleared after administration, or the like.

In certain embodiments, the compositions and/or formulations described herein are administered at least once a day. In certain embodiments, the formulations containing the ASBTI are administered at least twice a day, while in other embodiments the formulations containing the ASBTI are administered at least three times a day. In certain embodiments, the formulations containing the ASBTI are administered up to five times a day. It is to be understood that in certain embodiments, the dosage regimen of composition containing the ASBTI described herein to is determined by considering various factors such as the patient's age, sex, and diet.

The concentration of the ASBTI administered in the formulations described herein ranges from about 1 mM to about 1 M. In certain embodiments the concentration of the ASBTI administered in the formulations described herein ranges from about 1 mM to about 750 mM. In certain embodiments the concentration of the ASBTI administered in the formulations described herein ranges from about 1 mM to about 500 mM. In certain embodiments the concentration of the ASBTI administered in the formulations described herein ranges from about 5 mM to about 500 mM. In certain embodiments the concentration of the ASBTI administered in the formulations described herein ranges from about 10 mM to about 500 mM. In certain embodiments the concentration of the administered in the formulations described herein ranges from about 25 mM to about 500 mM. In certain embodiments the concentration of the ASBTI administered in the formulations described herein ranges from about 50 mM to about 500 mM. In certain embodiments the concentration of the ASBTI administered in the formulations described herein ranges from about 100 mM to about 500 mM. In certain embodiments the concentration of the ASBTI administered in the formulations described herein ranges from about 200 mM to about 500 mM.

In certain embodiments, by targeting the distal gastrointestinal tract (e.g., distal ileum, colon, and/or rectum), compositions and methods described herein provide efficacy (e.g., in reducing microbial growth and/or alleviating symptoms of cholestasis or a cholestatic liver disease) with a reduced dose of enteroendocrine peptide secretion enhancing agent (e.g., as compared to an oral dose that does not target the distal gastrointestinal tract).

Rectal Administration Formulations

The pharmaceutical compositions described herein for the non-systemic delivery of a compound described herein to the rectum and/or colon are formulated for rectal administration as rectal enemas, rectal foams, rectal gels, and rectal suppositories. The components of such formulations are described herein. It is to be understood that as used herein, pharmaceutical compositions and compositions are or comprise the formulations as described herein. In some embodiments, rectal formulations comprise rectal enemas, foams, gels, or suppositories.

In certain embodiments, liquid carrier vehicles or co-solvents in the compositions and/or formulations described herein include, by way of non-limiting example, purified water, propylene glycol, PEG200, PEG300, PEG400, PEG600, polyethyleneglycol, ethanol, 1-propanol, 2-propanol, 1-propen-3-ol (allyl alcohol), propylene glycol, glycerol, 2-methyl-2-propanol, formamide, methyl formamide, dimethyl formamide, ethyl formamide, diethyl formamide, acetamide, methyl acetamide, dimethyl acetamide, ethyl acetamide, diethyl acetamide, 2-pyrrolidone, N-methyl-2-pyrrolidone, N-ethyl-2-pyrrolidone, tetramethyl urea, 1,3-dimethyl-2-imidazolidinone, propylene carbonate, 1,2-butylene carbonate, 2,3-butylene carbonate, dimethyl sulfoxide, diethyl sulfoxide, hexamethyl phosphoramide, pyruvic aldehyde dimethylacetal, dimethylisosorbide and combinations thereof.

In some embodiments, stabilizers used in compositions and/or formulations described herein include, but are not limited to, partial glycerides of polyoxyethylenic saturated fatty acids.

In certain embodiments, surfactants/emulsifiers used in the compositions and/or formulations described herein include, by way of non-limiting example, mixtures of cetostearylic alcohol with sorbitan esterified with polyoxyethylenic fatty acids, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and combinations thereof.

In some embodiments, non-ionic surfactants used in compositions and/or formulations described herein include, by way of non-limiting example, phospholipids, alkyl poly (ethylene oxide), poloxamers (e.g., poloxamer 188), polysorbates, sodium dioctyl sulfosuccinate, Brij™-30 (Laureth-4), Brij™-58 (Ceteth-20) and Brij™-78 (Steareth-20), Brij™-721 (Steareth-21), Crillet-1 (Polysorbate 20), Crillet-2 (Polysorbate 40), Crillet-3 (Polysorbate 60), Crillet 45 (Polysorbate 80), Myrj-52 (PEG-40 Stearate), Myrj-53 (PEG-50 Stearate), Pluronic™ F77 (Poloxamer 217), Pluronic™ F87 (Poloxamer 237), Pluronic™ F98 (Poloxamer 288), Pluronic™ L62 (Poloxamer 182), Pluronic™ L64 (Poloxamer 184), Pluronic™ F68 (Poloxamer 188), Pluronic™ L81 (Poloxamer 231), Pluronic™ L92 (Poloxamer 282), Pluronic™ L101 (Poloxamer 331), Pluronic™ P103 (Poloxamer 333), Pluracare™ F 108 NF (Poloxamer 338), and Pluracare™ F 127 NF (Poloxamer 407) and combinations thereof. Pluronic™ polymers are commercially purchasable from BASF, USA and Germany.

In certain embodiments, anionic surfactants used in compositions and/or formulations described herein include, by way of non-limiting example, sodium laurylsulphate, sodium dodecyl sulfate (SDS), ammonium lauryl sulfate, alkyl sulfate salts, alkyl benzene sulfonate, and combinations thereof.

In some embodiments, the cationic surfactants used in compositions and/or formulations described herein include, by way of non-limiting example, benzalkonium chloride, benzethonium chloride, cetyl trimethylammonium bromide, hexadecyl trimethyl ammonium bromide, other alkyltrimethylammonium salts, cetylpyridinium chloride, polyethoxylated tallow and combinations thereof.

In certain embodiments, the thickeners used in compositions and/or formulations described herein include, by way of non-limiting example, natural polysaccharides, semi-synthetic polymers, synthetic polymers, and combinations thereof. Natural polysaccharides include, by way of non-limiting example, acacia, agar, alginates, carrageenan, guar, arabic, tragacanth gum, pectins, dextran, gellan and xanthan gums. Semi-synthetic polymers include, by way of non-limiting example, cellulose esters, modified starches, modified celluloses, carboxymethylcellulose, methyl cellulose, ethyl cellulose, hydroxyethyl cellulose, hydroxypropyl cellulose and hydroxypropyl methylcellulose. Synthetic polymers include, by way of non-limiting example, polyoxyalkylenes, polyvinyl alcohol, polyacrylamide, polyacrylates, carboxypolymethylene (carbomer), polyvinylpyrrolidone (povidones), polyvinylacetate, polyethylene glycols and poloxamer. Other thickeners include, by way of nonlimiting example, polyoxyethyleneglycol isostearate, cetyl alcohol, Polyglycol 300 isostearate, propyleneglycol, collagen, gelatin, and fatty acids (e.g., lauric acid, myristic acid, palmitic acid, stearic acid, palmitoleic acid, linoleic acid, linolenic acid, oleic acid and the like).

In some embodiments, chelating agents used in the compositions and/or formulations described herein include, by way of non-limiting example, ethylenediaminetetraacetic acid (EDTA) or salts thereof, phosphates and combinations thereof.

In some embodiments, the concentration of the chelating agent or agents used in the rectal formulations described herein is a suitable concentration, e.g., about 0.1%, 0.15%, 0.2%, 0.25%, 0.3%, 0.4%, or 0.5% (w/v).

In some embodiments, preservatives used in compositions and/or formulations described herein include, by way of non-limiting example, parabens, ascorbyl palmitate, benzoic acid, butylated hydroxyanisole, butylated hydroxytoluene, chlorobutanol, ethylenediamine, ethylparaben, methylparaben, butyl paraben, propylparaben, monothioglycerol, phenol, phenylethyl alcohol, propylparaben, sodium benzoate, sodium propionate, sodium formaldehyde sulfoxylate, sodium metabisulfite, sorbic acid, sulfur dioxide, maleic acid, propyl gallate, benzalkonium chloride, benzethonium chloride, benzyl alcohol, chlorhexidine acetate, chlorhexidine gluconate, sorbic acid, potassium sorbitol, chlorobutanol, phenoxyethanol, cetylpyridinium chloride, phenylmercuric nitrate, thimerosal, and combinations thereof.

In certain embodiments, antioxidants used in compositions and/or formulations described herein include, by way of non-limiting example, ascorbic acid, ascorbyl palmitate, butylated hydroxyanisole, butylated hydroxytoluene, hypophosphorous acid, monothioglycerol, propyl gallate, sodium ascorbate, sodium sulfite, sodium bisulfite, sodium formaldehyde sulfoxylate, potassium metabisulphite, sodium metabisulfite, oxygen, quinones, t-butyl hydroquinone, erythorbic acid, olive (*Olea europaea*) oil, pentasodium pentetate, pentetic acid, tocopheryl, tocopheryl acetate and combinations thereof.

In some embodiments, concentration of the antioxidant or antioxidants used in the rectal formulations described herein is sufficient to achieve a desired result, e.g., about 0.1%, 0.15%, 0.2%, 0.25%, 0.3%, 0.4%, or 0.5% (w/v).

The lubricating agents used in compositions and/or formulations described herein include, by way of non-limiting example, natural or synthetic fat or oil (e.g., a tris-fatty acid glycerate and the like). In some embodiments, lubricating agents include, by way of non-limiting example, glycerin (also called glycerine, glycerol, 1,2,3-propanetriol, and trihydroxypropane), polyethylene glycols (PEGs), polypropylene glycol, polyisobutene, polyethylene oxide, behenic acid, behenyl alcohol, sorbitol, mannitol, lactose, polydimethylsiloxane and combinations thereof.

In certain embodiments, mucoadhesive and/or bioadhesive polymers are used in the compositions and/or formulations described herein as agents for inhibiting absorption of the enteroendocrine peptide secretion enhancing agent across the rectal or colonic mucosa. Bioadhesive or mucoadhesive polymers include, by way of non-limiting example, hydroxypropyl cellulose, polyethylene oxide homopolymers, polyvinyl ether-maleic acid copolymers, methyl cellulose, ethyl cellulose, propyl cellulose, hydroxyethyl cellulose, hydroxypropyl cellulose, hydroxypropylmethyl cellulose, carboxymethylcellulose, polycarbophil, polyvinylpyrrolidone, carbopol, polyurethanes, polyethylene oxide-polypropylene oxide copolymers, sodium carboxymethyl cellulose, polyethylene, polypropylene, lectins, xanthan gum, alginates, sodium alginate, polyacrylic acid, chitosan, hyaluronic acid and ester derivatives thereof, vinyl acetate homopolymer, calcium polycarbophil, gelatin, natural gums, karaya, tragacanth, algin, chitosan, starches, pectins, and combinations thereof.

In some embodiments, buffers/pH adjusting agents used in compositions and/or formulations described herein include, by way of non-limiting example, phosphoric acid, monobasic sodium or potassium phosphate, triethanolamine (TRIS), BICINE, HEPES, Trizma, glycine, histidine, arginine, lysine, asparagine, aspartic acid, glutamine, glutamic acid, carbonate, bicarbonate, potassium metaphosphate, potassium phosphate, monobasic sodium acetate, acetic acid, acetate, citric acid, sodium citrate anhydrous, sodium citrate dihydrate and combinations thereof. In certain embodiments, an acid or a base is added to adjust the pH. Suitable acids or bases include, by way of non-limiting example, HCL, NaOH and KOH.

In certain embodiments, concentration of the buffering agent or agents used in the rectal formulations described herein is sufficient to achieve or maintain a physiologically desirable pH, e.g., about 0.1%, 0.2%, 0.3%, 0.4%, 0.5%, 0.6%, 0.8%, 0.9%, or 1.0% (w/w).

The tonicity modifiers used in compositions and/or formulations described herein include, by way of non-limiting example, sodium chloride, potassium chloride, sodium phosphate, mannitol, sorbitol or glucose.

Oral Administration for Colonic Delivery

In certain aspects, the composition or formulation containing one or more compounds described herein is orally administered for local delivery of an ASBTI, or a compound described herein to the colon and/or rectum. Unit dosage forms of such compositions include a pill, tablet or capsules formulated for enteric delivery to colon. In certain embodiments, such pills, tablets or capsule contain the compositions described herein entrapped or embedded in microspheres. In some embodiments, microspheres include, by way of non-limiting example, chitosan microcores HPMC capsules and cellulose acetate butyrate (CAB) microspheres. In certain embodiments, oral dosage forms are prepared using conventional methods known to those in the field of pharmaceutical formulation. For example, in certain embodiments, tablets are manufactured using standard tablet processing procedures and equipment. An exemplary method for forming tablets is by direct compression of a powdered, crystalline or granular composition containing the active agent(s), alone or in combination with one or more carriers, additives, or the like. In alternative embodiments, tablets are prepared using wet-granulation or dry-granulation processes. In some embodiments, tablets are molded rather than compressed, starting with a moist or otherwise tractable material.

In certain embodiments, tablets prepared for oral administration contain various excipients, including, by way of non-limiting example, binders, diluents, lubricants, disintegrants, fillers, stabilizers, surfactants, preservatives, coloring agents, flavoring agents and the like. In some embodiments, binders are used to impart cohesive qualities to a tablet, ensuring that the tablet remains intact after compression. Suitable binder materials include, by way of non-limiting example, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), Veegum, and combinations thereof. In certain embodiments, diluents are utilized to increase the bulk of the tablet so that a practical size tablet is provided. Suitable diluents include, by way of non-limiting example, dicalcium phosphate, calcium sulfate, lactose, cellulose, kaolin, mannitol, sodium chloride, dry starch, powdered sugar and combinations thereof. In certain embodiments, lubricants are used to facilitate tablet manufacture; examples of suitable lubricants include, by way of non-limiting example, vegetable oils such as peanut oil, cottonseed oil, sesame oil, olive oil, corn oil, and oil of theobroma, glycerin, magnesium stearate, calcium stearate, stearic acid and combinations thereof. In some embodiments, disintegrants are used to facilitate disintegration of the tablet, and include, by way of non-limiting example, starches, clays, celluloses, algins, gums, crosslinked polymers and combinations thereof. Fillers include, by way of non-limiting example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. In certain embodiments, stabilizers are used to inhibit or retard drug decomposition reactions that include, by way of example, oxidative reactions. In certain embodiments, surfactants are anionic, cationic, amphoteric or nonionic surface active agents.

In some embodiments, ASBTIs, or other compounds described herein are orally administered in association with a carrier suitable for delivery to the distal gastrointestinal tract (e.g., distal ileum, colon, and/or rectum).

In certain embodiments, a composition described herein comprises an ASBTI, or other compounds described herein in association with a matrix (e.g., a matrix comprising hypromellose) that allows for controlled release of an active agent in the distal part of the ileum and/or the colon. In some embodiments, a composition comprises a polymer that is pH sensitive (e.g., a MMX™ matrix from Cosmo Pharmaceuticals) and allows for controlled release of an active agent in the distal part of the ileum. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a composition suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an enteroendocrine peptide secretion enhancing agent to the distal ileum. In some embodiments, a dosage form comprising an enteroendocrine peptide secretion enhancing agent is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the distal ileum and/or the colon. In some embodiments, bacterially activated systems are suitable for targeted delivery to the distal part of the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical composition described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some embodiments, using standard coating procedures, such as those described in Remington's Pharmaceutical Sciences, 20th Edition (2000), a film coating is provided around the formulation of the compound of Formula I. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

In further embodiments, a tablet or capsule comprising an ASBTI or other compounds described herein is film-coated for delivery to targeted sites within the gastrointestinal tract. Examples of enteric film coats include and are not limited to hydroxypropylmethylcellulose, polyvinyl pyrrolidone, hydroxypropyl cellulose, polyethylene glycol 3350, 4500, 8000, methyl cellulose, pseudoethylcellulose, amylopectin and the like.

Pediatric Dosage Formulations and Compositions

Provided herein, in certain embodiments, is a pediatric dosage formulation or composition comprising a therapeutically effective amount of any compound described herein. In certain instances, the pharmaceutical composition comprises an ASBT inhibitor (e.g., any ASBTI described herein).

In certain embodiments, suitable dosage forms for the pediatric dosage formulation or composition include, by way of non-limiting example, aqueous or non-aqueous oral dispersions, liquids, gels, syrups, elixirs, slurries, suspensions, solutions, controlled release formulations, fast melt formulations, effervescent formulations, lyophilized formulations, chewable tablets, gummy candy, orally disintegrating tablets, powders for reconstitution as suspension or solution, sprinkle oral powder or granules, dragees, delayed release formulations, extended release formulations, pulsatile release formulations, multiparticulate formulations, and mixed immediate release and controlled release formulations. In some embodiments, provided herein is a pharmaceutical composition wherein the pediatric dosage form is selected from a solution, syrup, suspension, elixir, powder for reconstitution as suspension or solution, dispersible/effervescent tablet, chewable tablet, gummy candy, lollipop, freezer pops, troches, oral thin strips, orally disintegrating tablet, orally disintegrating strip, sachet, and sprinkle oral powder or granules.

In another aspect, provide herein is a pharmaceutical composition wherein at least one excipient is a flavoring agent or a sweetener. In some embodiments, provided herein is a coating. In some embodiments, provided herein is a taste-masking technology selected from coating of drug particles with a taste-neutral polymer by spray-drying, wet granulation, fluidized bed, and microencapsulation; coating with molten waxes of a mixture of molten waxes and other pharmaceutical adjuvants; entrapment of drug particles by complexation, flocculation or coagulation of an aqueous polymeric dispersion; adsorption of drug particles on resin and inorganic supports; and solid dispersion wherein a drug and one or more taste neutral compounds are melted and cooled, or co-precipitated by a solvent evaporation. In some embodiments, provided herein is a delayed or sustained release formulation comprising drug particles or granules in a rate controlling polymer or matrix.

Suitable sweeteners include sucrose, glucose, fructose or intense sweeteners, i.e. agents with a high sweetening power when compared to sucrose (e.g. at least 10 times sweeter than sucrose). Suitable intense sweeteners comprise aspartame, saccharin, sodium or potassium or calcium saccharin, acesulfame potassium, sucralose, alitame, xylitol, cyclamate, neonate, neohesperidine dihydrochalcone or mixtures thereof, thaumatin, palatinit, stevioside, rebaudioside, Magnasweet®. The total concentration of the sweeteners may range from effectively zero to about 300 mg/ml based on the liquid composition upon reconstitution.

In order to increase the palatability of the liquid composition upon reconstitution with an aqueous medium, one or more taste-making agents may be added to the composition in order to mask the taste of the ASBT inhibitor. A taste-masking agent can be a sweetener, a flavoring agent or a combination thereof. The taste-masking agents typically provide up to about 0.10% or 5% by weight of the total pharmaceutical composition. In a preferred embodiment of the present invention, the composition contains both sweetener(s) and flavor(s).

A flavoring agent herein is a substance capable of enhancing taste or aroma of a composition. Suitable natural or synthetic flavoring agents can be selected from standard reference books, for example Fenaroli's Handbook of Flavor Ingredients, 3rd edition (1995). Non-limiting examples of flavoring agents and/or sweeteners useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. Flavoring agents can be used singly or in combinations of two or more. In some embodiments, the aqueous liquid dispersion comprises a sweetening agent or flavoring agent in a concentration ranging from about 0.001% to about 5.0% the volume of the aqueous dispersion. In one embodiment, the aqueous liquid dispersion comprises a sweetening agent or flavoring agent in a concentration ranging from about 0.001% to about 1.0% the volume of the aqueous dispersion. In another embodiment, the aqueous liquid dispersion comprises a sweetening agent or flavoring agent in a concentration ranging from about 0.005% to about 0.5% the volume of the aqueous dispersion. In yet another embodiment, the aqueous liquid dispersion comprises a sweetening agent or flavoring agent in a concentration ranging from about 0.010% to about 1.0% the volume of the aqueous dispersion. In yet another embodiment, the aqueous liquid dispersion comprises a sweetening agent or flavoring agent in a concentration ranging from about 0.01% to about 0.5% the volume of the aqueous dispersion.

In certain embodiments, a pediatric pharmaceutical composition described herein includes one or more compound described herein as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be described herein.

A "carrier" for pediatric pharmaceutical compositions includes, in some embodiments, a pharmaceutically acceptable excipient and is selected on the basis of compatibility with compounds described herein, such as, compounds of any of Formula I-VI, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), all of which references are incorporated herein by reference in their entirety for all purposes.

Moreover, in certain embodiments, the pediatric pharmaceutical compositions described herein are formulated as a dosage form. As such, in some embodiments, provided herein is a dosage form comprising a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In certain aspects, the pediatric composition or formulation containing one or more compounds described herein is orally administered for local delivery of an ASBTI, or a compound described herein to the colon and/or rectum. Unit dosage forms of such compositions include a pill, tablet or capsules formulated for enteric delivery to colon. In certain embodiments, such pills, tablets or capsule contain the compositions described herein entrapped or embedded in microspheres. In some embodiments, microspheres include, by way of non-limiting example, chitosan microcores HPMC capsules and cellulose acetate butyrate (CAB) microspheres. In certain embodiments, oral dosage forms are prepared using conventional methods known to those in the field of pharmaceutical formulation. For example, in certain embodiments, tablets are manufactured using standard tablet processing procedures and equipment. An exemplary method for forming tablets is by direct compression of a powdered, crystalline or granular composition containing the active agent(s), alone or in combination with one or more carriers, additives, or the like. In alternative embodiments, tablets are prepared using wet-granulation or dry-granulation processes. In some embodiments, tablets are molded rather than compressed, starting with a moist or otherwise tractable material.

In certain embodiments, tablets prepared for oral administration contain various excipients, including, by way of non-limiting example, binders, diluents, lubricants, disintegrants, fillers, stabilizers, surfactants, preservatives, coloring agents, flavoring agents and the like. In some embodiments, binders are used to impart cohesive qualities to a tablet, ensuring that the tablet remains intact after compression. Suitable binder materials include, by way of non-limiting example, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), Veegum, and combinations thereof. In certain embodiments, diluents are utilized to increase the bulk of the tablet so that a practical size tablet is provided. Suitable diluents include, by way of non-limiting example, dicalcium phosphate, calcium sulfate, lactose, cellulose, kaolin, mannitol, sodium chloride, dry starch, powdered sugar and combinations thereof. In certain embodiments, lubricants are used to facilitate tablet manufacture; examples of suitable lubricants include, by way of non-limiting example, vegetable oils such as peanut oil, cottonseed oil, sesame oil, olive oil, corn oil, and oil of theobroma, glycerin, magnesium stearate, calcium stearate, stearic acid and combinations thereof. In some embodiments, disintegrants are used to facilitate disintegration of the tablet, and include, by way of non-limiting example, starches, clays, celluloses, algins, gums, crosslinked polymers and combinations thereof. Fillers include, by way of non-limiting example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. In certain embodiments, stabilizers are used to inhibit or retard drug decomposition reactions that include, by way of example, oxidative reactions. In certain embodiments, surfactants are anionic, cationic, amphoteric or nonionic surface active agents.

In some embodiments, ASBTIs, or other compounds described herein are orally administered in association with a carrier suitable for delivery to the distal gastrointestinal tract (e.g., distal ileum, colon, and/or rectum).

In certain embodiments, a pediatric composition described herein comprises an ASBTI, or other compounds described herein in association with a matrix (e.g., a matrix comprising hypromellose) that allows for controlled release of an active agent in the distal part of the ileum and/or the colon. In some embodiments, a composition comprises a polymer that is pH sensitive (e.g., a MMX™ matrix from Cosmo Pharmaceuticals) and allows for controlled release of an active agent in the distal part of the ileum. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a composition suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an enteroendocrine peptide secretion enhancing agent to the distal ileum. In some embodiments, a dosage form comprising an enteroendocrine peptide secretion enhancing agent is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the distal ileum and/or the colon. In some embodiments, bacterially activated systems are suitable for targeted delivery to the distal part of the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pediatric pharmaceutical composition described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the compound of Formula I. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

In further embodiments, a tablet or capsule comprising an ASBTI or other compounds described herein is film-coated for delivery to targeted sites within the gastrointestinal tract. Examples of enteric film coats include and are not limited to hydroxypropylmethylcellulose, polyvinyl pyrrolidone, hydroxypropyl cellulose, polyethylene glycol 3350, 4500, 8000, methyl cellulose, pseudo ethylcellulose, amylopectin and the like.

Solid Dosage Forms for Pediatric Administration

Solid dosage forms for pediatric administration of the present invention can be manufactured by standard manufacturing techniques. Non-limiting examples of oral solid dosage forms for pediatric administration are described below.

Effervescent Compositions

The effervescent compositions of the invention may be prepared according to techniques well-known in the art of pharmacy.

Effervescent formulations contain and effervescent couple of a base component and an acid component, which components reach in the presence of water to generate a gas. In some embodiments, the base component may comprise, for example, an alkali metal or alkaline earth metal carbonate, or bicarbonate. The acid component may comprise, for example, an aliphatic carboxylic acid or a salt thereof, such as citric acid. The base and acid components may each independently constitute, for example, 25% to 55% (w/w) of the effervescent composition. The ratio of acid component to base component may be within the range of 1:2 to 2:1.

The effervescent compositions of the invention may be formulated using additional pharmaceutically acceptable carriers or excipients as appropriate. For example, one or more taste masking agents may be used. Dyes may also be used, as pediatric patients often prefer colorful pharmaceutical combinations. The compositions may take the form of, for example, tablets, granules or powders, granules or powders presented in a sachet.

Chewable Tablets

The chewable tablets of the invention may be prepared according to techniques well-known in the art of pharmacy.

Chewable tablets are tablets that are intended to disintegrate in the mouth under the action of chewing or sucking and where, in consequence, the active ingredient has greater opportunity to come into contact with the bitter-taste receptors on the tongue.

One method of overcoming this issue is to absorb the active ingredient onto a suitable substrate. This approach is known in the art and described for example in U.S. Pat. No. 4,647,459, which is incorporated herein by reference in its entirety for all purposes.

Another approach involves forming the active ingredient into an aggregate along with a pre-swelled substantially anhydrous hydrocolloid. The hydrocolloid absorbs saliva and acquires a slippery texture which enables it to lubricate the particles of aggregate and mask the taste of the active ingredient. This approach is known in the art and described for example in European patent application 0190826, which is incorporated herein by reference in its entirety for all purposes.

Another approach involves employing a water-insoluble hygroscopic excipient such as microcrystalline cellulose. This approach is known in the art and described for example in U.S. Pat. No. 5,275,823, which is incorporated herein by reference in its entirety for all purposes.

In addition to the above approaches, the chewable tablets of the present invention can also contain other standard tableting excipients such as a disintegrant and a taste-masking agent.

Orodispersible Tablets

The orodispersible tablets of the invention may be prepared according to techniques well-known in the art of pharmacy.

In orodispersible tablets of the invention, the excipient mixtures are such as to provide it with a disintegration rate so that its disintegration in the buccal cavity occurs in an extremely short time and especially shorter than sixty seconds. In some embodiments, the excipient mixture is characterized by the fact that the active substance is in the form of coated or non-coated microcrystals of microgranules. In some embodiments, the orodispersible tablet comprises one or several disintegrating agents of the carboxymethylcellulose type or insoluble reticulated PVP type, one or several swelling agents which may comprise a carboxymethylcellulose, a starch, a modified starch, or a microcrystalline cellulose or optionally a direct compression sugar.

Powders for Reconstitution

The powder for reconstitution pharmaceutical compositions of the invention may be prepared according to techniques well-known in the art of pharmacy.

In some embodiments, the powder for reconstitution compositions of the invention comprise an effective amount of at least one internal dehydrating agent. The internal dehydrating agent can enhance the stability of the powder. In some embodiments, the internal dehydrating agent is magnesium citrate or disodium carbonate. In some embodiments, the powder composition comprises a pharmaceutically acceptable diluents, such as sucrose, dextrose, mannitol, xylitol, or lactose.

Powder compositions of the inventions may be placed in sachets or bottles for contemporaneous dissolution or for short term storage in liquid form (e.g. 7 days).

Gummy Candies

The gummy candies of the invention may be prepared according to techniques well-known in the art of pharmacy.

Traditional gummy candy is made from a gelatin base. Gelatin gives the candy its elasticity, the desired chewy consistency, and a longer shelf life. In some embodiments, the gummy candy pharmaceutical composition of the invention includes a binding agent, a sweetener, and an active ingredient.

In some embodiments, the binding agent is a pectin gel, gelatin, food starch, or any combination thereof.

In some embodiments, the gummy candy comprises sweeteners, a binding agent, natural and/or artificial flavors and colors and preservatives. In some embodiments, the gummy candy comprises glucose syrup, natural cane juice, gelatin, citric acid, lactic acid, natural colors, natural flavors, fractionated coconut oil, and carnauba wax.

Liquid Dosage Forms

The pharmaceutical liquid dosage forms of the invention may be prepared according to techniques well-known in the art of pharmacy.

A solution refers to a liquid pharmaceutical formulation wherein the active ingredient is dissolved in the liquid. Pharmaceutical solutions of the invention include syrups and elixirs. A suspension refers to a liquid pharmaceutical formulation wherein the active ingredient is in a precipitate in the liquid.

In a liquid dosage form, it is desirable to have a particular pH and/or to be maintained within a specific pH range. In order to control the pH, a suitable buffer system can be used. In addition, the buffer system should have sufficient capacity to maintain the desired pH range. Examples of the buffer system useful in the present invention include but are not limited to, citrate buffers, phosphate buffers, or any other suitable buffer known in the art. Preferably the buffer system include sodium citrate, potassium citrate, sodium bicarbonate, potassium bicarbonate, sodium dihydrogen phosphate and potassium dihydrogen phosphate, etc. The concentration of the buffer system in the final suspension varies according to factors such as the strength of the buffer system and the pH/pH ranges required for the liquid dosage form. In one embodiment, the concentration is within the range of 0.005 to 0.5 w/v % in the final liquid dosage form.

The pharmaceutical composition comprising the liquid dosage form of the present invention can also include a suspending/stabilizing agent to prevent settling of the active material. Over time the settling could lead to caking of the active to the inside walls of the product pack, leading to difficulties with redispersion and accurate dispensing. Suitable stabilizing agents include but are not limited to, the polysaccharide stabilizers such as xanthan, guar and tragacanth gums as well as the cellulose derivatives HPMC (hydroxypropyl methylcellulose), methyl cellulose and Avicel RC-591 (microcrystalline cellulose/sodium carboxymethyl cellulose). In another embodiment, polyvinylpyrrolidone (PVP) can also be used as a stabilizing agent.

In addition to the aforementioned components, the ASBTI oral suspension form can also optionally contain other excipients commonly found in pharmaceutical compositions such as alternative solvents, taste-masking agents, antioxidants, fillers, acidifiers, enzyme inhibitors and other components as described in Handbook of Pharmaceutical Excipients, Rowe et al., Eds., 4$^{th}$ Edition, Pharmaceutical Press (2003), which is hereby incorporated by reference in its entirety for all purposes.

Addition of an alternative solvent may help increase solubility of an active ingredient in the liquid dosage form, and consequently the absorption and bioavailability inside the body of a subject. Preferably the alternative solvents include methanol, ethanol or propylene glycol and the like.

In another aspect, the present invention provides a process for preparing the liquid dosage form. The process comprises steps of bringing ASBTI or its pharmaceutically acceptable salts thereof into mixture with the components including glycerol or syrup or the mixture thereof, a preservative, a buffer system and a suspending/stabilizing agent, etc., in a liquid medium. In general, the liquid dosage form is prepared by uniformly and intimately mixing these various components in the liquid medium. For example, the components such as glycerol or syrup or the mixture thereof, a preservative, a buffer system and a suspending/stabilizing agent, etc., can be dissolved in water to form the aqueous solution, then the active ingredient can be then dispersed in the aqueous solution to form a suspension.

In some embodiments, the liquid dosage form provided herein can be in a volume of between about 5 ml to about 50 ml. In some embodiments, the liquid dosage form provided herein can be in a volume of between about 5 ml to about 40 ml. In some embodiments, the liquid dosage form provided herein can be in a volume of between about 5 ml to about 30 ml. In some embodiments, the liquid dosage form provided herein can be in a volume of between about 5 ml to about 20 ml. In some embodiments, the liquid dosage form provided herein can be in a volume of between about 10 ml to about 30 ml. In some embodiments, the liquid dosage form provided herein can be in a volume of about 20 ml. In some embodiments, the ASBTI can be in an amount ranging from about 0.001% to about 90% of the total volume. In some embodiments, the ASBTI can be in an amount ranging from about 0.01% to about 80% of the total volume. In some embodiments, the ASBTI can be in an amount ranging from about 0.10% to about 70% of the total volume. In some embodiments, the ASBTI can be in an amount ranging from about 1% to about 60% of the total volume. In some embodiments, the ASBTI can be in an amount ranging from about 1% to about 50% of the total volume. In some embodiments, the ASBTI can be in an amount ranging from about 1% to about 40% of the total volume. In some embodiments, the ASBTI can be in an amount ranging from about 1% to about 30% of the total volume. In some embodiments, the ASBTI can be in an amount ranging from about 1% to about 20% of the total volume. In some embodiments, the ASBTI can be in an amount ranging from about 1% to about 10% of the total volume. In some embodiments, the ASBTI can be in an amount ranging from about 5% to about 70% of the total volume. In some embodiments, the ASBTI can be in an amount ranging from about 5% to about 60% of the total volume. In some embodiments, the ASBTI can be in an amount ranging from about 5% to about 50% of the total volume. In some embodiments, the ASBTI can be in an amount ranging from about 5% to about 40% of the total volume. In some embodiments, the ASBTI can be in an amount ranging from about 5% to about 30% of the total volume. In some embodiments, the ASBTI can be in an amount ranging from about 5% to about 20% of the total volume. In some embodiments, the ASBTI can be in an amount ranging from about 5% to about 10% of the total volume. In some embodiments, the ASBTI can be in an amount ranging from about 10% to about 50% of the total volume. In some embodiments, the ASBTI can be in an amount ranging from about 10% to about 40% of the total volume. In some embodiments, the ASBTI can be in an amount ranging from about 10% to about 30% of the total volume. In some embodiments, the ASBTI can be in an amount ranging from about 10% to about 20% of the total volume. In one embodiment, the resulted liquid dosage form can be in a liquid volume of 10 ml to 30 ml, preferably 20 ml, and the active ingredient can be in an amount ranging from about 0.001 mg/ml to about 16 mg/ml, or from about 0.025 mg/ml to about 8 mg/ml, or from about 0.1 mg/ml to about 4 mg/ml, or about 0.25 mg/ml, or about 0.5 mg/ml, or about 1 mg/ml, or about 2 mg/ml, or about 4 mg/ml, or about 5 mg/ml, or about 8 mg/ml, or about 10 mg/ml, or about 12 mg/ml, or about 14 mg/ml or about 16 mg/ml.

Bile Acid Sequestrant

In certain embodiments, an oral formulation for use in any method described herein is, e.g., an ASBTI in association with a labile bile acid sequestrant. A labile bile acid sequestrant is a bile acid sequestrant with a labile affinity for bile acids. In certain embodiments, a bile acid sequestrant described herein is an agent that sequesters (e.g., absorbs or is charged with) bile acid, and/or the salts thereof.

In specific embodiments, the labile bile acid sequestrant is an agent that sequesters (e.g., absorbs or is charged with) bile acid, and/or the salts thereof, and releases at least a portion of the absorbed or charged bile acid, and/or salts thereof in the distal gastrointestinal tract (e.g., the colon, ascending colon, sigmoid colon, distal colon, rectum, or any combination thereof). In certain embodiments, the labile bile acid sequestrant is an enzyme dependent bile acid sequestrant. In specific embodiments, the enzyme is a bacterial enzyme. In some embodiments, the enzyme is a bacterial enzyme found in high concentration in human colon or rectum relative to the concentration found in the small intestine. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like. In some embodiments, the labile bile acid sequestrant is a time dependent bile acid sequestrant (i.e., the bile acid sequesters the bile acid and/or salts thereof and after a time releases at least a portion of the bile acid and/or salts thereof). In some embodiments, a time dependent bile acid sequestrant is an agent that degrades in an aqueous environment over time. In certain embodiments, a labile bile acid sequestrant described herein is a bile acid sequestrant that has a low affinity for bile acid and/or salts thereof, thereby allowing the bile acid sequestrant to continue to sequester bile acid and/or salts thereof in an environ where the bile acids/salts and/or salts thereof are present in high concentration and release them in an environ wherein bile acids/salts and/or salts thereof are present in a lower relative concentration. In some embodiments, the labile bile acid sequestrant has a high affinity for a primary bile acid and a low affinity for a secondary bile acid, allowing the bile acid sequestrant to sequester a primary bile acid or salt thereof and subsequently release a secondary bile acid or salt thereof as the primary bile acid or salt thereof is converted (e.g., metabolized) to the secondary bile acid or salt thereof. In some embodiments, the labile bile acid sequestrant is a pH dependent bile acid sequestrant. In some embodiments, the pH dependent bile acid sequestrant has a high affinity for bile acid at a pH of 6 or below and a low affinity for bile acid at a pH above 6. In certain embodiments, the pH dependent bile acid sequestrant degrades at a pH above 6.

In some embodiments, labile bile acid sequestrants described herein include any compound, e.g., a macrostructured compound, that can sequester bile acids/salts and/or salts thereof through any suitable mechanism. For example, in certain embodiments, bile acid sequestrants sequester bile acids/salts and/or salts thereof through ionic interactions, polar interactions, static interactions, hydrophobic interactions, lipophilic interactions, hydrophilic interactions, steric interactions, or the like. In certain embodiments, macrostructured compounds sequester bile acids/salts and/or sequestrants by trapping the bile acids/salts and/or salts thereof in pockets of the macrostructured compounds and, optionally, other interactions, such as those described above. In some embodiments, bile acid sequestrants (e.g., labile bile acid sequestrants) include, by way of non-limiting example, lignin, modified lignin, polymers, polycationic polymers and copolymers, polymers and/or copolymers comprising anyone one or more of N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof, or any combination thereof.

Covalent Linkage of the Drug with a Carrier

In some embodiments, strategies used for colon targeted delivery include, by way of non-limiting example, covalent linkage of the ASBTI or other compounds described herein to a carrier, coating the dosage form with a pH-sensitive polymer for delivery upon reaching the pH environment of the colon, using redox sensitive polymers, using a time released formulation, utilizing coatings that are specifically degraded by colonic bacteria, using bioadhesive system and using osmotically controlled drug delivery systems.

In certain embodiments of such oral administration of a composition containing an ASBTI or other compounds described herein involves covalent linking to a carrier wherein upon oral administration the linked moiety remains intact in the stomach and small intestine. Upon entering the colon, the covalent linkage is broken by the change in pH, enzymes, and/or degradation by intestinal microflora. In certain embodiments, the covalent linkage between the ASBTI and the carrier includes, by way of non-limiting example, azo linkage, glycoside conjugates, glucuronide conjugates, cyclodextrin conjugates, dextran conjugates, and amino-acid conjugates (high hydrophilicity and long chain length of the carrier amino acid).

Coating with Polymers: pH-Sensitive Polymers

In some embodiments, the oral dosage forms described herein are coated with an enteric coating to facilitate the delivery of an ASBTI or other compounds described herein to the colon and/or rectum. In certain embodiments, an enteric coating is one that remains intact in the low pH environment of the stomach, but readily dissolved when the optimum dissolution pH of the particular coating is reached which depends upon the chemical composition of the enteric coating. The thickness of the coating will depend upon the solubility characteristics of the coating material. In certain embodiments, the coating thicknesses used in such formulations described herein range from about 25 µm to about 200 µm.

In certain embodiments, the compositions or formulations described herein are coated such that an ASBTI or other compounds described herein of the composition or formulation is delivered to the colon and/or rectum without absorbing at the upper part of the intestine. In a specific embodiment, specific delivery to the colon and/or rectum is achieved by coating of the dosage form with polymers that degrade only in the pH environment of the colon. In alternative embodiments, the composition is coated with an enteric coat that dissolves in the pH of the intestines and an outer layer matrix that slowly erodes in the intestine. In some of such embodiments, the matrix slowly erodes until only a core composition comprising an enteroendocrine peptide secretion enhancing agent (and, in some embodiments, an absorption inhibitor of the agent) is left and the core is delivered to the colon and/or rectum.

In certain embodiments, pH-dependent systems exploit the progressively increasing pH along the human gastrointestinal tract (GIT) from the stomach (pH 1-2 which increases to 4 during digestion), small intestine (pH 6-7) at the site of digestion and it to 7-8 in the distal ileum. In certain embodiments, dosage forms for oral administration of the compositions described herein are coated with pH-sensitive polymer(s) to provide delayed release and protect the enteroendocrine peptide secretion enhancing agents from gastric fluid. In certain embodiments, such polymers are be able to withstand the lower pH values of the stomach and of the proximal part of the small intestine but disintegrate at the neutral or slightly alkaline pH of the terminal ileum and/or ileocecal junction. Thus, in certain embodiments, provided herein is an oral dosage form comprising a coating, the coating comprising a pH-sensitive polymer. In some embodiments, the polymers used for colon and/or rectum targeting include, by way of non-limiting example, methacrylic acid copolymers, methacrylic acid and methyl methacrylate copolymers, Eudragit L100, Eudragit S100, Eudragit L-30D, Eudragit FS-30D, Eudragit L100-55, polyvinylacetate phthalate, hydroxypropyl ethyl cellulose phthalate, hydroxypropyl methyl cellulose phthalate 50, hydroxypropyl methyl cellulose phthalate 55, cellulose acetate trimellitate, cellulose acetate phthalate and combinations thereof.

In certain embodiments, oral dosage forms suitable for delivery to the colon and/or rectum comprise a coating that has a biodegradable and/or bacteria degradable polymer or polymers that are degraded by the microflora (bacteria) in the colon. In such biodegradable systems suitable polymers include, by way of non-limiting example, azo polymers, linear-type-segmented polyurethanes containing azo groups, polygalactomannans, pectin, glutaraldehyde crosslinked dextran, polysaccharides, amylose, guar gum, pectin, chitosan, inulin, cyclodextrins, chondroitin sulphate, dextrans, locust bean gum, chondroitin sulphate, chitosan, poly(-caprolactone), polylactic acid and poly(lactic-co-glycolic acid).

In certain embodiments of such oral administration of compositions containing one or more ASBTIs or other compounds described herein, the compositions are delivered to the colon without absorbing at the upper part of the intestine by coating of the dosage forms with redox sensitive polymers that are degraded by the microflora (bacteria) in the colon. In such biodegradable systems such polymers include, by way of non-limiting example, redox-sensitive polymers containing an azo and/or a disulfide linkage in the backbone.

In some embodiments, compositions formulated for delivery to the colon and/or rectum are formulated for time-release. In some embodiments, time release formulations resist the acidic environment of the stomach, thereby delaying the release of the enteroendocrine peptide secretion enhancing agents until the dosage form enters the colon and/or rectum.

In certain embodiments the time released formulations described herein comprise a capsule (comprising an enteroendocrine peptide secretion enhancing agent and an optional absorption inhibitor) with hydrogel plug. In certain embodiments, the capsule and hydrogel plug are covered by a water-soluble cap and the whole unit is coated with an enteric polymer. When the capsule enters the small intestine the enteric coating dissolves and the hydrogels plug swells and dislodges from the capsule after a period of time and the composition is released from the capsule. The amount of hydrogel is used to adjust the period of time to the release the contents.

In some embodiments, provided herein is an oral dosage form comprising a multi-layered coat, wherein the coat comprises different layers of polymers having different pH-sensitivities. As the coated dosage form moves along GIT the different layers dissolve depending on the pH encountered. Polymers used in such formulations include, by way of non-limiting example, polymethacrylates with appropriate pH dissolution characteristics, Eudragit® RL and Eudragit®RS (inner layer), and Eudragit® FS (outer layer). In other embodiments the dosage form is an enteric coated tablets having an outer shell of hydroxypropylcellulose or hydroxypropylmethylcellulose acetate succinate (HPMCAS).

In some embodiments, provided herein is an oral dosage form that comprises coat with cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxopropyl methylcellulose succinate, carboxymethyl ethylcellulose, hydroxypropyl methylcellulose acetate succinate, polymers and copolymers formed from acrylic acid, methacrylic acid, and combinations thereof.

Combination Therapy

In some embodiments, the methods provided herein comprise administering a compound (e.g., an ASBTI) or composition described herein in combination with one or more additional agents. In some embodiments, the present invention also provides a composition comprising a compound (e.g., an ASBTI) with one or more additional agents.

Fat Soluble Vitamins

In some embodiments, the methods provided herein further comprise administering one or more vitamins. In some embodiments, the vitamin is vitamin A, B1, B2, B3, B5, B6, B7, B9, B12, C, D, E, K, folic acid, pantothenic acid, niacin, riboflavin, thiamine, retinol, beta carotene, pyridoxine, ascorbic acid, cholecalciferol, cyanocobalamin, tocopherols, phylloquinone, menaquinone.

In some embodiments, the vitamin is a fat soluble vitamin such as vitamin A, D, E, K, retinol, beta carotene, cholecalciferol, tocopherols, phylloquinone. In a preferred embodiment, the fat soluble vitamin is tocopherol polyethylene glycol succinate (TPGS).

ASBTIs and PPAR Agonists

In various embodiments, the present invention provides methods of use of combinations of ASBTIs with PPAR (peroxisome proliferator-activated receptor) agonists. In various embodiments, the PPAR agonist is a fibrate drug. In some embodiments, the fibrate drug is clofibrate, gemfibrozil, ciprofibrate, benzafibrate, fenofibrate, or various combinations thereof. In various embodiments, the PPAR agonist is aleglitazar, muraglitazar, tesaglitazar, saroglitazar, GW501516, GW-9662, a thiazolidinedione (TZD), a NSAID (e.g., IBUPROFEN), an indole, or various combinations thereof.

ASBTIs and FXR Drugs

In various embodiments, the present invention provides methods of use of combinations of ASBTIs with farnesoid X receptor (FXR) targeting drugs. In various embodiments, the FXR targeting drug is avermectin B1a, bepridil, fluticasone propionate, GW4064, gliquidone, nicardipine, triclosan, CDCA, ivermectin, chlorotrianisene, tribenoside, mometasone furoate, miconazole, amiodarone, butoconazole, bromocryptine mesylate, pizotifen malate, or various combinations thereof.

Partial External Biliary Diversion (PEBD)

In some embodiments, the methods provided herein further comprise using partial external biliary diversion as a treatment for patients who have not yet developed cirrhosis. This treatment helps reduce the circulation of bile acids/salts in the liver in order to reduce complications and prevent the need for early transplantation in many patients.

This surgical technique involves isolating a segment of intestine 10 cm long for use as a biliary conduit (a channel for the passage of bile) from the rest of the intestine. One end of the conduit is attached to the gallbladder and the other end is brought out to the skin to form a stoma (a surgically constructed opening to permit the passage of waste). Partial external biliary diversion may be used for patients who are unresponsive to all medical therapy, especially older, larger patients. This procedure may not be of help to young patients such as infants. Partial external biliary diversion may decrease the intensity of the itching and abnormally low levels of cholesterol in the blood.

ASBTI and Ursodiol

In some embodiments, an ASBTI is administered in combination with ursodiol or ursodeoxycholic acid, chenodeoxycholic acid, cholic acid, taurocholic acid, ursocholic acid, glycocholic acid, glycodeoxycholic acid, taurodeoxycholic acid, taurocholate, glycochenodeoxycholic acid, tauroursodeoxycholic acid. In some instances, an increase in the concentration of bile acids/salts in the distal intestine induces intestinal regeneration, attenuating intestinal injury, reducing bacterial translocation, inhibiting the release of free radical oxygen, inhibiting production of proinflammatory cytokines, or any combination thereof or any combination thereof.

In certain embodiments, the patient is administered ursodiol at a daily dose of about or of at least about 5 mg, 10 mg, 15 mg, 20 mg, 25 mg, 30 mg, 35 mg, 36 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,250 mg, 1,500 mg, 1,750 mg, 2,000 mg, 2,250 mg, 2,500 mg, 2,750 mg, or 3,000 mg. In certain embodiments, the patient is administered ursodiol at a daily dose of about or of no more than about 10 mg, 15 mg, 20 mg, 25 mg, 30 mg, 35 mg, 36 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,250 mg, 1,500 mg, 1,750 mg, 2,000 mg, 2,250 mg, 2,500 mg, 2,750 mg, 3,000 mg, or 3,500 mg. In various embodiments, the patient is administered ursodiol at a daily dose of about or of at least about 3 mg to about 300 mg, about 30 mg to about 250 mg, from about 36 mg to about 200 mg, from about 10 mg to about 3000 mg, from about 1000 mg to about 2000 mg, or from about 1500 to about 1900 mg.

In various embodiments the ursodiol is administered as a tablet. In various embodiments, the ursodiol is administered as a suspension. In various embodiments, the concentration of ursodiol in the suspension is from about 10 mg/mL to about 200 mg/mL, from about 50 mg/mL to about 150 mg/mL, from about 10 mg/mL to about 500 mg/mL, or from about 40 mg/mL to about 60 mg/mL. In various embodiments, the concentration of ursodiol in suspension is about or is at least about 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, or 80 mg/mL. In various embodiments, the concentration of ursodiol in suspension is no more than about 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, or 85 mg/mL.

An ASBTI and a second active ingredient are used such that the combination is present in a therapeutically effective amount. That therapeutically effective amount arises from the use of a combination of an ASBTI and the other active ingredient (e.g., ursodiol) wherein each is used in a therapeutically effective amount, or by virtue of additive or synergistic effects arising from the combined use, each can also be used in a subclinical therapeutically effective amount, i.e., an amount that, if used alone, provides for reduced effectiveness for the therapeutic purposes noted herein, provided that the combined use is therapeutically effective. In some embodiments, the use of a combination of an ASBTI and any other active ingredient as described herein encompasses combinations where the ASBTI or the other active ingredient is present in a therapeutically effective amount, and the other is present in a subclinical therapeutically effective amount, provided that the combined use is therapeutically effective owing to their additive or synergistic effects. As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone. Any suitable combination of an ASBTI with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing; e.g, from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In certain embodiments, provided herein are combination therapies. In certain embodiments, the compositions described herein comprise an additional therapeutic agent. In some embodiments, the methods described herein comprise administration of a second dosage form comprising an additional therapeutic agent. In certain embodiments, combination therapies the compositions described herein are administered as part of a regimen. Therefore, additional therapeutic agents and/or additional pharmaceutical dosage form can be applied to a patient either directly or indirectly, and concomitantly or sequentially, with the compositions and formulations described herein.

Kits

In another aspect, provided herein are kits containing a device for rectal administration pre-filled a pharmaceutical composition described herein. In certain embodiments, kits contain a device for oral administration and a pharmaceutical composition as described herein. In certain embodiments the kits include prefilled sachet or bottle for oral administration, while in other embodiments the kits include prefilled bags for administration of rectal gels. In certain embodiments the kits include prefilled syringes for administration of oral enemas, while in other embodiments the kits include prefilled syringes for administration of rectal gels. In certain embodiments the kits include prefilled pressurized cans for administration of rectal foams.

Release in Distal Ileum and/or Colon

In certain embodiments, a dosage form comprises a matrix (e.g., a matrix comprising hypromellose) that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an ASBTI to the distal ileum. In some embodiments, a dosage form comprising an ASBTI is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the ASBTI. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An ASBT inhibitor may be used in the preparation of medicaments for the prophylactic and/or therapeutic treatment of cholestasis or a cholestatic liver disease. A method for treating any of the diseases or conditions described herein in an individual in need of such treatment, may involve administration of pharmaceutical compositions containing at least one ASBT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

EXAMPLES

The following examples are provided to further describe some of the embodiments disclosed herein. The examples are intended to illustrate, not to limit, the disclosed embodiments.

Example 1. Phase 2 Open-Label Efficacy and Safety Study of the Apical Sodium-Dependent Bile Acid Transporter Inhibitor Maralixibat in Children with Progressive Familial Intrahepatic Cholestasis (INDIGO Clinical Study)

Figure 2:
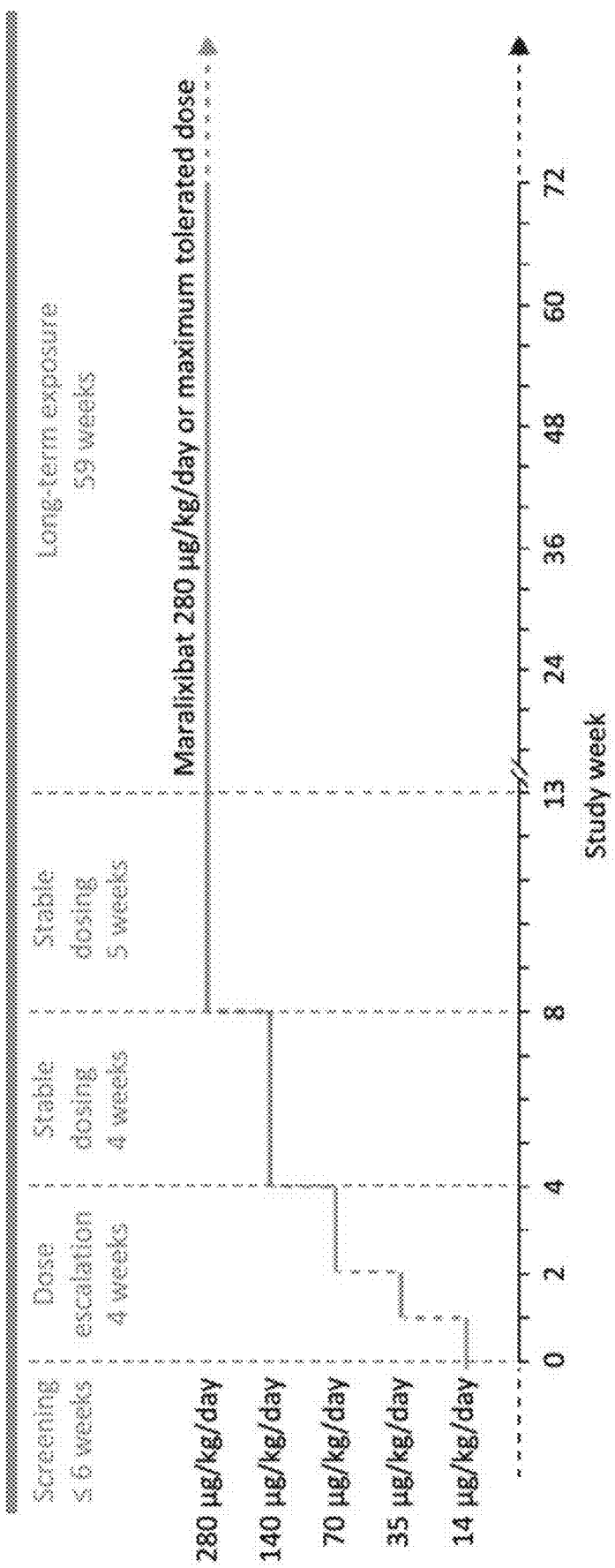
FIG. 2 shows a schematic providing an overview of a dosing regimen used in an INDIGO phase 2 open-label safety and efficacy clinical study (INDIGO clinical study) of maralixibat in children with PFIC. The clinical study investigated long-term exposure to maralixibat.

The dosing regimen used in the INDIGO clinical study is summarized in FIG. 2. In addition to the doses indicated in FIG. 2, some patients were administered a dose of 280 µg/kg twice a day (BID) after initially being administered a dose of 280 µg/kg daily (QD). Dosing was escalated up to 280 µg/kg QD over a period of 8 weeks.

Key inclusion criteria for the INDIGO clinical study were the following: 1) aged 1-18 years; 2) clinically diagnosed with PFIC; 3) two mutant ABCB11 or ATB8B1 alleles. Key exclusion criteria for the INDIGO clinical study were the following: 1) surgically disrupted enterohepatic circulation; 2) liver transplant; 3) decompensated cirrhosis.

The following cholestasis biomarkers were monitored in the INDIGO clinical study, among others: serum bile acid concentration (sBA); serum alanine aminotransferase (ALT) concentration; serum aspartate aminotransferase (AST) concentration; serum bilirubin concentration; and serum 7αC4 concentration. Fecal bile acid (fBA) concentration was also measured. Severity of pruritus was assessed throughout the INDIGO clinical study using observer-reported itch-reported outcome (ITCHRO(OBS)) weekly average score (parent-rated e-diary) and clinician scratch scale (CSS) score (investigator-rated). Patients were also administered a health-related quality of life (HRQoL) assessment throughout the INDIGO clinical study. The HRQoL used was the PEDIATRIC QUALITY OF LIFE INVENTORY (PedsQL). Multi-parameter response was defined by a greater than 70% reduction or normalization in sBA concentration and a greater than 1.0 reduction or lower than 1.0 in ITCHRO (OBS) score.

Figure 5A:
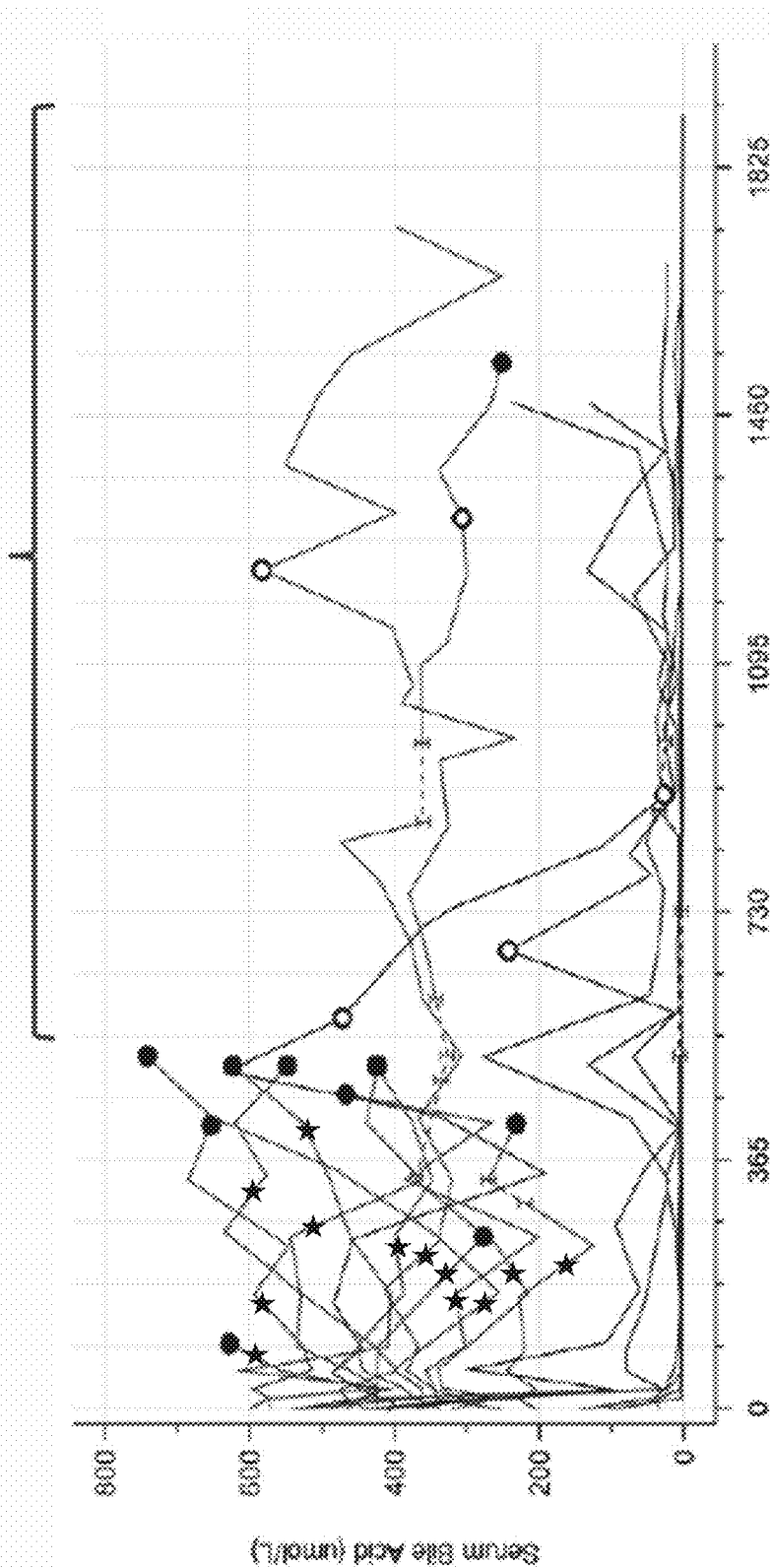
FIGS. 5A and 5B provide scatter plots plotting serum bile acids (sBA) concentration over time for patients that participated in the INDIGO clinical study.

Table 1 provides a summary of demographics and baseline health-related parameters for participants in the INDIGO clinical study. Of 25 participants suffering PFIC 2, 19 participants had non-truncating ABCB11 mutations (classified as mild or moderate) and 6 participants had truncating ABCB11 mutations, see Tables 2-3 and 5. 29 participants reached week 48, see Table 4. Mild PFIC 2 was defined as PFIC 2 resulting from a E297G or a D482G mutation, or both, to the ABCB11 gene while moderate PFIC 2 was defined as PFIC 2 resulting from an ABCB11 gene comprising missense mutations but not comprising a E297G or a D482G mutation, see Table 3. Of the 19 participants having non-truncating ABCB11 mutations, 7 suffered mild PFIC 2 and 12 suffered moderate PFIC 2, see Table 3 and Table 5. One patient (1 of 7 mild PFIC 2 patients) suffering mild PFIC 2 was a multi-parameter responder in the INDIGO clinical study at a dose of 280 µg/kg QD, see Tables 3, 4, and 6. One patient (1 of 12 moderate PFIC 2 patients) suffering moderate PFIC 2 only demonstrated responsiveness (high-dose responder) after being administered a dose of maralixibat of 280 µg/kg twice daily (discussed further below), see Tables 3, 4, and 8. Five patients (5 of 12 moderate PFIC 2 patients) were responders in the INDIGO clinical study at a dose of 280 µg/kg/day by week 48 of the INDIGO clinical study, see Tables 3-9. All PFIC 1 patients and all patients harboring a truncating ABCB11 mutation were not multi-parameter responders in the INDIGO clinical study, see Tables 3, 5 and FIG. 5.

Patients indicated as having no response in Table 3 demonstrated no response within the times and at the maximum dosages provided in Table 6. Patients showing no response, therefore, may have demonstrated a response if administered maralixibat at a higher dose or for a longer time duration.

TABLE 1

Baseline disease characteristics and demographics for participants in the INDIGO clinical study Patient Characteristics

| N = 33 | PFIC1, n = 8 FIC1 def. | PFIC2, n = 25 BSEP def. |
|---|---|---|
| Median Age (range), year | 2.0 (1-7) | 4.0 (1-13) |
| Boys, n (%) | 6 (75) | 8 (32) |
| White, n (%) | 6 (75) | 20 (80) |
| Serum bile acid (range) µmol/L | 261.9 (159.8-423.5) | 381.0 (34.4-602.1) |
| Mean (SD) z = scores | | |
| Height | −2.96 (1.47) | −1.29 (0.98) |
| Weight | −2.70 (2.82) | −0.63 (0.88) |

TABLE 2

Genetic status of participants in the INDIGO clinical study having PFIC 2

BSEP Genetic Status

| | Participants (n) |
|---|---|
| Non-truncating (mild/moderate) | 19 |
| Truncating | 6 |

TABLE 3

ABCB11 genotypes, PFIC 2 classifications, and observed responses for PFIC 2 participants in the INDIGO clinical study

| Subject ID | Mutation 1 cDNA | Mutation 1 Protein | Mutation 2 cDNA | Mutation 2 Protein | Classification | Response |
|---|---|---|---|---|---|---|
| 001051-J-D | c.149T>C | Leu50Ser | c.3667G>A | Glu1223Lys | Moderate | No reponse |
| 001053-M-E | c.890A>G | Glu297Gly | c.890A>G | Glu297Gly | Mild | No reponse |
| 001054-LOA | c.2495G>A | Arg832His | c.2842C>T | Arg948Cys | Moderate | Rapid complete response |
| 001055-H-B | c. 2611-2 A>T | Splice site | c. 2611-2 A>T | Splice site | Severe | No reponse |
| 001057-W-R | c.319T>C | Cys107Arg | c.319T>C | Cys107Arg | Moderate | No reponse |
| 001060 | c.319T>C | Cys107Arg | c.319T>C | Cys107Arg | Moderate | No reponse |
| 002052-M-H | c. 1145-1165del | p.Ala382_Ala388del | c.2787_2788insGAGAT | p.Lys930Glufs*79 | Severe | No reponse |
| 002053-E-B | c.499G>A | p.A167T | c.3457G>A | p.R1153S | Moderate | No reponse |
| 002054-KRD | c.149T>C | p.L50S | c.890A>G | p.E297G | Mild | No reponse |
| 003052-R-C | c.890A>G | Glu297Gly | c.2012-8T>G | Splice site | Mild | No reponse |
| 003053-A-J | c.890A>G | Glu297Gly | c.2842C>T | Arg948Cys | Mild | No reponse |
| 013051-T-C | c.403G>A | E135K | c.1012-8T>G | Splice site | Moderate | No reponse |
| 013052-JMC | c. 1408C>T | p.R470* | c.3945delC | p.T1316Lfs*64 | Severe | No reponse |
| 014051 | c.1460G>C | p.(Arg487Pro) | c.2944G>A | p.(Gly982Arg) | Moderate | No reponse |
| 016051 ---- | c.470A>G | p.Y157C | c.3892G>A | p.G1298R | Moderate | Rapid complete response |

TABLE 3-continued

ABCB11 genotypes, PFIC 2 classifications, and observed responses for PFIC 2 participants in the INDIGO clinical study

| Subject ID | Mutation 1 cDNA | Mutation 1 Protein | Mutation 2 cDNA | Mutation 2 Protein | Classification | Response |
|---|---|---|---|---|---|---|
| 016052 ---- | c.470A>G | p.Y157C | c.3892G>A | p.G1298R | Moderate | Rapid complete response |
| 016053 ---- | c.757G>A | Gly253 Arg | c. 1769A>G | Asp590Gly | Moderate | Good response |
| 016054 ---- | c.2783_2787dupGAGAT | Lys930Glufs*79 | c. 1769A>G | Asp590Gly | Moderate | No response until 560 reached |
| 027051-T-S | c.3457C>T | Arg1153Cys | c.3476T>C | Val1159Ala | Moderate | Rapid complete response |
| 027052-AJC | c.890A>G | Glu297Gly | c.3491delT | Val1164Glyfs7 | Mild | No reponse |
| 027053-VJB | c.890A>G | Glu297Gly | c.890A>G | Glu297Gly | Mild | No reponse |
| 052051-S-C | c.1826_1827insCA | Ile610fs | c. 1826_1827insCA | Ile610fs | Severe | No reponse |
| 052052-S-M | c.1827_1828insCA | Ile610fs | c. 1827_1828insCA | Ile610fs | Severe | No reponse |
| 052054 | c.1062T>A | Tyr354Ter | 1052T>A | Tyr354Ter | Severe | No reponse |
| 080051-L-M | c.1558A>T | p.(Arg520Ter) | c. 1445A>G | p.Asp482Gly | Mild | >70% reduction in BAs |

TABLE 4

Disposition of patients in the INDIGO study to week 48

| | |
|---|---|
| Reached week 48, n | 29 |
| Efficacy data available, n | 26 |
| PFIC1 | 6 |
| PFIC2 | 20 |
| Maralixibat dose, n | |
| 280 µg/kg/day | 23 |
| 140 µg/kg/day | 2 |
| <140 µg/kg/day[a] | 1 |

[a] One patient receiving 280 µ/kg/day had a treatment interruption and was re-escalated at week 48

TABLE 5

Summary of subject PFIC genotype status for responders in the INDIGO clinical study

| Subject Genotype Status | Multi-parameter Responders |
|---|---|
| Non-truncating BSEP (N = 19) | 7/19 (36.8%) |
| Mild (N = 7) | 1/7 (14.3%) |
| Moderate (N = 12) | 6/12 (50%) |
| Truncating BSEP (N = 6) | 0/6 (0%) |

TABLE 6

Study duration and max dose for participants in the INDIGO clinical study

| Subject ID | Max dose | Study duration |
|---|---|---|
| 001051-J-D | 280 | 72 weeks |
| 001053-M-E | 280 | 72 weeks |
| 001054-LOA | 280 | 1328 days |
| 001055-H-B | 280 | 124 weeks |
| 001057-W-R | 560 | 1247 days |
| 001060 | 280 | 60 weeks |
| 002052-M-H | 280 | 86 weeks |
| 002053-E-B | 280 | 60 weeks |
| 002054-KRD | 280 | 72 weeks |
| 003052-R-C | 280 | 72 weeks |
| 003053-A-J | 560 | 1127 days |
| 013051-T-C | 280 | 60 weeks |
| 013052-JMC | 280 | 122 weeks |
| 014051 | 280 | 60 weeks |
| 016051— | 280 | 1218 days |
| 016052— | 280 | 1218 days |
| 016053— | 560 | 1196 days |
| 016054— | 560 | 927 days |
| 027051-T-S | 280 | 1220 days |
| 027052-AJC | 280 | 72 weeks |
| 027053-VJB | 280 | 72 weeks |
| 052051-S-C | 280 | 72 weeks |
| 052052-S-M | 280 | 72 weeks |
| 052054 | 280 | 72 weeks |
| 080051-L-M | 560 | 924 days |

TABLE 7

Summary of efficacy measures at baseline and
changes at week 48 of the INDIGO clinical study

| sBA, μmol/L | ALT, UI/L | Total bilirubin, mg/dL | C4, ng/mL | ItchRO (Obs) score | PedsQL total score |
|---|---|---|---|---|---|
| Baseline, mean (range) | | | | | |
| 352 (34, 602) | 108 (13, 438) | 2.9 (0.1, 15.1) | 4.2 (0.1, 47.3) | 2.3 (0.1, 3.8) | 61.5 (18.1, 85.9) |
| Change from baseline to week 48, mean (95% CI) | | | | | |
| −32 (−110, +46) | −12 (−36, +13) | +0.8 (−0.1, +1.7) | +6.0 (−0.6, +12.5) | −1.0 (−1.4, -0.6) | +8.2 (+0.7, +15.6) |

TABLE 8

Summary of responders observed in PFIC
patients that participated in the INDIGO
clinical study (n = 6) by week 48

| | |
|---|---|
| Diagnosis, n | |
| PFIC1 (ATP8B1 mutation) | 0 |
| PFIC2 (ABCB11 mutation) | 6 |
| Reached week 48, n | 6 |
| Maralixibat dose, n | 6 |
| 280 μg/kg/day | |

TABLE 9

Overview of responses observed in responders in the
INDIGO clinical study (n = 6) by week 48

| | |
|---|---|
| sBA levels, n | |
| Normalized (+≤8.5 μmol/L) | 4 |
| Reduced by >70% or ≥80% from baseline | 2 |
| ItchRO score, n | |
| Zero (no pruritus) | 2 |
| Improved by ≥1.0 points from baseline | 4 |

Therefore, in view of the above observations, patient responsiveness to administration of maralixibat correlated with patient genotype. In particular, the INDIGO clinical study revealed the surprising result that only patients suffering PFIC 2 caused by a non-truncating ABCB11 gene mutation were responders to administration of maralixibat. Additionally, it was unexpectedly found that moderate PFIC 2 patients were more likely to show a response at 280 μg/kg/day of maralixibat than mild PFIC 2 patients, see Tables 3 and 5-6.

The six patients demonstrating a response at 280 μg/kg/day of maralixibat (low-dose responders) demonstrated a decrease in sBA concentration, serum ALT concentration, serum bilirubin concentration, ITCHRO(OBS) score, and PEDSQL score and increase in serum 7αC4 (C4) concentration by week 48 of the INDIGO clinical study, see Table 7. Two of the low-dose responders demonstrated a reduction in sBA from baseline of over 70% or over 80%, see Table 9. Four of the low-dose responders demonstrated a normalization in sBA, see Table 9. A detailed overview of each of the six low-dose responders to maralixibat administration is provided as FIG. 3. All low-dose responders demonstrated an increase in C4 levels of at least 2.5-fold relative to baseline within 13 weeks of first administration of maralixibat in the INDIGO clinical study. All low-dose responders demonstrated establishment of normalized or only mildly elevated concentrations of serum ALT, AST, and bilirubin concentrations over time (e.g., within 2-6 months of first administration of maralixibat) in the INDIGO clinical study.

Figure 3A:
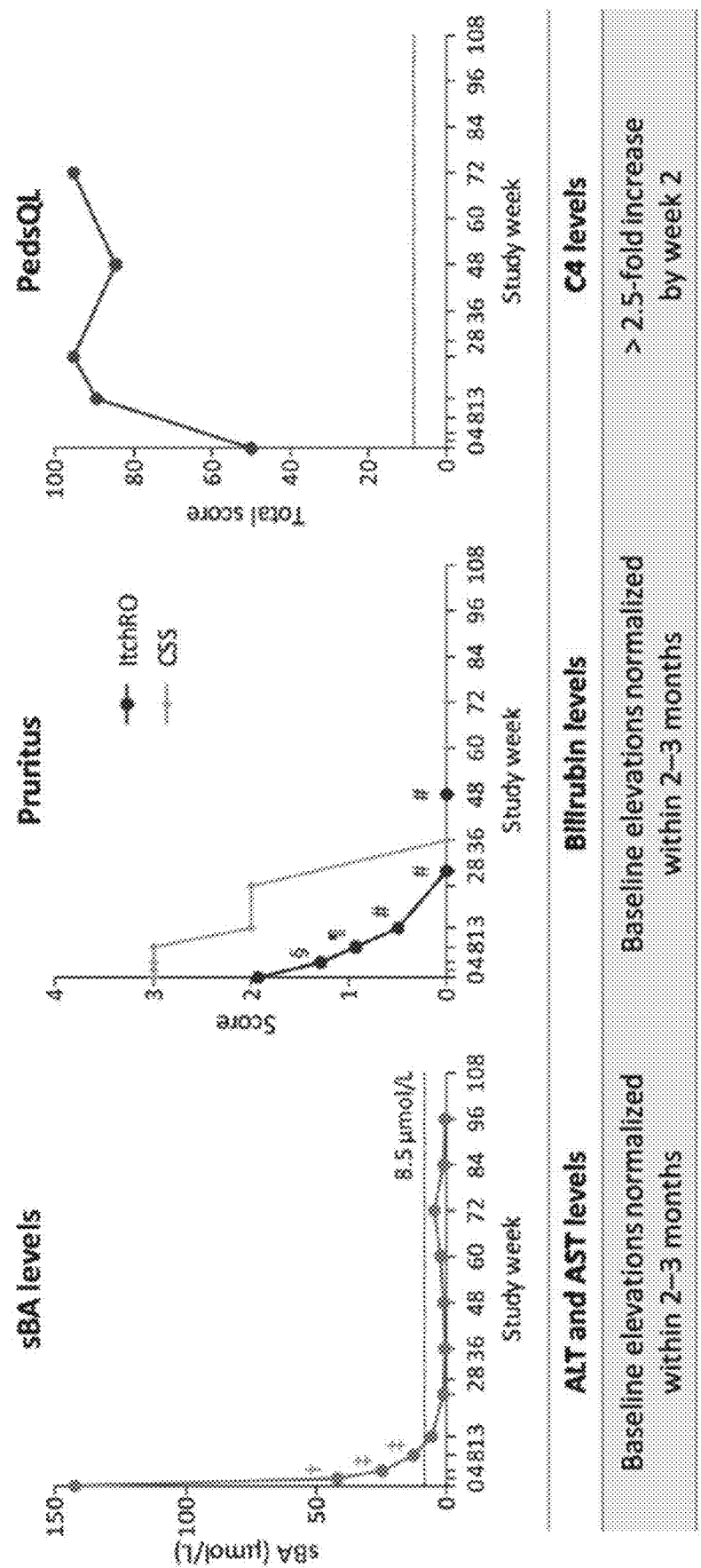
FIGS. 3A-3F each provide quantitative summaries of response indicators measured for six responders that participated in the INDIGO clinical study. The six responders were a girl aged 3 years (FIG. 3A), a boy aged 10 years (FIG. 3B), a girl aged 6 years and sister of the boy aged 10 years (FIG. 3C), a girl aged 4 years (FIG. 3D), a boy aged 3 years (FIG. 3E), and a girl aged 1 year (FIG. 3F). Each of FIGS. 3A-3F provides three scatter plots plotting sBA levels (concentrations), pruritus severity score, and PEDIATRIC QUALITY OF LIFE INVENTORY (PEDSQL) scores against study week, respectively. Pruritus severity score was measured according to the clinical scratch score (CSS) and Itch Reported Outcome (ITCHRO) score. Each of FIGS. 3A-3F also provides a summary of changes observed in ALT (alanine aminotransferase) and AST (aspartate aminotransferase) levels, bilirubin levels, and C4 levels for each responder.
Figure 3B:
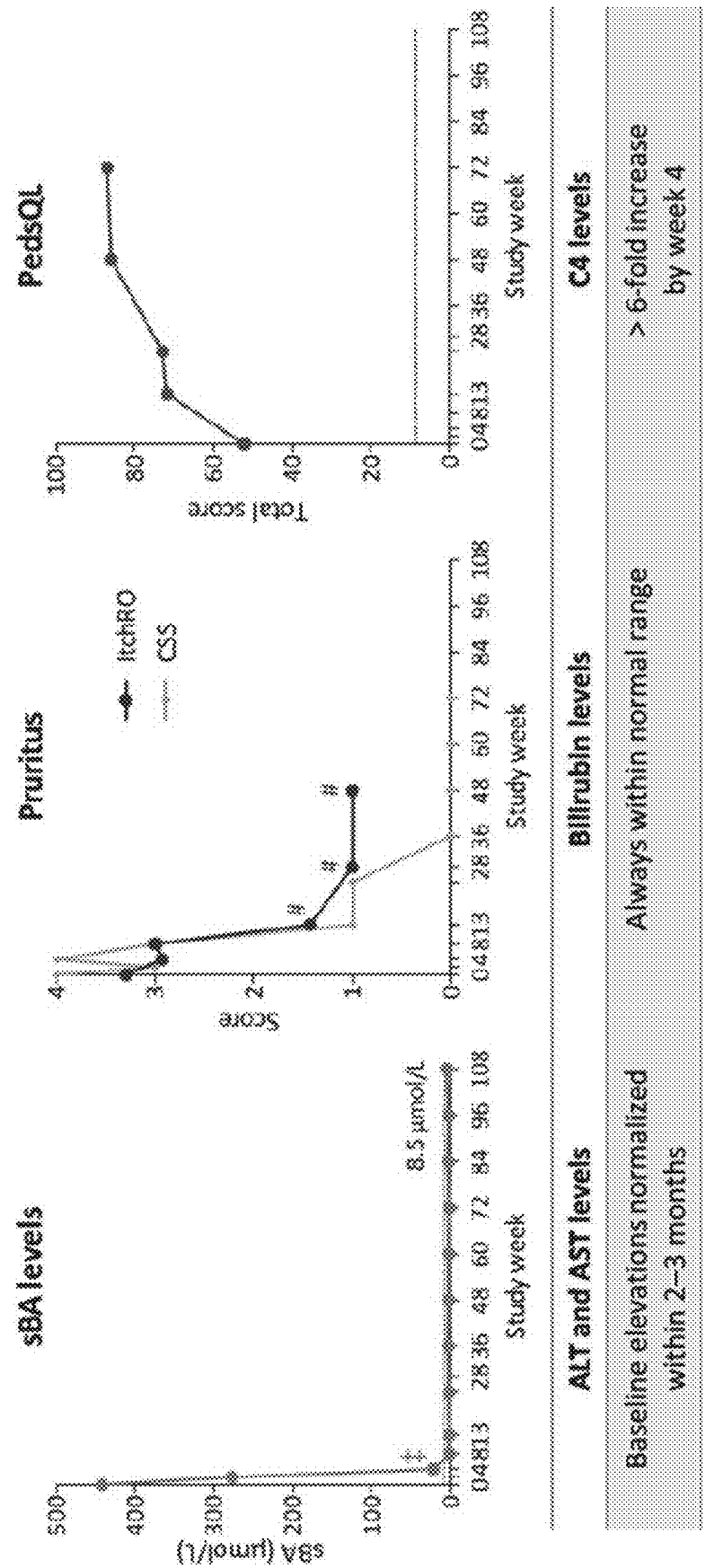
Figure 3C:
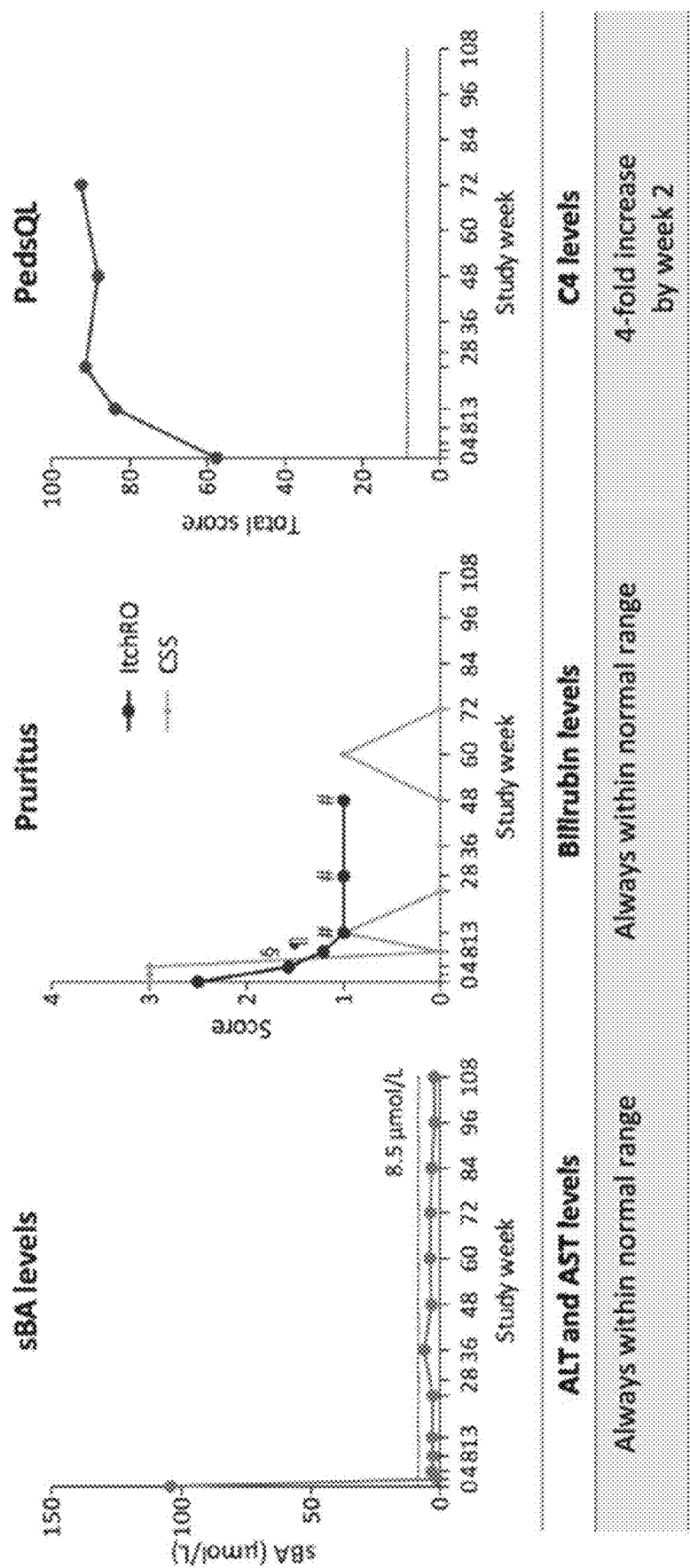
Figure 3D:
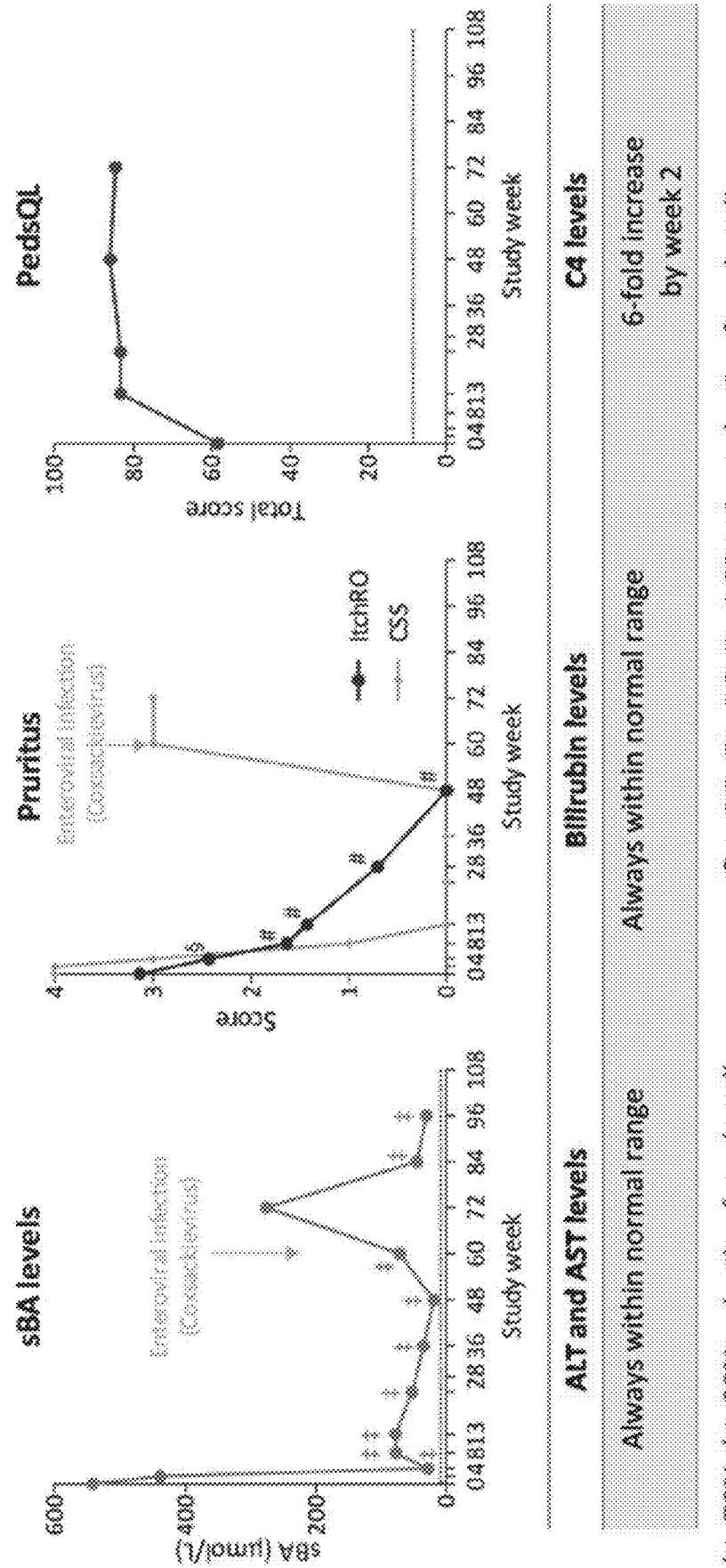
Figure 3E:
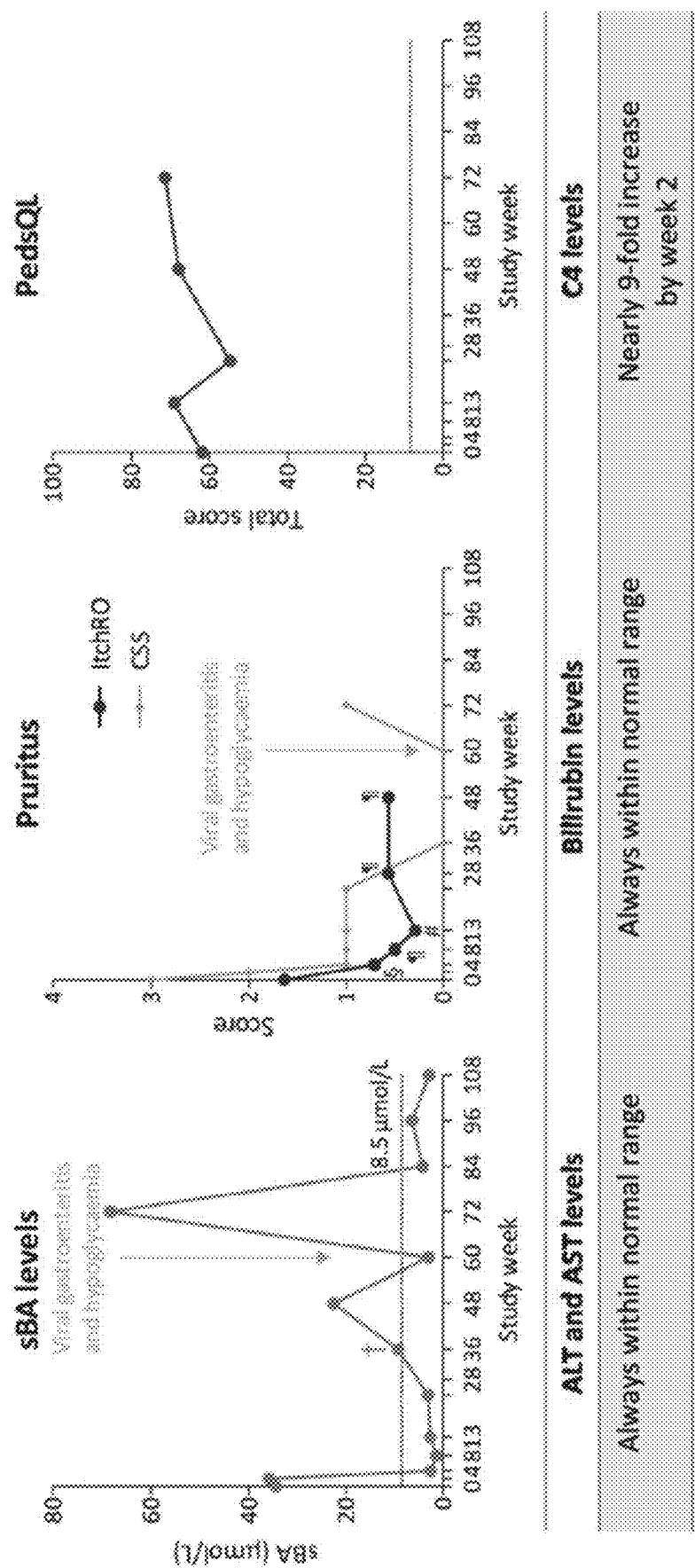
Figure 3F:
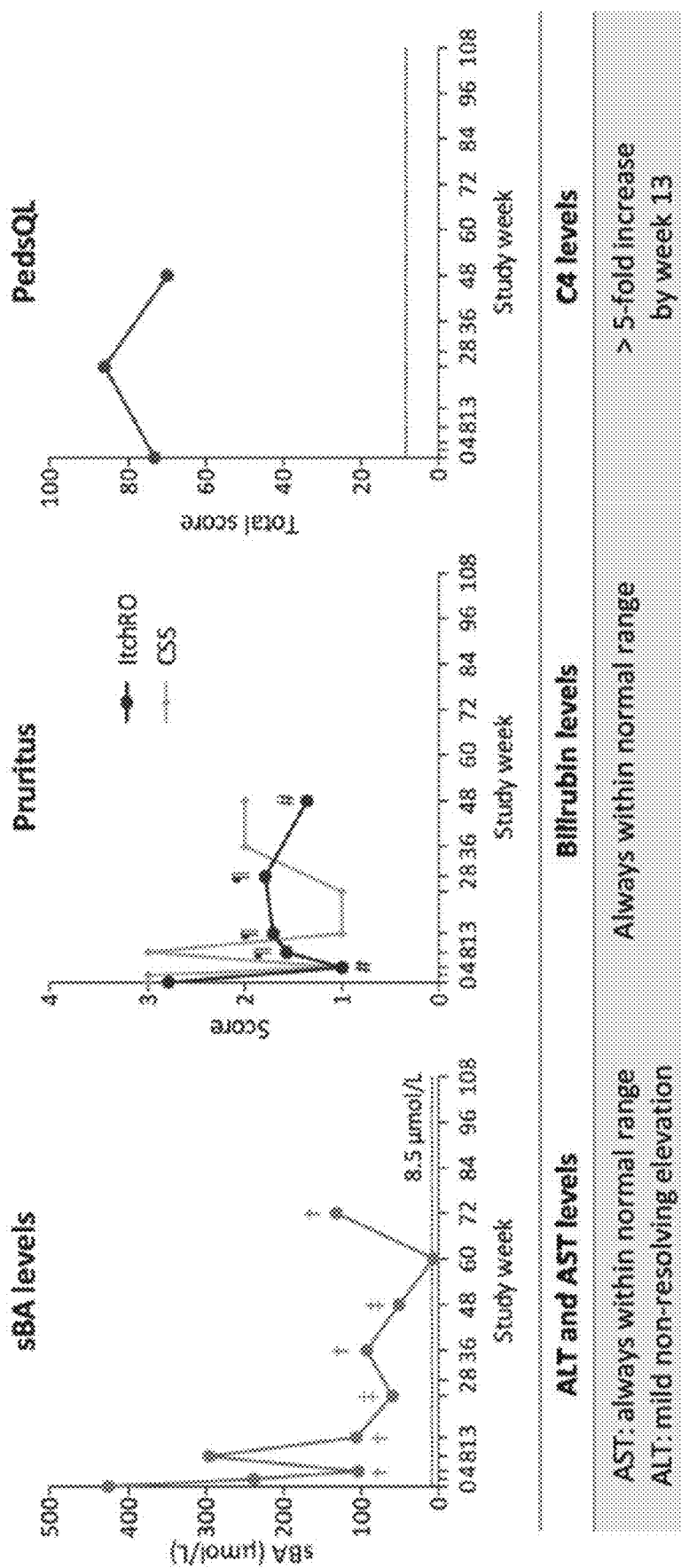

Gastrointestinal infections were found to interfere with of the treatment effect of maralixibat in PFIC 2, see FIGS. 3D and 3E. Therefore, gastrointestinal infections may cause otherwise responsive patients to appear non-responsive to administration of maralixibat.

Three patients that did not demonstrate a response at a dose of 280 μg/kg/day of maralixibat non-truncating PFIC 2 were administered 560 μg/kg/day of maralixibat and one (mentioned above) responded at the higher dose, see Tables 3 and 6.

The low-dose responders demonstrated 7αC4 concentrations at 48 weeks that were 14× baseline (range, 3-43). Non-responder 7αC4 concentrations were 1.8× baseline (range, 0.5-6) at 48 weeks. This demonstrates a correlation between response and increased BA synthesis. The mean change from baseline at week 48 in the ratio of 7αC4 concentration to sBA concentration (7αC4:sBA) for the low-dose responders was 1388 times baseline ratio (range, 5-3982), whereas the ratio was 1.9 times baseline ratio (range, 0.43-12) in non-responders. The high-dose responder demonstrated a 7αC4:sBA ratio of 12 times baseline prior to administration of 560 μg/kg/day of maralixibat, which increased to 1770 times baseline upon administration of the higher dose.

Not wishing to be limited by any particular mechanism of action, patients with greater retained canlicular transport (as in the mild PFIC 2 patients) may require higher doses of maralixibat to block absorption of BA than those patients with lower retained canlicular transport. Further, patients with biochemical effect (increase in 7αC4:sBA ratio) but not clinical response may be rescued with higher maralixibat doses.

Figure 4:
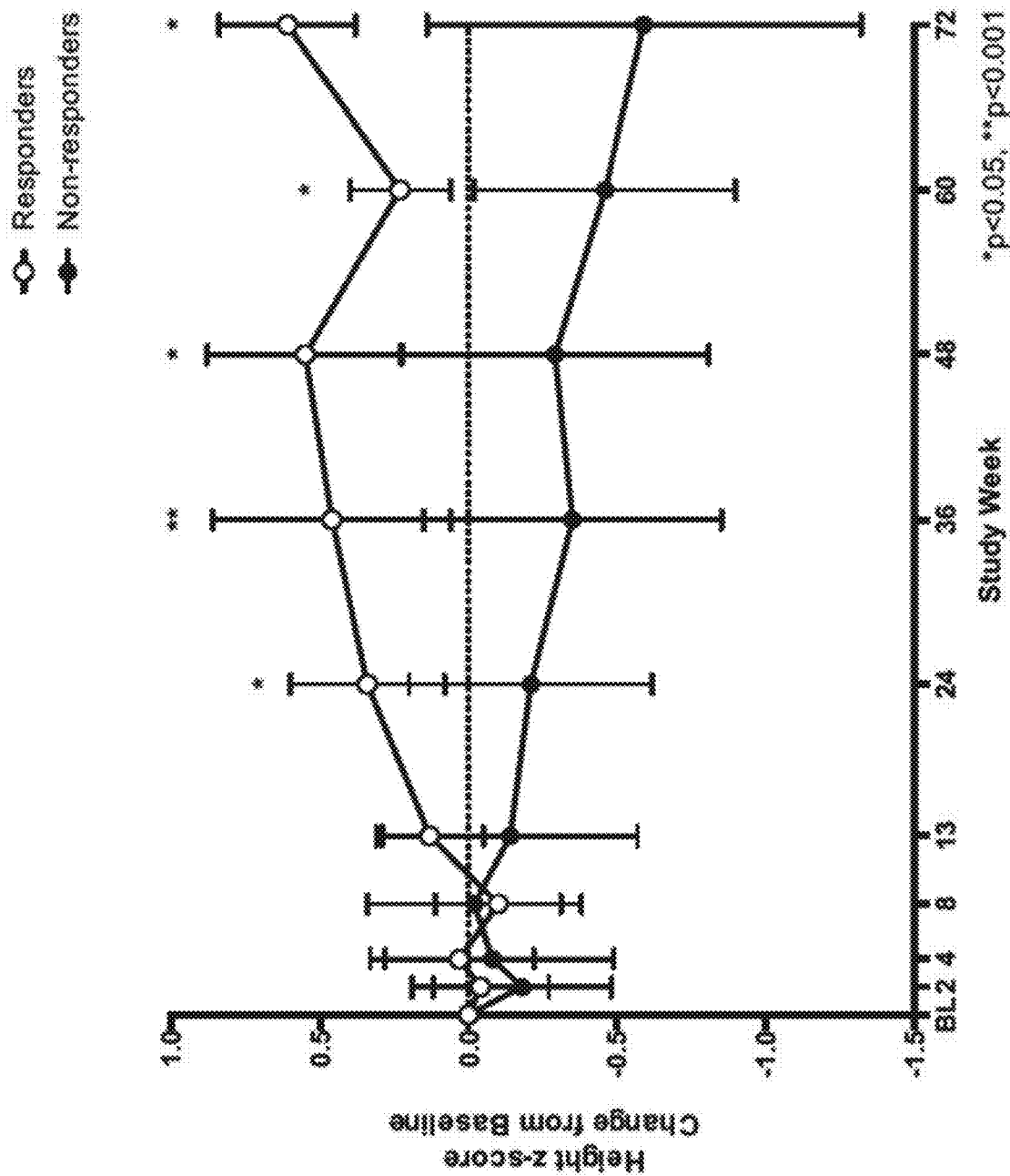
FIG. 4 depicts a scatter plot showing height Z-score change from baseline over time for responders and non-responders in the INDIGO clinical study. The decrease in average height Z-score at week 60 is due to one patient not having a measurement for that time point.

A further surprising result was observed in the INDIGO clinical study. Low-dose responders demonstrated improved growth relative to baseline, whereas non-responders did not, see FIG. 4. Improved growth was measured using height Z-score and was defined as a positive height Z-score change relative to baseline height Z-scores measured prior to administration of maralixibat. Furthermore, the high dose responder also exhibited an increase in height Z-score following treatment response on sBA.

Twelve patients participated in a long-term extension of the INDIGO clinical study. FIGS. 5-8 plot measurements of cholestasis markers taken for all participants in the INDIGO clinical study over time. The high-dose responder was first administered a daily dose of 560 μg/kg/day (2 equal doses of 280 μg/kg daily, BID) at between 547 and 638 days, see FIG. 5A. The high-dose responder demonstrated an increase in 7αC4:sBA ratio following administration of the higher dose, see FIG. 8. A low-dose responder demonstrating an increase in sBA concentration, a decrease in serum 7αC4 concentration, and a decrease in 7αC4:sBA ratio during the long-term extension was administered a higher dose of maralixibat (280 μg/kg BID) at between 640 and 730 days, see FIGS. 5A and 6-8. Following the administration of the higher dose, sBA concentration decreased, severity of pruritus decreased, serum 7αC4 concentration increased, and 7αC4:sBA ratio increased, see FIGS. 5A and 6-8. One low-dose responder demonstrated an increase in sBA during the long-term extension and was therefore administered a higher dose of maralixibat (280 μg/kg BID) at between 820 and 910 days, see FIG. 6. The severity of pruritus subsequently decreased, see FIG. 6, and the 7αC4:sBA ratio increased, see FIG. 8.

Figure 5B:
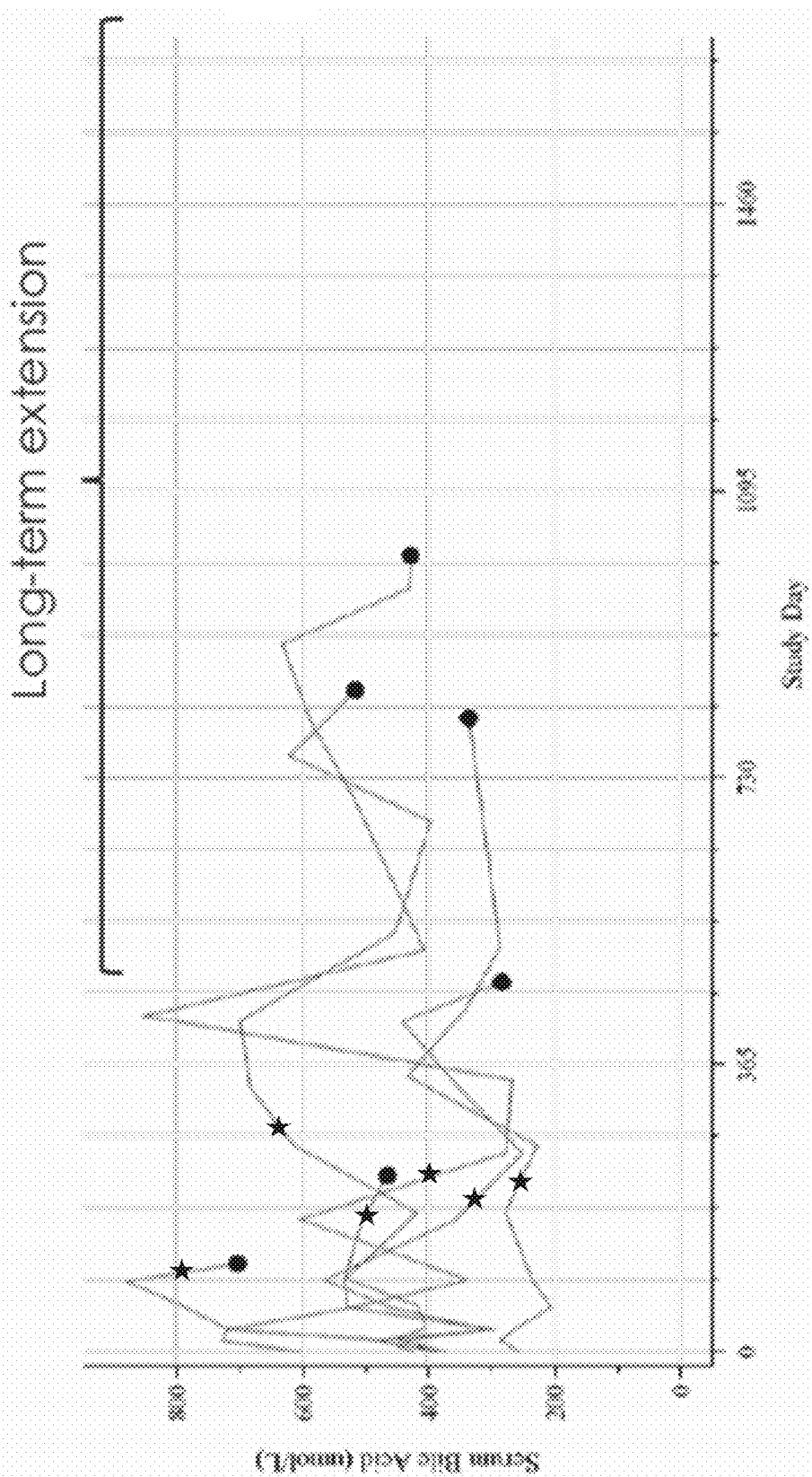
Figure 6:
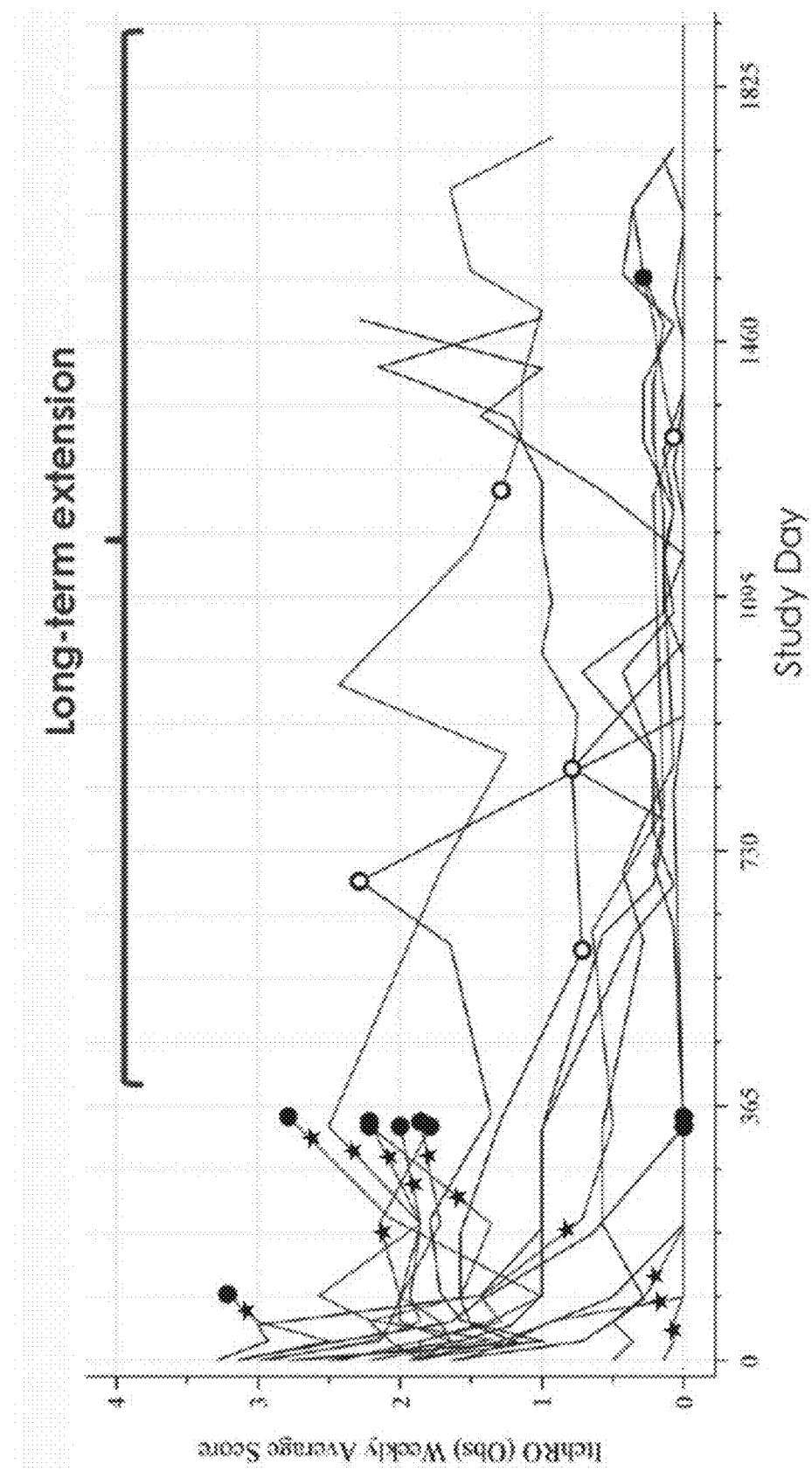
FIG. 6 provides a scatter plot plotting observer-reported itch reported outcome (ITCHRO(OBS)) weekly average scores for patients participating in the INDIGO clinical study and having non-truncating BSEP mutations.
Figure 7:
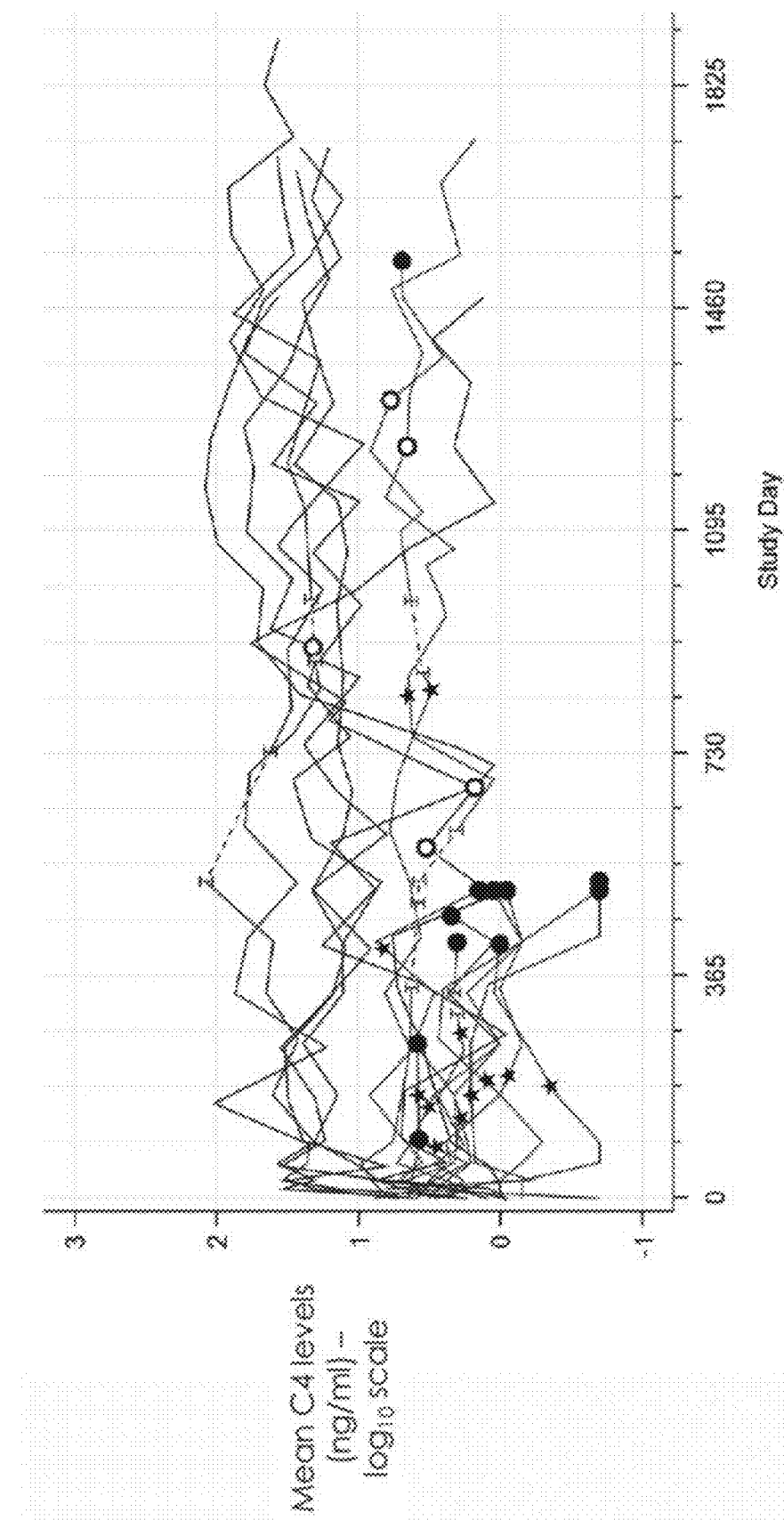
FIG. 7 provides a scatter plot plotting mean serum 7α-hydroxy-4-choesten-3-one (7αC4 or C4) concentration over time for patients participating in the INDIGO clinical study and having non-truncating BSEP mutations.

In the long-term extension of the INDIGO clinical study, no patients having an ABCB11 gene with a truncating mutation were responders, see FIG. 5B.

Figure 8:
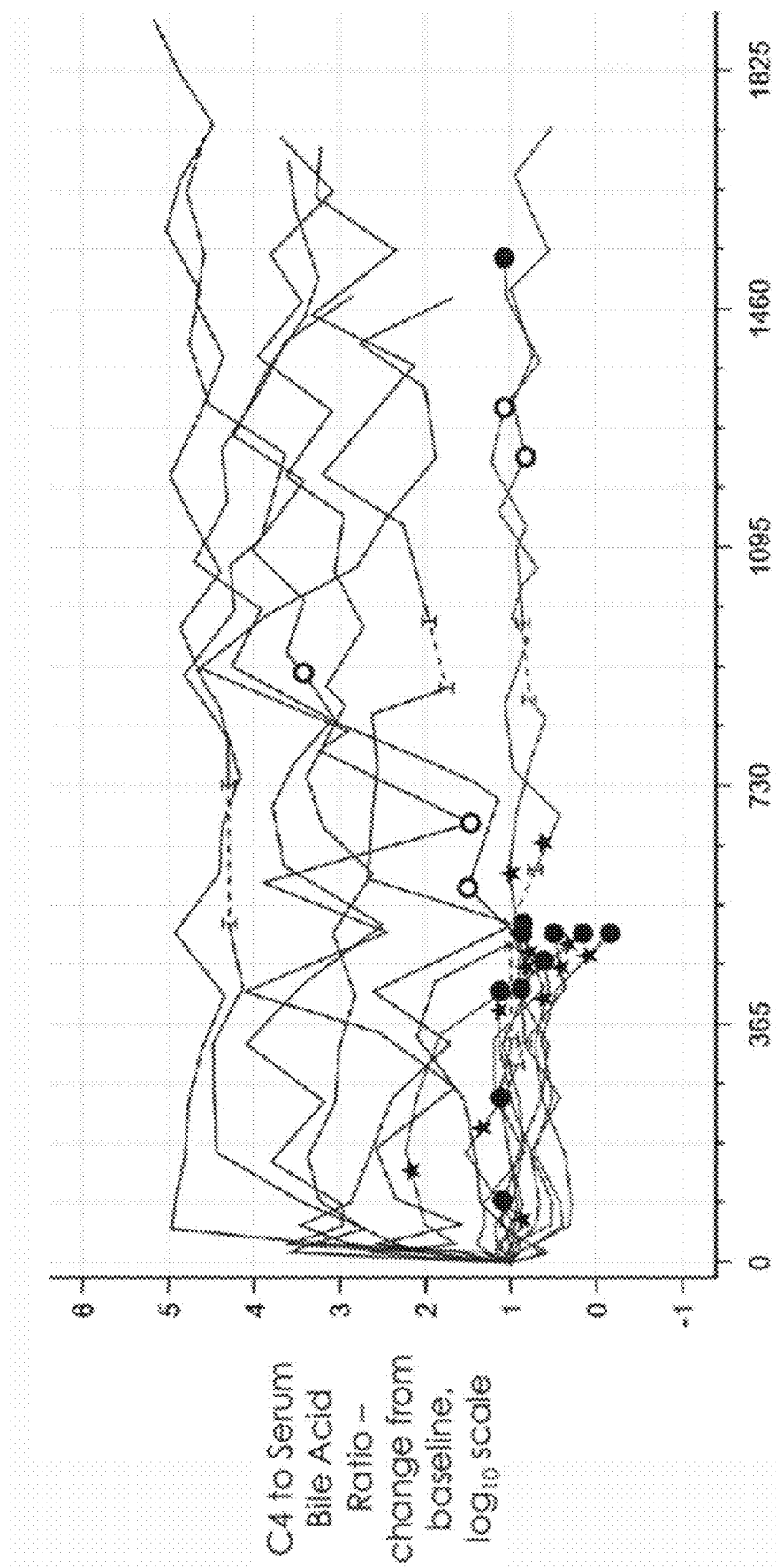
FIG. 8 provides a scatter plot showing the ratio of 7αC4 concentration to sBA concentration (7αC4:sBA) over time for patients participating in the INDIGO clinical study and having non-truncating BSEP mutations.

One non-responder demonstrated an initial increase in 7αC4:sBA ratio before 90 days, which subsequently decreased, see FIG. 8. This non-responder may have demonstrated a response if the non-responder had been administered a higher dose of maralixibat (e.g., 280 μg/kg BID) prior to being withdrawing from the INDIGO clinical study. The initial increase, or spike, in 7αC4:sBA ratio indicates that this patient may have been capable of demonstrating a response (i.e., a clinical response) to maralixibat administration.

Responders in the INDIGO study maintained a response to maralixibat for over a year and for up to or beyond 5 years, see FIGS. 5-8. Patients with non-truncating BSEP deficiency demonstrated durable control of pruritus and cholestasis with maralixibat, see FIGS. 5-8. FIGS. 5-8 demonstrate that 7αC4:sBA ratio is a good predictor of response to ASBTI.

Responders had genotypes consistent with residual BSEP function, whereas some non-responders had genotypes consistent with total lack of BSEP function.

Example 2. Dose-Dependent Fecal Bile Acid Excretion with Apical Sodium-Dependent Bile Acid Transporter Inhibitors Maralixibat and Volixibat in a Dose-Ranging Phase 1 Clinical Study (NTC02475317) in Overweight and Obese Adults Multiple oral doses of maralixibat, volixibat, or placebo were administered once (QD) or twice (BID) for 7 days in overweight and obese adults on a low-fiber diet. Participants had a body mass index of from 25 kg/m$^2$ to 35 kg/m$^2$. Participants consumed a low-fiber diet (<10 mg/day) for 2 days before randomization and during the 7-day treatment period. Measurements were taken of fBA, sBA concentration, and serum 7αC4 concentration (which is a biomarker of bile acid synthesis) prior to drug administration and at day 7.

A summary of demographics and baseline fBA for participants to which each drug at each indicated dosage was administered is provided in Table 10. Overall demographics for all patients participating in the study are also provided in Table 10.

TABLE 10

Summary of demographics and baseline characteristics for participants in a phase 1, blinded, placebo-controlled, dose-ranging clinical study (NCT02475317).

| | Placebo | Maralixibat | | | | | | Volixibat | | | Overall |
|---|---|---|---|---|---|---|---|---|---|---|---|
| | | 10 mg QD | 20 mg QD | 50 mg QD | 100 mg QD | 50 mg BID | All doses | 10 mg QD | 20 mg QD | All doses | |
| n | 14 | 10 | 10 | 10 | 10 | 10 | 50 | 10 | 10 | 20 | 84 |
| Mean age, year (SD) | 38.2 (9.32) | 45.4 (11.18) | 32.2 (8.92) | 36.4 (12.87) | 38.5 (9.87) | 39.4 (12.66) | 38.4 (11.58) | 37.5 (6.74) | 43.7 (14.40) | 40.6 (11.39) | 38.9 (11.11) |
| Race, n (%) | | | | | | | | | | | |
| White | 7 (50.0) | 6 (60.0) | 3 (30.0) | 7 (70.0) | 7 (70.0) | 6 (60.0) | 29 (58.0) | 6 (60.0) | 515201 | 11 (55.0) | 47 (56.0) |
| Black | 6 (42.9) | 4 (40.0) | 7 (70.0) | 3 (30.0) | 3 (30.0) | 4 (40.0) | 21 (420) | 4 (40.0) | 4 (40.0) | 8 (40.0) | 35 (41.7) |
| Black & White | 1 (7.1) | 0 | 0 | 0 | 0 | 0 | 0 | 0 | 1 (10.0) | 1 (5.0) | 0 |
| Mean fBA excretion, μmol (SD) | 246.44 (113.597) | 200.91 (176.918) | 138.46 (91.660) | 192.40 (235.828) | 230.39 (231.489) | 199.31 (147.859) | | 160.91 (129.561) | 263.19 (287.653) | | |

BID, twice daily; QD, once daily; SD, standard deviation; n, number of participants; multiple = mixed race (black and white).

Figure 9:
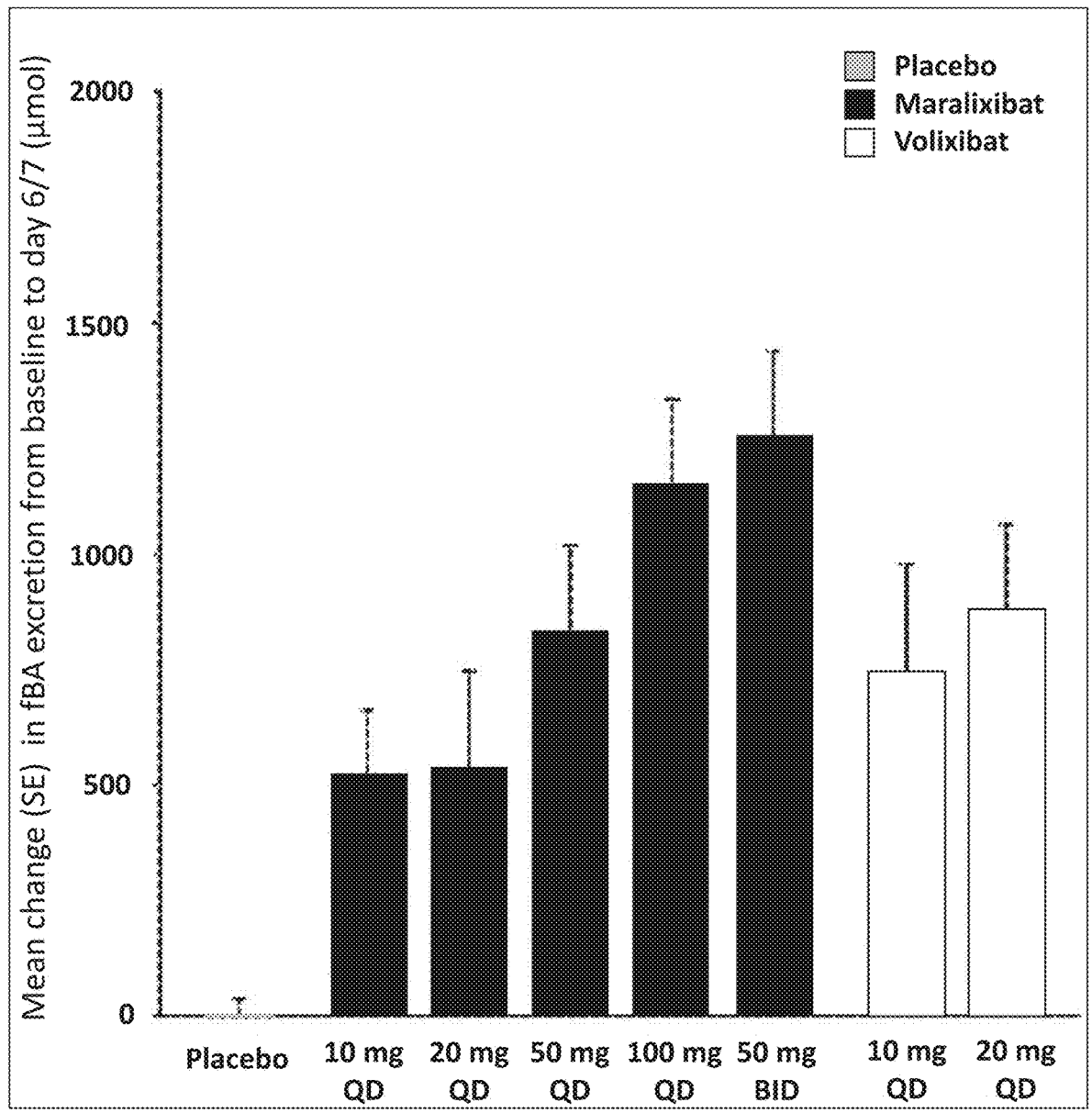
FIG. 9 provides a bar graph showing mean change from baseline to day 6 and 7 in fecal bile acid (fBA) excretion across indicated doses of maralixibat, volixibat, and placebo for a phase 1, blinded, placebo controlled, dose ranging clinical study (NCT02475317). BID, twice daily; QD, once daily; SE, standard error.

Of 84 participants, 50 were randomized to maralixibat, 20 to volixibat, and 14 to placebo, see Table 10. All participants completed the study. Mean baseline fBA excretion ranged from 138 μmol to 240 μmol (SD, 92-231) across maralixibat doses and 161 μmol to 263 μmol (SD, 130-288) across volixibat doses and was 246 μM (SD, 114) for placebo, see Table 10.

fBA excretion increased in a dose-dependent manner for maralixibat and volixibat, with no notable change for placebo, see FIG. 9. Mean change from baseline was similar at the highest maralixibat doses: 1251 μmol (95% confidence interval, 539-1963) for 50 mg BID and 1144 μmol (95% confidence interval, 823-1466) for 100 mg QD, see FIG. 9. At the 10 mg dose for maralixibat and volixibat, mean change from baseline was 515 μmol (95% confidence interval, 196-835) and 744 μmol (95% confidence interval, 230-1257), respectively, see FIG. 9. At the 20 mg dose for maralixibat and volixibat, mean change from baseline was 532 μmol (95% confidence interval, 60-1005) and 874 μmol (95% confidence interval, 457-1290), respectively, see FIG. 9.

Figure 10:
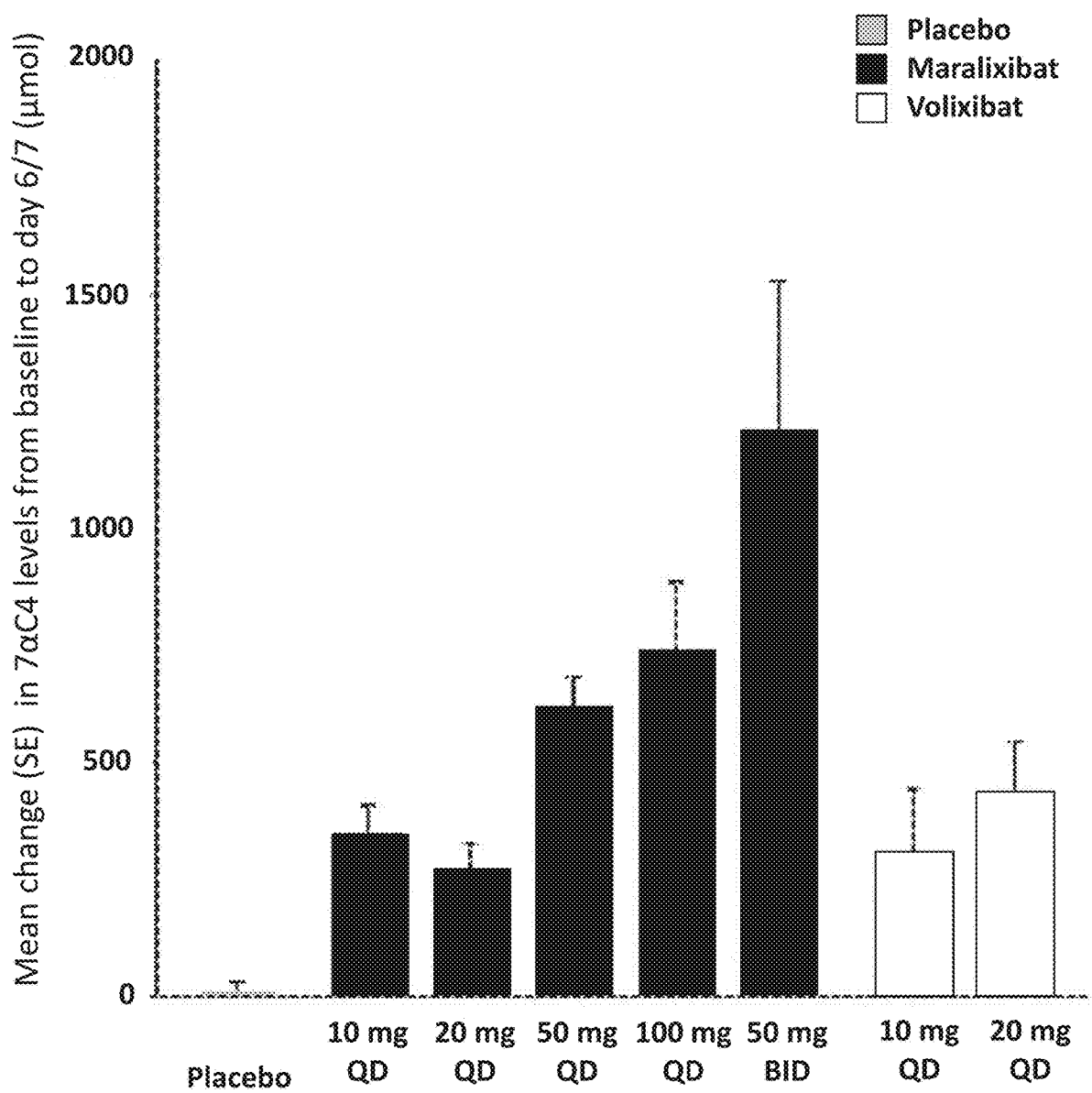
FIG. 10 provides a bar graph showing mean change from baseline to day 7 in serum 7αC4 concentration across indicated doses of maralixibat, volixibat, and placebo. BID, twice daily; fBA, fecal bile acids; QD, once daily; SE, standard error.

Mean serum 7αC4 increased with administration of maralixibat or volixibat, with the greatest change observed at a maralixibat dose of 50 mg BID, see FIG. 10.

No notable change in sBA or 7αC4 was observed with placebo, see FIGS. 9-10. Mean baseline sBA levels were not elevated with administration of maralixibat or volixibat but did increase by 2.6 ng/mL (95% confidence interval, 1.2-3.9) with placebo. All treatment-emergent adverse events were mild, and none were serious. The proportion of participants with treatment-emergent adverse events did not differ among volixibat and maralixibat doses, or between maralixibat and volixibat. The only treatment-emergent adverse events occurring in over 10% of participants were headache and diarrhea.

Increases in fBA excretion were dose-dependent up to the maximum tested doses of volixibat and maralixibat, see FIG. 9. Safety outcomes were similar across tested dose ranges and between compounds.

At the highest daily doses of maralixibat, increases in fBA excretion were numerically higher with 50 mg BID than with 100 mg QD, see FIG. 9.

Example 3. Safety and Efficacy of Maralixibat in Participants with Primary Sclerosing Cholangitis (PSC): A 14-Week, Single-Arm, Open-Label, Phase 2a, Proof-of-Concept Study of Maralixibat (the CAMEO Clinical Trial; ClinicalTrials.gov: NTC02061540)

The CAMEO clinical trial included a 6-week dose-escalation period (maralixibat 0.5 mg/day, 1 mg/day, 2.5 mg/day, 5 mg/day, and 7.5 mg/day) followed by an 8-week dose-maintenance period (maralixibat 10 mg/day) and a 4-week follow-up period.

Participants were adults aged 18-80 years with a diagnosis of PSC. PSC diagnosis included a documented history of alkaline phosphatase (ALP) levels greater than 1.5 times above the upper limit of normal, biliary obstruction, and histological findings consistent with PSC diagnosis (if previously biopsied). The study enrolled 27 adults.

Efficacy was assessed by measuring at baseline and throughout the study sBA concentration, serum 7αC4 concentration (a marker of de novo bile acid synthesis), serum autotaxin concentration, LDL-C concentration, serum total cholesterol concentration, serum liver enzyme concentrations, and pruritus severity. Pruritus severity was determined by calculating Adult Itch Reported Outcome (ITCHRO) weekly sum scores and average daily scores (mean score over a 7-day period). Participants self-reported the ITCHRO daily on a scale 0-10 (0=no pruritus; 10=most severe pruritus).

Baseline mean serum alkaline phosphatase concentration for participants in the CAMEO study was 471.6 U/L (SD, 316.9).

Outcomes were assessed in the overall study population and in subgroups of participants (A) with any pruritus at baseline or (B) with an ITCHRO average daily score ≥4 out of 10 at baseline. Efficacy endpoints were based on change from baseline to week 14 or early termination (ET) and were analyzed using paired t-tests or Wilcoxon signed rank tests.

Of 27 enrolled participants, 23 (85.2%) completed the study. Participants were predominantly male (66.7%) and white (85.2%), with a mean age of 43.7 years (standard deviation [SD], 11.35) at study enrollment. Mean time since PSC diagnosis was 94 months (SD, 75.4). PSC symptoms of inflammatory bowel disease and ulcerative colitis were reported by 44.4% and 55.6% of participants, respectively.

Figure 11:
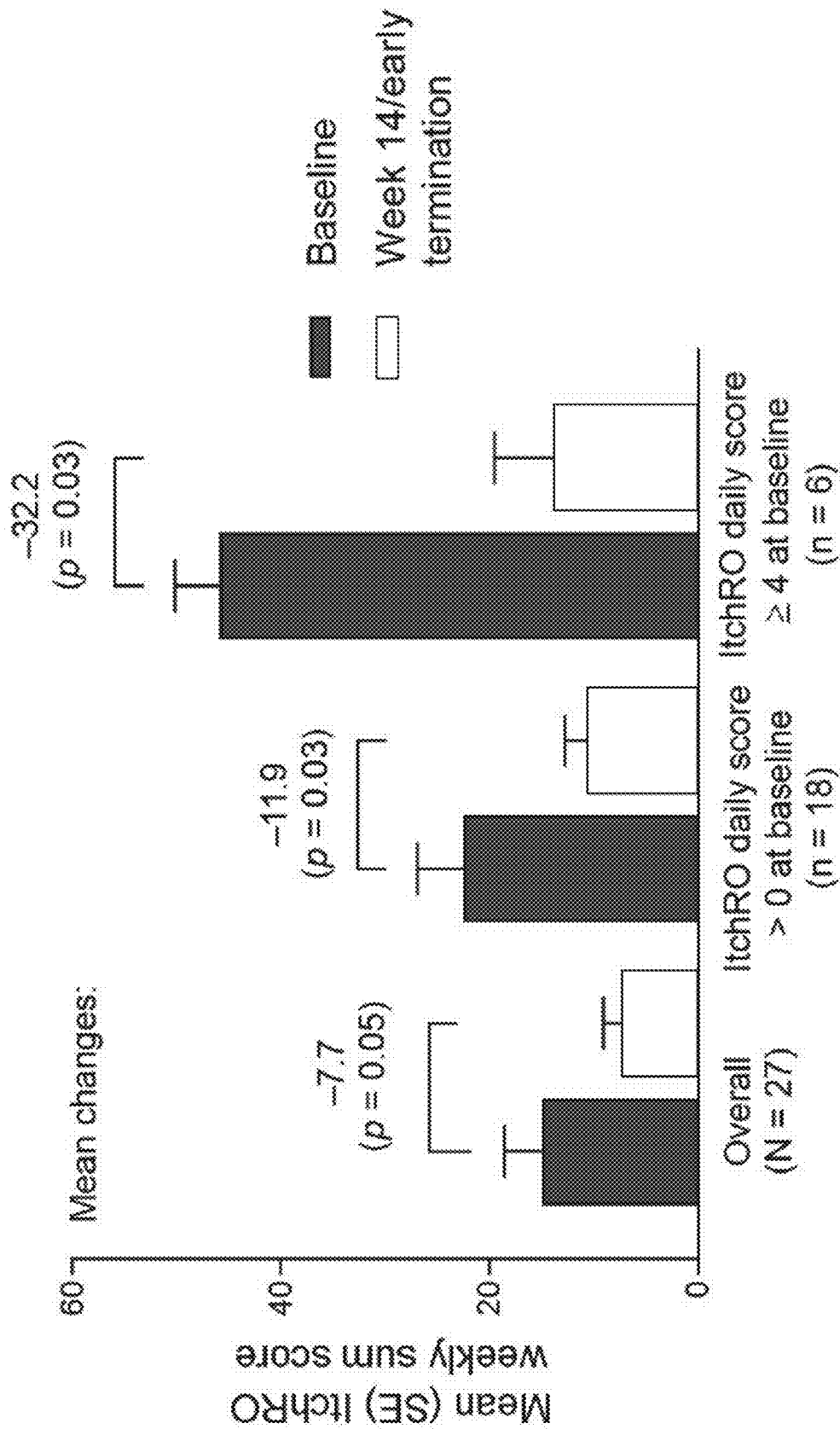
FIG. 11 provides a bar graph showing mean ITCHRO weekly sum scores in an overall population of participants in a 14-week, single-arm, open-label, phase 2a, proof-of-concept study of maralixibat (CAMEO clinical study) having any pruritus at baseline, and participants with ITCHRO daily scores ≥4 at baseline.

ITCHRO weekly sum scores decreased from baseline by 51% (p=0.0495) overall, by 53% (p=0.0275) in participants with any pruritus at baseline (n=18), and by 70% (p=0.0313) in participants with an ITCHRO daily score ≥4 out of 10 at baseline (n=6), see FIG. 11. ITCHRO average daily score improved by >3 points in 6 of 27 (22.2%) participants and improved by >1 point in 8 out of 27 (29.6%) participants. No participants experienced worsening of pruritus by >1 point from baseline to week 14. Pruritus improved in all 6 participants with an ITCHRO score ≥4 at baseline, see Table 11 and FIG. 11.

TABLE 11

ITCHRO scores for participants in the CAMEO clinical study with an ITCHRO daily score ≥4 at baseline

| | ItchRO average daily score (0-10 scale) | | |
|---|---|---|---|
| Participant | Baseline | Week 14/ET | Change from baseline to week 14/ET |
| A | 9.1 | 0 | −9.1 |
| B | 4.7 | 0 | −4.7 |
| C | 5.9 | 1.3 | −4.6 |
| D | 6.9 | 5.1 | −1.7 |
| E | 6.9 | 3.1 | −3.7 |
| F | 6.0 | 2.3 | −3.7 |

Figure 12:
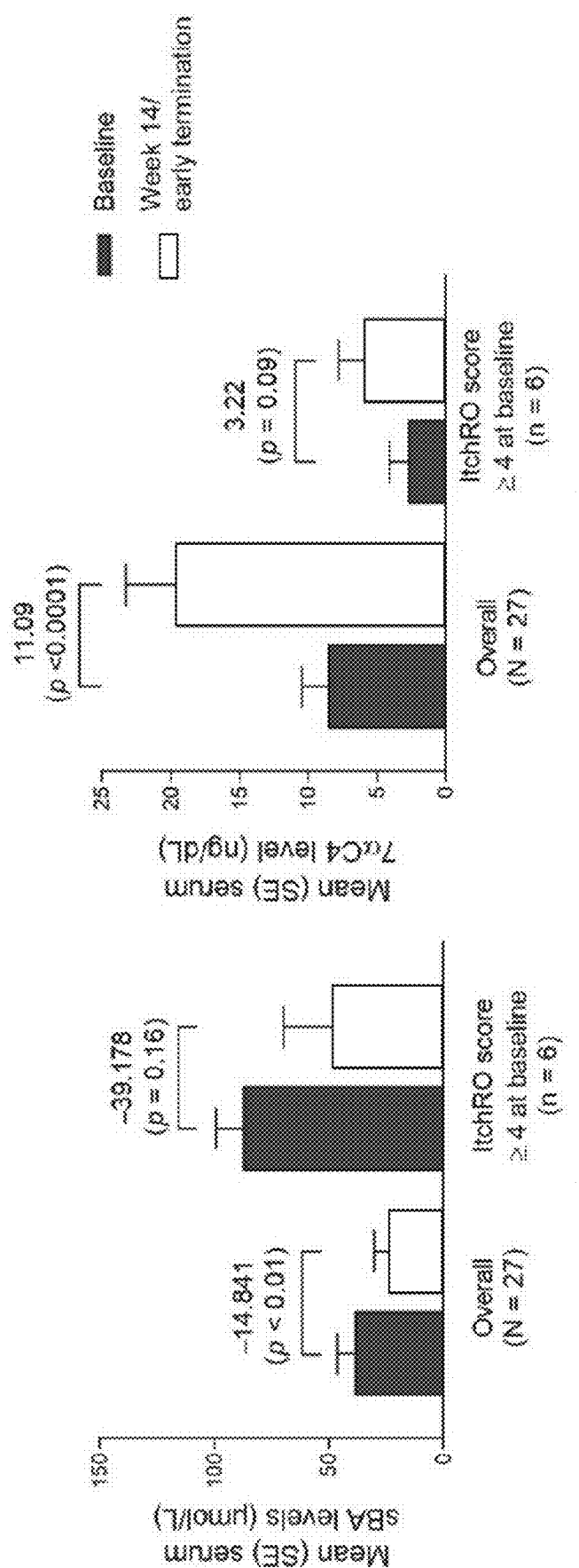
FIG. 12 shows bar plots of sBA concentration (left panel) and 7αC4 concentration (right panel) in an overall population participating in the CAMEO clinical study and in participants with ITCHRO daily scores ≥4 at baseline.

ET, early termination; ItchRO, Itch Reported Outcome.

sBA levels decreased from baseline by 38% (mean −14.8 μmol/L [SD, 31.4]; p=0.0043) overall and by 45% in participants with an ITCHRO daily score ≥4 at baseline, see FIG. 12. Mean levels of 7αC4 increased from baseline by 130% (mean, 11.1 ng/mL [SD, 13.6]; p<0.0001) overall and by 107% in participants with an ITCHRO daily score ≥4 at baseline, see FIG. 12.

Figure 13:
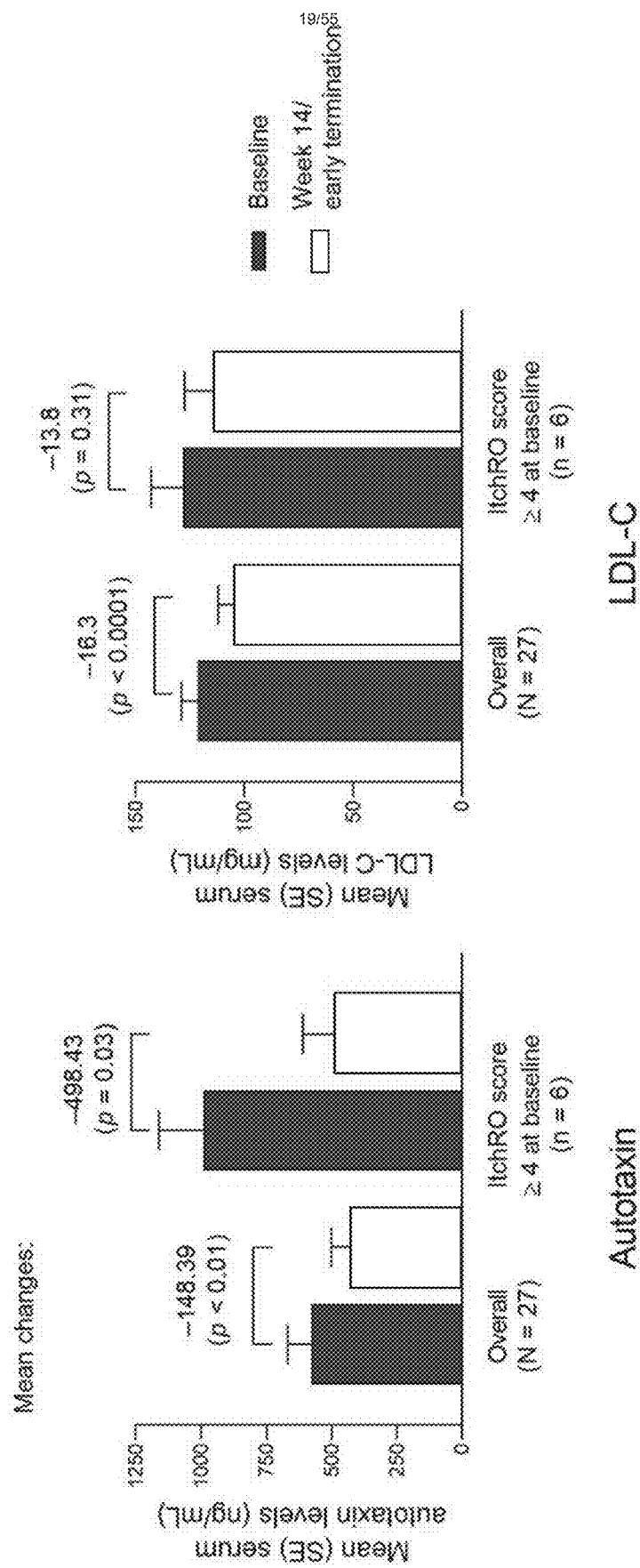
FIG. 13 shows bar plots of serum autotaxin concentration (left panel) and serum low-density lipoprotein cholesterol (LDL-C) concentration (right panel) in the overall population participating in the CAMEO clinical study and in participants with ITCHRO daily scores ≥4 at baseline.

In the overall population of participants in the CAMEO clinical trial, significant reductions were observed in serum autotaxin concentration (−148 ng/mL [SD, 319]; p=0.0462) and serum LCL-C concentration (−16.3 mg/dL [SD, 17.6]; P<0.0001), see FIG. 13. In participants with an ITCHRO daily score ≥4 at baseline, significant reductions were observed in autotaxin levels, see FIG. 13. Reductions were observed in levels of total cholesterol in the overall population (mean change, −21.2 mg/dL [SE, 4.90; SD, 25.5]; p=0.0002) and in participants with an ITCHRO daily score ≥4 at baseline (mean change, −32.0 mg/dL [SE, 13.38]; p=0.06).

Mean conjugated bilirubin levels increased by 0.19 mg/dL (SE, 0.09, p<0.0462; SE, 0.450) in the overall population, with no significant change in participants with ITCHRO daily score ≥0 at baseline. Changes in serum total bilirubin, alanine aminotransferase, aspartate aminotransferase, and alkaline phosphatase concentrations were not statistically significant in participants in the CAMEO clinical study.

Figure 14:
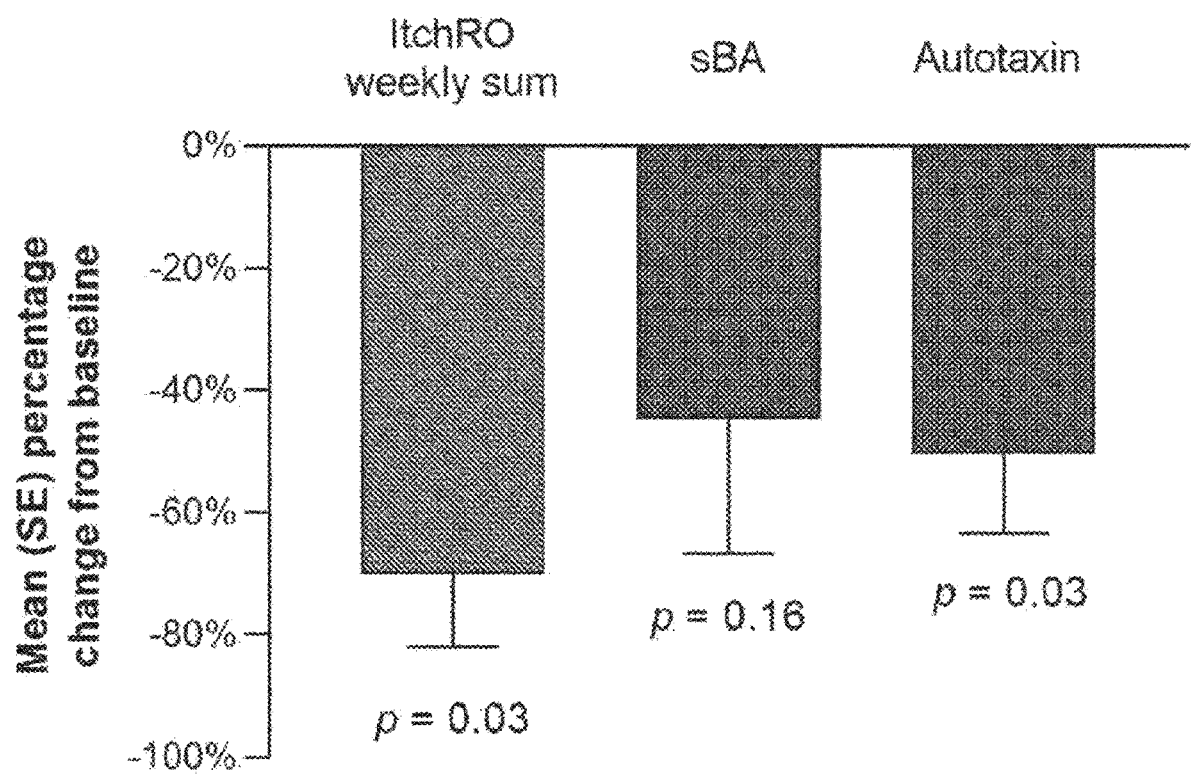
FIG. 14 shows a bar plot of percentage change from baseline to week 14 or early termination on efficacy measures including ITCHRO score (1-10 daily score), sBA concentration, and serum autotaxin concentration in six participants in the CAMEO clinical study with ITCHRO daily scores ≥4 at baseline.

Statistically significant reductions in pruritus and sBA were observed after 14 weeks of treatment with maralixibat in the CAMEO clinical study, which is consistent with a proposed mechanism of action for maralixibat, see FIG. 1. Levels of serum autotaxin, a potential marker for cholestatic pruritus, also improved in a statistically significant manner, see FIG. 13. Mean percent reductions were greater in pruritus and sBA and autotaxin levels in participants with an ITCHRO daily score ≥4 at baseline than in the overall participant population for the CAMEO study, see FIG. 14.

Statistically significant reductions in serum LDL-C levels and statistically significant increases in serum 7αC4 levels indicated de novo synthesis of bile acids from cholesterol, which is consistent with ASBT inhibition.

Maralixibat was well tolerated in the CAMEO study and associated with reduced serum BA levels in adults with PSC. In addition, autotaxin levels reduced and pruritus improved significantly from BL, with the greatest reductions in those with worst pruritus at baseline.

Example 4. Durability of Treatment Effect with Long-Term Maralixibat in Children with Alagille Syndrome: 4-Year Efficacy Results from a Phase 2b Double-Blind, Randomized, Placebo-Controlled Drug-Withdrawal Study with a Long-Term Open-Label Pretreatment Period of Maralixibat 400 µg/kg/Day Twice Daily (BID) (the ICONIC Clinical Study)

Children aged 1-18 years with a diagnosis of ALGS and evidence of cholestasis were eligible to enroll in the ICONIC clinical study, see Tables 12-14. During a long-term extension, participants with sBA levels above the upper limit of normal and/or an ITCHRO(OBS) score >1.5 were eligible for the 400 µg/kg BID dose (all participants received the 400 µg/kg BID dose). Inclusion criteria for the ICONIC study included having cholestasis, which was defined as at least one of 1) sBA concentration (total sBA)>3× the upper limit of normal, 2) serum conjugated bilirubin concentration >1 mg/dL, 3) fat-soluble vitamin deficiency not otherwise explained, 4) serum gamma-glutamyl transferase concentration >3× the upper limit of normal, and 3) intractable pruritus explainable only by liver disease. Inclusion criteria also included having significant pruritus, which was defined as an average daily score of >2 on the ITCHRO(OBS) scale for 2 consecutive weeks (0=no pruritus; 4=most severe pruritus). Exclusion criteria included having surgically disrupted enterohepatic circulation, a liver transplant, decompensated cirrhosis, or having any liver disease other than ALGS.

TABLE 12

Disposition and demographics for participants in the ICONIC clinical study.

| Disposition and demographics | |
|---|---|
| Median Age (range), years | 5.4 (1-15) |
| Male, % | 61.3 |
| Genotype, n (%) | |
| JAG1 | 31 (100) |
| Enrolled, n | 31 |
| Randomized week 18, n | 29 |
| Maralixibat | 13 |
| Placebo | 16 |
| Completed week 48, n | 28 |

TABLE 13

Baseline characteristics for participants in the ICONIC clinical study. ALT, alanine transaminase.

| Baseline characteristics, mean (SD) | |
|---|---|
| ItchRO (Obs), 0-4 | 2.9 (0.5) |
| CSS, 0-4 | 3.3 (0.9) |
| sBA, µmol/L | 283 (211) |
| C4, ng/ml | 10.3 (14.7) |
| Total bilirubin, mg/dL | 6.1 (5.8) |
| Direct bilirubin, mg/dL | 4.6 (3.7) |
| ALT, U/L | 181 (109) |

TABLE 13-continued

Baseline characteristics for participants in the ICONIC clinical study. ALT, alanine transaminase.

| Baseline characteristics, mean (SD) | |
|---|---|
| Clinician xanthoma scale, 0-4 | 0.9 (1.26) |
| PedsQL, 0-100 | 61.2 (17.3) | sBA responders were defined as those patients achieving ≥50% reduction from baseline in sBA at week 12 or 18. ITCHRO responders were defined as those patients achieving at least a 1-point reduction from Baseline in weekly morning ITCHRO(OBS) score at week 12 or 18.

Figure 15:
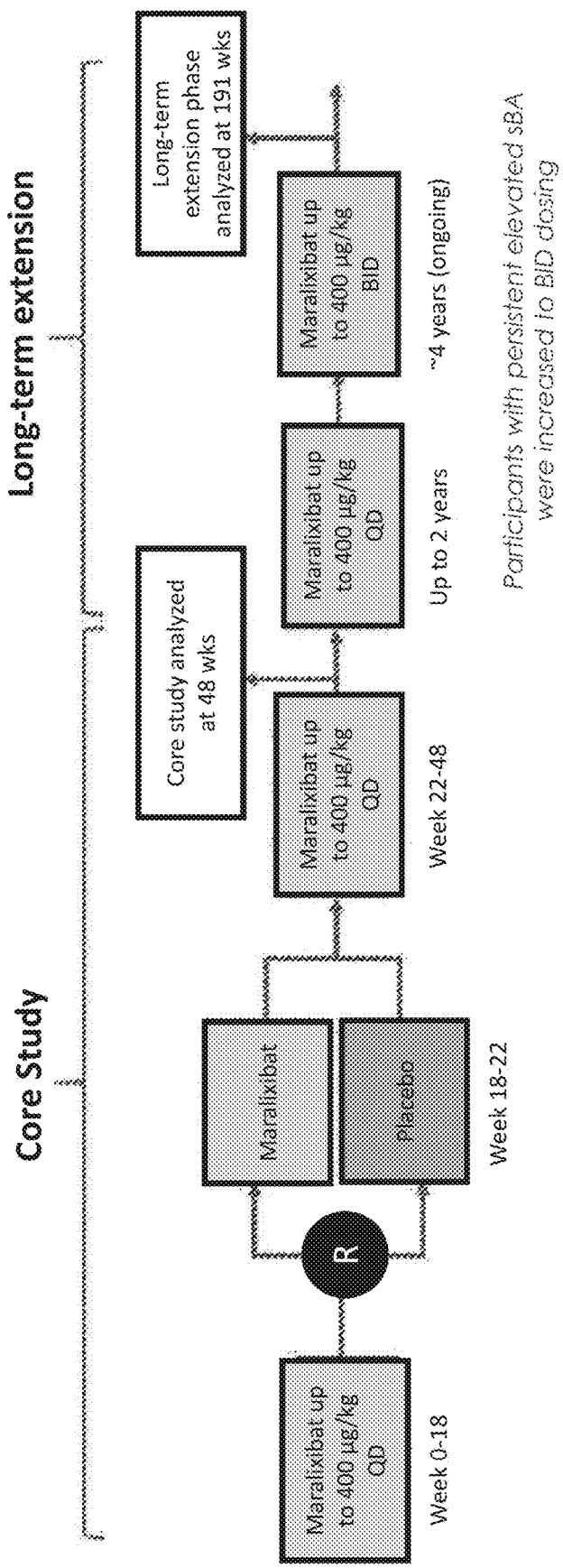
FIG. 15 provides a diagram summarizing the clinical study design for a double blind, randomized, placebo controlled drug withdrawal study with a long-term open label treatment period of maralixibat 400 μg/kg QD (ICONIC clinical study).

A summary of the experimental design for the ICONIC clinical study is provided as FIG. 15. After completion of the 48-week core study at a dose of 400 µg/kg daily (QD), participants were able to continue long-term treatment with maralixibat 400 µg/kg QD (the extension portion of the study). In the open label extension, the effect of higher doses was explored by increasing dosage to a maximum of 400 µg/kg BID in eligible participants.

Efficacy assessments were based on changes from baseline in sBA concentration, weekly average ITCHRO(OBS) scores (0, none; 4, most severe), CSS score (0, none; 4 most severe), and Clinician Xanthoma Scale score (0, none; 4, disabling). During a randomized withdrawal period (week 18-22), differences between maralixibat and placebo in sBA concentration and ITCHRO(OBS) scores were evaluated. During the long-term extension, efficacy assessments were conducted every 12 weeks. Serum total cholesterol and serum 7αC4 concentration were also monitored during the ICONIC clinical study, among other measures.

sBA were measured using a fully validated liquid chromatography-electrospray ionization-mass electrospray (LC-ESI-MS) method using stable-isotope dilution analysis to measure serum concentrations of principal bile acids (cholic, chenodeoxycholic, ursodeoxycholic, deoxycholic acid, lithocholic, and their corresponding glycine and taurine conjugates). Serum samples were analyzed in the Division of Pathology and Laboratory Medicine, Cincinnati Children's Hospital Medical Center according to SOP #PATH.CMS.1033. Calibration standards of individual bile acids were in the range of 50-25,000 ng/mL and Quality Control samples were prepared at concentrations of 100, 500, 1000, 2500, and 20000 ng/mL. The intra- and inter-assay imprecision of the method for individual bile acids measured was within the accepted GLP quality assurance guidelines of <15% coefficient of variance for these QC samples. The lower limit of quantification of the assay was set at 100 ng/mL and the imprecision at this concentration was <20%. The limit of detection of the assay was 5 ng/mL. Total sBA is represented by the sum of the individual bile acid species measured.

Figure 16:
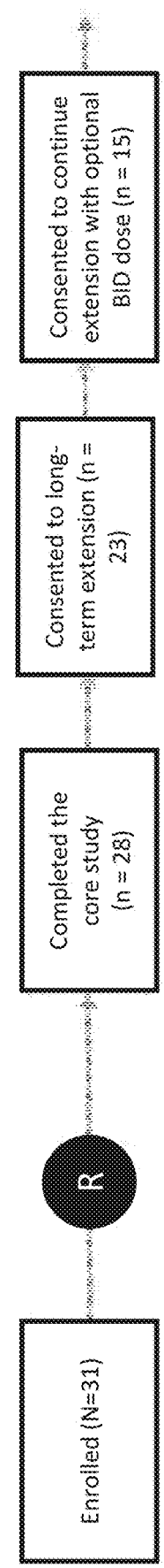
FIG. 16 provides a diagram summarizing the disposition of participants in the ICONIC clinical study.

Of the 28 participants who completed the core study (up to week 48), 23 consented to long-term extension. After 2 years, 15 participants continued in the extension phase with a dose increase to 400 µg/kg BID, see FIGS. 15-16. Table 14 provides baseline characteristics and demographics for participants in the long-term extension.

TABLE 14

Baseline characteristics and demographics for participants enrolled in the ICONIC clinical study and participants in the long-term extension of the ICONIC clinical study

| | Enrolled participants (N = 31) | Extension participants (N = 15) |
|---|---|---|
| Median age (range), years | 5.0 (1-15) | 5.0 (1-12) |
| Male, n (%) | 19 (61.3) | 10 (66.7) |
| JAG1 mutation, n (%) | 31 (100.0) | 15 (100.0) |
| Serum bile acid level, μmol/L | 283.4 (37.8) | 259.0 (55.3) |
| Total Bilirubin mg/dL | 6.1 (1.0) | 3.2 (0.9) |
| ItchRO(Obs) score (0-4) | 2.9 (0.1) | 2.8 (0.1) |
| CSS score (0-4) | 3.3 (0.2) | 3.2 (0.3) |
| Height z-score | -1.7 (0.2) | -1.8 (0.3) |

Figure 17A:
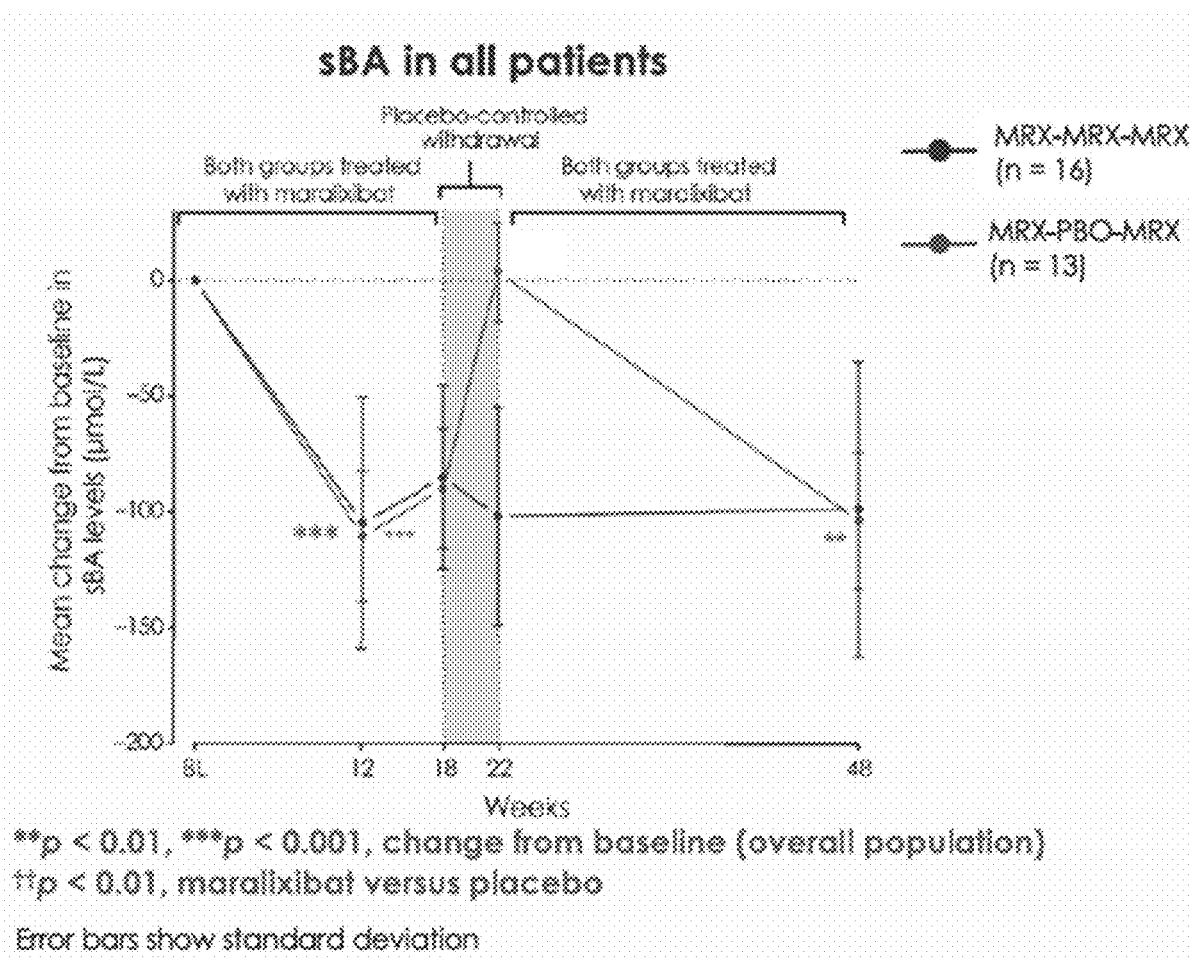
FIGS. 17A and 17B demonstrate significant improvements in sBA levels versus baseline and placebo in participants in the ICONIC clinical study.
Figure 17B:
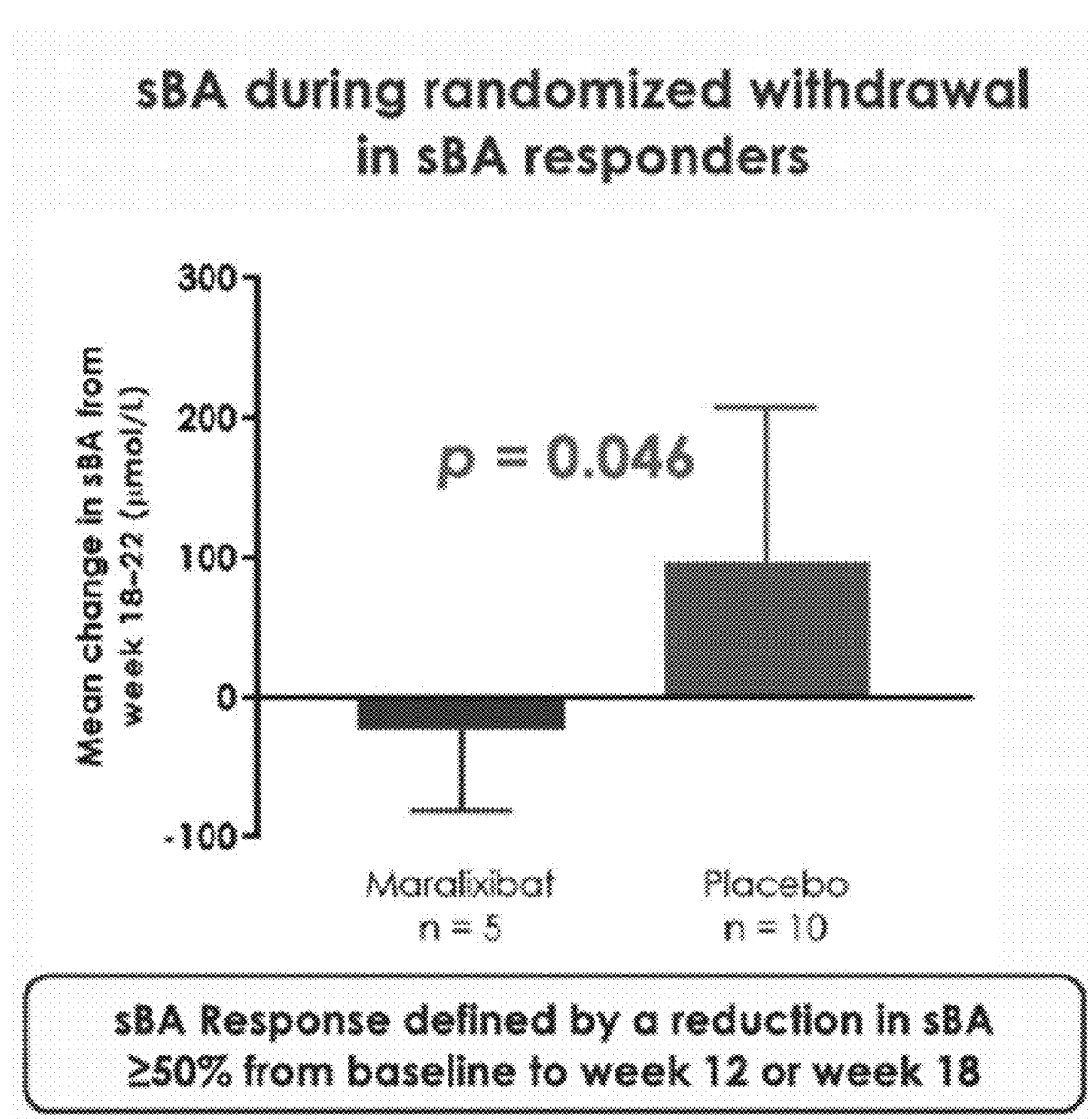
Figure 18:
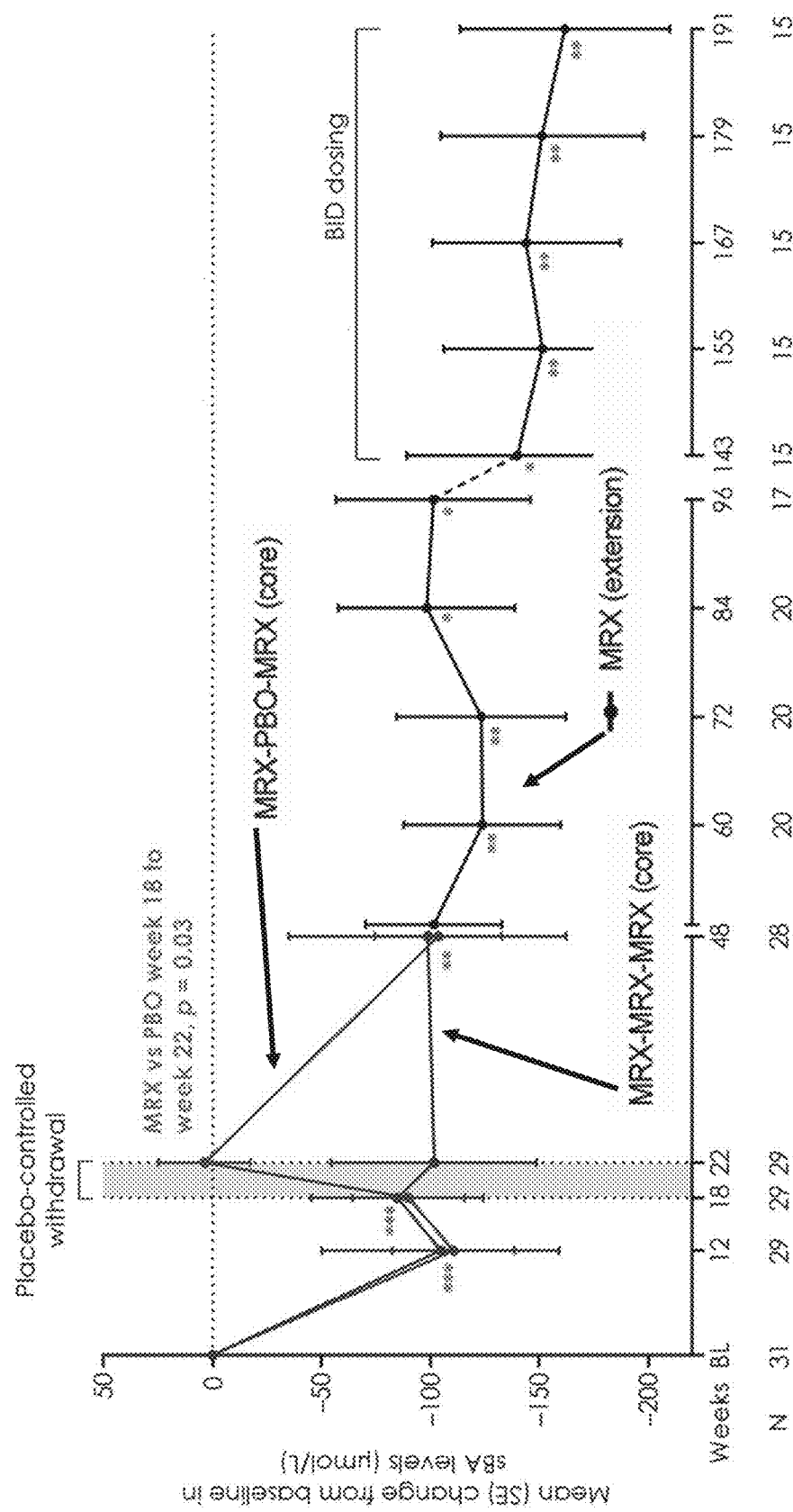
FIG. 18 shows a plot of mean sBA concentrations for participants in the ICONIC clinical study during the core study (first 48 weeks) and during the extension (period after 48 weeks). MRX=maralixibat; PLA=placebo.
Figure 19:
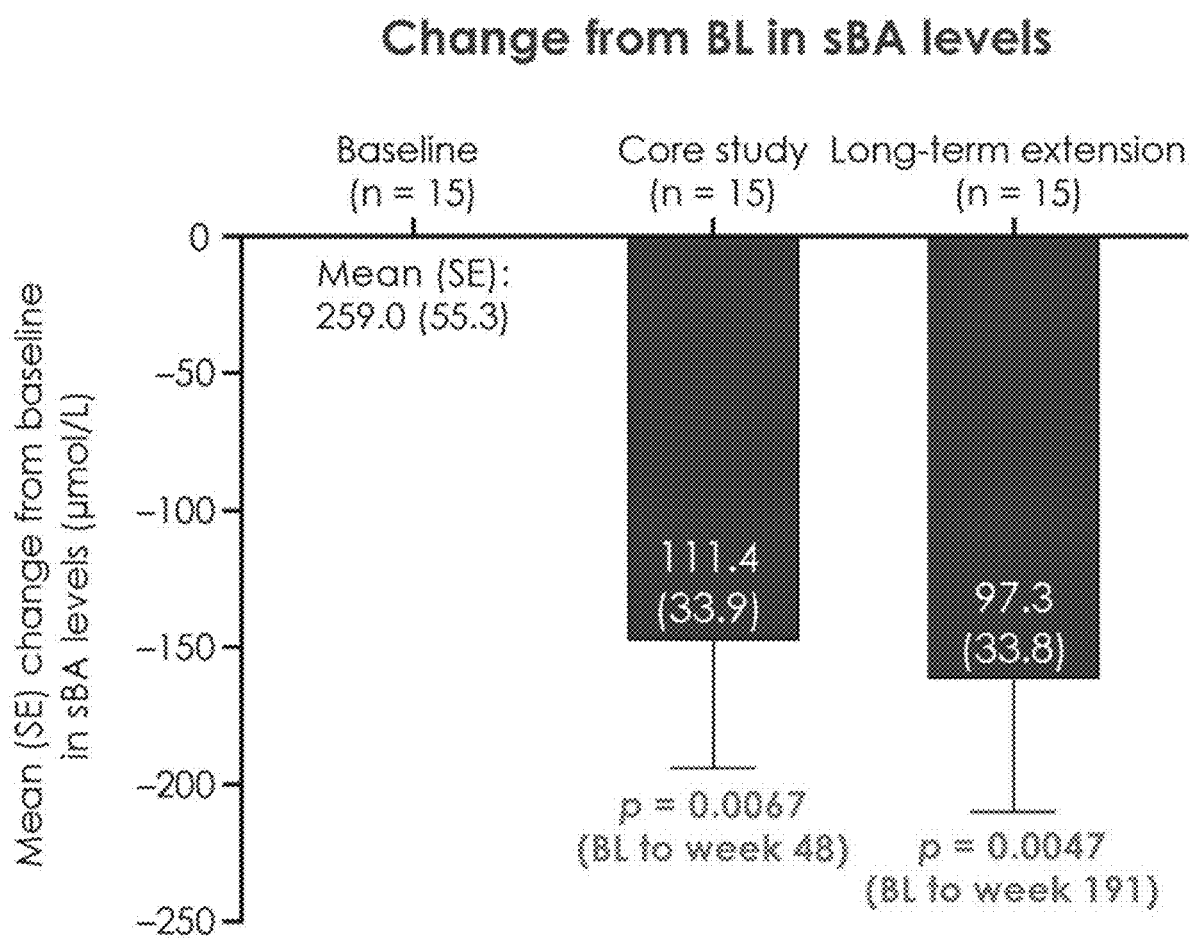
FIG. 19 provides a bar graph showing mean change from baseline (BL) in sBA levels observed in the ICONIC clinical study.

Data presented as mean (SE) unless otherwise specified.

sBA concentration decreased by 31% (p=0.0005) during the first 18 weeks of treatment with maralixibat at 400 μg/kg QD, see FIGS. 17-18 and 32. During randomized withdrawal, sBA levels returned to baseline in the placebo group but were maintained in the maralixibat groups (least squares [LS] mean difference, -114.0; SE, 48.0; p=0.03), see FIGS. 17-18 and 32. Reductions in sBA levels were maintained and continued to improve during the long-term extension, see FIGS. 18 and 19. At 191 weeks, sBA levels were reduced by about 57% from baseline (p=0.0047), see FIG. 19.

Serum total cholesterol concentration and serum 7αC4 concentration both showed a statistically significant decrease from baseline by week 48 and week 191, see Table 15. A statistically significant decrease observed in serum total cholesterol concentration and serum 7αC4 concentration observed by week 49 was maintained through week 191 of the ICONIC clinical study, see Table 15.

TABLE 15

Serum cholesterol concentration (mg/dL) and serum 7αC4 concentration (ng/mL) at baseline, week 48, and week 191 and a comparison of the week 49 and week 191 measurements to the baseline measurements for participants in the ICONIC clinical study.

| Mean (SD) | Baseline n = 15 | Week 48 n = 15 | Week 191 n = 15 |
|---|---|---|---|
| Serum cholesterol, mg/dL | 414.3 (182.1) | 340.3 (149.9) | 277.5 (65.7) |
| p value<sup>a</sup> | | <0.01 | <0.01 |
| C4, ng/mL | 7.4 (8.7) | 20.4 (32.2) | 30.4 (44.6) |
| p value<sup>a</sup> | | 0.1 | 0.04 |

Figure 20A:
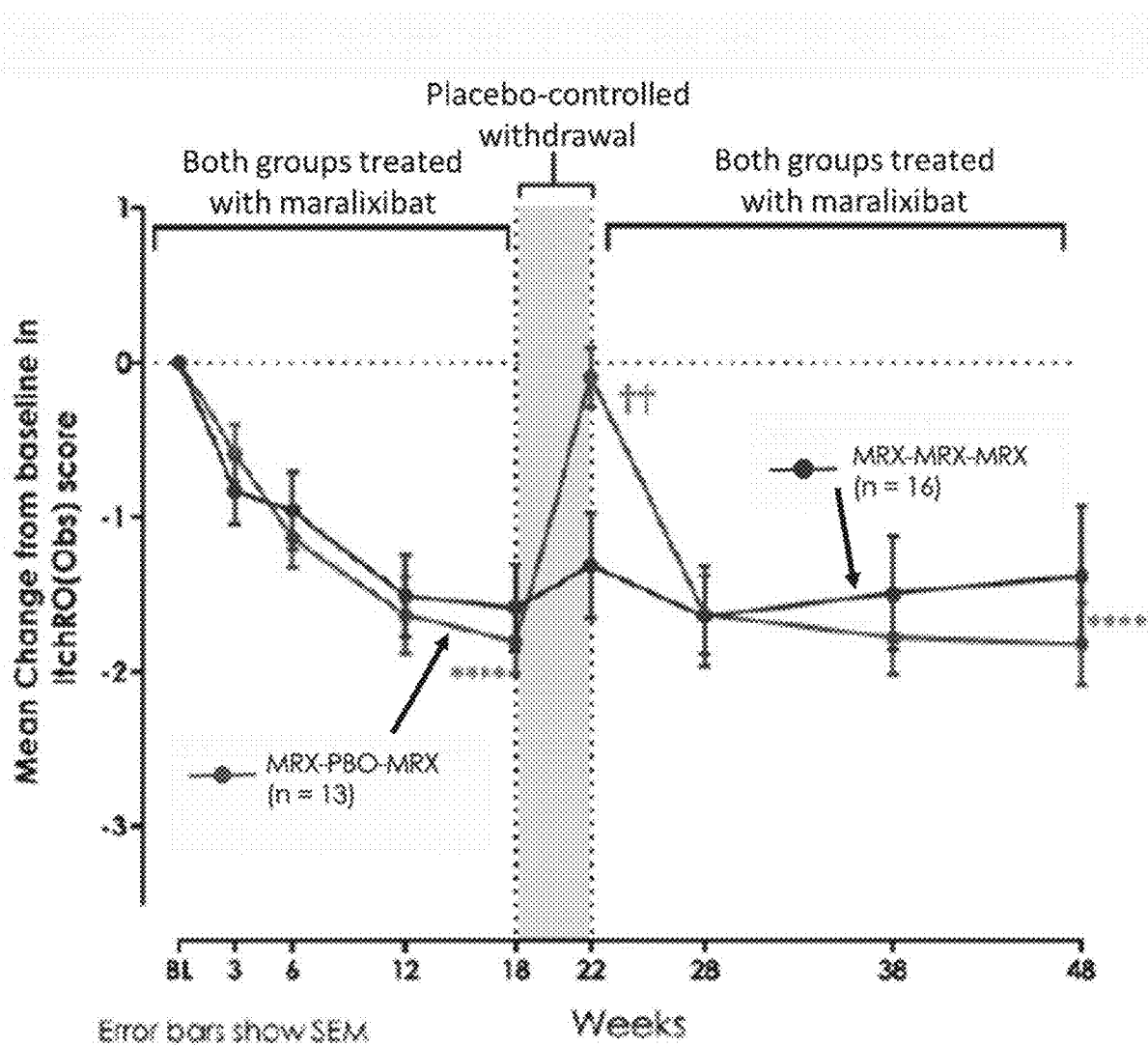
FIGS. 20A and 20B demonstrate improvements in ITCHRO(Obs) scores maintained during randomized withdrawal with maralixibat in participants in the ICONIC clinical study.
Figure 20B:
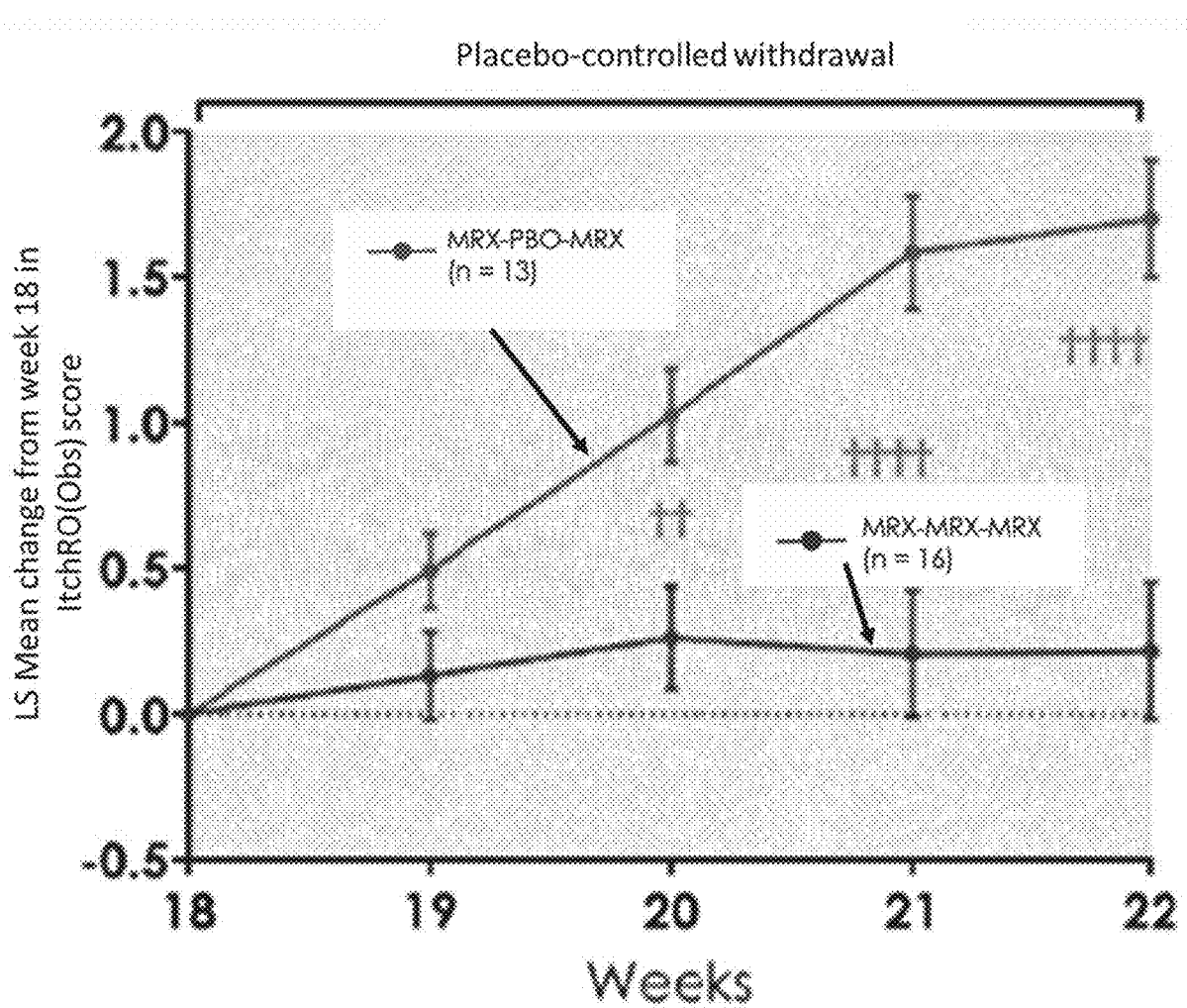
Figure 21B:
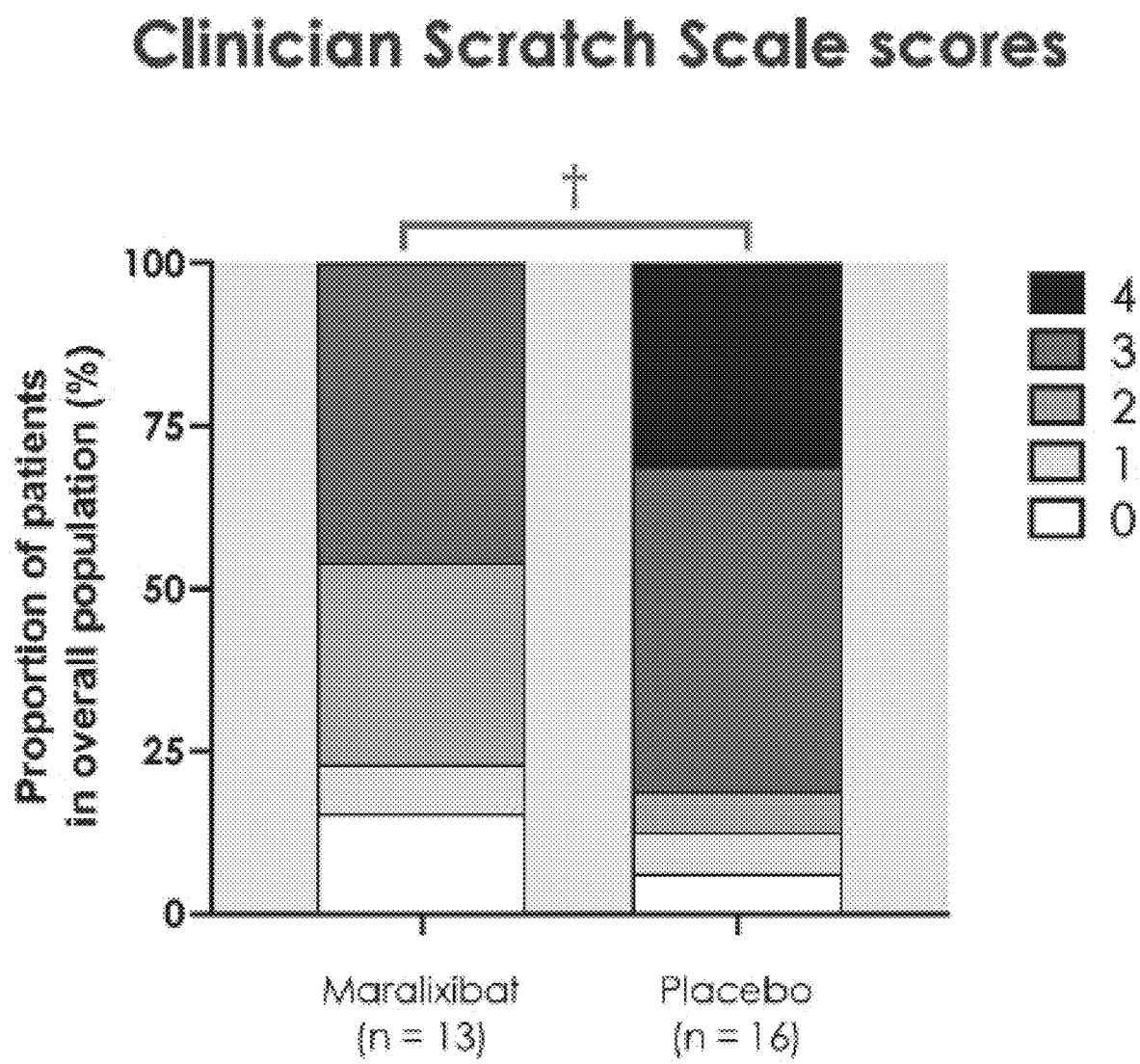
Figure 22:
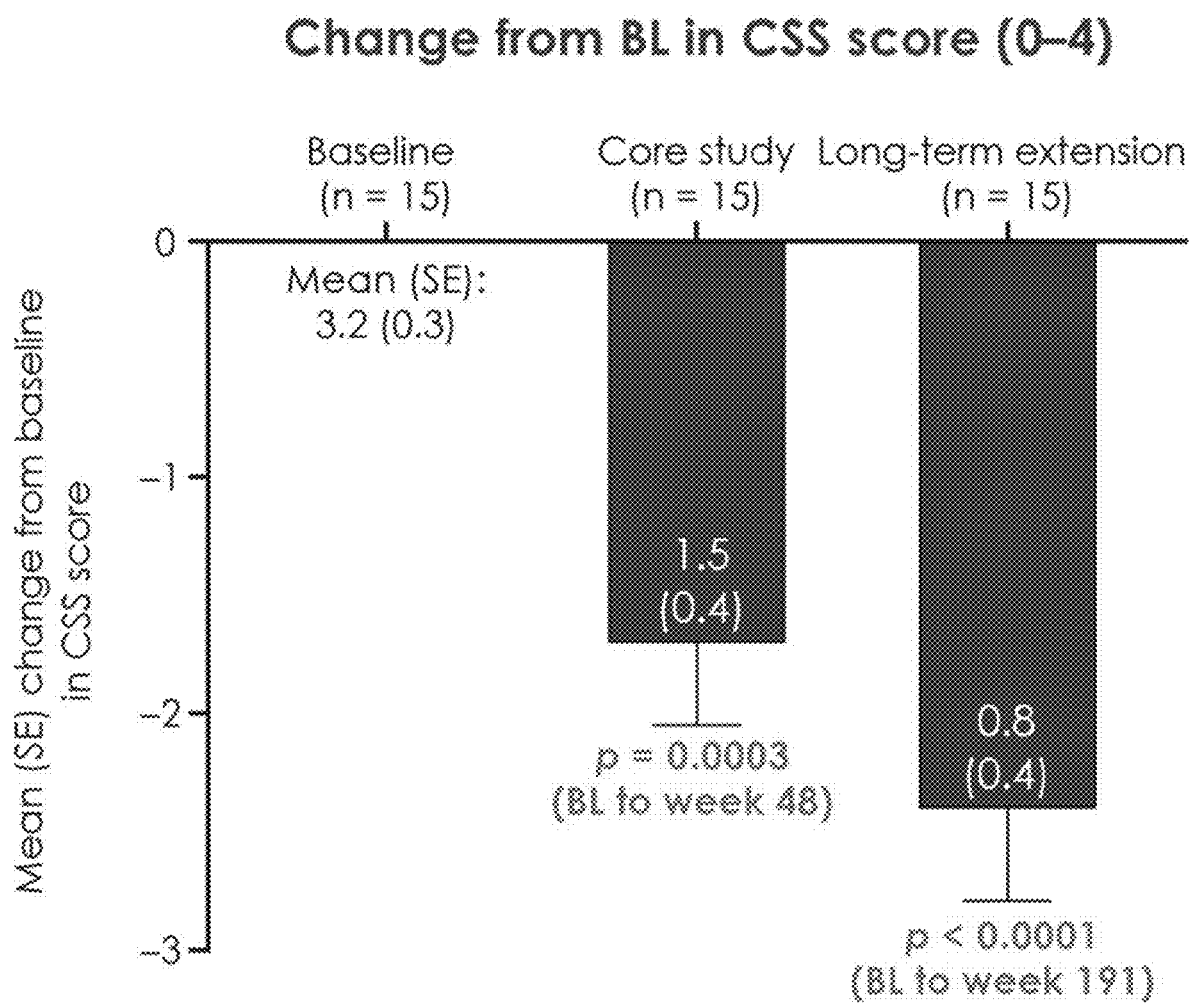
FIG. 22 shows change from baseline (BL) in CSS score for participants in the ICONIC clinical study at week 48 and at week 191.
Figure 23B:
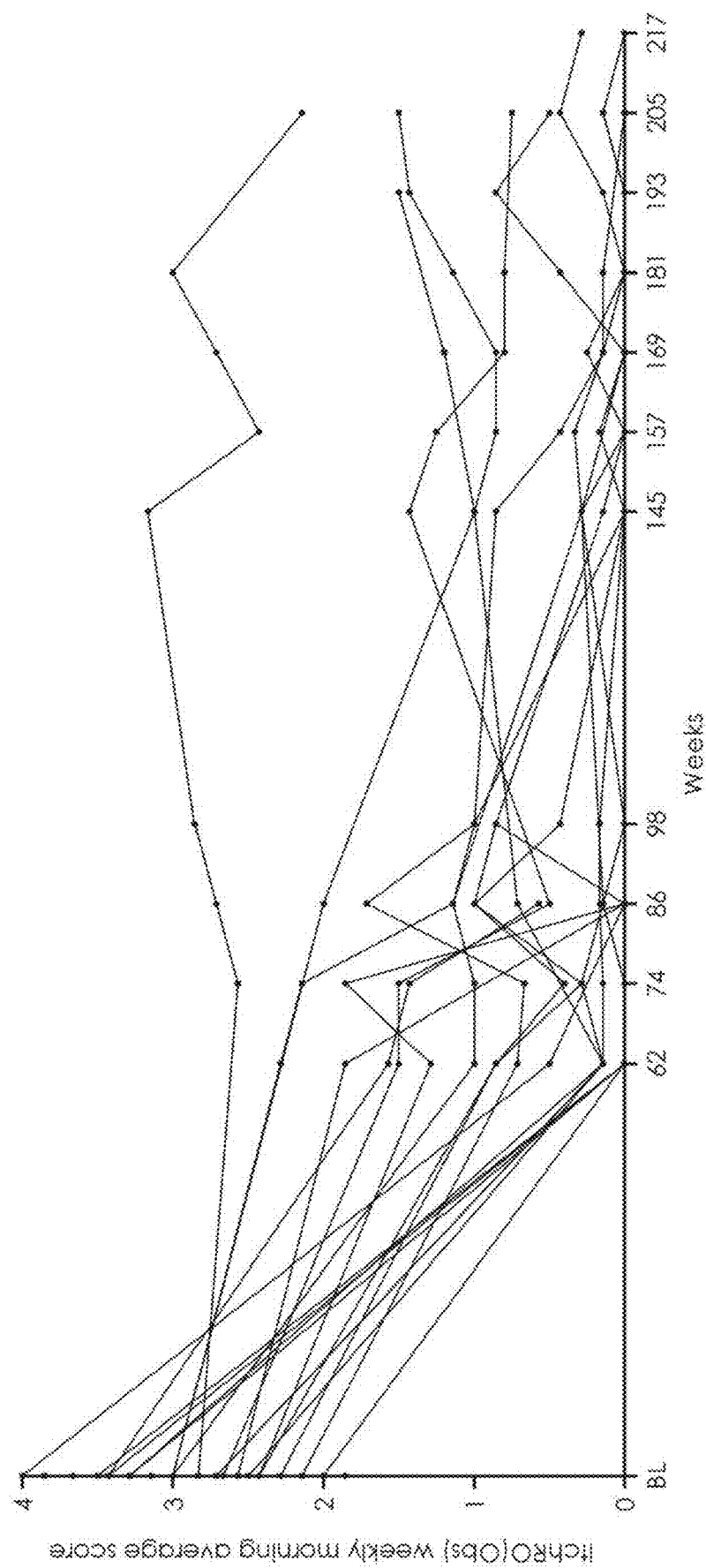
Figure 23C:
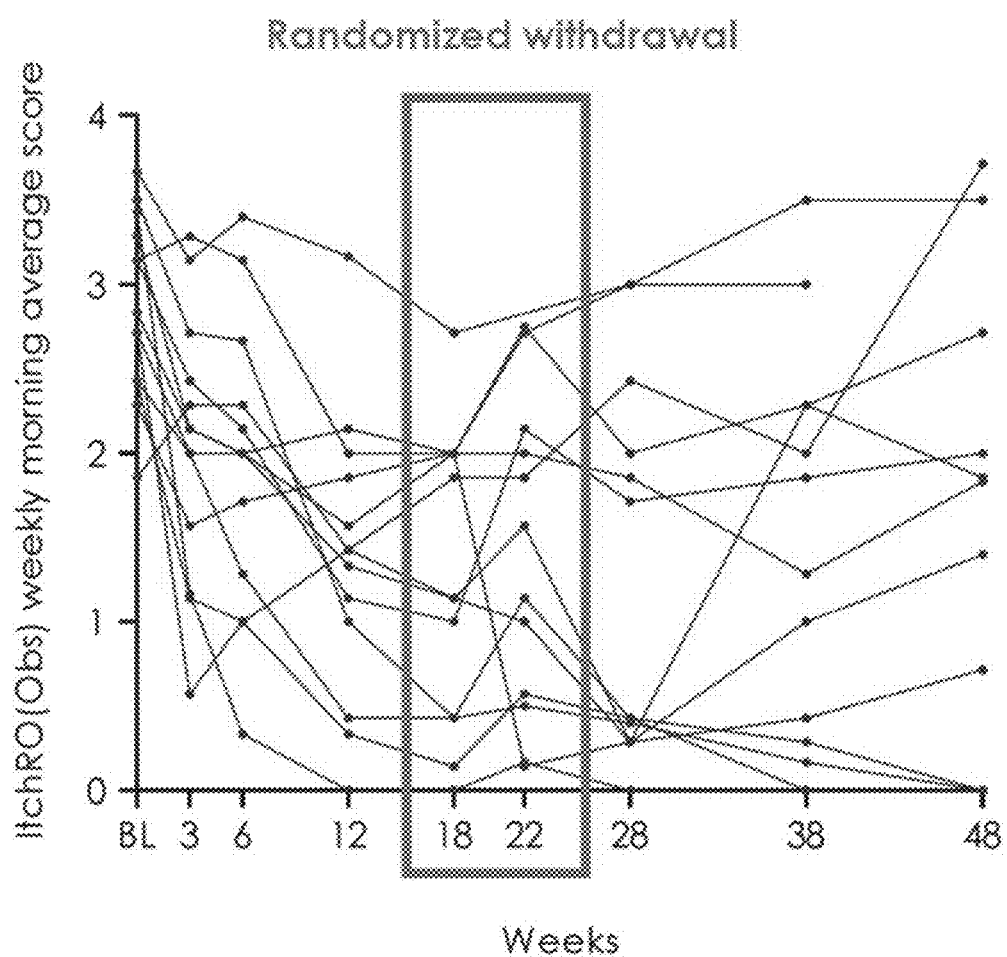
Figure 23D:
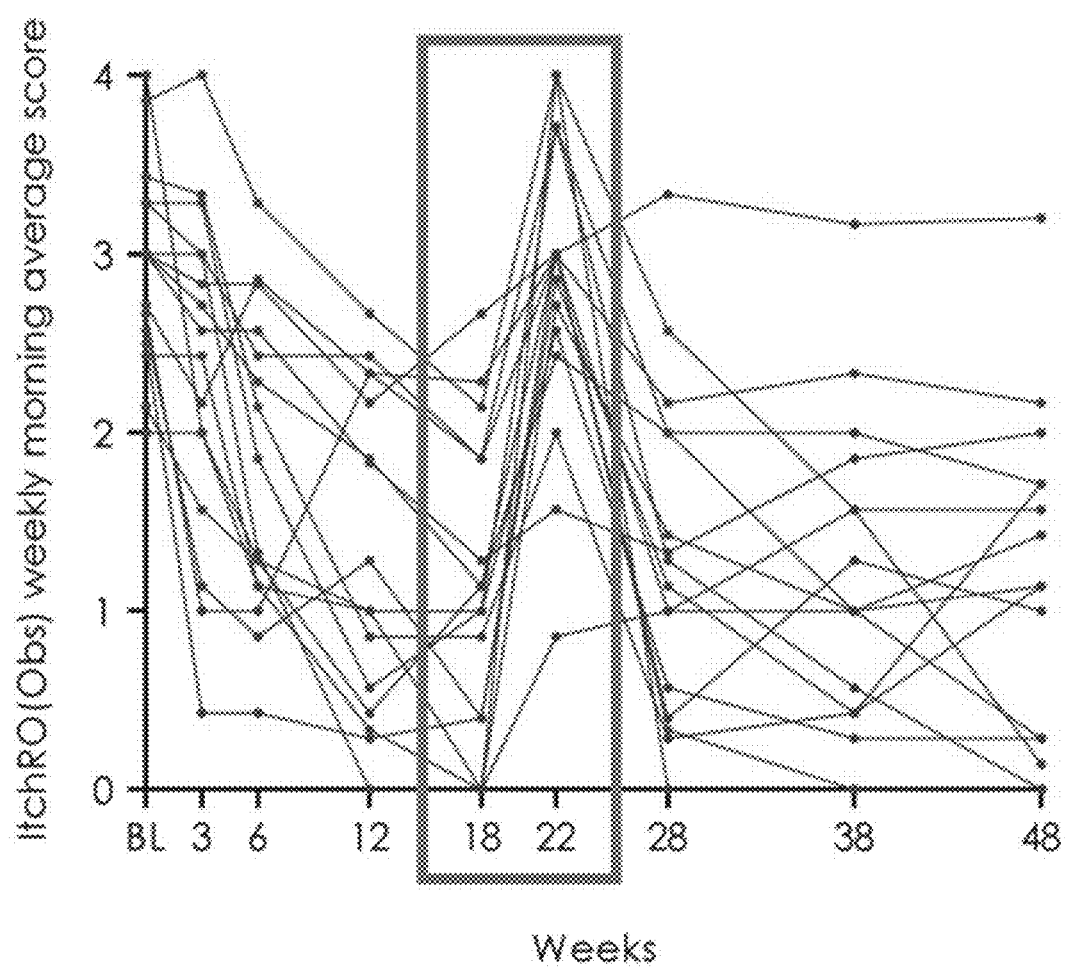
Figure 24:
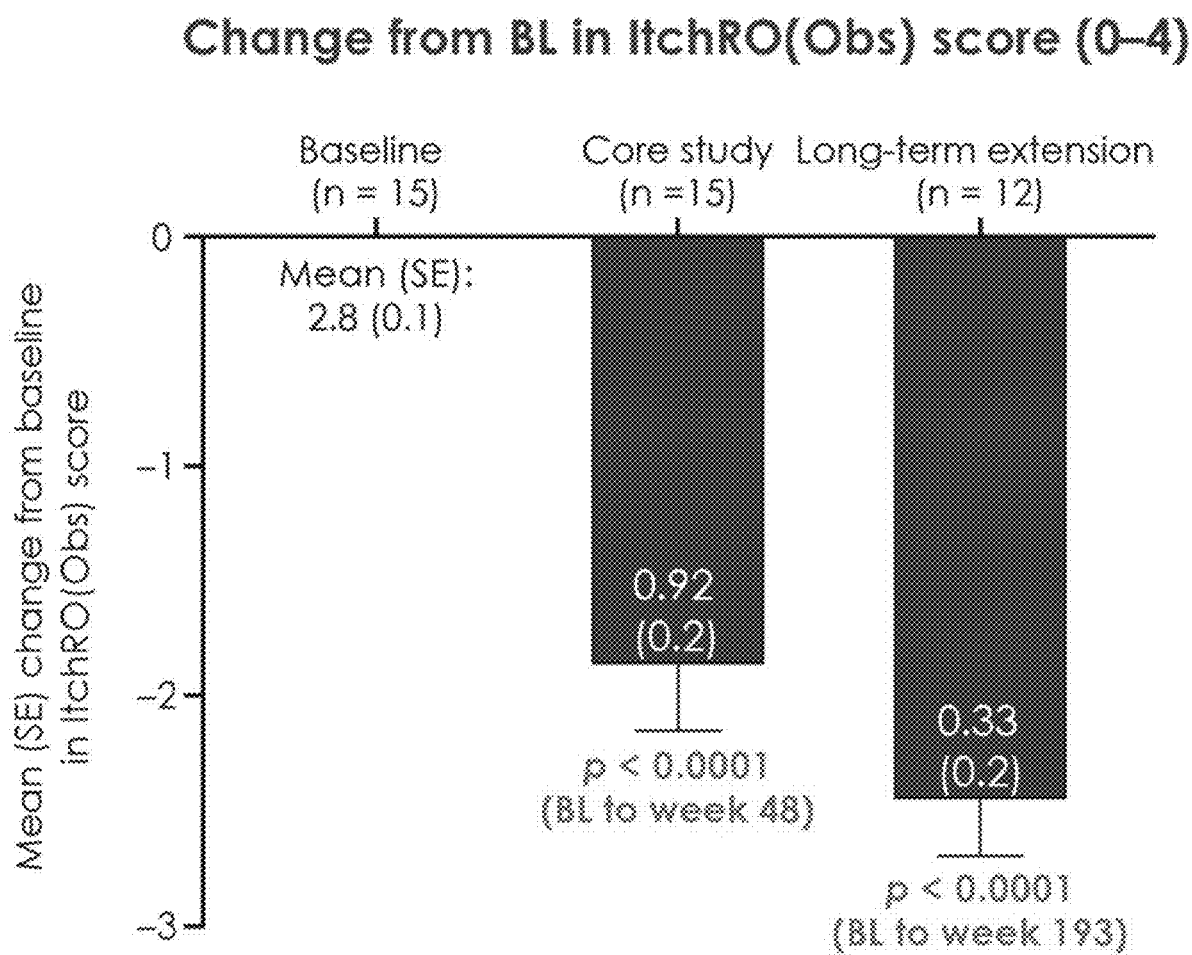
FIG. 24 shows change from baseline (BL) in ITCHRO (OBS) score at 48 weeks and at 193 weeks for participants in the ICONIC clinical study.
Figure 25:
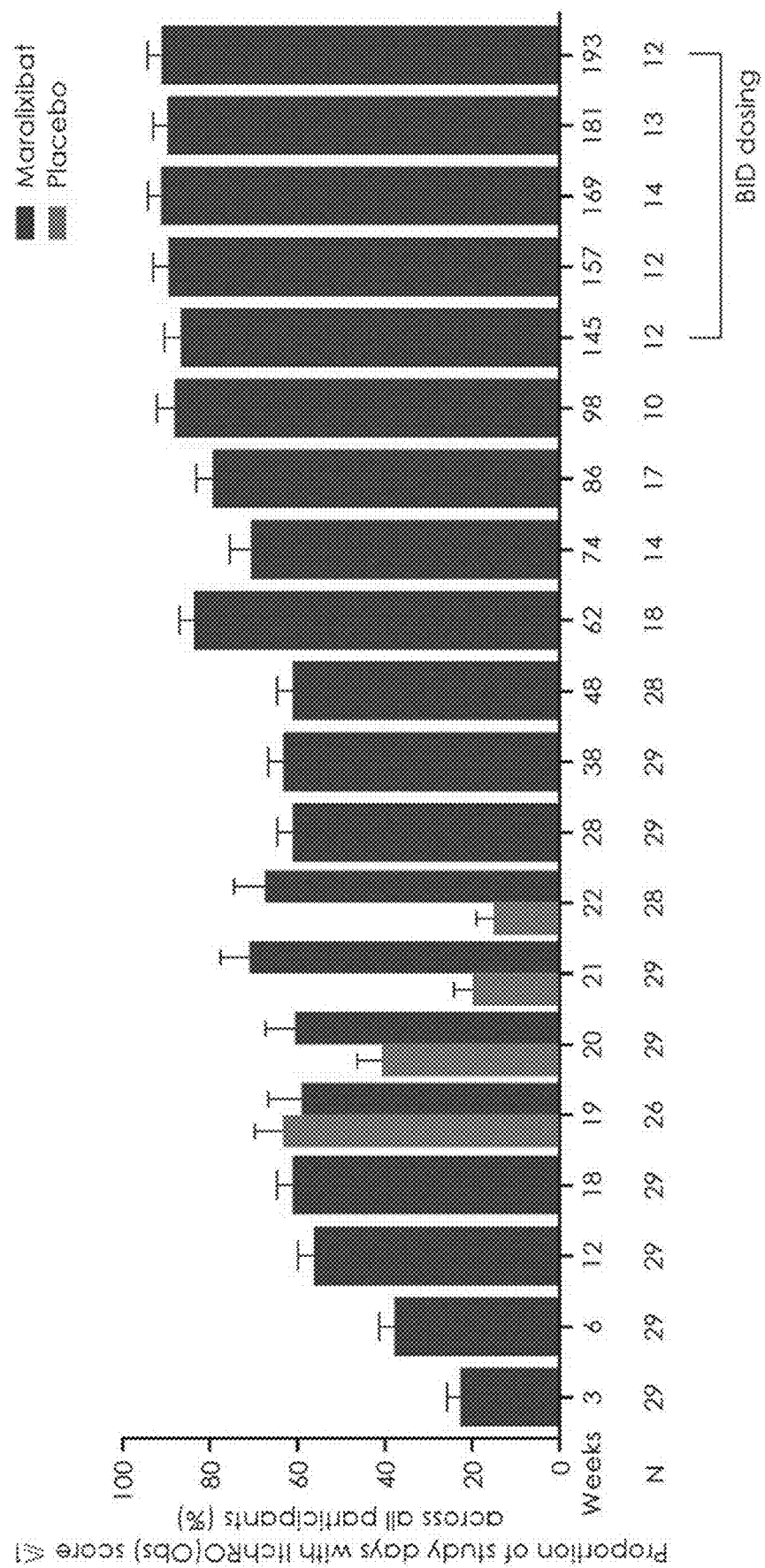
FIG. 25 provides a bar graph showing proportion of study days with ITCHRO(OBS) score ≤1 across all participants (%) in the ICONIC clinical during administration of placebo and during administration of maralixibat.

ITCHRO(OBS) scores decreased from baseline (mean change, -1.7; SE, 0.2; p<0.0001) during the first 18 weeks of treatment with maralixibat at 400 μg/kg QD, see FIGS. 20, 23 and 32. During randomized withdrawal, pruritus worsened in the placebo group but not in the maralixibat group (LS mean difference, -1.5; SE, 0.3, p=0.0001), see FIGS. 20, 21, 23, 25 and 32 and Table 16. At 191 weeks, ITCHRO(OBS) score was reduced from baseline (mean change, -2.5; SE, 0.2; p<0.0001), see FIGS. 22-23. Improvement in pruritus was also demonstrated by a mean reduction in CSS score at 191 weeks of 2.4 points (SE, 0.4; p<0.0001), FIG. 22, and a mean reduction in ITCHRO (OBS) score at 193 weeks of over 2 points to a final score of about 0.33 (SE, 0.2; p<0.0001), see FIGS. 23 and 24. Also, CSS scores decreased by over 1.5 points (final average score of about 1.5) on average by week 48 across all participants, FIG. 22, and ITCHRO(OBS) scores decreased by over 1.5 points on average (final average score of about 0.33) relative to baseline by week 193, see FIGS. 23 and 24. Control of pruritus improved over time, with over 89% of study days across participants reported by observers as minimal or no pruritus (ITCHRO(OBS)≤1) after 98 weeks, see FIGS. 21-25.

TABLE 16

A greater proportion of ITCHRO (OBS) responders were observed in a maralixibat group than placebo during withdrawal in the ICONIC clinical study

| ItchRO (Obs) responder criteria | Open-label Week 18 | Withdrawal-Week 22 | | Open-label Week 48 |
|---|---|---|---|---|
| | | Maralixibat | Placebo | |
| Decrease from baseline ≥1 | 67.7% | 53.8% (p = 0.14) | 25.0% | 72.4% |
| Decrease from baseline ≥1.25 | 58.1% | 46.2% (p = 0.09)<sup>a</sup> | 12.5% | 58.6% |
| Decrease from baseline ≥1.5 | 51.6% | 23.1% (p = 0.01)<sup>a</sup> | 0% | 51.7% |

Figure 26:
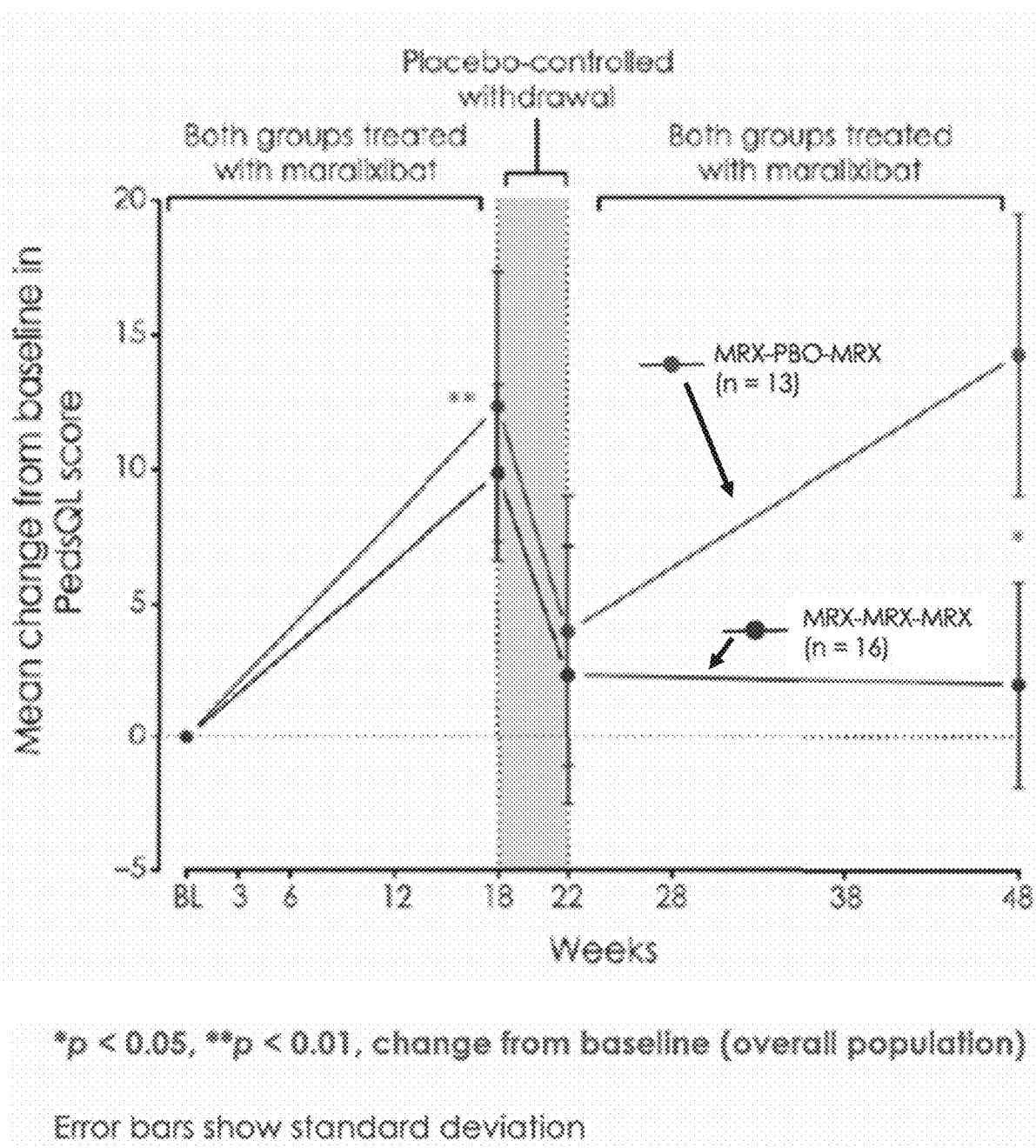
FIG. 26 shows a plot of HRQoL scores over time for patients participating in the ICONIC clinical study. HRQoL scores were measured as PEDSQL scores.
Figure 27:
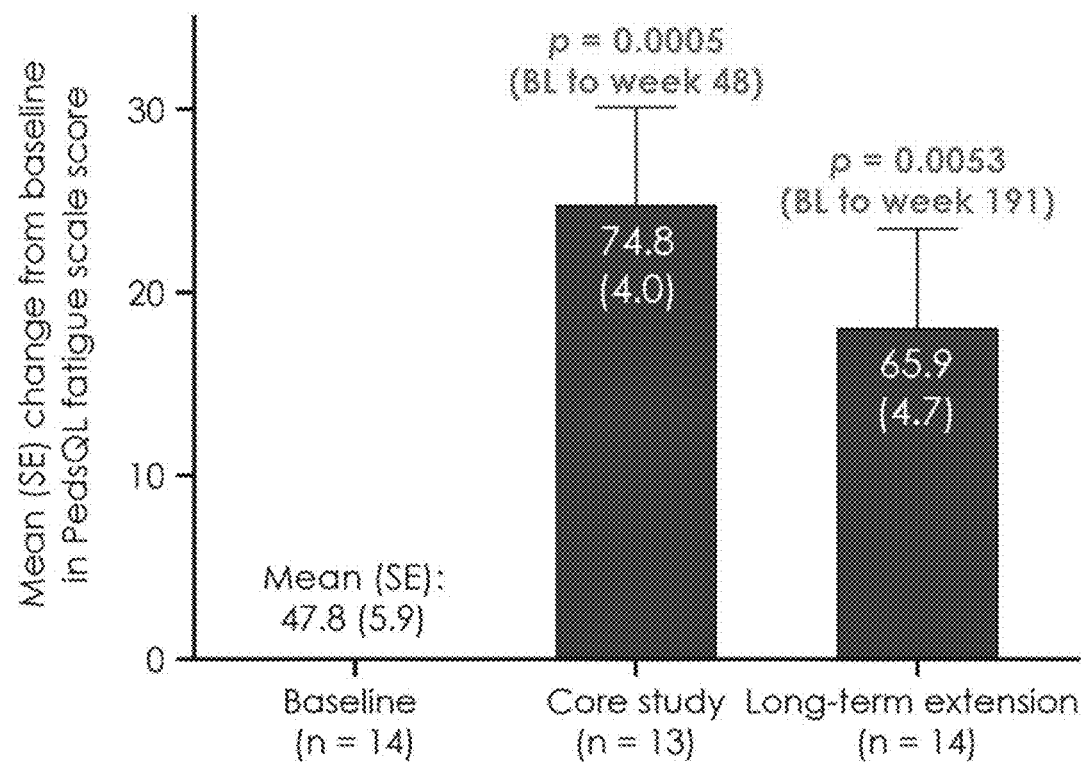
FIG. 27 provides a bar graph showing change from baseline (BL) in PEDSQL fatigue scale score (scale of 0-100) at week 48 and at week 191 for participants in the ICONIC clinical study. n=number of participants represented at an indicated time point.
Figure 29:
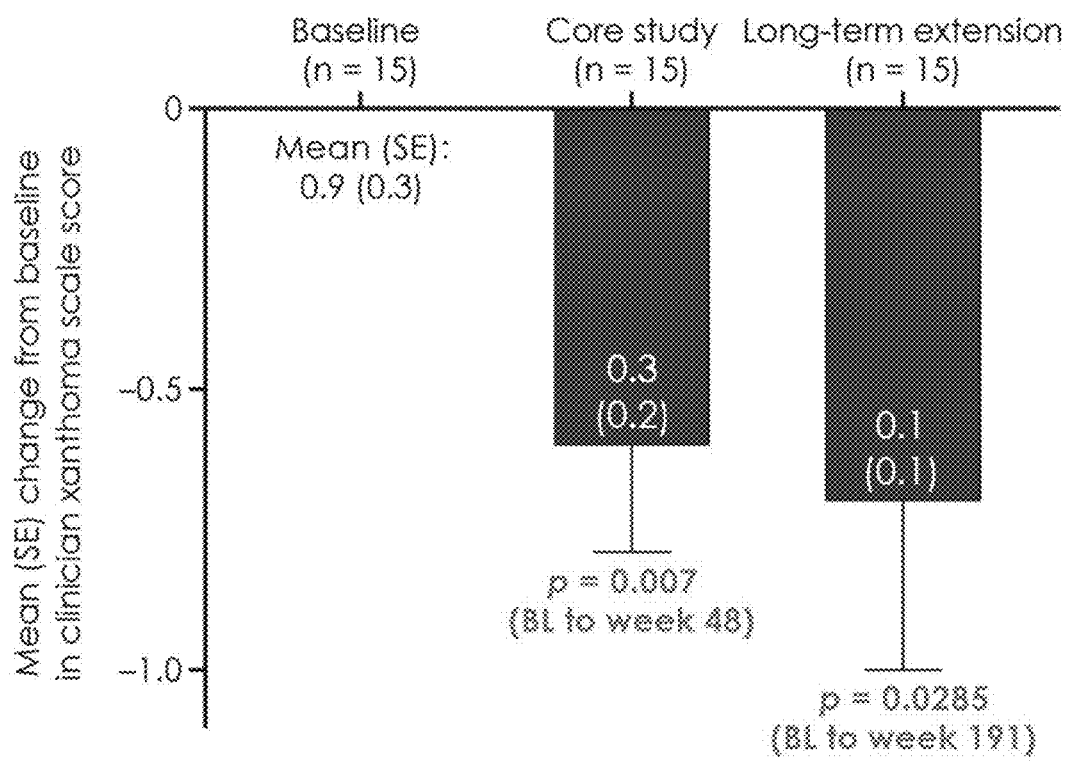
FIG. 29 provides a bar graph showing change from baseline (BL) in clinician xanthoma scale score for participants in the ICONIC clinical study at week 48 and at week 191.

Reductions in sBA concentration and pruritus severity continued and were further improved during the extension, see FIGS. 18-19 and 22-24, and xanthomas continued to be re-absorbed (p<0.05), see FIG. 29. CSS scores continued to improve during the extension (p<0.0001). Improvements were seen in PedsQL Multidimensional Fatigue Scale scores (p<0.01) during the ICONIC core study and extension, see FIGS. 26-27. Therefore, maralixibat improved quality of life.

Figure 28:
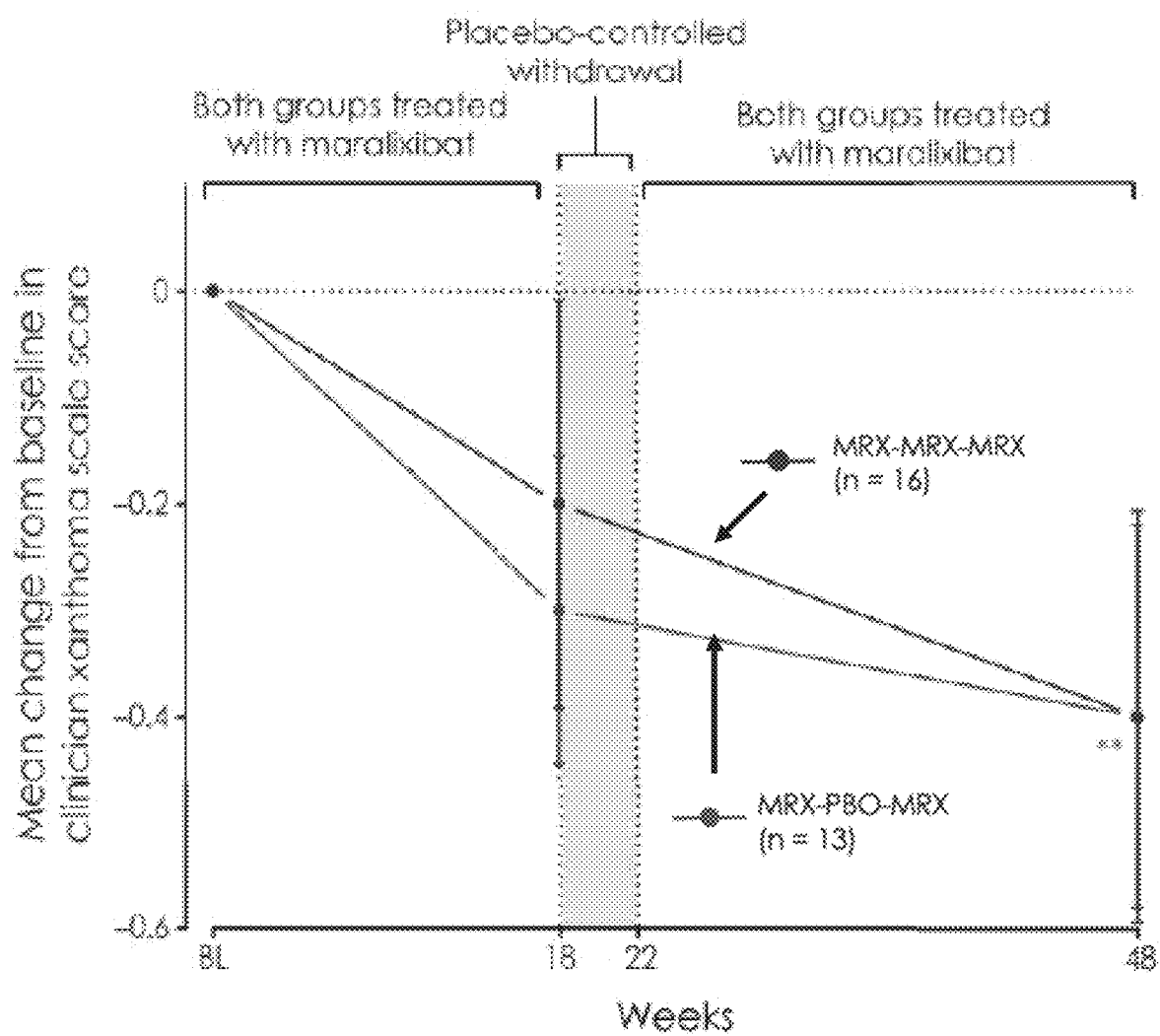
FIG. 28 shows a plot of Clinician Xanthoma Scale scores over time for patients participating in the ICONIC clinical study.

Clinician Xanthoma Score was reduced by 0.7 points (SE, 0.3; p=0.0285) from baseline in participants in the ICONIC clinical study by week 191. Clinician xanthoma scale scores improved significantly (p<0.01) across all participants by week 48, see FIG. 28. Xanthomas continued to be reabsorbed during the long-term extension, see FIG. 29. Thus, maralixibat improved xanthomas.

Figure 30:
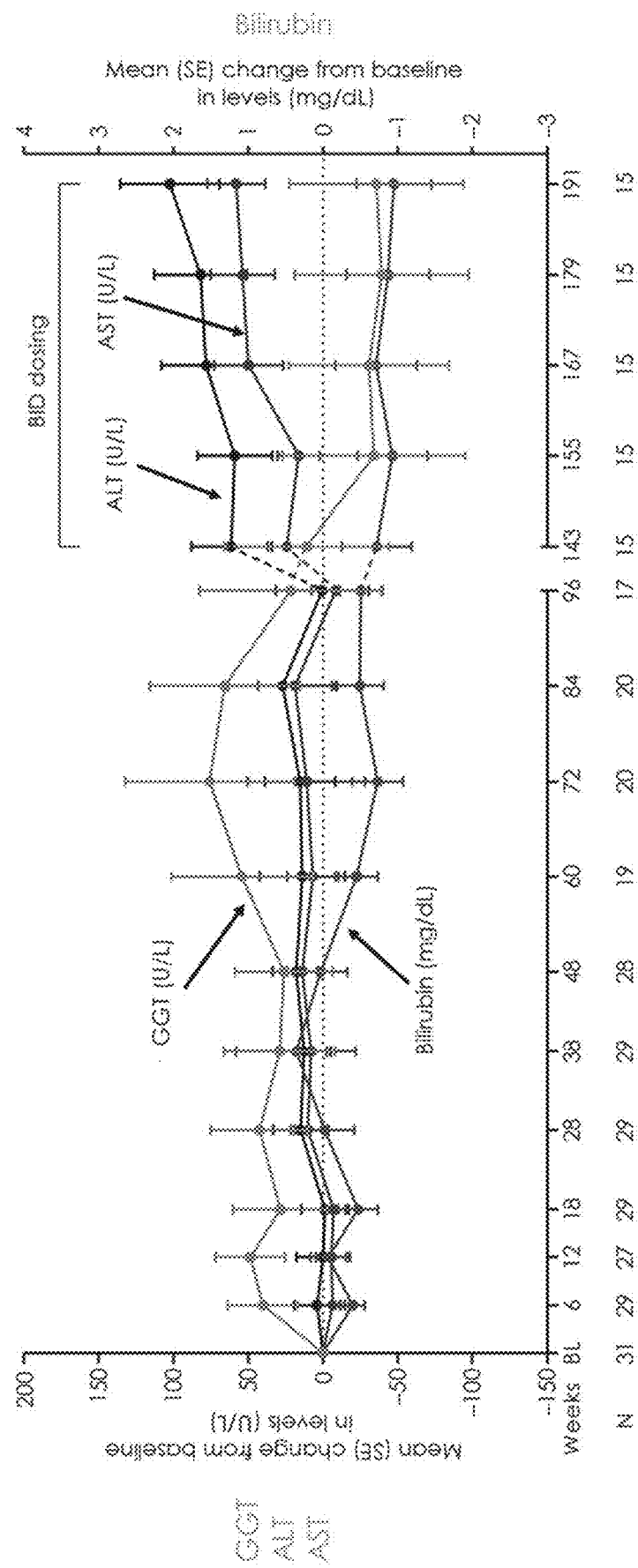
FIG. 30 provides a scatter plot showing serum concentrations of indicators of liver function over time for participants in the ICONIC clinical study. GGT, gamma-glutamyl transpeptidase.

Maralixibat was well tolerated during the core study and extension of the ICONIC clinical study for a period of over three years. Treatment effect was maintained over a period exceeding 48 weeks. Serum concentrations of GGT, ALT, AST, and bilirubin were monitored throughout the ICONIC clinical study, see FIG. 30.

Therapeutic benefits of maralixibat in children with ALGS were clinically relevant and statistically significant. Continuation of maralixibat treatment following a withdrawal period maintained significantly lower sBA levels and less severe pruritus than placebo during the randomized placebo-controlled drug-withdrawal period. Maralixibat significantly reduced pruritus and sBA levels over time and versus placebo in children with ALGS. Long-term maralixibat treatment was associated with durable control of sBA levels, pruritus, and xanthomas, as well as improved growth (discussed further below). Maralixibat was generally well tolerated at doses up to 800 µg/kg/day and with treatment duration up to 4 years.

Figure 31:
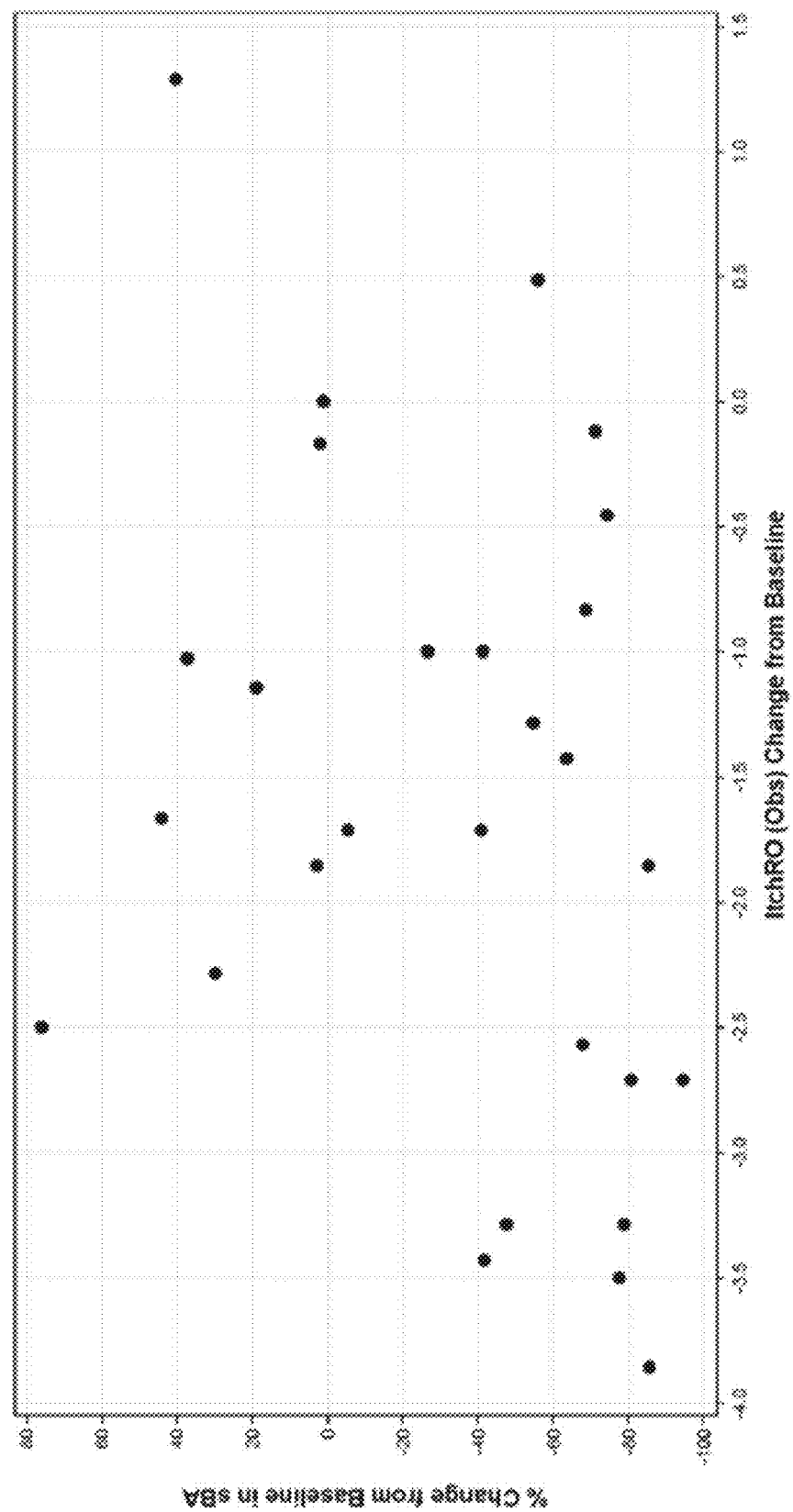
FIG. 31 shows a plot of percent change from baseline in sBA against ITCHRO(OBS) weekly morning average score change from baseline for participants in the ICONIC clinical study at week 48.
Figure 32A:
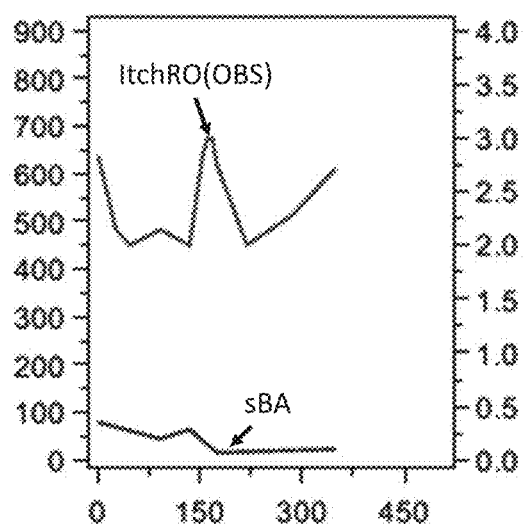
FIG. 32A-32H show lattice plots for each participant (identified by subject number above each plot) in the ICONIC clinical study through week 48.
Figure 32A:
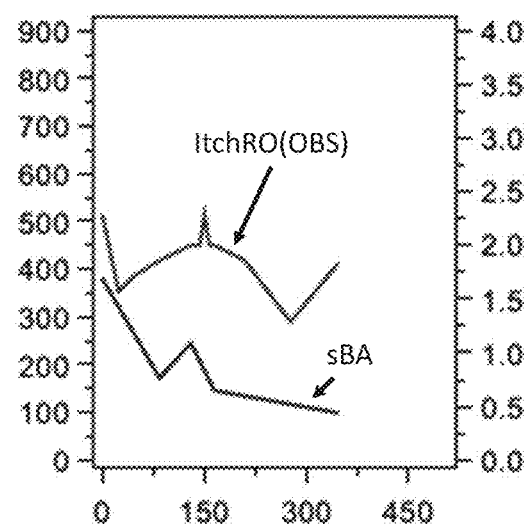
Figure 32A:
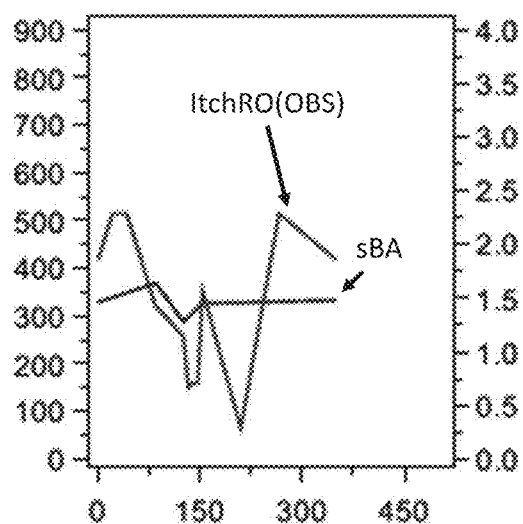
Figure 32A:
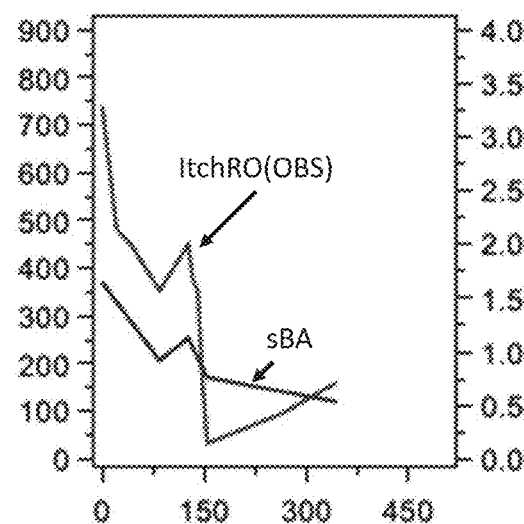
Figure 32B:
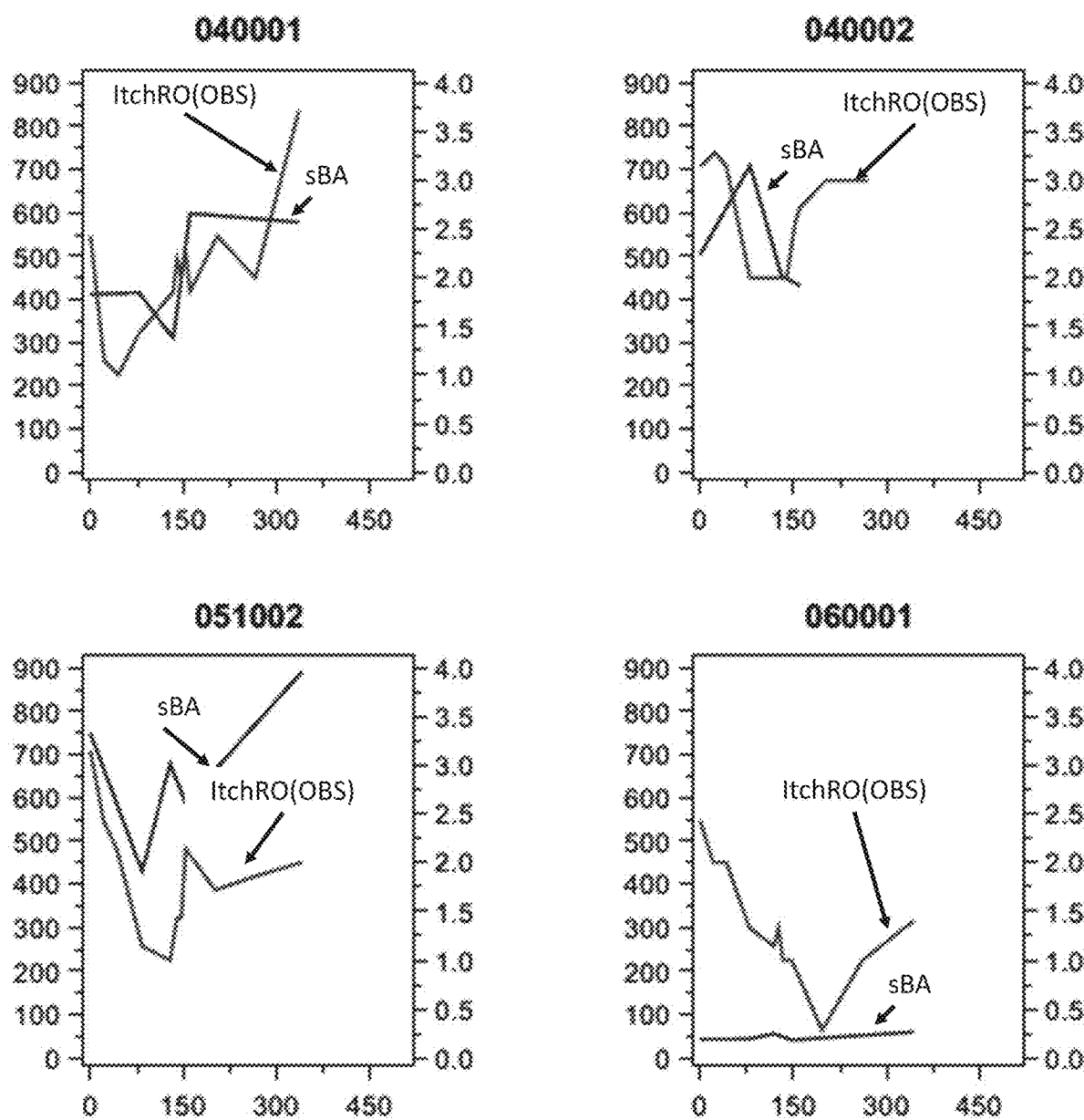
Figure 32C:
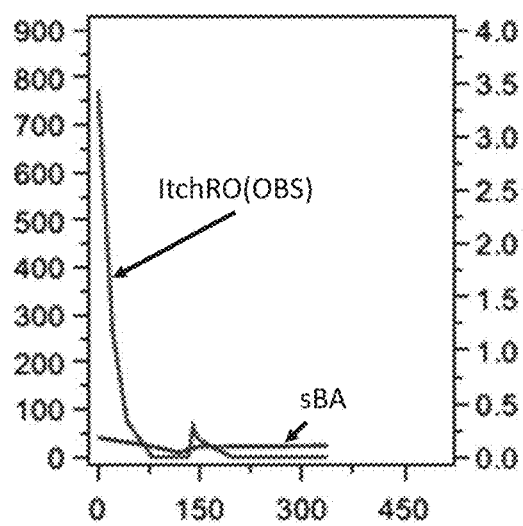
Figure 32C:
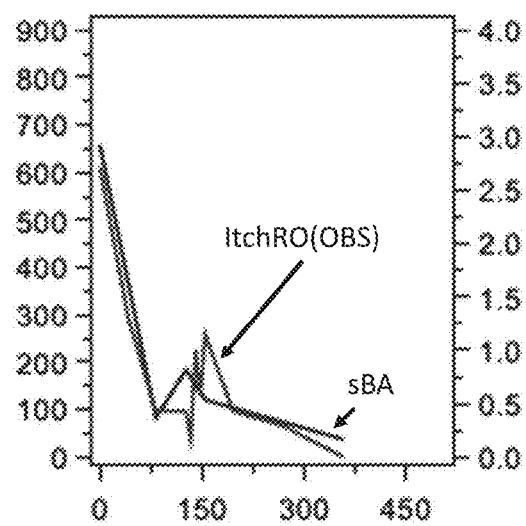
Figure 32C:
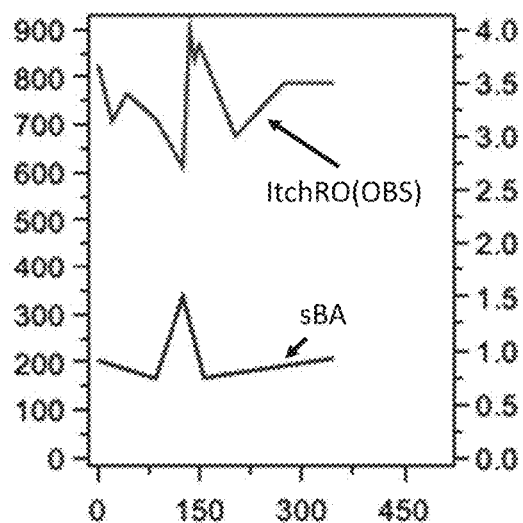
Figure 32C:
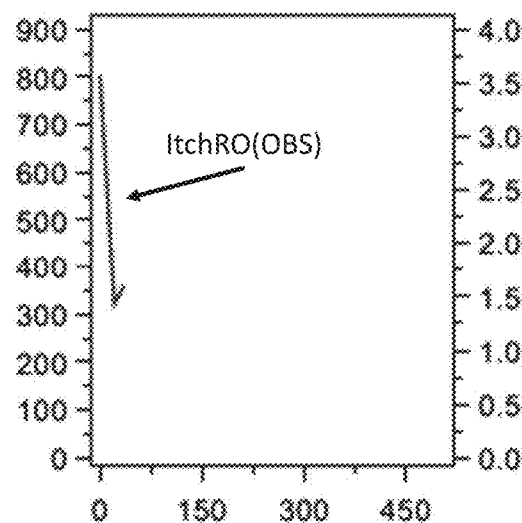
Figure 32D:
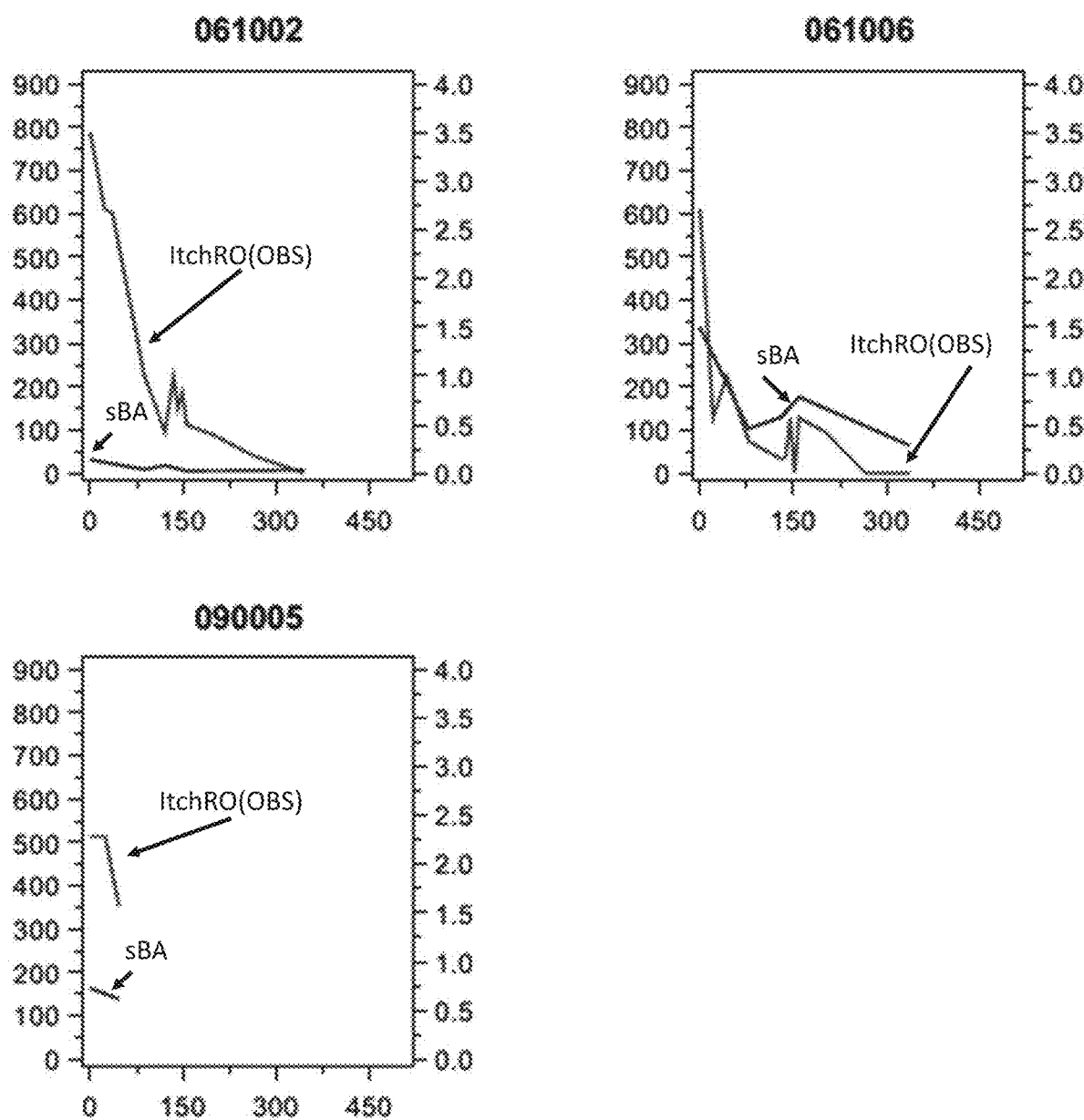
Figure 32E:
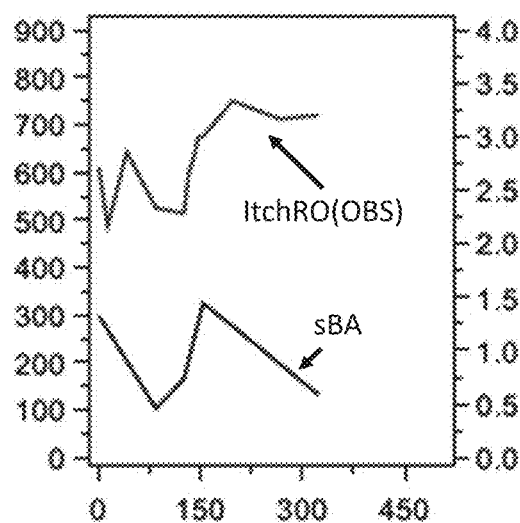
Figure 32E:
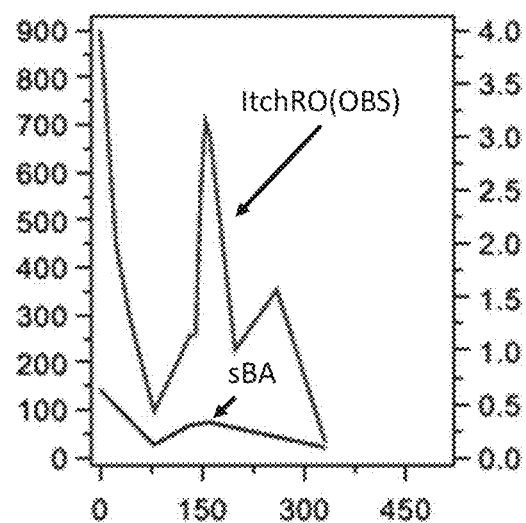
Figure 32E:
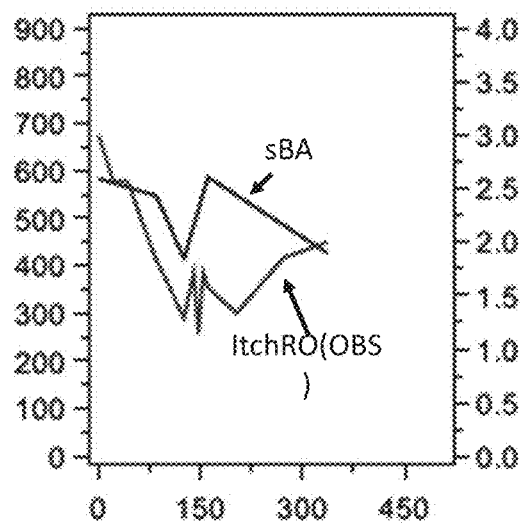
Figure 32E:
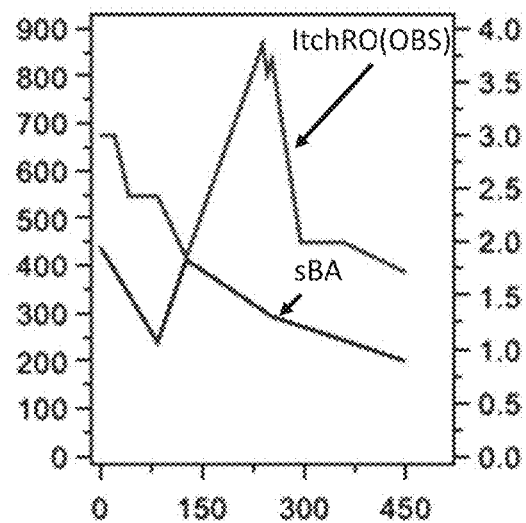
Figure 32F:
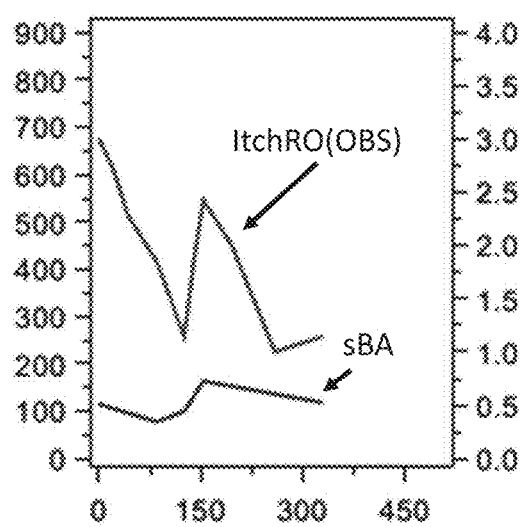
Figure 32F:
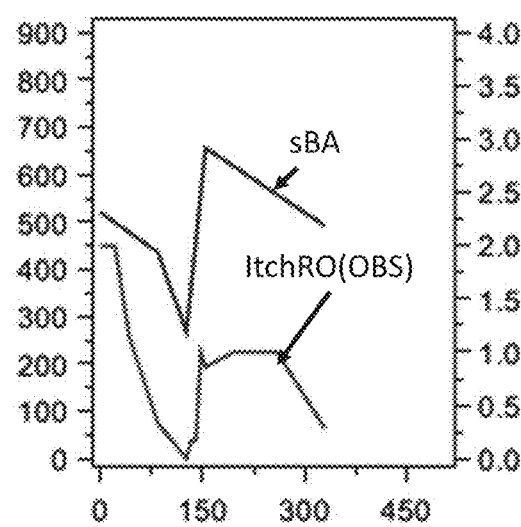
Figure 32F:
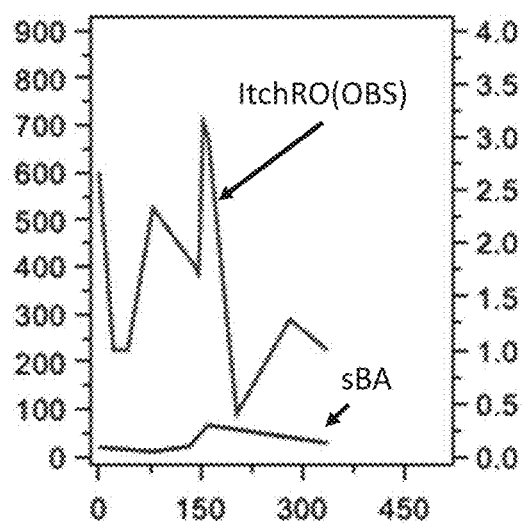
Figure 32F:
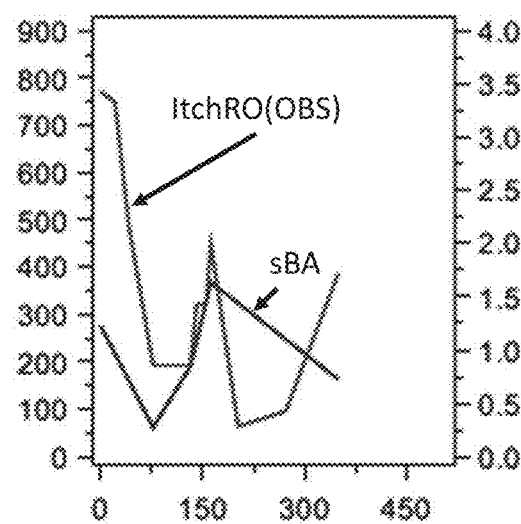
Figure 32G:
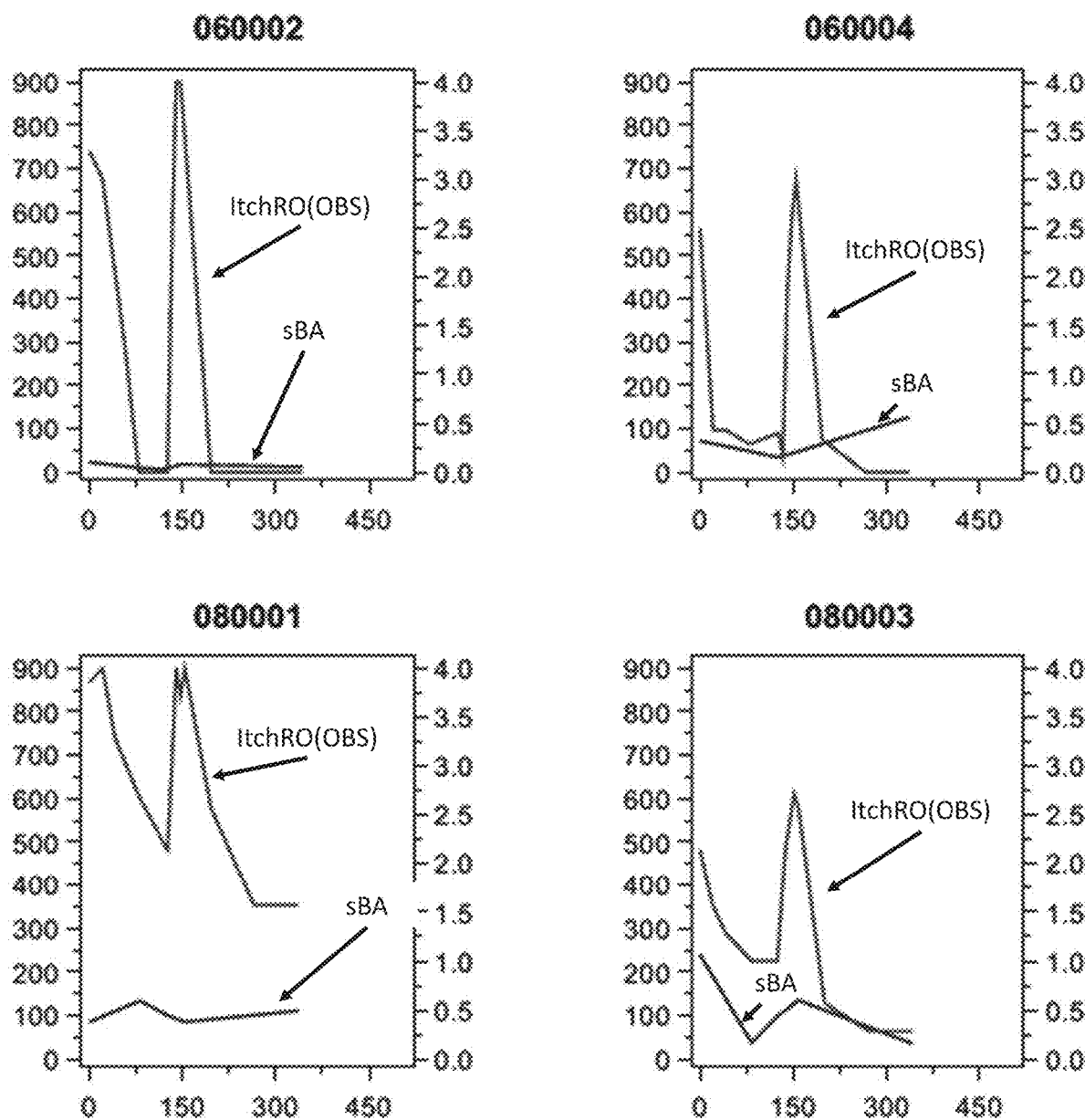
Figure 32H:
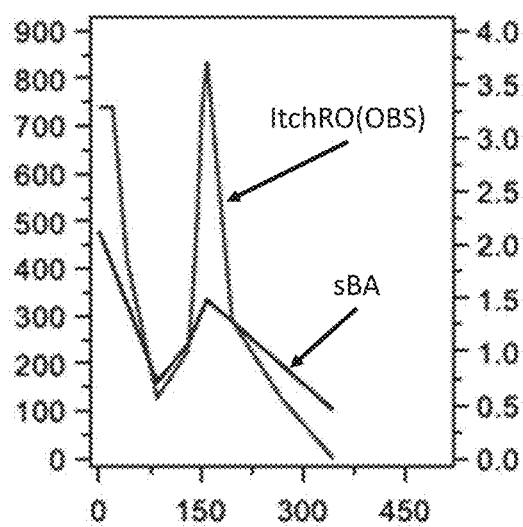
Figure 32H:
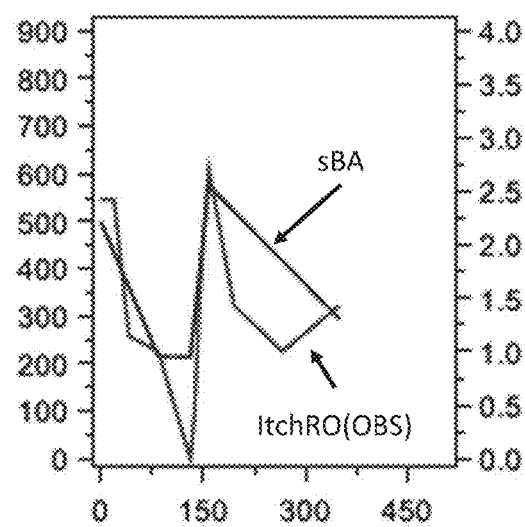
Figure 32H:
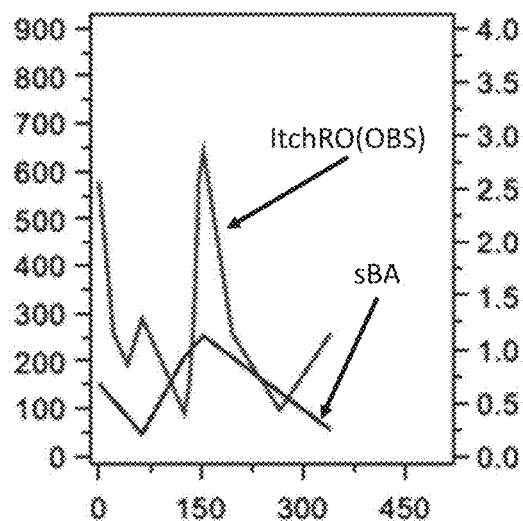
Figure 32H:
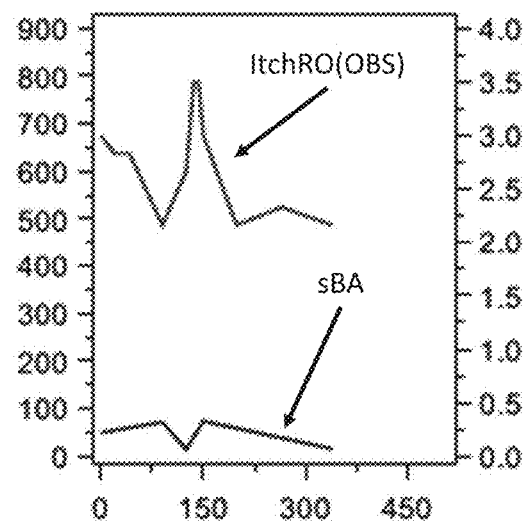

A positive correlation was observed between reduction in sBA concentration and reduction of severity of pruritus as measured by the ITCHRO(OBS) scale, see FIGS. 31-32 and Tables 17-19.

TABLE 17

ITCHRO (OBS) weekly morning average score by sBA response definition for participants in the ICONIC clinical study. A reduction in sBA concentration showed a positive correlation with a reduction in ITCHRO (OBS) weekly morning average score, as compared to baseline.

| | | ItchRO (Obs) Weekly Morning Average Score | |
|---|---|---|---|
| sBA Response Definition | Week 48 (N = 28) n (%) | Week 48 Average Score | Average Change from Baseline |
| ≥50% Reduction | 13 (46.4%) | 1.07 | −1.86 |
| ≥60% Reduction | 11 (39.3%) | 0.82 | −2.12 |
| ≥70% Reduction | 8 (28.6%) | 0.62 | −2.31 |
| ≥80% Reduction | 4 (14.3%) | 0.11 | −2.79 |
| ≥90% Reduction | 1 (3.6%) | 0.00 | −2.71 |
| Normalization (<8.5 µmol/L) | 1 (3.6%) | 0.00 | −3.50 |

TABLE 18 sBA concentrations and change in ITCHRO (OBS) weekly morning average score from baseline for participants (subjects) in the ICONIC clinical study at week 48.

| | Serum Bile Acid (µmol/L) | | | |
|---|---|---|---|---|
| Subject ID | Baseline | Week 48 | Change from Baseline to Week 48 | Change in ItchRO from Baseline to Week 48 |
| 001021 | 79.4 | 22.9 | −56.4 | −0.12 |
| 001022 | 298.1 | 131.8 | −166.3 | 0.49 |
| 001023 | 379.9 | 98.5 | −281.4 | −0.45 |
| 040001 | 411.8 | 578.1 | 166.4 | 1.29 |
| 040002[a] | 503.2 | | | |
| 040003 | 142.0 | 20.8 | −121.1 | −3.86 |
| 050001 | 328.7 | 333.0 | 4.3 | 0.00 |
| 050003 | 370.5 | 119.6 | −251.0 | −2.57 |
| 050004 | 114.5 | 117.7 | 3.3 | −1.86 |
| 050005 | 519.9 | 492.6 | −27.3 | −1.71 |
| 050006 | 583.4 | 427.9 | −155.5 | −1.00 |
| 050007 | 440.0 | 199.8 | −240.2 | −1.29 |
| 051001 | 20.2 | 29.2 | 9.0 | −1.67 |
| 051002 | 748.5 | 891.6 | 143.1 | −1.14 |
| 052002 | 275.6 | 163.4 | −112.2 | −1.71 |
| 060001 | 43.8 | 60.2 | 16.4 | −1.03 |
| 060002 | 22.8 | 12.0 | −10.9 | −3.29 |
| 060003 | 40.5 | 23.6 | −16.9 | −3.43 |
| 060004 | 71.6 | 126.1 | 54.5 | −2.50 |
| 061001 | 657.4 | 37.0 | −620.4 | −2.71 |
| 061002 | 30.9 | 7.0 | −23.9 | −3.50 |
| 061004 | 479.2 | 101.9 | −377.3 | −3.29 |
| 061005 | 499.2 | 293.3 | −205.9 | −1.00 |
| 061006 | 335.4 | 65.0 | −270.4 | −2.71 |
| 080001 | 85.4 | 110.9 | 25.5 | −2.29 |
| 80003 | 239.4 | 35.8 | −203.6 | −1.86 |
| 090001 | 203.7 | 208.0 | 4.3 | −0.17 |
| 090002 | 152.2 | 55.8 | −96.4 | −1.43 |
| 090003 | 49.5 | 15.6 | −33.9 | −0.83 |
| 090004[a] | 496.9 | | | |
| 090005[a] | 162.8 | | | |

[a]Subjects do not have data beyond baseline due to early discontinuations prior to Week 48.

TABLE 19

ITCHRO (OBS) morning average score and sBA reduction levels
for participants (subjects) in the ICONIC clinical study.

| | ItchRO (Obs) Weekly Morning Average Score | | | Serum Bile Acid | |
| --- | --- | --- | --- | --- | --- |
| Subject ID | Baseline | Week 48 | Change from Baseline to Week 48 | Normalization at Week 48 (<8.5 μmol/L) (Y or N) | Reduction of ≥80% from Baseline to Week 48 (Y or N) |
| 001021 | 2.83 | 2.71 | −0.12 | N | N |
| 001022 | 2.71 | 3.20 | 0.49 | N | N |
| 001023 | 2.29 | 1.83 | −0.45 | N | N |
| 040001 | 2.43 | 3.71 | 1.29 | N | N |
| 040002[a] | 3.14 | | | | |
| 040003 | 4.00 | 0.14 | −3.86 | N | Y |
| 050001 | 1.86 | 1.86 | 0.00 | N | N |
| 050003 | 3.29 | 0.71 | −2.57 | N | N |
| 050004 | 3.00 | 1.14 | −1.86 | N | N |
| 050005 | 2.00 | 0.29 | −1.71 | N | N |
| 050006 | 3.00 | 2.00 | −1.00 | N | N |
| 050007 | 3.00 | 1.71 | −1.29 | N | N |
| 051001 | 2.67 | 1.00 | −1.67 | N | N |
| 051002 | 3.14 | 2.00 | −1.14 | N | N |
| 052002 | 3.43 | 1.71 | −1.71 | N | N |
| 060001 | 2.43 | 1.40 | −1.03 | N | N |
| 060002 | 3.29 | 0.00 | −3.29 | N | N |
| 060003 | 3.43 | 0.00 | −3.43 | N | N |
| 060004 | 2.50 | 0.00 | −2.50 | N | N |
| 061001 | 2.71 | 0.00 | −2.71 | N | Y |
| 061002 | 3.50 | 0.00 | −3.50 | Y | N |
| 061004 | 3.29 | 0.00 | −3.29 | N | N |
| 061005 | 2.43 | 1.43 | −1.00 | N | N |
| 061006 | 2.71 | 0.00 | −2.71 | N | Y |
| 080001 | 3.86 | 1.57 | −2.29 | N | N |
| 080003 | 2.14 | 0.29 | −1.86 | N | Y |
| 090001 | 3.67 | 3.50 | −0.17 | N | N |
| 090002 | 2.57 | 1.14 | −1.43 | N | N |
| 090003 | 3.00 | 2.17 | −0.83 | N | N |
| 090004[a] | 3.57 | | | | |
| 090005[a] | 2.29 | | | | |

[a]Subjects do not have data beyond baseline due to early discontinuations prior to Week 48.

Figure 33:
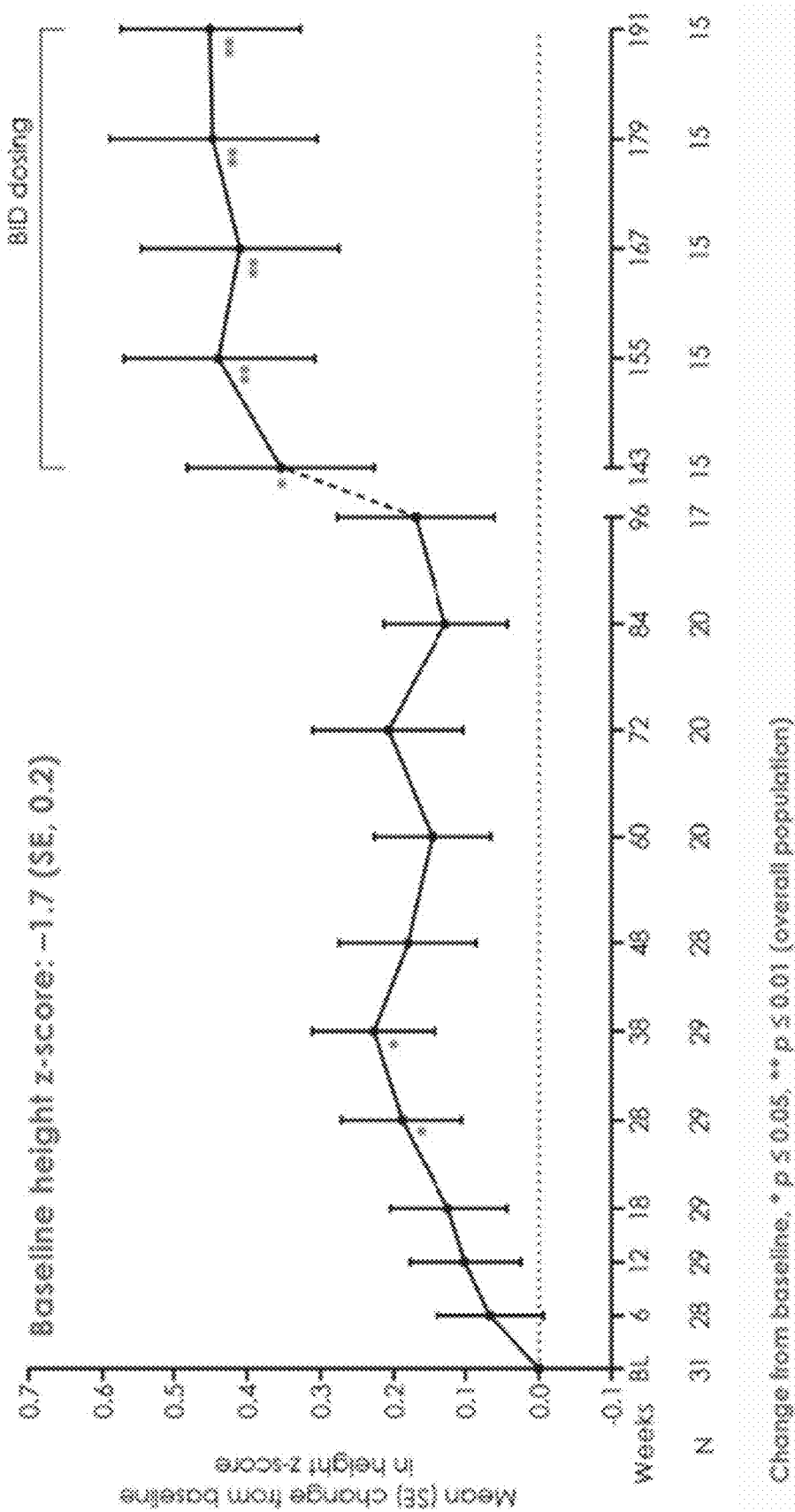
FIG. 33 shows a scatter plot of mean change from baseline in height Z-score over time for all participants in the ICONIC clinical study. The number of patients (N) measured at each data point is indicated beneath the x-axis. BL=baseline.
Figure 34:
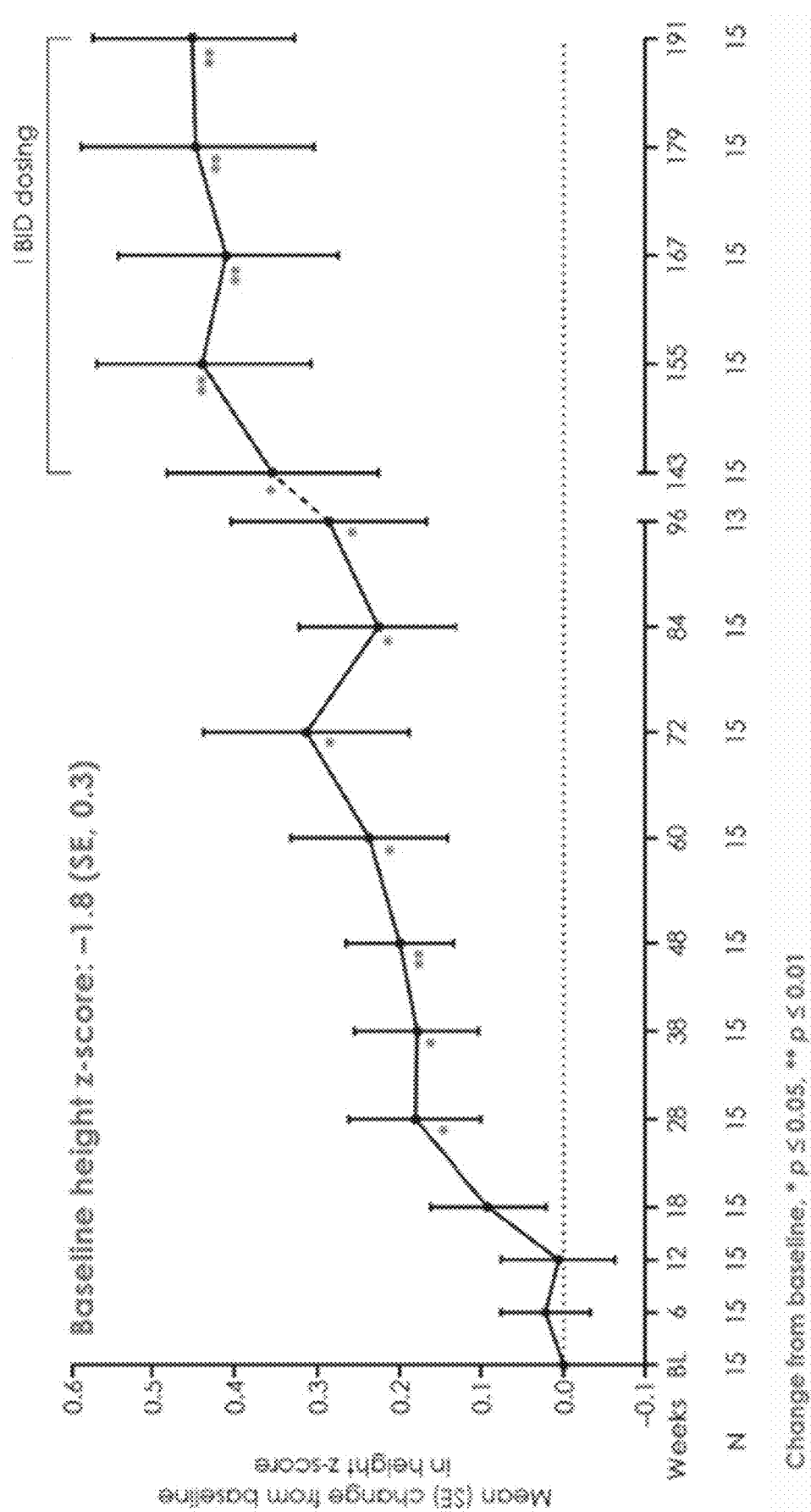
FIG. 34 shows a scatter plot of mean change from baseline in height Z-score over time for participants in the ICONIC clinical study who consented to a long-term extension of the ICONIC clinical study and made it to approximately four years as participants in the study (n=15). The number of patients (N) measured at each data point is indicated beneath the x-axis. BL=baseline.
Figure 35:
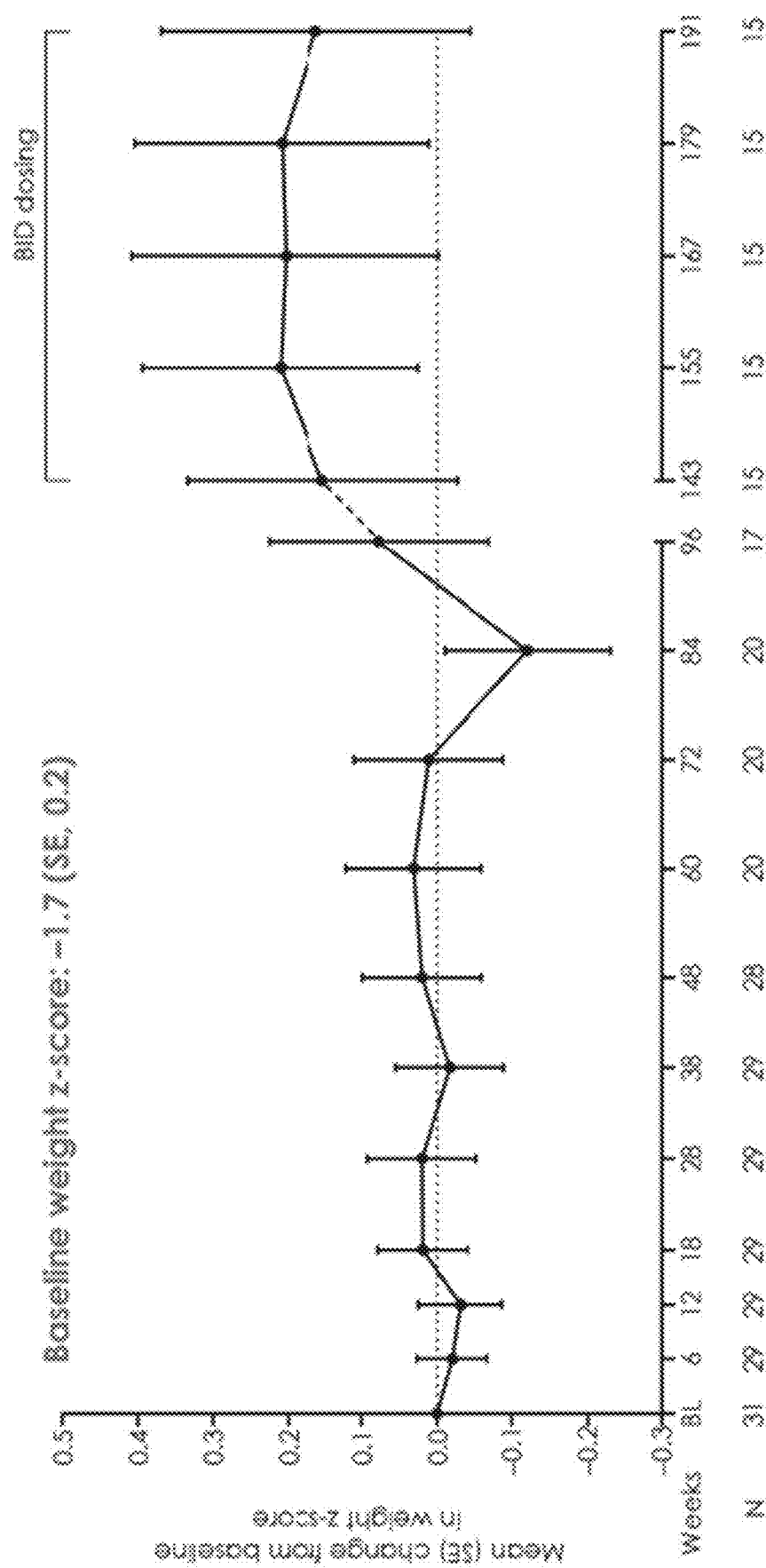
FIG. 35 shows a scatter plot of mean change from baseline in weight Z-score over time for all participants in the ICONIC clinical study (n=31). The number of patients (N) measured at each data point is indicated beneath the x-axis. BL=baseline.
Figure 36:
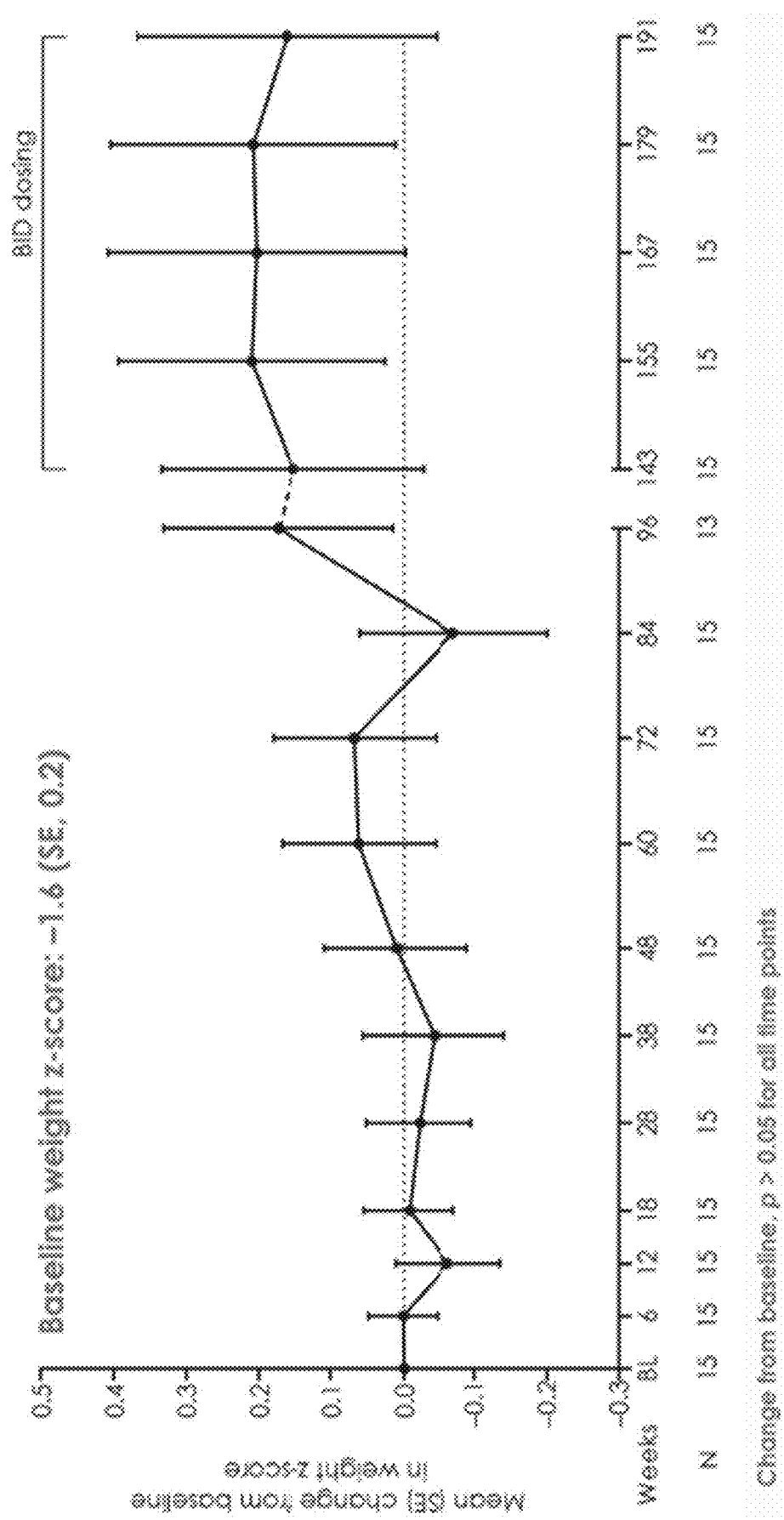
FIG. 36 shows a scatter plot of mean change from baseline in height Z-score over time for participants in the ICONIC clinical study who consented to a long-term extension of the ICONIC clinical study and made it to approximately four years as participants in the study (n=15). The number of patients (N) measured at each data point is indicated beneath the x-axis. BL=baseline.

Height Z-score increased by 0.5 (SE, 0.1; p=0.0027) from baseline in participants in the ICONIC clinical study, see FIGS. 33-34. This corresponds to a statistically significant acceleration in height growth. Therefore, maralixibat improved growth relative to baseline in patients suffering ALGS. Moreover, a further increase in growth from baseline was observed when patients (N=15) were administered 400 μg/kg BID of maralixibat after having been administered a 400 μg/kg QD of maralixibat for a period in excess of about 40 weeks. Also, further improvements in sBA, pruritus, and growth were observed following administration of the higher daily dose relative to improvements observed with administration of 400 μg/kg QD of maralixibat, see FIGS. 18 and 23. The increase in growth was also observed as an increase in weight Z-scores, see FIGS. 35-36. As with the height Z-score, administration of maralixibat caused a dose-dependent increase in weight Z-scores, see FIGS. 35-36. Participants administered maralixibat at a dose of 400 μg/kg BID of maralixibat after having been administered a 400 μg/kg QD of maralixibat for a period in excess of about 40 weeks demonstrated a greater increase in weight Z-score at 400 μg/kg BID than at 400 μg/kg QD.

All references cited anywhere within this specification are incorporated herein by reference in their entirety for all purposes.

While preferred embodiments of the present invention have been shown and described herein, it will be obvious to those skilled in the art that such embodiments are provided by way of example only.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating cholestatic pruritus in a subject having Alagille Syndrome (ALGS) comprising administering to the subject maralixibat in an amount of from about 400 μg/kg/day to about 800 μg/kg/day, wherein maralixibat is administered as a liquid pharmaceutical composition comprising about 0.001 mg/mL to about 16 mg/mL of maralixibat.

2. The method of claim 1, wherein maralixibat is administered in an amount of about 400 μg/kg/day.

3. The method of claim 1, wherein maralixibat is administered in an amount of 360 μg/kg/day to 400 μg/kg/day.

4. The method of claim 1, wherein maralixibat is administered once daily (QD).

5. The method of claim 1, wherein maralixibat is administered once daily in an amount of about 400 μg/kg/day.

6. The method of claim 1, wherein maralixibat is administered once daily in an amount of 360 μg/kg/day to 400 μg/kg/day.

7. The method of claim 1, wherein maralixibat is administered for at least 18 weeks.

8. The method of claim 1, wherein maralixibat is administered for at least 2 years.

9. The method of claim 1, wherein maralixibat is administered for at least 3 years.

10. The method of claim 1, wherein the subject is a pediatric subject.

11. The method of claim 1, wherein the subject is at least 1 year of age.

12. The method of claim 1, wherein maralixibat is administered prior to ingestion of food.

13. The method of claim 1, wherein maralixibat is administered orally.

14. The method of claim 1, wherein the liquid pharmaceutical composition comprises about 10 mg/mL of maralixibat.

15. The method of claim 1, wherein the liquid pharmaceutical composition is administered orally.

16. The method of claim 1, wherein the liquid pharmaceutical composition is an oral solution.

17. The method of claim 1, wherein the liquid pharmaceutical composition is an aqueous solution.

* * * * *